US011326171B2

(12) United States Patent
Feinberg et al.

(10) Patent No.: US 11,326,171 B2
(45) Date of Patent: May 10, 2022

(54) HETEROLOGOUS EXPRESSION OF TAURINE IN MICROORGANISMS

(71) Applicant: KnipBio, Inc., Lowell, MA (US)

(72) Inventors: Lawrence F. Feinberg, Lowell, MA (US); Christopher J. Marx, Lowell, MA (US); Max A. Wall, Lowell, MA (US); Daniel R. Smith, Lowell, MA (US); Catherine J. Pujol-Baxley, Lowell, MA (US); Bonnie D. McAvoy, Lowell, MA (US)

(73) Assignee: KnipBio, Inc., Lowell, MA (US)

( * ) Notice: Subject to any disclaimer, the term of this patent is extended or adjusted under 35 U.S.C. 154(b) by 0 days.

(21) Appl. No.: 15/774,731

(22) PCT Filed: Nov. 9, 2016

(86) PCT No.: PCT/US2016/061081
§ 371 (c)(1),
(2) Date: May 9, 2018

(87) PCT Pub. No.: WO2017/083351
PCT Pub. Date: May 18, 2017

(65) Prior Publication Data

US 2019/0062757 A1 Feb. 28, 2019

Related U.S. Application Data

(60) Provisional application No. 62/252,971, filed on Nov. 9, 2015.

(51) Int. Cl.

| | |
|---|---|
| ***C12N 9/96*** | (2006.01) |
| ***C12N 15/52*** | (2006.01) |
| ***A23K 10/12*** | (2016.01) |
| ***A23K 50/80*** | (2016.01) |
| ***A23L 33/175*** | (2016.01) |
| ***C12P 13/00*** | (2006.01) |
| ***C12P 21/00*** | (2006.01) |
| ***C12P 11/00*** | (2006.01) |
| ***A23L 5/44*** | (2016.01) |
| ***A23K 20/10*** | (2016.01) |
| ***A23L 33/15*** | (2016.01) |
| ***A23K 20/142*** | (2016.01) |

(52) U.S. Cl.
CPC .............. *C12N 15/52* (2013.01); *A23K 10/12* (2016.05); *A23K 20/10* (2016.05); *A23K 20/142* (2016.05); *A23K 50/80* (2016.05); *A23L 5/44* (2016.08); *A23L 33/15* (2016.08); *A23L 33/175* (2016.08); *C12P 11/00* (2013.01); *C12P 13/001* (2013.01); *C12P 21/00* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 6,551,795 B1 * | 4/2003 | Rubenfield ............ | C07K 14/21 435/253.3 |
| 7,517,684 B2 * | 4/2009 | Rubenfield ............ | C07K 14/21 435/320.1 |
| 2005/0108791 A1 * | 5/2005 | Edgerton ............ | C07K 14/415 800/284 |
| 2012/0107360 A1 | 5/2012 | Le Butt et al. | |
| 2012/0222148 A1 | 8/2012 | Furano et al. | |
| 2015/0044327 A1 | 2/2015 | Feinberg et al. | |

FOREIGN PATENT DOCUMENTS

| | | |
|---|---|---|
| EP | 1298200 A2 | 4/2003 |
| KR | 101214632 B1 | 12/2012 |
| WO | 2011/053764 A2 | 5/2011 |
| WO | WO2017/083351 A1 | 5/2017 |

OTHER PUBLICATIONS

Spencer et al. (J. Bacteriol. 185(4), pp. 1316-1325, 2003).*
Bruland et al. (J. Biol. Chem., Jan. 2009, 284 (1), pp. 660-672).*
Krog et al. (PLOS One, Mar. 2013, vol. 8, issue 3, pp. 1-11).*
Zuniga et al. (Nature Communications, 11:3803, 2020, pp. 1-13).*
Abe, Y., et al., Role of the osmolyte taurine on the folding of a model protein, hen egg white lysozyme, under a crowding condition, Amino Acids 47(5):909-15, Jan. 21, 2015.
Agnello, G., et al., Discovery of a Substrate Selectivity Motif in Amino Acid Decarboxylases Unveils a Taurine Biosynthesis Pathway in Prokaryotes, ACS Chemical Biology 8(10):2264-2271, Aug. 23, 2013.
Mou, S., et al., Separation methods for taurine analysis in biological samples, Journal of Chromatography B, 781:251-267, 2002.
Salze, G., et al., Taurine: a critical nutrient for future fish feeds, Aquaculture 437:215-229, 2015.
Tevatia, R., et al., The taurine biosynthetic pathway of microalgae, Algal Research 9:21-26, 2015.
Gaylord, T., et al., Supplementation of taurine and methionine to all-plant protein diets for rainbow trout (Oncorhynchus mykiss), Aquaculture 269:514-524, 2007.
Denger, K., et al., Bifurcated Degradative Pathway of 3-Sulfolactate in Roseovarius nubinhibens ISM via Sulfolacetaldehyde Acetyltransferase and (S)-Cysteate Sulfolyase, J Biol Chem 191(18):5648-5656, 2009. Denger, K., et al., Rhodococcus opacus expresses the xsc gene to utilize taurine as a carbon source or as a nitrogen source but not as a sulfur source, Microbiology 150:1859-1867, 2004.

(Continued)

*Primary Examiner* — Hope A Robinson
(74) *Attorney, Agent, or Firm* — FisherBroyles, LLP; Jill A. Jacobson

(57) ABSTRACT

Non-naturally occurring microorganisms are provided that produce taurine and/or taurine precursors, e.g., hypotaurine, sulfoacetaldehyde, or cysteate, utilizing exogenously added enzyme activities. Methods of producing taurine and/or taurine precursors in microbial cultures, and feed and nutritional supplement compositions that include taurine and/or taurine precursors produced in the microbial cultures, such as taurine- and/or taurine precursor-containing biomass, are also provided.

8 Claims, 13 Drawing Sheets

Specification includes a Sequence Listing.

(56) References Cited

OTHER PUBLICATIONS

McKusker, S., et al., Amino acid content of selected plant, algae and insect species: a search for alternative protein sources for use in pet foods, J Nutr Sci 3:e39, 2014.
Denger, K., et al., Rhodococcus opacus expresses the xsc gene to utilize taurine as a carbon source or as a nitrogen source but not as a sulfur source, Microbiology 150:1859-1867, 2004. McKusker, S., et al., Amino acid content of selected plant, algae and insect species: a search for alternative protein sources for use in pet foods, J Nutr Sci 3:e39, 2014.
Brosnan, J., et al., The Sulfur-Containing Amino Acids: An Overview,J Nutr 1 36(6 Suppl):1636S-1640S, 2006.
Honjoh, K., et al., Enhancement of menadione stress tolerance in yeast by accumulation of hypotaurine and taurine: co-expression of cDNA clones, from Cyprinus carpio, for cysteine dioxygenase and cysteine sulfinate decarboxylase in *Saccharomyces cerevisiae*, Amino Acids 38:1173-1183, 2010.
Graham, D., et al., Convergent evolution of coenzyme M biosynthesis in the Methanosarcinales: cysteate synthase evolved from an ancestral threonine synthase, Biochem J 424:467-478, 2009.
Takeuchi, K., et al., A hyperosmotic stress-induced mRNA of carp cell encodes Na+- and Cl-dependent high affinity taurine transporter, Biochimica et Biophysica Acta 1464(2):219-230, 2000.
Warskulat, U., et al., Phenotype of the Taurine Transporter Knockout Mouse, Methods Enzymol 428:439-58, 2007.
Fujii, T., et al., Stable Supply of Large Amounts of Human Fab from the Inclusion Bodies in *E. coli*, J Biochem 141 (5):697-707, 2007.
Wu, Y., et al., Replacement of fishmeal by soy protein concentrate with taurine supplementation in diets for golden pompano (*Trachinotus ovatus*), Aquae Nutr 2192):214-222, 2015.
Ripps, H., et al., Review: Taurine: A "very essential" amino acid, Molecular Vision 18:2673-2786, 2012.
Matsunari, H., et al., Effect of feeding rotifers enriched with taurine on the growth and survival of larval amberjack Seriola dumerili, Fish Sci 79(5): 815-821, 2013.
Langdon, C., et al. , Microparticle types for delivering nutrients to marine fish larvae, Aquaculture 227(1-4):259-275, 2003.
Francis, G., et al., Antinutriional factors present in plant-derived alternate fish feed ingredient and their effects in fish, Aquaculture 199(3-4):197-227, 2001.
Oliveira, M., et al., Scavenging and antioxidant potential of physiological taurine concentrations against different reactive oxygen/nitrogen species, Pharmacological Reports 62:185-193, 2010.
Aruoma, O, et al., The antioxidant action of taurine, hypotaurine and their metabolic precursors, Biochem J 256:251-55, 1988.
Bucolo, C., et al., Taurine exerts antioxidant and osmoprotecting activity: an in vitro and in vivo study, Acta Ophthalmologic 95 (S256), 2016.
Patel, S., et al., Comparison of taurine and pantoyltaurine as antioxidants in vitro and in the central nervous system of rdiabetic rats, Exp Toxic Pathol 68(2-3):103-12, 2016.
Fontana, M., et al., Antioxidant Properties of Sulfinates: Protective Effect of Hypotaurine on Peroxynitrite-Dependent Damage, Neurochemical Research 29(1):111-116, 2004.
Altschul, S., et al., Basic Local Alignment Search Tool, J Mol Biol 215:403-410, 1990.
Henikoff, S., et al., Amino acid substitution matrices from protein blocks, Proc Natl Acad Sci USA 89:10915-10919, 1992.
Pearson, W.R., et al., Improved tools for biological sequence comparison, Proc Natl Acad Sci USA 85:2444-2448, 1988.
Marx, C., et al., Development of improved versatile broad-host-range vectors for use in methylotrophs and other Gram-negative bacteria, Microbiology 147:2065-2075, 2001.
Chou, H.-H., et al., Fast Growth Increase the Selective Advantage of a Mutation Arising Recurrently during Evolution under Metal Limitation, PLoS Genetics 5(9):e 1000652, 2009.
Chubiz, L., et al., A novel pair of inducible expression vectors for use in Methylobacterium extorquens, BMC Research Notes 6:183, 2013.
Marx, C. et al., Broad-Host-Range cre-lox System for Antibiotic Marker Recycling in Gram-Negative Bacteria, BioTechniques 33:1062-1067, 2002.
D'Argenio, D., et al., *Drosophila* as a Model Host for Pseudomonas aeruginosa Infection, Journal of Bacteriology 183(4):1466-1471, 2001.
Marx, C., et al., Novel Mehtylotrophy Genes of Methylobactrium extorquens AM1 Identified by using Transposon Mutagenesis Including a Putative Dihydromethanopterin Reductase, Journal of Bacteriology 185(2):669-673, 2003.
Lee, M.-C., et al., Asymmetric, Bimodal Trade-Offs during Adaptation of Methylobacterium toDistinct Growth Substrates, Evolution 63:2813-2830, 2009.
Marx, C, Development of a broad-host-range sacB-based vector for unmarked allelic exchange, BMC Research Notes 1:1, 2008.
Delaney, N., et al., Development of an Optimized Medium, Strain and High-Throughput Culturing Methods for methylobacterium extorquens, PLoS One 8(4):e62957), 2013.
Choi, J., et al., Optimization of Growth Medium and Poly-B-hydroxybutyric Acid Production from Methanol in Methylobacterium organophilum Appl Microbiol Bioeng 17:392-6, 1989.
Marco, A., et al., Native folding of aggregation-prone recombinant proteins in *Escherichia coli* by osmolytes, plasmid-or benzyl alcohol-overexpressed molecular chaperones, Cell Stress & Chaperones 10(4):329-339, 2005.
Karlin, S., et al., Applications and statistics for multiple high-socring segments in molecular sequences, Proc Natl Acad Sci USA 90:5873-5877, 1993.
Higgins, D., et al., CLUSTAL: A package for performing multiple sequence alignment on a microcomputer, Gene 73:237-244, 1989.

* cited by examiner taurine hypotaurine cysteine sulfinic acid

L-cysteine taurine cysteate 2-aminoacrylate

L-serine taurine cysteate 2-aminoacrylate

L-serine

L-phosphoserine taurine cysteate

L-cystathione

L-cysteine taurine cysteate pyruvate taurine cysteate sulfopyruvate (R)-sulfolactate (R)-phospho-sulfolactate phosphoenolpyruvate taurine sulfoacetaldehyde acetyl phosphate pyruvate
taurine
sulfoacetaldehyde
cysteine sulfinic acid
cysteate
sulfopyruvate
L-cysteine
2-aminoacrylate
L-cystathione
L-serine
L-phosphoserine

HETEROLOGOUS EXPRESSION OF TAURINE IN MICROORGANISMS

CROSS-REFERENCE TO RELATED APPLICATIONS

This application is a U.S. national stage application under 35 U.S.C. § 371 of PCT/US2016/061081, filed Nov. 9, 2016, which claims the benefit of U.S. Provisional Application No. 62/252,971, filed Nov. 9, 2015, which is incorporated herein by reference in its entirety.

SEQUENCE LISTING

The instant application contains a Sequence Listing which has been submitted electronically in ASCII format and is hereby incorporated by reference in its entirety. Said ASCII copy, created on May 8, 2018, is named 05291_001US1_SL.txt and is 145,624 bytes in size.

FIELD OF THE INVENTION

The invention relates to recombinant production of taurine in microbial organisms, and use in feed compositions, in particular for aquaculture, animal feeds and human nutrition.

BACKGROUND

Taurine (2-aminoethanesulfonic acid) is a 2-carbon (β)-amino acid found in a broad swath of organisms, from birds to mammals, fish to plants, fungi and bacteria (McCusker et al. (2014) *J Nutr Sci* 3:e39). While some proteins contain taurine, it does not form peptide bonds due to the lack of a carboxyl group. In fact, taurine is the most abundant free amino acid (FAA) present in animal tissues, constituting 19% of the FAA in the brain, 50% in kidney, and 53% in muscle. (Brosnan et al. (2006) *J Nutr.* 136(6):16365-16405)

Taurine is critical in many basic cellular processes, including osmoregulation, membrane stabilization, and antioxidation. (Honjoh et al. (2010) *Amino Acids.* 38(4):1173-1183; Takeuchi et al. (2000) *Biochim Biophys Acta.* 1464 (2):219-230) In addition, taurine participates in a variety of more complex physiological functions, such as bile conjugation and calcium signaling. (Salze et al. (2015) *Aquaculture* 437:215-229). Taurine and hypotaurine have also been shown to aid in protein folding (Warskulat et al. (2007) *Methods Enzymol* 428:439-58; Abe et al. (2015) *Amino acids* 47(5):909-15; Fujii et al. (2007) *J Biochem* 141(5): 697-707).

While taurine can be detected at high levels in a variety of fish species, some taurine has been suggested as a conditionally essential nutrient for many carnivorous fish species, from trout to snakehead, and its supplementation has been shown to increase their growth rate. (Gibson et al. (2007) *Aquaculture* 269(1-4):514-524; Wu et al. (2015) *Aquac Nutr.* 21(2):214-222) Furthermore, it appears that taurine supplementation can complement the reduction of fishmeal in the feedstock, a critical objective for achieving a more sustainable form of aquaculture.

For cats, dietary taurine is often a necessary addition to feed. Inadequate levels of taurine may cause severe degenerative changes in the retina, visual cortex and brain development. Taurine has also been reported to have anti-epilepsy properties. (Ripps and Shen (2012) *Molecular Vision* 18:2673-2786)

Chemical synthesis of taurine is undoubtedly the predominant means of production, via a plethora of known synthetic mechanisms. (Salze et al. (2015) *Aquaculture* 437:215-229) The biosynthesis of taurine in plant cells has also been described. (US2012/0222148 A1) Contrary to prior belief, a series of recent publications indicate that a large number of bacteria, fungi, and algae contain individual enzymes, or in some cases entire anabolic pathways, which are capable of taurine synthesis. (Tevatia et al. (2015) *Algal Res.* 9:21-26; Agnello et al. (2013) *ACS Chem Biol.* 8(10): 2264-2271)

There is a need for a combined protein/taurine feedstock to serve the fields of animal nutrition. The need is especially pressing in aquaculture during the larval stage of fish. Larval feed, which can sit in the water longer than adult feed, can result in significant loss of taurine due to dissipation. Chemically synthesized taurine in crystalline form is particularly susceptible to this process. Enriching rotifers with taurine is an effective solution (Matsunari et al. (2013) *Fish Sci.* 79(5):815-821), but a potentially uneconomical one, as live feeds tend to be expensive. An alternative strategy is to encapsulate taurine in microparticles, such as lipid-walled capsules (Langdon et al. (2003) *Aquaculture* 227(1-4):259-275). Plant-based production systems could achieve this objective by employing the cell membrane as a natural lipid-capsule. This approach is imperfect, however, as direct feeding with plant cells suffers from the anti-nutritional factors found in plant-based feeds. (Francis et al. (2001) *Aquaculture* 199(3-4):197-227) Therefore, there exists a need for an aquaculture feed that protects taurine from dissolving in water, while eschewing solutions involving plant-based biosynthesis or live feeds. The invention herein describes just such a solution.

BRIEF SUMMARY OF THE INVENTION

In one aspect, non-naturally occurring microorganisms are provided that express one or more polynucleotide(s) expressing exogenous enzyme(s) for production of taurine. For example, a non-naturally occurring microorganism expresses the following enzyme activities: (a) cysteamine (2-aminoethanethiol) dioxygenase (ADO); (b) cysteine dioxygenase (CDO), and cysteine sulfinic acid decarboxylase (CSAD) or glutamate decarboxylase (GAD); (c) 3-mercaptopropionate dioxygenase (p3MDO), and CSAD or GAD; (d) L-serine dehydratase; sulfate adenyltransferase and adenylyl-sulfate kinase (APSK), and/or 3'-phosphoadenosine 5'-phosphosulfate synthase (PAPSS1)); 3'-phosphoadenylyl sulfate:2-aminoacrylate C-sulfotransferase (PAPS-AS), and CSAD or GAD; (e) cysteate synthase, optionally L-serine dehydratase, and CSAD or GAD; (f) L-cysteine desulfydrase (CD) activity; optionally cystathionine gamma-lyase (CGL) activity; sulfate adenyltransferase and APSK, and/or PAPSS1); PAPS-AS, and CSAD or GAD; (g) CD) activity; optionally CGL activity; cysteate synthase, and CSAD or GAD; (h) cysteate sulfo-lyase (CuyA), and CSAD or GAD; (i) phosphosulfolactate synthase (ComA), 2-phospho-3-sulfolactate phosphohydrolase (ComB), sulfolactate dehydrogenase (ComC), aspartate aminotransferase (AspAT), and CSAD or GAD; (j) sulfoacetaldehyde acetyltransferase (Xsc) and taurine-pyruvate aminotransferase (Tpa); (k) ComA, ComB, ComC, sulfopyruvate decarboxylase (ComDE), and Tpa; or (1) AspAT, ComDE and Tpa, wherein at least one of said enzyme activities is encoded by an exogenous polynucleotide that is expressed in the microorganism.

In some embodiments, the non-naturally occurring microorganism is derived from a host cell from genera selected from *Methylobacterium, Methylomonas, Methylobacter. Methylococcus, Methylosinus, Methylocyctis, Methylomicrobium, Methylomonas, Methylpophilus, Methylobacillus, Methylobacterium, Hyphomicrobium, Xanthobacter, Bacillus, Paracoccus, Nocardia, Arthrobacter, Rhodopseudomonas, Pseudomonas, Candida, Hansenula, Pichia, Torulopsis, Rhodotorula, Escherichia*, and *Saccharomyces*. For example, the microorganism may be selected from *Methylobacterium, Escherichia, Saccharomyces*, and *Bacillus*. In some embodiments, the non-naturally occurring microorganism is a methylotrophic bacterium. For example, the non-naturally occurring microorganism may be a *Methylobacterium* species, such as but not limited to, *Methylobacterium extorquens*.

In some embodiments, the one or more exogenous polynucleotide(s) is/are codon optimized for expression in the microorganism. In some embodiments, the one or more exogenous polynucleotide(s) is/are operably linked to promoter(s) for expression in the microorganism.

In some embodiments, the non-naturally occurring microorganism includes deletion of one or more genes that encode enzyme(s) that degrade taurine or the taurine precursor cysteate or sulfoacetaldehyde or modification of one or more genes that encode enzyme(s) that degrade taurine, cysteate, or sulfoacetaldehyde such that activity of the one or more enzyme(s) that degrade taurine, cysteate, or sulfoacetaldehyde is lower than in the microorganism parent strain from which the non-naturally microorganism is derived. In some embodiments, the one or more enzyme(s) that degrade taurine, cysteate, or sulfoacetaldehyde includes taurine dehydrogenase, taurine dioxygenase, Xsc, CuyA, Tpa, and/or gamma-glutamyltransferase.

In some embodiments, the non-naturally occurring microorganism is genetically modified or artificially pre-selected to produce elevated levels of a carotenoid compound relative to the corresponding unmodified or unselected microorganism. For example, the microorganism may produce elevated levels of one or more carotenoid compound(s) selected from β-carotene, lycopene, rhodopsin, zeaxanthin, lutein, canthaxanthin, astaxanthin, and sprilloxanthin, in comparison to the host cell from which the carotenoid producing microorganism is derived.

In some embodiments, the non-naturally occurring microorganism accumulates intracellular taurine and/or hypotaurine, wherein the taurine and/or hypotaurine aids in the folding of one or more native and/or heterologous protein(s), e.g., for the purpose of increased enzymatic activity and/or protein yield in comparison to the parent microorganism from which the non-naturally occurring microorganism is derived, e.g., a parent microorganism that does not include the one or more exogenous polynucleotide(s).

In another aspect, methods are provided for producing biomass that includes taurine and/or taurine precursors such as cysteate, sulfoacetaldehyde, and/or hypotaurine. The methods include culturing a non-naturally occurring microorganism as described herein in a culture medium under conditions suitable for growth of the microorganism and expression of exogenous enzyme(s) for production of taurine and/or taurine precursors, wherein biomass comprising taurine and/or taurine precursors is produced in the culture.

In another aspect, a feed or nutritional supplement is provided that includes taurine- and/or taurine precursor-containing biomass produced as described herein.

DETAILED DESCRIPTION

Figure 1:
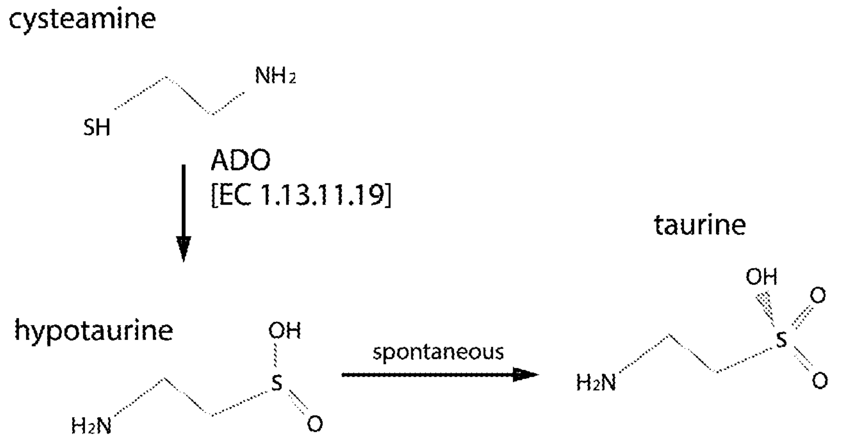
FIG. 1 depicts an embodiment of a biosynthetic pathway for production of taurine from cysteamine.

The invention described herein addresses the dual challenge of producing taurine from an inexpensive feedstock, and encapsulating it to prevent dissolution in water for aquaculture. Microbial systems for taurine production are described as well as feed products in which the taurine is encapsulated in a natural lipid bilayer (microbial cells).

Provided herein are non-naturally occurring microorganisms, e.g., bacteria, yeast, Archaea, that are capable of producing taurine and/or the taurine precursor(s), e.g., hypotaurine or cysteate. Also provided are methods of engineering and culturing such microorganisms, methods of using such microorganisms to produce taurine, and methods of producing taurine-containing compositions, such as feed compositions that contain the microorganisms or compositions that contain taurine recovered from such organisms.

One aspect pertains to the field of aquaculture. Another aspect is the field of pet foods, for example, for cats and dogs. A further aspect is in the field of human nutrition and supplements. More specifically, aquaculture feeds, pet food, and nutritional supplement compositions are provided that include taurine-containing microbial biomass and a complete protein nutrition, that is, containing most or all amino acids necessary for healthy growth of the animal to which it is administered. In some embodiments, the aquaculture feed compositions herein contain one or more carotenoid(s) produced by the microorganism that produces taurine and/or taurine precursor(s), e.g., hypotaurine or cysteate. The microbial biomass can be blended with other ingredients to form a portion or whole of a feed, or may be consumed directly as a protein-rich powder.

Another aspect pertains to the field of industrial protein production. Osmolytes such as betaine, glycine, trimethylamine N-Oxide (TMAO), and taurine can aid in protein folding (Warskulat et al. (2007) *Methods Enzymol* 428:439-58; Abe et al. (2015) *Amino acids* 47(5):909-15; Fujii et al. (2007) *J Biochem* 141(5):697-707). Microorganisms engineered to accumulate intracellular taurine as a chemical chaperone could produce higher yields or more active proteins of interest. As antioxidants, taurine, hypotaurine, and their precursors also promote protein activity by limiting protein inactivation through oxidation (Oliveira et al. (2010) *Pharmacological Reports* 62:185-193; Aruoma et al. (1988) *Biochem J* 256:251-55; Bucolo et al. (2016) *Acta Ophthalmologic* 95(256); Patel et al. (2016) *Exp Toxic Pathol* 68(2-3):103-12; Fontana et al. (2004) *Neurochemical Research* 29(1):111-116).

Definitions

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, N.Y. (1991) provide one of skill with a general dictionary of many of the terms used in this invention. Any methods and materials similar or equivalent to those described herein can be used in the practice or testing of the present invention.

The practice of the present invention will employ, unless otherwise indicated, conventional techniques of molecular biology (including recombinant techniques), microbiology, cell biology, and biochemistry, which are within the skill of the art. Such techniques are explained fully in the literature, for example, *Molecular Cloning: A Laboratory Manual*, second edition (Sambrook et al., 1989); *Oligonucleotide Synthesis* (M. J. Gait, ed., 1984; *Current Protocols in Molecular Biology* (F. M. Ausubel et al., eds., 1994); *PCR: The Polymerase Chain Reaction* (Mullis et al., eds., 1994); and *Gene Transfer and Expression: A Laboratory Manual* (Kriegler, 1990).

Numeric ranges provided herein are inclusive of the numbers defining the range.

Unless otherwise indicated, nucleic acids are written left to right in 5' to 3' orientation; amino acid sequences are written left to right in amino to carboxy orientation, respectively.

"A," "an" and "the" include plural references unless the context clearly dictates otherwise.

As used herein, the term "polynucleotide" refers to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Because the genetic code is degenerate, more than one codon may be used to encode a particular amino acid, and the present invention encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms "polynucleotide," "nucleic acid," and "oligonucleotide" are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR.sub.2 ("amidate"), P(O)R, P(O)OR', CO or CH.sub.2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, a "vector" refers to a polynucleotide sequence designed to introduce nucleic acids into one or more cell types. Vectors include cloning vectors, expression vectors, shuttle vectors, plasmids, phage particles, cassettes and the like.

As used herein, the term "expression" refers to the process by which a polypeptide is produced based on the nucleic acid sequence of a gene. The process includes both transcription and translation.

As used herein, "expression vector" refers to a DNA construct containing a DNA coding sequence (e.g., gene sequence) that is operably linked to one or more suitable control sequence(s) capable of effecting expression of the coding sequence in a host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. The plasmid is the most commonly used form of expression vector. However, the invention is intended to include such other forms of expression vectors that serve equivalent functions and which are, or become, known in the art.

A "promoter" refers to a regulatory sequence that is involved in binding RNA polymerase to initiate transcription of a gene. A promoter may be an inducible promoter or a constitutive promoter. An "inducible promoter" is a promoter that is active under environmental or developmental regulatory conditions.

The term "operably linked" refers to a juxtaposition or arrangement of specified elements that allows them to perform in concert to bring about an effect. For example, a promoter is operably linked to a coding sequence if it controls the transcription of the coding sequence.

"Under transcriptional control" is a term well understood in the art that indicates that transcription of a polynucleotide sequence depends on its being operably linked to an element which contributes to the initiation of, or promotes transcription.

"Under translational control" is a term well understood in the art that indicates a regulatory process which occurs after mRNA has been formed.

A "gene" refers to a DNA segment that is involved in producing a polypeptide and includes regions preceding and following the coding regions as well as intervening sequences (introns) between individual coding segments (exons).

As used herein, the term "host cell" refers to a cell or cell line into which a recombinant expression vector for production of a polypeptide may be transfected for expression of the polypeptide. Host cells include progeny of a single host cell, and the progeny may not necessarily be completely identical (in morphology or in total genomic DNA complement) to the original parent cell due to natural, accidental, or deliberate mutation. A host cell includes cells transfected or transformed in vivo with an expression vector.

The term "recombinant," refers to genetic material (i.e., nucleic acids, the polypeptides they encode, and vectors and cells comprising such polynucleotides) that has been modified to alter its sequence or expression characteristics, such as by mutating the coding sequence to produce an altered polypeptide, fusing the coding sequence to that of another gene, placing a gene under the control of a different promoter, expressing a gene in a heterologous organism, expressing a gene at a decreased or elevated levels, expressing a gene conditionally or constitutively in manner different from its natural expression profile, and the like. Generally recombinant nucleic acids, polypeptides, and cells based thereon, have been manipulated by man such that they are not identical to related nucleic acids, polypeptides, and cells found in nature.

A "signal sequence" refers to a sequence of amino acids bound to the N-terminal portion of a protein which facilitates the secretion of the mature form of the protein from the cell. The mature form of the extracellular protein lacks the signal sequence which is cleaved off during the secretion process.

The term "selective marker" or "selectable marker" refers to a gene capable of expression in a host cell that allows for ease of selection of those hosts containing an introduced nucleic acid or vector. Examples of selectable markers include but are not limited to antimicrobial substances (e.g., hygromycin, bleomycin, or chloramphenicol) and/or genes that confer a metabolic advantage, such as a nutritional advantage, on the host cell.

The term "derived from" encompasses the terms "originated from," "obtained from," "obtainable from," "isolated from," and "created from," and generally indicates that one specified material finds its origin in another specified material or has features that can be described with reference to the another specified material.

The term "culturing" refers to growing a population of cells, e.g., microbial cells, under suitable conditions for growth, in a liquid or solid medium.

The term "heterologous" or "exogenous," with reference to a polynucleotide or protein, refers to a polynucleotide or protein that does not naturally occur in a specified cell, e.g., a host cell. It is intended that the term encompass proteins that are encoded by naturally occurring genes, mutated genes, and/or synthetic genes. In contrast, the term "homologous," with reference to a polynucleotide or protein, refers to a polynucleotide or protein that occurs naturally in the cell.

The term "introduced," in the context of inserting a nucleic acid sequence into a cell, includes "transfection," "transformation," or "transduction" and refers to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed.

"Transfection" or "transformation" refers to the insertion of an exogenous polynucleotide into a host cell. The exogenous polynucleotide may be maintained as a non-integrated vector, for example, a plasmid, or alternatively, may be integrated into the host cell genome. The term "transfecting" or "transfection" is intended to encompass all conventional techniques for introducing nucleic acid into host cells. Examples of transfection techniques include, but are not limited to, calcium phosphate precipitation, DEAE-dextran-mediated transfection, lipofection, electroporation, and microinjection.

As used herein, the terms "transformed," "stably transformed," and "transgenic" refer to a cell that has a non-native (e.g., heterologous) nucleic acid sequence integrated into its genome or as an episomal plasmid that is maintained through multiple generations.

The terms "recovered," "isolated," "purified," and "separated" as used herein refer to a material (e.g., a protein, nucleic acid, or cell) that is removed from at least one component with which it is naturally associated. For example, these terms may refer to a material which is substantially or essentially free from components which normally accompany it as found in its native state, such as, for example, an intact biological system.

A "signal sequence" (also termed "presequence," "signal peptide," "leader sequence," or "leader peptide") refers to a sequence of amino acids at the amino terminus of a nascent polypeptide that targets the polypeptide to the secretory pathway and is cleaved from the nascent polypeptide once it is translocated in the endoplasmic reticulum membrane.

Related (and derivative) proteins encompass "variant" proteins. Variant proteins differ from a parent protein and/or from one another by a small number of amino acid residues. In some embodiments, the number of different amino acid residues is any of about 1, 2, 3, 4, 5, 10, 20, 25, 30, 35, 40, 45, or 50. In some embodiments, variants differ by about 1 to about 10 amino acids. Alternatively or additionally, variants may have a specified degree of sequence identity with a reference protein or nucleic acid, e.g., as determined using a sequence alignment tool, such as BLAST, ALIGN, and CLUSTAL (see, infra). For example, variant proteins or nucleic acid may have at least about 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% amino acid sequence identity with a reference sequence.

As used herein, the term "analogous sequence" refers to a polypeptide sequence within a protein that provides a similar function, tertiary structure, and/or conserved residues with respect to a reference protein. For example, in epitope regions that contain an alpha helix or a beta sheet structure, replacement amino acid(s) in an analogous sequence maintain the same structural element. In some embodiments, analogous sequences are provided that result in a variant enzyme exhibiting a similar or improved function with respect to the parent protein from which the variant is derived.

As used herein, "homologous protein" refers to a protein that has similar function and/or structure as a reference protein. Homologs may be from evolutionarily related or unrelated species. In some embodiments, a homolog has a quaternary, tertiary and/or primary structure similar to that of a reference protein, thereby potentially allowing for replacement of a segment or fragment in the reference protein with an analogous segment or fragment from the homolog, with reduced disruptiveness of structure and/or function of the reference protein in comparison with replacement of the segment or fragment with a sequence from a non-homologous protein.

As used herein, "wild-type," "native," and "naturally-occurring" proteins are those found in nature. The terms "wild-type sequence" refers to an amino acid or nucleic acid sequence that is found in nature or naturally occurring. In some embodiments, a wild-type sequence is the starting point of a protein engineering project, for example, production of variant proteins.

The phrases "substantially similar" and "substantially identical" in the context of at least two nucleic acids or polypeptides typically means that a polynucleotide, polypeptide, or region or domain of a polypeptide that comprises a sequence that has at least about 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) polynucleotide, polypeptide, or region or domain of a polypeptide. A region or domain of a polypeptide may contain, for example, at least about 20, 50, 100, or 200 amino acids within a longer polypeptide sequence. Sequence identity may be determined using known programs such as BLAST, ALIGN, and CLUSTAL using standard parameters. (See, e.g., Altshul et al. (1990) *J Mol. Biol.* 215:403-410; Henikoff et al. (1989) *Proc. Natl. Acad. Sci.* 89:10915; Karin et al. (1993) *Proc. Natl. Acad. Sci.* 90:5873; and Higgins et al. (1988) *Gene* 73:237). Software for performing BLAST analyses is publicly available through the National Center for Biotechnology Information. Also, databases may be searched using FASTA (Person et al. (1988) Proc. Natl. Acad. Sci. 85:2444-2448.) In some embodiments, substantially identical polypeptides differ only by one or more conservative amino acid substitutions. In some embodiments, substantially identical polypeptides are immunologically cross-reactive. In some embodiments, substantially identical nucleic acid molecules hybridize to each other under stringent conditions (e.g., within a range of medium to high stringency).

The term "carotenoid" is understood in the art to refer to a structurally diverse class of pigments derived from isoprenoid pathway intermediates. The commitment step in carotenoid biosynthesis is the formation of phytoene from geranylgeranyl pyrophosphate. Carotenoids can be acyclic or cyclic, and may or may not contain oxygen, so that the term carotenoids include both carotenes and xanthophylls. In general, carotenoids are hydrocarbon compounds having a conjugated polyene carbon skeleton formally derived from the five-carbon compound IPP, including triterpenes ($C_{30}$ diapocarotenoids) and tetraterpenes ($C_{40}$ carotenoids) as well as their oxygenated derivatives and other compounds that are, for example, $C_{35}$, $C_{50}$, $C_{60}$, $C_{70}$, $C_{80}$ in length or other lengths. Many carotenoids have strong light absorbing properties and may range in length in excess of $C_{2OO}$-$C_{3O}$ diapocarotenoids typically consist of six isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{3O}$ carotenoids may be formally derived from the acyclic $C_{3O}H_{42}$ structure, having a long central chain of conjugated double bonds, by: (i) hydrogenation (ii) dehydrogenation, (iii) cyclization, (iv) oxidation, (v) esterification/glycosylation, or any combination of these processes. $C_{40}$ carotenoids typically consist of eight isoprenoid units joined in such a manner that the arrangement of isoprenoid units is reversed at the center of the molecule so that the two central methyl groups are in a 1,6-positional relationship and the remaining non-terminal methyl groups are in a 1,5-positional relationship. Such $C_{40}$ carotenoids may be formally derived from the acyclic $C_{40}H_{56}$ structure, having a long central chain of conjugated double bonds, by (i) hydrogenation, (ii) dehydrogenation, (iii) cyclization, (iv) oxidation, (v) esterification/glycosylation, or any combination of these processes. The class of $C_{40}$ carotenoids also includes certain compounds that arise from rearrangements of the carbon skeleton, or by the (formal) removal of part of this structure. More than 600 different carotenoids have been identified in nature. Carotenoids include but are not limited to: antheraxanthin, adonirubin, adonixanthin, astaxanthin, canthaxanthin, capsorubrin, β-cryptoxanthin, a-carotene, β-carotene, β,ψ-carotene, δ-carotene, ε-carotene, echinenone, 3-hydroxyechinenone, 3'-hydroxyechinenone, γ-carotene, ψ-carotene, 4-keto-Y-carotene, ζ-carotene, a-cryptoxanthin, deoxyflexixanthin, diatoxanthin, 7,8-didehydroastaxanthin, didehydrolycopene, fucoxanthin, fucoxanthinol, isorenieratene, β-isorenieratene, lactucaxanthin, lutein, lycopene, myxobactone, neoxanthin, neurosporene, hydroxyneurosporene, peridinin, phytoene, rhodopin, rhodopin glucoside, 4-keto-rubixanthin, siphonaxanthin, spheroidene, spheroidenone, spirilloxanthin, torulene, 4-keto-torulene, 3-hydroxy-4-keto-torulene, uriolide, uriolide acetate, violaxanthin, zeaxanthin-β-diglucoside, zeaxanthin, and C30 carotenoids. Additionally, carotenoid compounds include derivatives of these molecules, which may include hydroxy-, methoxy-, oxo-, epoxy-, carboxy-, or aldehydic functional groups. Further, included carotenoid compounds include ester (e.g., glycoside ester, fatty acid ester) and sulfate derivatives (e.g., esterified xanthophylls).

The "isoprenoid pathway" is understood in the art to refer to a metabolic pathway that either produces or utilizes the five-carbon metabolite isopentyl pyrophosphate (IPP). As discussed herein, two different pathways can produce the common isoprenoid precursor IPP—the "mevalonate pathway" and the "non-mevalonate pathway." The term "isoprenoid pathway" is sufficiently general to encompass both of these types of pathway. Biosynthesis of isoprenoids from IPP occurs by polymerization of several five-carbon isoprene subunits. Isoprenoid metabolites derived from IPP vary greatly in chemical structure, including both cyclic and acyclic molecules. Isoprenoid metabolites include, but are not limited to, monoterpenes, sesquiterpenes, diterpenes, sterols, and polyprenols such as carotenoids.

The term "isoprenoid compound" refers to any compound which is derived via the pathway beginning with isopentenyl pyrophosphate (IPP) and formed by the head-to-tail condensation of isoprene units which may be of 5, 10, 15, 20, 30 or 40 carbons in length. There term "isoprenoid pigment" refers to a class of isoprenoid compounds which typically have strong light absorbing properties.

The term "feed premix" refers to the crude mixture of aquaculture feed or animal/pet food components prior to processing, optionally at high temperature, into an aquaculture feed or animal or pet food composition that is in the form of pellets or flakes.

An aquaculture feed composition is used in the production of an "aquaculture product," wherein the product is a harvestable aquacultured species (e.g., finfish, crustaceans), which is often sold for human consumption. For example, salmon are intensively produced in aquaculture and thus are aquaculture products. Aquaculture compositions may also be used as feed for aquaculture feed organisms such as small fish like krill, rotifers, and the like, that are food sources for larger aquaculture organisms such as carnivorous fish. In addition, aquaculture compositions described herein can be used as feed for ornamental fish, shrimp, hobbyist aquaculture, and the like, that are not intended as food for other organisms.

The term "aquaculture meat product" refers to food products intended for human consumption comprising at least a portion of meat from an aquaculture product as defined above. An aquaculture meat product may be, for example, a whole fish or a filet cut from a fish, each of which may be consumed as food. In some embodiments, such a product can be referred to as a fish or seafood product.

The term "biomass" refers to microbial cellular material. Biomass may be produced naturally, or may be produced from the fermentation of a native host or a recombinant production host. The biomass may be in the form of whole cells, whole cell lysates, homogenized cells, partially hydrolyzed cellular material, and/or partially purified cellular material (e.g., microbially produced oil).

The term "processed biomass" refers to biomass that has been subjected to additional processing such as drying, pasteurization, disruption, etc., each of which is discussed in greater detail below.

The term "C-1 carbon substrate" refers to any carbon-containing molecule that lacks a carbon-carbon bond. Examples are methane, methanol, formaldehyde, formic acid, formate, methylated amines (e.g., mono-, di-, and tri-methyl amine), methylated thiols, and carbon dioxide.

The term "C1 metabolizer" refers to a microorganism that has the ability to use a single carbon substrate as a sole source of energy and biomass. C1 metabolizers will typically be methylotrophs and/or methanotrophs capable of growth.

The term "methylotroph" means an organism capable of oxidizing organic compounds which do not contain carbon-carbon bonds. Where the methylotroph is able to oxidize $CH_4$, the methylotroph is also a methanotroph.

The term "methanotroph" means a prokaryote capable of utilizing methane as a substrate. Complete oxidation of methane to carbon dioxide occurs by aerobic degradation pathways. Typical examples of methanotrophs useful in the present invention include but are not limited to the genera *Methylomonas, Methylobacter, Methylococcus*, and *Methylosinus*.

The term "high growth methanotrophic bacterial strain" refers to a bacterium capable of growth using methane as its sole carbon and energy source.

Microorganisms

Non-naturally occurring microorganisms are provided for production of taurine or the taurine precursors hypotaurine, cysteate, or sulfoacetaldehyde. Non-naturally occurring, e.g., recombinant, microorganisms herein include, e.g., bacteria, yeast, Archaea, that have been engineered to express at least one (i.e., one or more) enzyme(s) for biosynthesis of taurine or taurine precursors and that produce taurine or taurine precursors when cultured under conditions suitable for microbial growth and taurine production.

Non-naturally occurring microorganisms as described herein include one or more exogenous polynucleotide(s) that encode and express one or more enzyme or enzyme activity for biosynthesis of taurine or the taurine precursors cysteate, sulfoacetaldehyde, or hypotaurine. The exogenous polynucleotide(s) may include one or more coding sequence for one or more enzyme or enzyme activity for biosynthesis of taurine or taurine precursors, operably linked to one or more promoter for expression in the non-naturally occurring microorganism. Such promoters may include, but are not limited to, P_R (e.g., SEQ ID NO:42), P_Lac (e.g., SEQ ID NO:41), P_tac (e.g., SEQ ID NO:39), P_tacA (e.g., SEQ ID NO:40), PmxaF (e.g., SEQ ID NO:43), P_rrnB, and P_T7. In some embodiments, the polynucleotide(s) are codon optimized for expression in the microorganism.

In some embodiments, the non-naturally occurring microorganism includes one or more exogenous and/or endogenous polynucleotide(s) that encodes one or more enzymes or enzyme activities for taurine biosynthesis, as described herein, that has been modified for improved stability and/or activity relative to the stability and/or activity of the enzyme or enzyme activity in the host cell from which it is derived or relative to the wild-type stability and/or activity of the enzyme or enzyme activity. For example, the non-naturally occurring microorganism may express a variant of an enzyme of taurine biosynthesis that has greater stability and/or activity than the wild-type enzyme from which it is derived.

In some embodiments, the host cell from which a non-naturally occurring microorganism as described herein is derived has one or more endogenous taurine, cysteate, or sulfoacetaldehyde degrading activity, for example, but not limited to, taurine dehydrogenase, Tpa, CuyA, gamma-glutamyltransferase, Xsc, and/or taurine dioxygenase. In some embodiments, the non-naturally occurring microorganism includes deletion of one or more genes that encode taurine, cysteate, or sulfoacetaldehyde degrading enzyme(s). In some embodiments, the host cell from which a non-naturally occurring microorganism includes modification of one or more genes that encode taurine, cysteate, or sulfoacetaldehyde degrading enzyme(s), such that the taurine, cysteate, or sulfoacetaldehyde degrading activity of the enzyme(s) is lower in the non-naturally occurring microorganism than in the host cell from which it is derived. In some embodiments, the host cell is *Methylobacterium extorquens* and the non-naturally occurring microorganism derived from the host cell includes deletion or modification of the gene that encodes gamma-glutamyltransferase in the host cell.

In certain embodiments, the host cell comprises one or more of endogenous genes in the described pathway. In certain embodiments, the host cell is modified so that one or more genes producing enzymes that divert compounds and taurine precursors away from a taurine biosynthetic pathway are blocked or deleted. In certain embodiments, the one or more blocked or deleted genes are selected from genes involved in the degradation of taurine, cysteate, or sulfoacetaldehyde. In certain embodiments, the host cell is a spontaneous mutant whose rate of growth is increased relative to a corresponding non-mutant. In certain embodiments, the host cell is cultured under stress conditions selected from light depletion, nutrient depletion, nitrogen depletion, high salt, or a chemical that inhibits growth of the host cell, wherein the stress conditions induce changes in gene expression leading to increased taurine or taurine precursor production.

In some embodiments, the non-naturally occurring microorganism or the host cell from which the non-naturally occurring microorganism is derived is genetically modified or artificially pre-selected to produce elevated levels of one or more carotenoid compound(s) relative to the corresponding unmodified or unselected microorganism. The one or more carotenoid compound(s) may include, but are not limited to, β-carotene, lycopene, zeaxanthin, lutein, canthaxanthin, rhodopin, astaxanthin, and/or sprilloxanthin. Non-limiting examples of host cells that produce elevated levels of one or more carotenoid compound(s) and methods for producing such microorganisms are provided in WO2015/021352 A2.

Non-limiting examples of genera from which the non-naturally occurring microorganism may be derived include *Methylobacterium, Methylomonas, Methylobacter. Methylococcus, Methylosinus, Methylocyctis, Methylomicrobium, Methylomonas, Methylpophilus, Methylobacillus, Methylobacterium, Hyphomicrobium, Xanthobacter, Bacillus, Paracoccus, Nocardia, Arthrobacter, Rhodopseudomonas, Pseudomonas, Candida, Hansenula, Pichia, Torulopsis, Rhodotorula, Escherichia*, and *Saccharomyces*. Non-limiting examples of microbial species from which the non-naturally occurring microorganism may be derived include *Methylobacterium extorquens* (e.g., strains AM1, DM4, CM4, PA1, or BJ001 (formerly *Methylobacterium populi*)), *Methylobacterium radiotolerans, Methylobacterium nodulans, Methylobacterium* spp. 4-46, and *Escherichia coli.*

In some embodiments, the non-naturally occurring microorganism is a methylotrophic bacterium.

Conversion of Cysteamine to Taurine

In some embodiments, a non-naturally occurring microorganism is provided that expresses an exogenous enzyme activity of 2-aminoethanol (cysteamine) dioxygenase (ADO) (EC1.13.11.19), which converts cysteamine to hypotaurine, for biosynthesis of taurine, as shown in FIG. 1.

In some embodiments, the non-naturally occurring microorganism includes an exogenous polynucleotide that encodes ADO comprising or consisting of the amino acid sequence depicted in SEQ ID NO:44, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:44. In some embodiments, the polynucleotide that encodes ADO comprises or consists of the polynucleotide sequence depicted in SEQ ID NO:45 or SEQ ID NO:57 or a polynucleotide having at least about 30, 35, 40, 45, 50, 55, 60, 65, 70, 75, 80, 85, 90, 95, 98, or 99% identity to SEQ ID NO:45 or SEQ ID NO:57. In some embodiments, the polynucleotide sequence is codon optimized for expression in the microorganism, e.g., SEQ ID NO:57.

In some embodiments, the non-naturally occurring microorganism is a *Methylobacterium, Escherichia, Saccharomyces*, or *Bacillus* microorganism that includes an exogenous polynucleotide that encodes ADO.

Conversion of Cysteine to Taurine Via CDO

In some embodiments, a non-naturally occurring microorganism is provided that expresses one or more exogenous enzyme activity/ies for the conversion of cysteine to taurine via the enzyme cysteine dioxygenase (CDO), for example, exogenous enzyme(s) of the CDO/CSAD or GAD pathway for biosynthesis of taurine. The CDO/CSAD or GAD pathway for taurine biosynthesis is shown schematically in FIG. 2.

In some embodiments, the non-naturally occurring microorganism that expresses exogenous enzyme activities of the CDO/CSAD or GAD pathway is not of genera *Escherichia* or species *Escherichia coli*. In some embodiments, the non-naturally occurring microorganism is not of genera *Saccharomyces* or species *Saccharomyces cerevisiae.*

Non-naturally occurring microorganisms are provided that include the following enzymes or enzyme activities: cysteine dioxygenase (CDO) (EC 1.13.11.20); and cysteine sulfuric acid decarboxylase (CSAD) (EC 4.1.1.29), wherein at least one of these enzymes or enzyme activities is encoded by an exogenous polynucleotide with which the microorganism has been transformed. In some embodiments, CDO and CSAD enzymes or enzyme activities are encoded by one or more exogenous polynucleotide(s) (e.g., one or two exogenous polynucleotide(s)) in the microorganism. In some embodiments, one of CDO and CSAD enzymes or enzyme activities is encoded an exogenous polynucleotide in the microorganism and the remaining activity is endogenously expressed in the host cell from which the non-naturally occurring microorganism is derived, i.e., not expressed from an exogenous polynucleotide. In one embodiment, the microorganism expresses an endogenous CSAD activity and CDO is encoded by an exogenous polynucleotide in the microorganism. In one embodiment, the microorganism expresses an endogenous CDO activity and CSAD is encoded by an exogenous polynucleotide in the microorganism.

Non-naturally occurring microorganisms are provided that include the following enzymes or enzyme activities: cysteine dioxygenase (CDO) (EC 1.13.11.20); and glutamate decarboxylase (GAD) (EC 4.1.1.15), wherein at least one of these enzymes or enzyme activities is encoded by an exogenous polynucleotide with which the microorganism has been transformed. In some embodiments, CDO and GAD enzymes or enzyme activities are encoded by one or more exogenous polynucleotide(s) (e.g., one or two exogenous polynucleotide(s)) in the microorganism. In some embodiments, one of CDO and GAD enzymes or enzyme activities is encoded by an exogenous polynucleotide in the microorganism and the remaining activity is endogenously expressed in the host cell from which the non-naturally occurring microorganism is derived, i.e., not expressed from an exogenous polynucleotide. In one embodiment, the microorganism expresses an endogenous GAD activity and CDO is encoded by an exogenous polynucleotide in the microorganism. In one embodiment, the microorganism expresses an endogenous CDO activity and GAD is encoded by an exogenous polynucleotide in the microorganism.

In some embodiments, the non-naturally occurring microorganism includes an exogenous polynucleotide that encodes CDO comprising or consisting of the amino acid sequence depicted in SEQ ID NO:15, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:15. In some embodiments, the polynucleotide that encodes CDO comprises or consists of the polynucleotide sequence depicted in SEQ ID NO:16, SEQ ID NO:50, or SEQ ID NO:58 or a polynucleotide having at least about 30, 35, 40, 45, 50, 55, 60, 65, 70, 75, 80, 85, 90, 95, 98, or 99% identity to SEQ ID NO:16, SEQ ID NO:50, or SEQ ID NO:58. In some embodiments, the polynucleotide sequence is codon optimized for expression in the microorganism, e.g., SEQ ID NO:58.

In some embodiments, the non-naturally occurring microorganism includes an exogenous polynucleotide that encodes CDO comprising or consisting of the amino acid sequence depicted in SEQ ID NO:35, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:35. In some embodiments, the polynucleotide that encodes CDO comprises or consists of the polynucleotide sequence depicted in SEQ ID NO:36, SEQ ID NO:51, or SEQ ID NO:59 or a polynucleotide having at least about 30, 35, 40, 45, 50, 55, 60, 65, 70, 75, 80, 85, 90, 95, 98, or 99% identity to SEQ ID NO:36, SEQ ID NO:51, or SEQ ID NO:59. In some embodiments, the polynucleotide sequence is codon optimized for expression in the microorganism, e.g., SEQ. NO:51 or SEQ ID NO: 59.

In some embodiments, the non-naturally occurring microorganism includes an exogenous polynucleotide that encodes CSAD comprising or consisting of the amino acid sequence depicted in SEQ ID NO:11, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:11. In some embodiments, the polynucleotide that encodes CSAD comprises or consists of the polynucleotide sequence depicted in SEQ ID NO:12, SEQ ID NO:53, or SEQ ID NO:54 or a polynucleotide having at least about 30, 35, 40, 45, 50, 55, 60, 65, 70, 75, 80, 85, 90, 95, 98, or 99% identity to SEQ ID NO:12, SEQ ID NO:53, or SEQ ID NO:54. In some embodiments, the polynucleotide sequence is codon optimized for expression in the microorganism, e.g., SEQ ID NO:53 or SEQ ID NO:54.

In some embodiments, the non-naturally occurring microorganism includes an exogenous polynucleotide that encodes GAD comprising or consisting of the amino acid sequence depicted in SEQ ID NO:13, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:13. In some embodiments, the polynucleotide that encodes GAD comprises or consists of the polynucleotide sequence depicted in SEQ ID NO:14 or a polynucleotide having at least about 30, 35, 40, 45, 50, 55, 60, 65, 70, 75, 80, 85, 90, 95, 98, or 99% identity to SEQ ID NO:14. In some embodiments, the polynucleotide sequence is codon optimized for expression in the microorganism.

In one embodiment, a non-naturally occurring *Methylobacterium* microorganism is provided that includes one or more exogenous polynucleotide(s) encoding CDO and CSAD. In another embodiment, a non-naturally occurring *Methylobacterium* microorganism is provided that includes one or more exogenous polynucleotide(s) encoding CDO and GAD.

In one embodiment, a non-naturally occurring *Escherichia* microorganism is provided that includes an exogenous polynucleotide encoding CDO. In one embodiment, a non-naturally occurring *Escherichia* microorganism is provided that includes one or more exogenous polynucleotide(s) encoding CDO and CSAD.

In one embodiment, a non-naturally occurring *Saccharomyces* microorganism is provided that includes an exogenous polynucleotide encoding CDO. In one embodiment, a non-naturally occurring *Saccharomyces* microorganism is provided that includes one or more exogenous polynucleotide(s) encoding CDO and CSAD.

In one embodiment, a non-naturally occurring *Bacillus* microorganism is provided that includes an exogenous polynucleotide encoding CSAD.

Conversion of Cysteine to Taurine Via p3MDO

Figure 3:
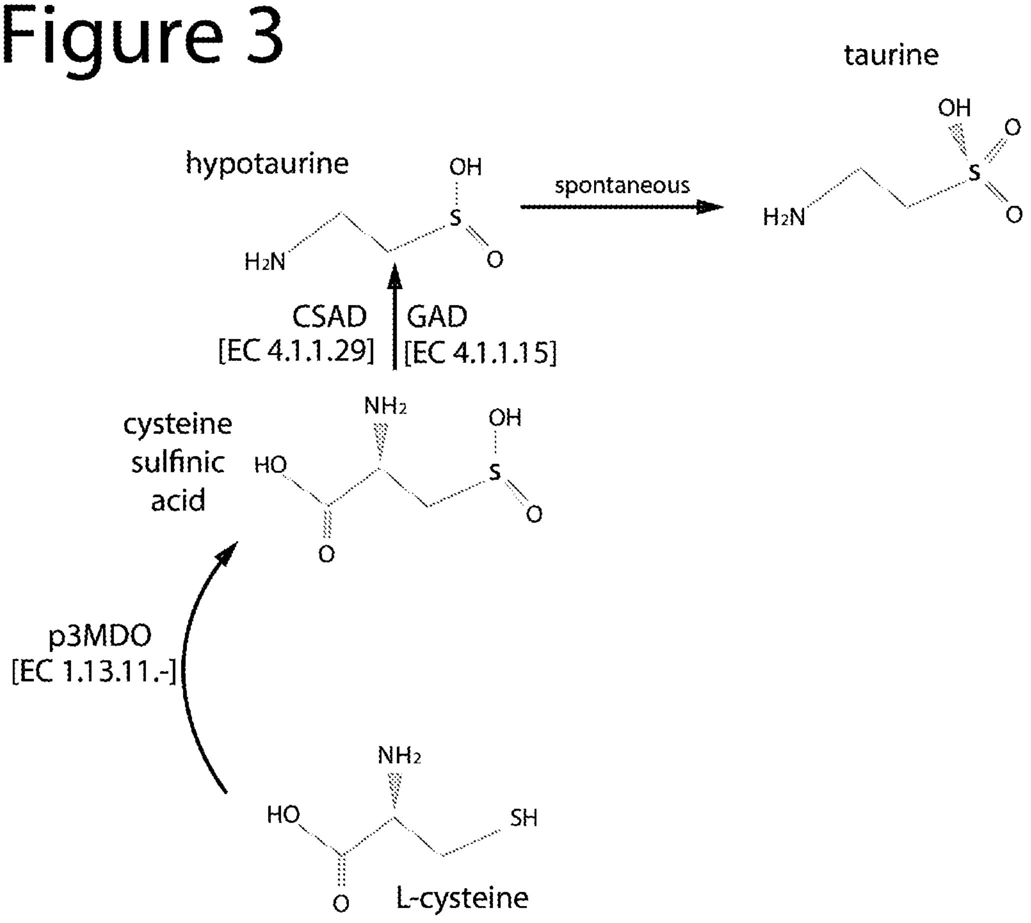
FIG. 3 depicts an embodiment of a biosynthetic pathway for production of taurine from L-cysteine.

In some embodiments, a non-naturally occurring microorganism is provided that expresses one or more exogenous enzyme activity/ies for the conversion of cysteine to taurine via the enzyme 3-mercaptopropionate dioxygenase (p3MDO), for example, exogenous enzyme(s) of the p3MDO/CSAD or GAD pathway for biosynthesis of taurine. The p3MDO/CSAD or GAD pathway for taurine biosynthesis is shown schematically in FIG. 3.

Non-naturally occurring microorganisms are provided that include the following enzymes or enzyme activities: 3-mercaptopropionate dioxygenase (MDO; p3MDO) (EC 1.13.11.-); and cysteine sulfinic acid decarboxylase (CSAD) (EC 4.1.1.29), wherein at least one of these enzymes or enzyme activities is encoded by an exogenous polynucleotide with which the microorganism has been transformed. In some embodiments, p3MDO and CSAD enzymes or enzyme activities are encoded by one or more exogenous polynucleotide(s) (e.g., one or two, exogenous polynucleotide(s)) in the microorganism. In some embodiments, one of p3MDO and CSAD enzymes or enzyme activities is encoded by an exogenous polynucleotide in the microorganism and the remaining activity is endogenously expressed in the host cell from which the non-naturally occurring microorganism is derived, i.e., not expressed from an exogenous polynucleotide. In one embodiment, the microorganism expresses an endogenous CSAD activity and p3MDO is encoded by an exogenous polynucleotide in the microorganism. In one embodiment, the microorganism expresses an endogenous p3MDO activity and CSAD is encoded by an exogenous polynucleotide in the microorganism.

Non-naturally occurring microorganisms are provided that include the following enzymes or enzyme activities: 3-mercaptopropionate dioxygenase (MDO; p3MDO) (EC 1.13.11.-); and glutamate decarboxylase (GAD) (EC 4.1.1.15), wherein at least one of these enzymes or enzyme activities is encoded by an exogenous polynucleotide with which the microorganism has been transformed. In some embodiments, p3MDO and GAD enzymes or enzyme activities are encoded by one or more exogenous polynucleotide(s) (e.g., one or two, exogenous polynucleotide(s)) in the microorganism. In some embodiments, one of p3MDO and GAD enzymes or enzyme activities is encoded an exogenous polynucleotide in the microorganism and the remaining activity is endogenously expressed in the host cell from which the non-naturally occurring microorganism is derived, i.e., not expressed from an exogenous polynucleotide. In one embodiment, the microorganism expresses an endogenous GAD activity and p3MDO is encoded by an exogenous polynucleotide in the microorganism. In one embodiment, the microorganism expresses an endogenous p3MDO activity and GAD is encoded by an exogenous polynucleotide in the microorganism.

In some embodiments, the non-naturally occurring microorganism includes an exogenous polynucleotide that encodes p3MDO comprising or consisting of the amino acid sequence depicted in SEQ ID NO:33, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:33. In some embodiments, the polynucleotide that encodes p3MDO comprises or consists of the polynucleotide sequence depicted in SEQ ID NO:34 or SEQ ID NO:60 or a polynucleotide having at least about 30, 35, 40, 45, 50, 55, 60, 65, 70, 75, 80, 85, 90, 95, 98, or 99% identity to SEQ ID NO:34 or SEQ ID NO:60. In some embodiments, the polynucleotide sequence is codon optimized for expression in the microorganism, e.g., SEQ ID NO:60.

In some embodiments, the non-naturally occurring microorganism includes an exogenous polynucleotide that encodes CSAD comprising or consisting of the amino acid sequence depicted in SEQ ID NO:11, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:11. In some embodiments, the polynucleotide that encodes CSAD comprises or consists of the polynucleotide sequence depicted in SEQ ID NO:12, SEQ ID NO:53, or SEQ ID NO:54 or a polynucleotide having at least about 30, 35, 40, 45, 50, 55, 60, 65, 70, 75, 80, 85, 90, 95, 98, or 99% identity to SEQ ID NO:12, SEQ ID NO:53, or SEQ ID NO:54. In some embodiments, the polynucleotide sequence is codon optimized for expression in the microorganism, e.g. SEQ ID NO: 53 or SEQ ID NO:54.

In some embodiments, the non-naturally occurring microorganism includes an exogenous polynucleotide that encodes GAD comprising or consisting of the amino acid sequence depicted in SEQ ID NO:13, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:13. In some embodiments, the polynucleotide that encodes GAD comprises or consists of the polynucleotide sequence depicted in SEQ ID NO:14 or a polynucleotide having at least about 30, 35, 40, 45, 50, 55, 60, 65, 70, 75, 80, 85, 90, 95, 98, or 99% identity to SEQ ID NO:14. In some embodiments, the polynucleotide sequence is codon optimized for expression in the microorganism.

In one embodiment, a non-naturally occurring *Methylobacterium* microorganism is provided that includes one or more exogenous polynucleotide(s) encoding p3MDO and CSAD. In another embodiment, a non-naturally occurring *Methylobacterium* microorganism is provided that includes one or more exogenous polynucleotide(s) encoding p3MDO and GAD.

In one embodiment, a non-naturally occurring *Escherichia* microorganism is provided that includes an exogenous polynucleotide encoding p3MDO. In one embodiment, a non-naturally occurring *Escherichia* microorganism is provided that includes one or more exogenous polynucleotide(s) encoding p3MDO and CSAD.

In one embodiment, a non-naturally occurring *Saccharomyces* microorganism is provided that includes an exogenous polynucleotide encoding p3MDO. In one embodiment, a non-naturally occurring *Saccharomyces* microorganism is provided that includes one or more exogenous polynucleotide(s) encoding p3MDO and CSAD.

In one embodiment, a non-naturally occurring *Bacillus* microorganism is provided that includes an exogenous polynucleotide encoding p3MDO. In one embodiment, a non-naturally occurring *Bacillus* microorganism is provided that includes one or more exogenous polynucleotide(s) encoding p3MDO and CSAD.

Conversion of Serine to Taurine

Figure 4:
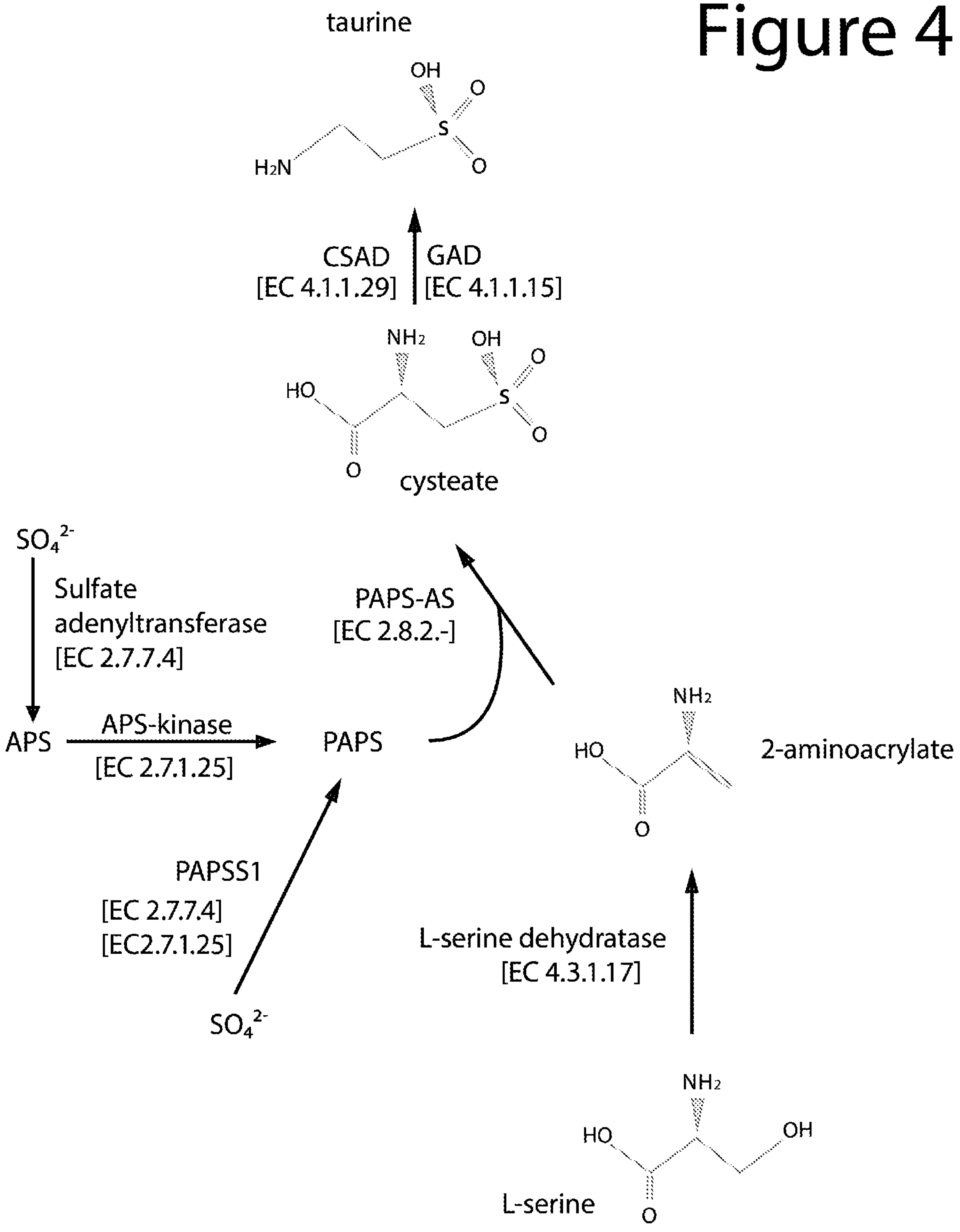
FIG. 4 depicts an embodiment of a biosynthetic pathway for production of taurine from L-serine.

In some embodiments, a non-naturally occurring microorganism is provided that expresses one or more exogenous enzyme activity/ies of the serine/sulfate pathway for biosynthesis of taurine. The serine/sulfate pathway for taurine biosynthesis is shown schematically in FIG. 4.

In some embodiments, the non-naturally occurring microorganism includes one or more mutations that cause accumulation of serine in the microorganism. For example, a methylotrophic strain that uses ribulose monophosphate (RuMP) for carbon assimilation from methanol may include a deletion or mutation in HprA (hydroxypyruvate reductase), which blocks the serine cycle from being completed, resulting in serine accumulation.

Non-naturally occurring microorganisms are provided that include the following enzymes or enzyme activities: L-serine dehydratase (EC 4.3.1.17); sulfate adenyltransferase (EC 2.7.7.4) and adenylyl-sulfate kinase (APS kinase) (EC 2.7.1.25), and/or 3'-phosphoadenosine 5'-phosphosulfate synthase (PAPSS1) (EC 2.7.7.4/EC 2.7.1.25); 3'-phosphoadenylyl sulfate: 2-aminoacrylate C-sulfotransferase (PAPS-AS) (EC 2.8.2.-); and cysteine sulfinic acid decarboxylase (CSAD) (EC 4.1.1.29), wherein at least one of these enzymes or enzyme activities is encoded by an exogenous polynucleotide with which the microorganism has been transformed. In some embodiments, L-serine dehydratase; sulfate adenyltransferase and APS kinase, and/or PAPSS1; PAPS-AS; and CSAD enzymes or enzyme activities are encoded by one or more exogenous polynucleotide(s) (e.g., one, two, three, four, five, six, or seven exogenous polynucleotide(s)) in the microorganism. In some embodiments, one, two, three, four, five, or six of L-serine dehydratase, sulfate adenyltrasnferase, APS kinase, PAPSS1, PAPS-AS, and CSAD enzymes or enzyme activities is encoded by one or more exogenous polynucleotide(s) in the microorganism and the remaining activity/ies is/are endogenously expressed in the host cell from which the non-naturally occurring microorganism is derived, i.e., not expressed from exogenous polynucleotide(s). In one embodiment, the microorganism expresses an endogenous L-serine dehydratase activity, and sulfate adenyltransferase and APS kinase, and/or PAPSS1, PAPS-AS, and CSAD are expressed from exogenous polynucleotide(s). In one embodiment, the microorganism expresses endogenous L-serine dehydratase, sulfate adenyltransferase, and APS kinase activity, and PAPS-AS and CSAD are expressed from exogenous polynucleotide(s). In one embodiment, the microorganism expresses endogenous L-serine dehydratase, sulfate adenyltransferase, APS kinase, and CSAD activities, and PAPS-AS is expressed from an exogenous polynucleotide.

Non-naturally occurring microorganisms are provided that include the following enzymes or enzyme activities: L-serine dehydratase (EC 4.3.1.17); sulfate adenyltransferase (EC 2.7.7.4) and adenylyl-sulfate kinase (APS kinase) (EC 2.7.1.25), and/or 3'-phosphoadenosine 5'-phosphosulfate synthase (PAPSS1) (EC 2.7.7.4/EC 2.7.1.25); 3'-phosphoadenylyl sulfate: 2-aminoacrylate C-sulfotransferase (PAPS-AS) (EC 2.8.2.-); and glutamate decarboxylase (GAD) (EC 4.1.1.15), wherein at least one of these enzymes or enzyme activities is encoded by an exogenous polynucleotide with which the microorganism has been transformed. In some embodiments, L-serine dehydratase; sulfate adenyltrasnferase and APS kinase, and/or PAPSS1; PAPS-AS; and GAD enzymes or enzyme activities are encoded by one or more exogenous polynucleotide(s) (e.g., one, two, three, four, five, six, or seven exogenous polynucleotide(s)) in the microorganism. In some embodiments, one, two, three, four, five, or six of L-serine dehydratase, sulfate adenyltransferase, APS kinase, PAPSS1, PAPS-AS, and GAD enzymes or enzyme activities is encoded by one or more exogenous polynucleotide(s) in the microorganism and the remaining activity/ies is/are endogenously expressed in the host cell from which the non-naturally occurring microorganism is derived, i.e., not expressed from exogenous polynucleotide(s). In one embodiment, the microorganism expresses an endogenous L-serine dehydratase activity, and sulfate adenyltransferase and APS kinase, and/or PAPSS1, PAPS-AS, and GAD are expressed from exogenous polynucleotide(s). In one embodiment, the microorganism expresses endogenous L-serine dehydratase, sulfate adenyltransferase, APS kinase activity, and PAPS-AS and GAD are expressed from exogenous polynucleotide(s). In one embodiment, the microorganism expresses endogenous L-serine dehydratase, sulfate adenyltransferase, APS kinase, and GAD activities, and PAPS-AS is expressed from an exogenous polynucleotide.

In some embodiments, the non-naturally occurring microorganism includes an exogenous polynucleotide that encodes L-serine dehydratase comprising or consisting of the amino acid sequence depicted in SEQ ID NO:1, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:1. In some embodiments, the polynucleotide that encodes L-serine dehydratase comprises or consists of the polynucleotide sequence depicted in SEQ ID NO:2 or a polynucleotide having at least about 30, 35, 40, 45, 50, 55, 60, 65, 70, 75, 80, 85, 90, 95, 98, or 99% identity to SEQ ID NO:2. In some embodiments, the polynucleotide sequence is codon optimized for expression in the microorganism.

In some embodiments, the non-naturally occurring microorganism includes exogenous polynucleotides that encode sulfate adenyltransferase comprising or consisting of the amino acid sequences depicted in SEQ ID NO:3 and SEQ ID NO:5, or a variant or homolog thereof. In some embodiments, the exogenous polynucleotides encode polypeptides comprising or consisting of amino acid sequences having at least about 30, 35, 40, 45, 50, 55, 60, 65, 70, 75, 80, 85, 90, 95, 98, or 99% identity to SEQ ID NO:3 or SEQ ID NO:5. In some embodiments, the polynucleotides that encode sulfate adenyltransferase comprise or consists of the polynucleotide sequences depicted in SEQ ID NO:4 and SEQ ID NO:6 or polynucleotides having at least about 30, 35, 40, 45, 50, 55, 60, 65, 70, 75, 80, 85, 90, 95, 98, or 99% identity to SEQ ID NO:4 or SEQ ID NO:6. In some embodiments, the polynucleotide sequences are codon optimized for expression in the microorganism.

In some embodiments, the non-naturally occurring microorganism includes an exogenous polynucleotide that encodes APS kinase comprising or consisting of the amino acid sequence depicted in SEQ ID NO:7, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:7. In some embodiments, the polynucleotide that encodes APS kinase comprises or consists of the polynucleotide sequence depicted in SEQ ID NO:8 or SEQ ID NO:62 or a polynucleotide having at least about 30, 35, 40, 45, 50, 55, 60, 65, 70, 75, 80, 85, 90, 95, 98, or 99% identity to SEQ ID NO:8 or SEQ ID NO:62. In some embodiments, the polynucleotide sequence is codon optimized for expression in the microorganism, e.g. SEQ ID NO:62.

In some embodiments, the non-naturally occurring microorganism includes an exogenous polynucleotide that encodes PAPSS1 comprising or consisting of the amino acid sequence depicted in SEQ ID NO:31, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:31. In some embodiments, the polynucleotide that encodes PAPSS1 comprises or consists of the polynucleotide sequence depicted in SEQ ID NO:32 or SEQ ID NO:63 or a polynucleotide having at least about 30, 35, 40, 45, 50, 55, 60, 65, 70, 75, 80, 85, 90, 95, 98, or 99% identity to SEQ ID NO:32 or SEQ ID NO:63. In some embodiments, the polynucleotide sequence is codon optimized for expression in the microorganism, e.g., SEQ ID NO:63.

In some embodiments, the non-naturally occurring microorganism includes an exogenous polynucleotide that encodes PAPS-AS comprising or consisting of the amino acid sequence depicted in SEQ ID NO:9, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:9. In some embodiments, the polynucleotide that encodes PAPS-AS comprises or consists of the polynucleotide sequence depicted in SEQ ID NO:10 or SEQ ID NO:61 or a polynucleotide having at least about 30, 35, 40, 45, 50, 55, 60, 65, 70, 75, 80, 85, 90, 95, 98, or 99% identity to SEQ ID NO:10 or SEQ ID NO:61. In some embodiments, the polynucleotide sequence is codon optimized for expression in the microorganism, e.g., SEQ ID NO:61.

In some embodiments, the non-naturally occurring microorganism includes an exogenous polynucleotide that encodes CSAD comprising or consisting of the amino acid sequence depicted in SEQ ID NO:11, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:11. In some embodiments, the polynucleotide that encodes CSAD comprises or consists of the polynucleotide sequence depicted in SEQ ID NO:12, SEQ ID NO:53, or SEQ ID NO:54 or a polynucleotide having at least about 30, 35, 40, 45, 50, 55, 60, 65, 70, 75, 80, 85, 90, 95, 98, or 99% identity to SEQ ID NO:12, SEQ ID NO:53, or SEQ ID NO:54. In some embodiments, the polynucleotide sequence is codon optimized for expression in the microorganism, e.g., SEQ ID NO:53 or SEQ ID NO:54.

In some embodiments, the non-naturally occurring microorganism includes an exogenous polynucleotide that encodes GAD comprising or consisting of the amino acid sequence depicted in SEQ ID NO:13, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:13. In some embodiments, the polynucleotide that encodes GAD comprises or consists of the polynucleotide sequence depicted in SEQ ID NO:14 or a polynucleotide having at least about 30, 35, 40, 45, 50, 55, 60, 65, 70, 75, 80, 85, 90, 95, 98, or 99% identity to SEQ ID NO:14. In some embodiments, the polynucleotide sequence is codon optimized for expression in the microorganism.

In one embodiment, a non-naturally occurring *Methylobacterium* microorganism is provided that includes one or more exogenous polynucleotide(s) encoding: sulfate adenyltransferase and APS kinase, and/or PAPSS1; PAPS-AS; and CSAD. In one embodiment, a non-naturally occurring *Methylobacterium* microorganism is provided that includes one or more exogenous polynucleotide(s) encoding PAPS-AS and CSAD. In another embodiment, a non-naturally occurring *Methylobacterium* microorganism is provided that includes one or more exogenous polynucleotide(s) encoding: sulfate adenyltransferase and APS kinase, and/or PAPSS1; PAPS-AS; and GAD. In one embodiment, a non-naturally occurring *Methylobacterium* microorganism is provided that includes one or more exogenous polynucleotide(s) encoding PAPS-AS and GAD.

In one embodiment, a non-naturally occurring *Escherichia* microorganism is provided that includes an exogenous polynucleotide encoding PAPS-AS. In one embodiment, a non-naturally occurring *Escherichia* microorganism is provided that includes one or more exogenous polynucleotide(s) encoding PAPSS1 and PAPS-AS. In one embodiment, a non-naturally occurring *Escherichia* microorganism is provided that includes one or more exogenous polynucleotide(s) encoding PAPSS1, PAPS-AS, and CSAD.

In one embodiment, a non-naturally occurring *Saccharomyces* microorganism is provided that includes an exogenous polynucleotide encoding PAPS-AS. In one embodiment, a non-naturally occurring *Saccharomyces* microorganism is provided that includes one or more exogenous polynucleotide(s) encoding PAPSS1 and PAPS-AS. In one embodiment, a non-naturally occurring *Saccharomyces* microorganism is provided that includes one or more exogenous polynucleotide(s) encoding PAPSS1, PAPS-AS, and CSAD.

In one embodiment, a non-naturally occurring *Bacillus* microorganism is provided that includes an exogenous polynucleotide encoding PAPS-AS. In one embodiment, a non-naturally occurring *Bacillus* microorganism is provided that includes one or more exogenous polynucleotide(s) encoding PAPSS1 and PAPS-AS. In one embodiment, a non-naturally occurring *Bacillus* microorganism is provided that includes one or more exogenous polynucleotide(s) encoding PAPSS1, PAPS-AS, and CSAD.

Conversion of Phosphoserine or Serine to Taurine

Figure 5:
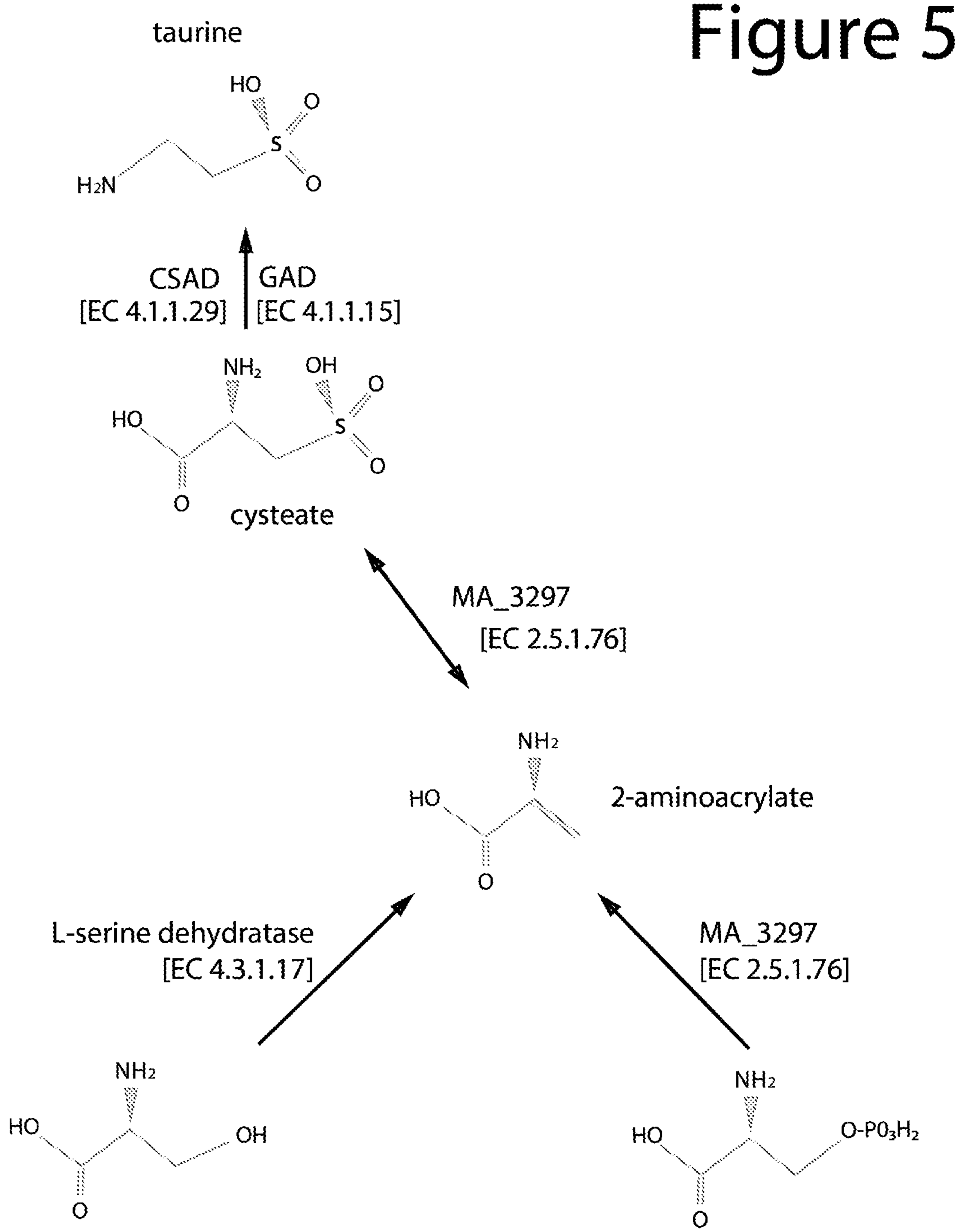
FIG. 5 depicts an embodiment of a biosynthetic pathway for production of taurine from L-phosphoserine or L-serine.

In some embodiments, a non-naturally occurring microorganism is provided that expresses one or more exogenous enzyme activity/ies for the conversion of phosphoserine to taurine via the enzyme cysteate synthase, for example, enzyme(s) of the cysteate synthase (e.g., MA_3297)/CSAD or GAD pathway for biosynthesis of taurine, and/or expresses one or more exogenous enzyme activity/ies for the conversion of serine to taurine via the enzymes L-serine dehydratase, cysteate synthase (e.g., MA_3297), and CSAD/GAD. The cysteate synthase (e.g., MA_3297)/CSAD or GAD, and L-serine dehydratase cysteate synthase (e.g., MA_3297)/CSAD or GAD pathways for taurine biosynthesis are shown schematically in FIG. 5.

Non-naturally occurring microorganisms are provided that include the following enzymes or enzyme activities: cysteate synthase, e.g., MA_3297 (EC 2.5.1.76); optionally L-serine dehydratase (EC 4.3.1.17); and cysteine sulfinic acid decarboxylase (CSAD) (EC 4.1.1.29), wherein at least one of these enzymes or enzyme activities is encoded by an exogenous polynucleotide with which the microorganism has been transformed. In some embodiments, cysteate synthase, optionally L-serine dehydratase, and CSAD enzymes or enzyme activities are encoded by one or more exogenous polynucleotide(s) (e.g., one, two, or three, exogenous polynucleotide(s)) in the microorganism. In some embodiments, one of cysteate synthase, L-serine dehydratase, or CSAD enzymes or enzyme activities is encoded by an exogenous polynucleotide in the microorganism and the remaining activity/ies is/are endogenously expressed in the host cell from which the non-naturally occurring microorganism is derived, i.e., not expressed from exogenous polynucleotide(s). In one embodiment, the microorganism expresses endogenous CSAD and optionally L-serine dehydratase activity, and cysteate synthase (e.g., MA_3297) is encoded by an exogenous polynucleotide in the microorganism. In one embodiment, the microorganism expresses an endogenous cysteate synthase and CSAD is encoded by an exogenous polynucleotide in the microorganism.

Non-naturally occurring microorganisms are provided that include the following enzymes or enzyme activities: cysteate synthase, e.g., MA_3297 (EC 2.5.1.76); optionally L-serine dehydratase (EC 4.3.1.17); and glutamate decarboxylase (GAD) (EC 4.1.1.15), wherein at least one of these enzymes or enzyme activities is encoded by an exogenous polynucleotide with which the microorganism has been transformed. In some embodiments, cysteate synthase, optionally L-serine dehydratase, and GAD enzymes or enzyme activities are encoded by one or more exogenous polynucleotide(s) (e.g., one, two, or three, exogenous polynucleotide(s)) in the microorganism. In some embodiments, one of cysteate synthase, L-serine dehydratase, or GAD enzymes or enzyme activities is encoded by an exogenous polynucleotide in the microorganism and the remaining activity/ies is/are endogenously expressed in the host cell from which the non-naturally occurring microorganism is derived, i.e., not expressed from exogenous polynucleotide(s). In one embodiment, the microorganism expresses endogenous GAD and optionally L-serine dehydratase activity and cysteate synthase (e.g., MA_3297) is encoded by an exogenous polynucleotide in the microorganism. In one embodiment, the microorganism expresses an endogenous cysteate synthase and GAD is encoded by an exogenous polynucleotide in the microorganism.

In some embodiments, the non-naturally occurring microorganism includes an exogenous polynucleotide that encodes cysteate synthase comprising or consisting of the amino acid sequence depicted in SEQ ID NO:17, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:17. In some embodiments, the polynucleotide that encodes cysteate synthase comprises or consists of the polynucleotide sequence depicted in SEQ ID NO:18, SEQ ID NO:52, or SEQ ID NO:64 or a polynucleotide having at least about 30, 35, 40, 45, 50, 55, 60, 65, 70, 75, 80, 85, 90, 95, 98, or 99% identity to SEQ ID NO:18, SEQ ID NO:52, or SEQ ID NO:64. In some embodiments, the polynucleotide sequence is codon optimized for expression in the microorganism, e.g., SEQ ID NO:52 or SEQ ID NO:64.

In some embodiments, the non-naturally occurring microorganism includes an exogenous polynucleotide that encodes L-serine dehydratase comprising or consisting of the amino acid sequence depicted in SEQ ID NO:1, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:1. In some embodiments, the polynucleotide that encodes L-serine dehydratase comprises or consists of the polynucleotide sequence depicted in SEQ ID NO:2 or a polynucleotide having at least about 30, 35, 40, 45, 50, 55, 60, 65, 70, 75, 80, 85, 90, 95, 98, or 99% identity to SEQ ID NO:2. In some embodiments, the polynucleotide sequence is codon optimized for expression in the microorganism.

In some embodiments, the non-naturally occurring microorganism includes an exogenous polynucleotide that encodes CSAD comprising or consisting of the amino acid sequence depicted in SEQ ID NO:11, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:11. In some embodiments, the polynucleotide that encodes CSAD comprises or consists of the polynucleotide sequence depicted in SEQ ID NO:12, SEQ ID NO:53, or SEQ ID NO:54 or a polynucleotide having at least about 30, 35, 40, 45, 50, 55, 60, 65, 70, 75, 80, 85, 90, 95, 98, or 99% identity to SEQ ID NO:12, SEQ ID NO:53, or SEQ ID NO:54. In some embodiments, the polynucleotide sequence is codon optimized for expression in the microorganism, e.g., SEQ ID NO:53 or SEQ ID NO:54.

In some embodiments, the non-naturally occurring microorganism includes an exogenous polynucleotide that encodes GAD comprising or consisting of the amino acid sequence depicted in SEQ ID NO:13, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:13. In some embodiments, the polynucleotide that encodes GAD comprises or consists of the polynucleotide sequence depicted in SEQ ID NO:14 or a polynucleotide having at least about 30, 35, 40, 45, 50, 55, 60, 65, 70, 75, 80, 85, 90, 95, 98, or 99% identity to SEQ ID NO:14. In some embodiments, the polynucleotide sequence is codon optimized for expression in the microorganism.

In one embodiment, a non-naturally occurring *Methylobacterium* microorganism is provided that includes one or more exogenous polynucleotide(s) encoding cysteate synthase (e.g., MA_3297) and CSAD. In another embodiment, a non-naturally occurring *Methylobacterium* microorganism is provided that includes one or more exogenous polynucleotide(s) encoding cysteate synthase (e.g., MA_3297) and GAD.

In one embodiment, a non-naturally occurring *Escherichia* microorganism is provided that includes one or more exogenous polynucleotide(s) encoding cysteate synthase (e.g., MA_3297) and optionally L-serine dehydratase. In one embodiment, a non-naturally occurring *Escherichia* microorganism is provided that includes one or more exogenous polynucleotide(s) encoding cysteate synthase (e.g., MA_3297), optionally L-serine dehydratase, and CSAD.

In one embodiment, a non-naturally occurring *Saccharomyces* microorganism is provided that includes one or more exogenous polynucleotide(s) encoding cysteate synthase (e.g., MA_3297) and optionally L-serine dehydratase. In one embodiment, a non-naturally occurring *Saccharomyces* microorganism is provided that includes one or more exogenous polynucleotide(s) encoding cysteate synthase (e.g., MA_3297), optionally L-serine dehydratase, and CSAD.

In one embodiment, a non-naturally occurring *Bacillus* microorganism is provided that includes one or more exogenous polynucleotide(s) encoding cysteate synthase (e.g., MA_3297) and optionally L-serine dehydratase. In one embodiment, a non-naturally occurring *Bacillus* microorganism is provided that includes one or more exogenous polynucleotide(s) encoding cysteate synthase (e.g., MA_3297), optionally L-serine dehydratase, and CSAD.

Conversion of Cysteine to Taurine, Via CGL/CD; PAPS-AS, and CSAD or GAD

Figure 6:
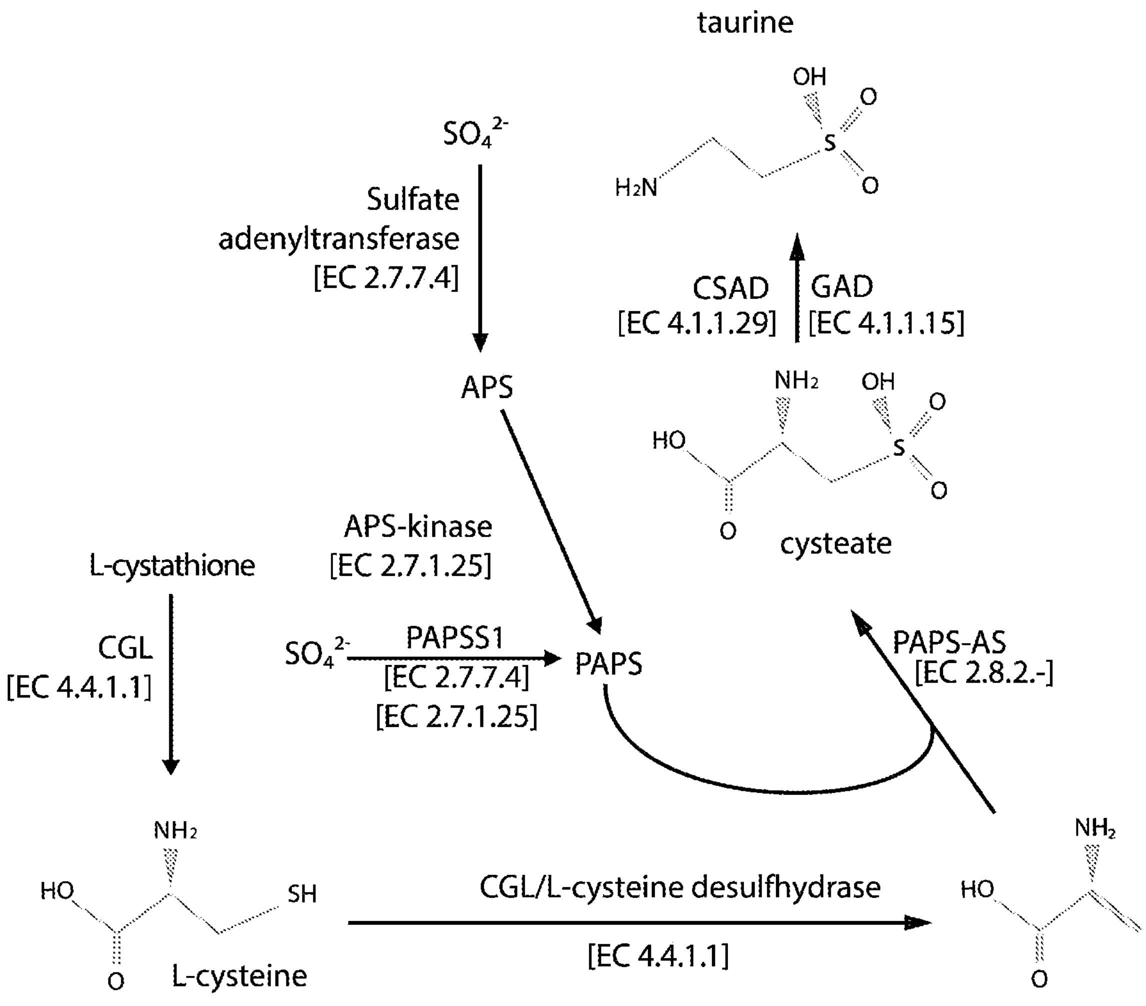
FIG. 6 depicts an embodiment of a biosynthetic pathway for production of taurine from L-cysteine.

In some embodiments, a non-naturally occurring microorganism is provided that expresses one or more exogenous enzyme activity/ies for the conversion of cysteine to taurine via the enzymes cystathionine gamma-lyase (CGL)/L-cysteine desulfhydrase (CD), 3' phosphoadenylyl sulfate:2-aminoacrylate C-sulfotransferase (PAPS-AS), and cysteine sulfinic acid decarboxylase (CSAD) or glutamate decarboxylase (GAD). This pathway for taurine biosynthesis is shown schematically in FIG. 6. Several proteins have been found to have L-cysteine desulfhydrase (CD) activity (EC 4.4.1.1) including cystathionine gamma-lyase (CGL), tryptophanase, cysteine synthases, and MalY (Awano et al. (2005) *Appl Environ Microbiol* 71(7):4149-52.). In some embodiments, a single enzyme includes both CGL and CD activities. In other embodiments, CGL and CD activities are provided by two separate enzymes. In some embodiments, CD activity is provided by an enzyme and CGL activity is absent. When CGL activity is present, it may provide greater flux via production of L-cysteine, which serves as a substrate for CD activity. In some embodiments, a first enzyme that includes both CGL and CD activities and a second enzyme that includes only CD activity are provided.

Non-naturally occurring microorganisms are provided that include the following enzymes or enzyme activities: cystathionine gamma-lyase (CGL)/L-cysteine desulfhydrase (CD) (EC 4.4.1.1); sulfate adenyltransferase (EC 2.7.7.4) and adenylyl-sulfate kinase (APS kinase) (EC 2.7.1.25), and/or 3'-phosphoadenosine 5'-phosphosulfate synthase (PAPSS1) (EC 2.7.7.4/EC 2.7.1.25); 3'-phosphoadenylyl sulfate: 2-aminoacrylate C-sulfotransferase (PAPS-AS) (EC 2.8.2.-); and cysteine sulfinic acid decarboxylase (CSAD) (EC 4.1.1.29), wherein at least one of these enzymes or enzyme activities is encoded by an exogenous polynucleotide with which the microorganism has been transformed. In some embodiments, CGL/CD; sulfate adenyltransferase and APS kinase, and/or PAPSS1; PAPS-AS; and CSAD enzymes or enzyme activities are encoded by one or more exogenous polynucleotide(s) (e.g., one, two, three, four, five, six, or seven exogenous polynucleotide(s)) in the microorganism. In some embodiments, one, two, three, four, five, or six of CGL/CD, sulfate adenyltransferase, APS kinase, PAPSS1, PAPS-AS, and CSAD enzymes or enzyme activities is encoded by one or more exogenous polynucleotide(s) in the microorganism and the remaining activity/ies is/are endogenously expressed in the host cell from which the non-naturally occurring microorganism is derived, i.e., not expressed from exogenous polynucleotide(s). In one embodiment, the microorganism expresses an endogenous activity, and sulfate adenyltransferase and APS kinase and/or PAPSS1, PAPS-AS, and CSAD are expressed from exogenous polynucleotide(s). In one embodiment, the microorganism expresses endogenous CGL/CD and sulfate adenyltransferase, APS kinase activities, and PAPS-AS and CSAD activities are expressed from exogenous polynucleotide(s). In one embodiment, the microorganism expresses endogenous CGL/CD, sulfate adenyltransferase, APS kinase, and CSAD activities, and PAPS-AS is expressed from an exogenous polynucleotide.

Non-naturally occurring microorganisms are provided that include the following enzymes or enzyme activities:

cystathionine gamma-lyase (CGL)/L-cysteine desulfhydrase (CD) (EC 4.4.1.1); sulfate adenyltransferase (EC 2.7.7.4) and adenylyl-sulfate kinase (APS kinase) (EC 2.7.1.25), and/or 3'-phosphoadenosine 5'-phosphosulfate synthase (PAPSS1) (EC 2.7.7.4/EC 2.7.1.25); 3'-phosphoadenylyl sulfate: 2-aminoacrylate C-sulfotransferase (PAPS-AS) (EC 2.8.2.-); and glutamate decarboxylase (GAD) (EC 4.1.1.15), wherein at least one of these enzymes or enzyme activities is encoded by an exogenous polynucleotide with which the microorganism has been transformed. In some embodiments, CGL/CD, sulfate adenyltransferase and APS kinase, and/or PAPSS1, PAPS-AS, and GAD enzymes or enzyme activities are encoded by one or more exogenous polynucleotide(s) (e.g., one, two, three, four, five, six, or seven exogenous polynucleotide(s)) in the microorganism. In some embodiments, one, two, three, four, five, or six of CGL/CD, sulfate adenyltransferase, APS kinase, PAPSS1, PAPS-AS, and GAD enzymes or enzyme activities is encoded by one or more exogenous polynucleotide(s) in the microorganism and the remaining activity/ies is/are endogenously expressed in the host cell from which the non-naturally occurring microorganism is derived, i.e., not expressed from exogenous polynucleotide(s). In one embodiment, the microorganism expresses an endogenous activity, and sulfate adenyltransferase and APS kinase, and/or PAPSS1, PAPS-AS, and GAD are expressed from exogenous polynucleotide(s). In one embodiment, the microorganism expresses endogenous CGL/CD, sulfate adenyltransferase, and APS kinase activities, and PAPS-AS and GAD activities are expressed from exogenous polynucleotide(s). In one embodiment, the microorganism expresses endogenous CGL/CD, sulfate adenyltransferase, APS kinase, and GAD activities, and PAPS-AS is expressed from an exogenous polynucleotide.

In some embodiments, the non-naturally occurring microorganism includes one or more exogenous polynucleotide(s) that encode(s) CGL/CD comprising or consisting of the amino acid sequence(s) depicted in SEQ ID NO:46, SEQ ID NO:70, and/or SEQ ID NO:72 or variant(s) or homolog(s) thereof. In some embodiments, the exogenous polynucleotide(s) encode(s) polypeptide(s) comprising or consisting of amino acid sequence(s) having at least about 30, 35, 40, 45, 50, 55, 60, 65, 70, 75, 80, 85, 90, 95, 98, or 99% identity to SEQ ID NO:46, SEQ ID NO:70, and/or SEQ ID NO:72. In some embodiments, the polynucleotide(s) that encode(s) CGL/CD comprise or consist of the polynucleotide sequence(s) depicted in SEQ ID NO:47, SEQ ID NO:65, SEQ ID NO:71 and/or SEQ ID NO:73, or polynucleotide(s) having at least about 30, 35, 40, 45, 50, 55, 60, 65, 70, 75, 80, 85, 90, 95, 98, or 99% identity to SEQ ID NO:47, SEQ ID NO:65, SEQ ID NO:71, and/or SEQ ID NO:73. In some embodiments, the polynucleotide sequence is codon optimized for expression in the microorganism, e.g., SEQ ID NO:65.

In some embodiments, the non-naturally occurring microorganism includes exogenous polynucleotides that encode sulfate adenyltransferase comprising or consisting of the amino acid sequences depicted in SEQ ID NO:3 and SEQ ID NO:5, or a variant or homolog thereof. In some embodiments, the exogenous polynucleotides encode polypeptides comprising or consisting of an amino acid sequences having at least about 30, 35, 40, 45, 50, 55, 60, 65, 70, 75, 80, 85, 90, 95, 98, or 99% identity to SEQ ID NO:3 or SEQ ID NO:5. In some embodiments, the polynucleotides that encode sulfate adenyltransferase comprises or consists of the polynucleotide sequences depicted in SEQ ID NO:4 or SEQ ID NO:6 or polynucleotides having at least about 30, 35, 40, 45, 50, 55, 60, 65, 70, 75, 80, 85, 90, 95, 98, or 99% identity to SEQ ID NO:4 or SEQ ID NO:6. In some embodiments, the polynucleotide sequences are codon optimized for expression in the microorganism.

In some embodiments, the non-naturally occurring microorganism includes an exogenous polynucleotide that encodes APS kinase comprising or consisting of the amino acid sequence depicted in SEQ ID NO:7, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:7. In some embodiments, the polynucleotide that encodes APS kinase comprises or consists of the polynucleotide sequence depicted in SEQ ID NO:8 or SEQ ID NO:62 or a polynucleotide having at least about 30, 35, 40, 45, 50, 55, 60, 65, 70, 75, 80, 85, 90, 95, 98, or 99% identity to SEQ ID NO:8 or SEQ ID NO:62. In some embodiments, the polynucleotide sequence is codon optimized for expression in the microorganism, e.g., SEQ ID NO:62.

In some embodiments, the non-naturally occurring microorganism includes an exogenous polynucleotide that encodes PAPSS1 comprising or consisting of the amino acid sequence depicted in SEQ ID NO:31, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:31. In some embodiments, the polynucleotide that encodes PAPSS1 comprises or consists of the polynucleotide sequence depicted in SEQ ID NO:32 or SEQ ID NO:63 or a polynucleotide having at least about 30, 35, 40, 45, 50, 55, 60, 65, 70, 75, 80, 85, 90, 95, 98, or 99% identity to SEQ ID NO:32 or SEQ ID NO:63. In some embodiments, the polynucleotide sequence is codon optimized for expression in the microorganism, e.g., SEQ ID NO:63.

In some embodiments, the non-naturally occurring microorganism includes an exogenous polynucleotide that encodes PAPS-AS comprising or consisting of the amino acid sequence depicted in SEQ ID NO:9, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:9. In some embodiments, the polynucleotide that encodes PAPS-AS comprises or consists of the polynucleotide sequence depicted in SEQ ID NO:10 or SEQ ID NO:61 or a polynucleotide having at least about 30, 35, 40, 45, 50, 55, 60, 65, 70, 75, 80, 85, 90, 95, 98, or 99% identity to SEQ ID NO:10 or SEQ ID NO:61. In some embodiments, the polynucleotide sequence is codon optimized for expression in the microorganism, e.g., SEQ ID NO:61.

In some embodiments, the non-naturally occurring microorganism includes an exogenous polynucleotide that encodes CSAD comprising or consisting of the amino acid sequence depicted in SEQ ID NO:11, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:11. In some embodiments, the polynucleotide that encodes CSAD comprises or consists of the polynucleotide sequence depicted in SEQ ID NO:12, SEQ ID NO:53, or SEQ ID NO:54 or a polynucleotide having at least about 30, 35, 40, 45, 50, 55, 60, 65, 70, 75, 80, 85, 90, 95, 98, or 99% identity to SEQ ID NO:12, SEQ ID NO:53, or SEQ ID NO:54. In some embodiments, the polynucleotide sequence is codon optimized for expression in the microorganism, e.g., SEQ ID NO:53 or SEQ ID NO:54.

In some embodiments, the non-naturally occurring microorganism includes an exogenous polynucleotide that encodes GAD comprising or consisting of the amino acid sequence depicted in SEQ ID NO:13, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:13. In some embodiments, the polynucleotide that encodes GAD comprises or consists of the polynucleotide sequence depicted in SEQ ID NO:14 or a polynucleotide having at least about 30, 35, 40, 45, 50, 55, 60, 65, 70, 75, 80, 85, 90, 95, 98, or 99% identity to SEQ ID NO:14. In some embodiments, the polynucleotide sequence is codon optimized for expression in the microorganism.

In one embodiment, a non-naturally occurring *Methylobacterium* microorganism is provided that includes one or more exogenous polynucleotide(s) encoding: CGL/CD, sulfate adenyltransferase and APS kinase, and/or PAPSS1; PAPS-AS, and CSAD. In one embodiment, a non-naturally occurring *Methylobacterium* microorganism is provided that includes one or more exogenous polynucleotide(s) encoding CGL/CD, PAPS-AS and CSAD. In another embodiment, a non-naturally occurring *Methylobacterium* microorganism is provided that includes one or more exogenous polynucleotide(s) encoding: CGL/CD; sulfate adenyltransferase and APS kinase, and/or PAPSS1, PAPS-AS, and GAD. In one embodiment, a non-naturally occurring *Methylobacterium* microorganism is provided that includes one or more exogenous polynucleotide(s) encoding CGL/CD, PAPS-AS and GAD.

In one embodiment, a non-naturally occurring *Escherichia* microorganism is provided that includes an exogenous polynucleotide encoding PAPS-AS. In one embodiment, a non-naturally occurring *Escherichia* microorganism is provided that includes one or more exogenous polynucleotide(s) encoding PAPSS1 and PAPS-AS. In one embodiment, a non-naturally occurring *Escherichia* microorganism is provided that includes one or more exogenous polynucleotide(s) encoding PAPSS1, PAPS-AS, and CSAD.

In one embodiment, a non-naturally occurring *Saccharomyces* microorganism is provided that includes an exogenous polynucleotide encoding PAPS-AS. In one embodiment, a non-naturally occurring *Saccharomyces* microorganism is provided that includes one or more exogenous polynucleotide(s) encoding PAPSS1 and PAPS-AS. In one embodiment, a non-naturally occurring *Saccharomyces* microorganism is provided that includes one or more exogenous polynucleotide(s) encoding PAPSS1, PAPS-AS, and CSAD.

In one embodiment, a non-naturally occurring *Bacillus* microorganism is provided that includes an exogenous polynucleotide encoding PAPS-AS. In one embodiment, a non-naturally occurring *Bacillus* microorganism is provided that includes one or more exogenous polynucleotide(s) encoding PAPSS1 and PAPS-AS. In one embodiment, a non-naturally occurring *Bacillus* microorganism is provided that includes one or more exogenous polynucleotide(s) encoding PAPSS1, PAPS-AS, and CSAD.

Conversion of Cysteine to Taurine Via CGL/CD and Cysteate Synthase

Figure 7:
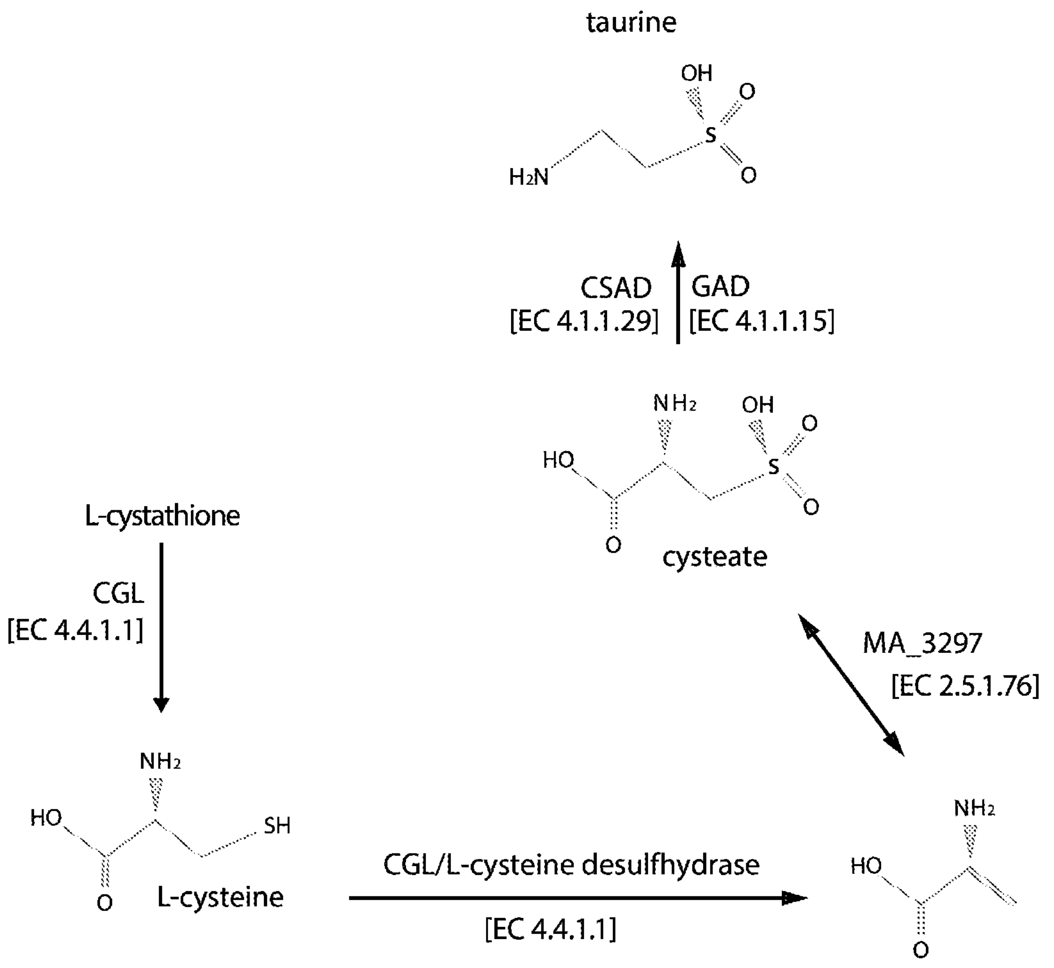
FIG. 7 depicts an embodiment of a biosynthetic pathway for production of taurine from L-cysteine.

In some embodiments, a non-naturally occurring microorganism is provided that expresses one or more exogenous enzyme activity/ies for the conversion of cysteine to taurine via the enzymes cystathionine gamma-lyase/L-cysteine desulfhydrase, cysteate synthase (e.g., MA_3297), and cysteine sulfinic acid decarboxylase (CSAD) or glutamate decarboxylase (GAD). The CGL/CD, cysteate synthase (e.g., MA_3297), CSAD or GAD pathway for taurine biosynthesis is shown schematically in FIG. 7. Several proteins have been found to have L-cysteine desulfhydrase (CD) activity (EC 4.4.1.1) including cystathionine gamma-lyase (CGL), tryptophanase, cysteine synthases, and MalY (Awano et al. (2005) *Appl Environ Microbiol* 71(7):4149-52.). In some embodiments, a single enzyme includes both CGL and CD activities. In other embodiments, CGL and CD activities are provided by two separate enzymes. In some embodiments, CD activity is provided by an enzyme and CGL activity is absent. When CGL activity is present, it may provide greater flux via production of L-cysteine, which serves as a substrate for CD activity. In some embodiments, a first enzyme that includes both CGL and CD activities and a second enzyme that includes only CD activity are provided.

Non-naturally occurring microorganisms are provided that include the following enzymes or enzyme activities: cystathionine gamma-lyase (CGL)/L-cysteine desulfhydrase (CD) (EC4.4.4.1), cysteate synthase, e.g., MA_3297 (EC 2.5.1.76); and cysteine sulfinic acid decarboxylase (CSAD) (EC 4.1.1.29), wherein at least one of these enzymes or enzyme activities is encoded by an exogenous polynucleotide with which the microorganism has been transformed. In some embodiments, CGL/CD, cysteate synthase, and CSAD enzymes or enzyme activities are encoded by one or more exogenous polynucleotide(s) (e.g., one, two, three, or four exogenous polynucleotide(s)) in the microorganism. In some embodiments, one or more of CGL/CD, cysteate synthase, and CSAD enzymes or enzyme activities is encoded by one or more exogenous polynucleotide(s) in the microorganism and the remaining activity/ies is/are endogenously expressed in the host cell from which the non-naturally occurring microorganism is derived, i.e., not expressed from exogenous polynucleotide(s). In one embodiment, the microorganism expresses an endogenous CSAD activity and CGL/CD and cysteate synthase (e.g., MA_3297) are encoded by exogenous polynucleotide(s) in the microorganism. In one embodiment, the microorganism expresses endogenous CGL/CD and CSAD activities and cysteate synthase (e.g., MA_3297) is encoded by an exogenous polynucleotide in the microorganism.

Non-naturally occurring microorganisms are provided that include the following enzymes or enzyme activities: cystathionine gamma-lyase (CGL)/L-cysteine desulfhydrase (CD) (EC4.4.4.1), cysteate synthase, e.g., MA_3297 (EC 2.5.1.76); and glutamate decarboxylase (GAD) (EC 4.1.1.15), wherein at least one of these enzymes or enzyme activities is encoded by an exogenous polynucleotide with which the microorganism has been transformed. In some embodiments, CGL/CD, cysteate synthase, and GAD enzymes or enzyme activities are encoded by one or more exogenous polynucleotide(s) (e.g., one, two, three, or four exogenous polynucleotide(s)) in the microorganism. In some embodiments, one or more of CGL/CD, cysteate synthase, and GAD enzymes or enzyme activities is encoded by one or more exogenous polynucleotide(s) in the micro-organism and the remaining activity/ies is/are endogenously expressed in the host cell from which the non-naturally occurring microorganism is derived, i.e., not expressed from exogenous polynucleotide(s). In one embodiment, the microorganism expresses an endogenous GAD activity and CGL/CD and cysteate synthase (e.g., MA_3297) are encoded by exogenous polynucleotide(s) in the microorganism. In one embodiment, the microorganism expresses endogenous CGL/CD and GAD activities and cysteate synthase (e.g., MA_3297) is encoded by an exogenous polynucleotide in the microorganism.

In some embodiments, the non-naturally occurring microorganism includes one or more exogenous polynucleotide(s) that encode(s) CGL/CD comprising or consisting of the amino acid sequence(s) depicted in SEQ ID NO:46, SEQ ID NO:70, and/or SEQ ID NO:72 or variant(s) or homolog(s) thereof. In some embodiments, the exogenous polynucleotide(s) encode(s) polypeptide(s) comprising or consisting of amino acid sequence(s) having at least about 30, 35, 40, 45, 50, 55, 60, 65, 70, 75, 80, 85, 90, 95, 98, or 99% identity to SEQ ID NO:46, SEQ ID NO:70, and/or SEQ ID NO:72. In some embodiments, the polynucleotide(s) that encode(s) CGL/CD comprise or consist of the polynucleotide sequence(s) depicted in SEQ ID NO:47, SEQ ID NO:65, SEQ ID NO:71, and/or SEQ ID NO:73 or a polynucleotide having at least about 30, 35, 40, 45, 50, 55, 60, 65, 70, 75, 80, 85, 90, 95, 98, or 99% identity to SEQ ID NO:47, SEQ ID NO:65, SEQ ID NO:71, and/or SEQ ID NO:73. In some embodiments, the polynucleotide sequence is codon optimized for expression in the microorganism, e.g., SEQ ID NO:65.

In some embodiments, the non-naturally occurring microorganism includes an exogenous polynucleotide that encodes cysteate synthase comprising or consisting of the amino acid sequence depicted in SEQ ID NO:17, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:17. In some embodiments, the polynucleotide that encodes cysteate synthase comprises or consists of the polynucleotide sequence depicted in SEQ ID NO:18, SEQ ID NO:52, or SEQ ID NO:64 or a polynucleotide having at least about 30, 35, 40, 45, 50, 55, 60, 65, 70, 75, 80, 85, 90, 95, 98, or 99% identity to SEQ ID NO:18, SEQ ID NO:52, or SEQ ID NO:64. In some embodiments, the polynucleotide sequence is codon optimized for expression in the microorganism, e.g., SEQ ID NO:52 or SEQ ID NO:64.

In some embodiments, the non-naturally occurring microorganism includes an exogenous polynucleotide that encodes CSAD comprising or consisting of the amino acid sequence depicted in SEQ ID NO:11, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:11. In some embodiments, the polynucleotide that encodes CSAD comprises or consists of the polynucleotide sequence depicted in SEQ ID NO:12, SEQ ID NO:53, or SEQ ID NO:54 or a polynucleotide having at least about 30, 35, 40, 45, 50, 55, 60, 65, 70, 75, 80, 85, 90, 95, 98, or 99% identity to SEQ ID NO:12, SEQ ID NO:53, or SEQ ID NO:54. In some embodiments, the polynucleotide sequence is codon optimized for expression in the microorganism, e.g., SEQ ID NO:53 or SEQ ID NO:54.

In some embodiments, the non-naturally occurring microorganism includes an exogenous polynucleotide that encodes GAD comprising or consisting of the amino acid sequence depicted in SEQ ID NO:13, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:13. In some embodiments, the polynucleotide that encodes GAD comprises or consists of the polynucleotide sequence depicted in SEQ ID NO:14 or a polynucleotide having at least about 30, 35, 40, 45, 50, 55, 60, 65, 70, 75, 80, 85, 90, 95, 98, or 99% identity to SEQ ID NO:14. In some embodiments, the polynucleotide sequence is codon optimized for expression in the microorganism.

In one embodiment, a non-naturally occurring *Methylobacterium* microorganism is provided that includes one or more exogenous polynucleotide(s) encoding CGL/CD, cysteate synthase (e.g., MA_3297), and CSAD. In another embodiment, a non-naturally occurring *Methylobacterium* microorganism is provided that includes one or more exogenous polynucleotide(s) encoding CGL/CD, cysteate synthase (e.g., MA_3297), and GAD.

In one embodiment, a non-naturally occurring *Escherichia* microorganism is provided that includes one or more exogenous polynucleotide(s) encoding CGL/CD and cysteate synthase (e.g., MA_3297). In one embodiment, a non-naturally occurring *Escherichia* microorganism is provided that includes one or more exogenous polynucleotide(s) encoding CGL/CD, cysteate synthase, and CSAD.

In one embodiment, a non-naturally occurring *Saccharomyces* microorganism is provided that includes one or more exogenous polynucleotide(s) encoding CGL/CD and cysteate synthase (e.g., MA_3297). In one embodiment, a non-naturally occurring *Saccharomyces* microorganism is provided that includes one or more exogenous polynucleotide(s) encoding CGL/CD, cysteate synthase, and CSAD.

In one embodiment, a non-naturally occurring *Bacillus* microorganism is provided that includes one or more exogenous polynucleotide(s) encoding cysteate synthase (e.g., MA_3297) and CSAD.

Conversion of Pyruvate to Taurine

Figure 8:
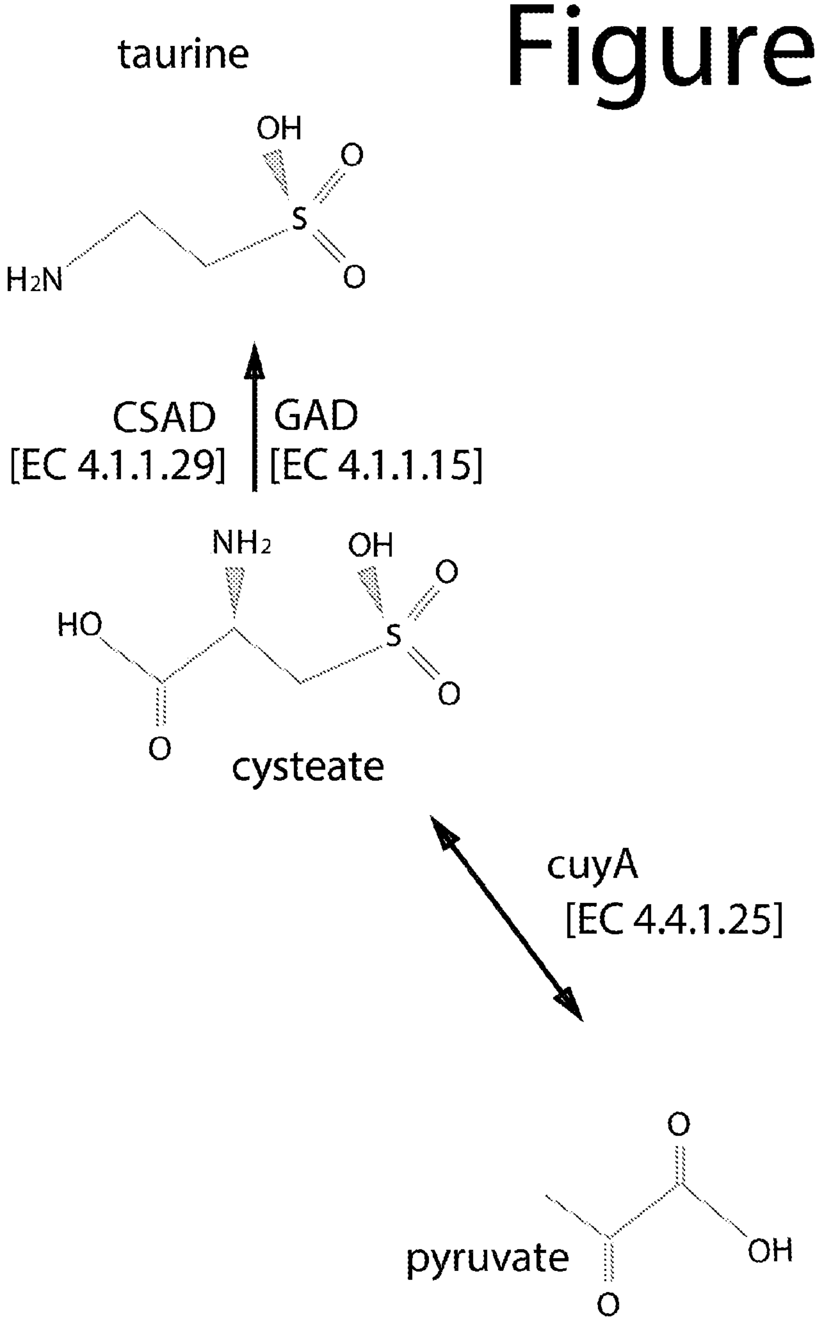
FIG. 8 depicts an embodiment of a biosynthetic pathway for production of taurine from pyruvate.

In some embodiments, a non-naturally occurring microorganism is provided that expresses exogenous enzyme activity/ies for the conversion of pyruvate to taurine via the enzyme L-cysteate sulfo-lyase (cuyA), for example, exogenous enzyme(s) of the L-cysteate sulfo-lyase (cuyA)/CSAD or GAD pathway for biosynthesis of taurine. The cuyA/CSAD or GAD pathway for taurine biosynthesis is shown schematically in FIG. 8.

Non-naturally occurring microorganisms are provided that include the following enzymes or enzyme activities: L-cysteate sulfo-lyase (cuyA) (EC 4.4.1.25); and cysteine sulfuric acid decarboxylase (CSAD) (EC 4.1.1.29), wherein at least one of these enzymes or enzyme activities is encoded by an exogenous polynucleotide with which the microorganism has been transformed. In some embodiments, cuyA and CSAD enzymes or enzyme activities are encoded by one or more exogenous polynucleotide(s) (e.g., one or two exogenous polynucleotide(s)) in the microorganism. In some embodiments, one of cuyA and CSAD enzymes or enzyme activities is encoded by an exogenous polynucleotide in the microorganism and the remaining activity is endogenously expressed in the host cell from which the non-naturally occurring microorganism is derived, i.e., not expressed from an exogenous polynucleotide. In one embodiment, the microorganism expresses an endogenous CSAD activity and cuyA is encoded by an exogenous polynucleotide in the microorganism. In one embodiment, the microorganism expresses an endogenous cuyA activity and CSAD is encoded by an exogenous polynucleotide in the microorganism.

Non-naturally occurring microorganisms are provided that include the following enzymes or enzyme activities: L-cysteate sulfo-lyase (cuyA) (EC 4.4.1.25); and glutamate decarboxylase (GAD) (EC 4.1.1.15), wherein at least one of these enzymes or enzyme activities is encoded by an exogenous polynucleotide with which the microorganism has been transformed. In some embodiments, cuyA and GAD enzymes or enzyme activities are encoded by one or more exogenous polynucleotide(s) (e.g., one or two exogenous polynucleotide(s)) in the microorganism. In some embodiments, one of cuyA and GAD enzymes or enzyme activities is encoded by an exogenous polynucleotide in the microorganism and the remaining activity is endogenously expressed in the host cell from which the non-naturally occurring microorganism is derived, i.e., not expressed from an exogenous polynucleotide. In one embodiment, the microorganism expresses an endogenous GAD activity and cuyA is encoded by an exogenous polynucleotide in the microorganism. In one embodiment, the microorganism expresses an endogenous cuyA activity and GAD is encoded by an exogenous polynucleotide in the microorganism.

In some embodiments, the non-naturally occurring microorganism includes an exogenous polynucleotide that encodes cuyA comprising or consisting of the amino acid sequence depicted in SEQ ID NO:37, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:37. In some embodiments, the polynucleotide that encodes cuyA comprises or consists of the polynucleotide sequence depicted in SEQ ID NO:38 or SEQ ID NO:66 or a polynucleotide having at least about 30, 35, 40, 45, 50, 55, 60, 65, 70, 75, 80, 85, 90, 95, 98, or 99% identity to SEQ ID NO:38 or SEQ ID NO:66. In some embodiments, the polynucleotide sequence is codon optimized for expression in the microorganism, e.g., SEQ ID NO:66.

In some embodiments, the non-naturally occurring microorganism includes an exogenous polynucleotide that encodes CSAD comprising or consisting of the amino acid sequence depicted in SEQ ID NO:11, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:11. In some embodiments, the polynucleotide that encodes CSAD comprises or consists of the polynucleotide sequence depicted in SEQ ID NO:12, SEQ ID NO:53, or SEQ ID NO:54 or a polynucleotide having at least about 30, 35, 40, 45, 50, 55, 60, 65, 70, 75, 80, 85, 90, 95, 98, or 99% identity to SEQ ID NO:12, SEQ ID NO:53, or SEQ ID NO:54. In some embodiments, the polynucleotide sequence is codon optimized for expression in the microorganism, e.g., SEQ ID NO:53 or SEQ ID NO:54.

In some embodiments, the non-naturally occurring microorganism includes an exogenous polynucleotide that encodes GAD comprising or consisting of the amino acid sequence depicted in SEQ ID NO:13, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:13. In some embodiments, the polynucleotide that encodes GAD comprises or consists of the polynucleotide sequence depicted in SEQ ID NO:14 or a polynucleotide having at least about 30, 35, 40, 45, 50, 55, 60, 65, 70, 75, 80, 85, 90, 95, 98, or 99% identity to SEQ ID NO:14. In some embodiments, the polynucleotide sequence is codon optimized for expression in the microorganism.

In one embodiment, a non-naturally occurring *Methylobacterium* microorganism is provided that includes one or more exogenous polynucleotide(s) encoding cuyA and CSAD. In another embodiment, a non-naturally occurring *Methylobacterium* microorganism is provided that includes one or more exogenous polynucleotide(s) encoding cuyA and GAD.

In one embodiment, a non-naturally occurring *Escherichia* microorganism is provided that includes an exogenous polynucleotide encoding cuyA. In one embodiment, a non-naturally occurring *Escherichia* microorganism is provided that includes one or more exogenous polynucleotide(s) encoding cuyA and CSAD.

In one embodiment, a non-naturally occurring *Saccharomyces* microorganism is provided that includes an exogenous polynucleotide encoding cuyA. In one embodiment, a non-naturally occurring *Saccharomyces* microorganism is provided that includes one or more exogenous polynucleotide(s) encoding cuyA and CSAD.

In one embodiment, a non-naturally occurring *Bacillus* microorganism is provided that includes an exogenous polynucleotide encoding cuyA. In one embodiment, a non-naturally occurring *Bacillus* microorganism is provided that includes one or more exogenous polynucleotide(s) encoding cuyA and CSAD.

Conversion of Phosphoenolpyruvate to Taurine Via CSAD or GAD

Figure 9:
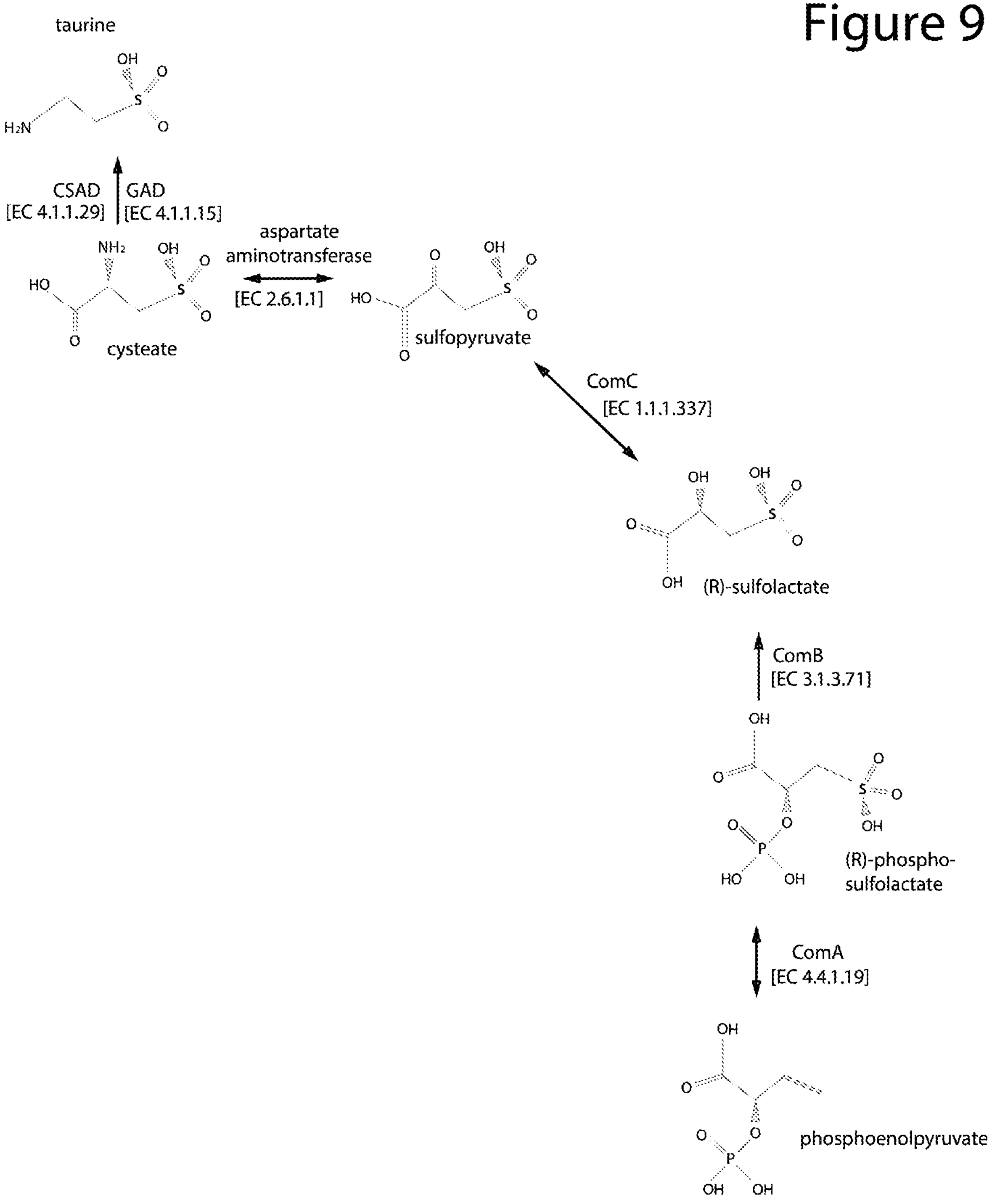
FIG. 9 depicts an embodiment of a biosynthetic pathway for production of taurine from phosphoenolpyruvate.

In some embodiments, a non-naturally occurring microorganism is provided that expresses one or more exogenous enzyme activity/ies for the conversion of phosphoenolpyruvate to taurine via the enzymes phosphosulfolactate synthase (ComA), 2-phospho-e-sulfolactate dehydrogenase (ComB), sulfolactate dehydrogenase (ComC), and aspartate aminotransferase (AspAT), for example, one or more exogenous enzyme(s) of the ComA/ComB/ComC/AspAT/CSAD or GAD pathway for biosynthesis of taurine. The ComA/ComB/ComC/AspAT/CSAD or GAD pathway for taurine biosynthesis is shown schematically in FIG. 9.

Non-naturally occurring microorganisms are provided that include the following enzymes or enzyme activities: phosphosulfolactate synthase (ComA) (EC 4.4.1.19), 2-phospho-3-sulfolactate phosphohydrolase (ComB) (EC 3.1.3.71), sulfolactate dehydrogenase (ComC) (EC 1.1.1.337), aspartate aminotransferase (AspAT) (EC 2.6.1.1), and cysteine sulfinic acid decarboxylase (CSAD) (EC 4.1.1.29), wherein at least one of these enzymes or enzyme activities is encoded by an exogenous polynucleotide with which the microorganism has been transformed. In some embodiments, ComA, ComB, ComC, AspAT, and CSAD enzymes or enzyme activities are encoded by one or more exogenous polynucleotide(s) (e.g., one, two, three, four, or five exogenous polynucleotide(s)) in the microorganism. In some embodiments, one or more of ComA, ComB, ComC, AspAT, and CSAD enzymes or enzyme activities is encoded by one or more exogenous polynucleotide(s) in the microorganism and the remaining activity/ies is/are endogenously expressed in the host cell from which the non-naturally occurring microorganism is derived, i.e., not expressed from exogenous polynucleotide(s). In one embodiment, the microorganism expresses endogenous CSAD and AspAT activities, and ComA, ComB, and ComC are encoded by exogenous polynucleotide(s) in the microorganism. In one embodiment, the microorganism expresses endogenous AspAT activity, and ComA, ComB, ComC, and CSAD are encoded by exogenous polynucleotide(s) in the microorganism.

Non-naturally occurring microorganisms are provided that include the following enzymes or enzyme activities: phosphosulfolactate synthase (ComA) (EC 4.4.1.19), 2-phospho-3-sulfolactate phosphohydrolase (ComB) (EC 3.1.3.71), sulfolactate dehydrogenase (ComC) (EC 1.1.1.337), aspartate aminotransferase (AspAT) (EC 2.6.1.1), and glutamate decarboxylase (GAD) (EC 4.1.1.15), wherein at least one of these enzymes or enzyme activities is encoded by an exogenous polynucleotide with which the microorganism has been transformed. In some embodiments, ComA, ComB, ComC, AspAT, and GAD enzymes or enzyme activities are encoded by one or more exogenous polynucleotide(s) (e.g., one, two, three, four, or five exogenous polynucleotide(s)) in the microorganism. In some embodiments, one or more of ComA, ComB, ComC, AspAT, and GAD enzymes or enzyme activities is encoded by one or more exogenous polynucleotide(s) in the microorganism and the remaining activity/ies is/are endogenously expressed in the host cell from which the non-naturally occurring microorganism is derived, i.e., not expressed from exogenous polynucleotide(s). In one embodiment, the microorganism expresses endogenous GAD and AsPAT activities, and ComA, ComB, and ComC are encoded by exogenous polynucleotide(s) in the microorganism. In one embodiment, the microorganism expresses endogenous AsPAT activity, and ComA, ComB, ComC, and GAD are encoded by exogenous polynucleotide(s) in the microorganism.

In some embodiments, the non-naturally occurring microorganism includes an exogenous polynucleotide that encodes ComA comprising or consisting of the amino acid sequence depicted in SEQ ID NO:19, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:19. In some embodiments, the polynucleotide that encodes ComA comprises or consists of the polynucleotide sequence depicted in SEQ ID NO:20 or SEQ ID NO:67 or a polynucleotide having at least about 30, 35, 40, 45, 50, 55, 60, 65, 70, 75, 80, 85, 90, 95, 98, or 99% identity to SEQ ID NO:20 or SEQ ID NO:67. In some embodiments, the polynucleotide sequence is codon optimized for expression in the microorganism, e.g., SEQ ID NO:67.

In some embodiments, the non-naturally occurring microorganism includes an exogenous polynucleotide that encodes ComB comprising or consisting of the amino acid sequence depicted in SEQ ID NO:21, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:21. In some embodiments, the polynucleotide that encodes ComB comprises or consists of the polynucleotide sequence depicted in SEQ ID NO:22 or SEQ ID NO:68 or a polynucleotide having at least about 30, 35, 40, 45, 50, 55, 60, 65, 70, 75, 80, 85, 90, 95, 98, or 99% identity to SEQ ID NO:22 or SEQ ID NO:68. In some embodiments, the polynucleotide sequence is codon optimized for expression in the microorganism, e.g., SEQ ID NO:68.

In some embodiments, the non-naturally occurring microorganism includes an exogenous polynucleotide that encodes ComC comprising or consisting of the amino acid sequence depicted in SEQ ID NO:23, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:23. In some embodiments, the polynucleotide that encodes ComC comprises or consists of the polynucleotide sequence depicted in SEQ ID NO:24 or SEQ ID NO:69 or a polynucleotide having at least about 30, 35, 40, 45, 50, 55, 60, 65, 70, 75, 80, 85, 90, 95, 98, or 99% identity to SEQ ID NO:24 or SEQ ID NO:69. In some embodiments, the polynucleotide sequence is codon optimized for expression in the microorganism, e.g. SEQ ID NO:69.

In some embodiments, the non-naturally occurring microorganism includes an exogenous polynucleotide that encodes CSAD comprising or consisting of the amino acid sequence depicted in SEQ ID NO:11, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:11. In some embodiments, the polynucleotide that encodes CSAD comprises or consists of the polynucleotide sequence depicted in SEQ ID NO:12, SEQ ID NO:53, or SEQ ID NO:54 or a polynucleotide having at least about 30, 35, 40, 45, 50, 55, 60, 65, 70, 75, 80, 85, 90, 95, 98, or 99% identity to SEQ ID NO:12, SEQ ID NO:53, or SEQ ID NO:54. In some embodiments, the polynucleotide sequence is codon optimized for expression in the microorganism, e.g., SEQ ID NO:53 or SEQ ID NO:54.

In some embodiments, the non-naturally occurring microorganism includes an exogenous polynucleotide that encodes GAD comprising or consisting of the amino acid sequence depicted in SEQ ID NO:13, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:13. In some embodiments, the polynucleotide that encodes GAD comprises or consists of the polynucleotide sequence depicted in SEQ ID NO:14 or a polynucleotide having at least about 30, 35, 40, 45, 50, 55, 60, 65, 70, 75, 80, 85, 90, 95, 98, or 99% identity to SEQ ID NO:14. In some embodiments, the polynucleotide sequence is codon optimized for expression in the microorganism.

In one embodiment, a non-naturally occurring *Methylobacterium* microorganism is provided that includes one or more exogenous polynucleotide(s) encoding ComA, ComB, ComC, and CSAD. In another embodiment, a non-naturally occurring *Methylobacterium* microorganism is provided that includes one or more exogenous polynucleotide(s) encoding ComA, ComB, ComC, and GAD.

In one embodiment, a non-naturally occurring *Escherichia* microorganism is provided that includes one or more exogenous polynucleotide(s) encoding ComA, ComB, and ComC. In one embodiment, a non-naturally occurring *Escherichia* microorganism is provided that includes one or more exogenous polynucleotide(s) encoding ComA, ComB, ComC, and CSAD.

In one embodiment, a non-naturally occurring *Saccharomyces* microorganism is provided that includes one or more exogenous polynucleotide(s) encoding ComA, ComB, and ComC. In one embodiment, a non-naturally occurring *Saccharomyces* microorganism is provided that includes one or more exogenous polynucleotide(s) encoding ComA, ComB, ComC, and CSAD.

In one embodiment, a non-naturally occurring *Bacillus* microorganism is provided that includes one or more exogenous polynucleotide(s) encoding ComA, ComB, and ComC. In one embodiment, a non-naturally occurring *Bacillus* microorganism is provided that includes one or more exogenous polynucleotide(s) encoding ComA, ComB, ComC, and CSAD.

Conversion of Acetyl Phosphate to Taurine

Figure 10:
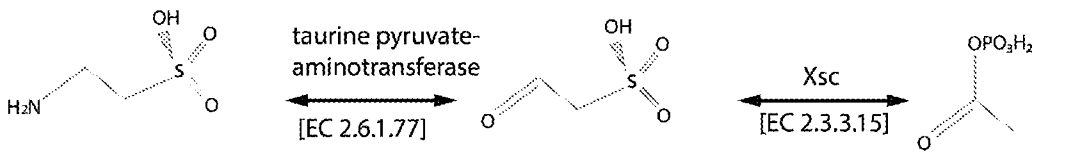
FIG. 10 depicts an embodiment of a biosynthetic pathway for production of taurine from acetyl phosphate.

In some embodiments, a non-naturally occurring microorganism is provided that expresses one or more exogenous enzyme activity/ies for the conversion of acetyl phosphate to taurine, for example, enzymes of the Xsc/Tpa pathway for biosynthesis of taurine. The Xsc/Tpa pathway of taurine biosynthesis is shown schematically in FIG. 10.

Non-naturally occurring microorganisms are provided that include the following enzymes or enzyme activities: sulfoacetaldehyde acetyltransferase (Xsc) (EC 2.3.3.15); and taurine-pyruvate aminotransferase (Tpa) (EC 2.6.1.77), wherein at least one of these enzymes or enzyme activities is encoded by an exogenous polynucleotide with which the microorganism has been transformed. In some embodiments, Xsc and Tpa enzymes or enzyme activities are encoded by one or more exogenous polynucleotides in the microorganism (e.g., one or two exogenous polynucleotide(s). In some embodiments, one of Xsc and Tpa enzymes or enzyme activities is encoded an exogenous polynucleotide in the microorganism and the remaining activity is endogenously expressed in the host cell from which the non-naturally occurring microorganism is derived, i.e., not expressed from an exogenous polynucleotide.

In some embodiments, the non-naturally occurring microorganism includes an exogenous polynucleotide that encodes Xsc comprising or consisting of the amino acid sequence depicted in SEQ ID NO:48, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:48. In some embodiments, the polynucleotide that encodes Xsc comprises or consists of the polynucleotide sequence depicted in SEQ ID NO:49 or a polynucleotide having at least about 30, 35, 40, 45, 50, 55, 60, 65, 70, 75, 80, 85, 90, 95, 98, or 99% identity to SEQ ID NO:49. In some embodiments, the polynucleotide sequence is codon optimized for expression in the microorganism.

In some embodiments, the non-naturally occurring microorganism includes an exogenous polynucleotide that encodes Tpa comprising or consisting of the amino acid sequence depicted in SEQ ID NO:27, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:27. In some embodiments, the polynucleotide that encodes Tpa comprises or consists of the polynucleotide sequence depicted in SEQ ID NO:28 or SEQ ID NO:56 or a polynucleotide having at least about 30, 35, 40, 45, 50, 55, 60, 65, 70, 75, 80, 85, 90, 95, 98, or 99% identity to SEQ ID NO:28 or SEQ ID NO:56. In some embodiments, the polynucleotide sequence is codon optimized for expression in the microorganism, e.g., SEQ ID NO:56.

In one embodiment, a non-naturally occurring *Methylobacterium* microorganism is provided that includes one or more exogenous polynucleotide(s) encoding Xsc and Tpa.

In one embodiment, a non-naturally occurring *Escherichia* microorganism is provided that includes an exogenous polynucleotide encoding Xsc and Tpa.

In one embodiment, a non-naturally occurring *Saccharomyces* microorganism is provided that includes an exogenous polynucleotide encoding Xsc and Tpa.

In one embodiment, a non-naturally occurring *Bacillus* microorganism is provided that includes an exogenous polynucleotide encoding Xsc and Tpa.

Conversion of Phosphoenolpyruvate to Taurine Via Tpa

Figure 11:
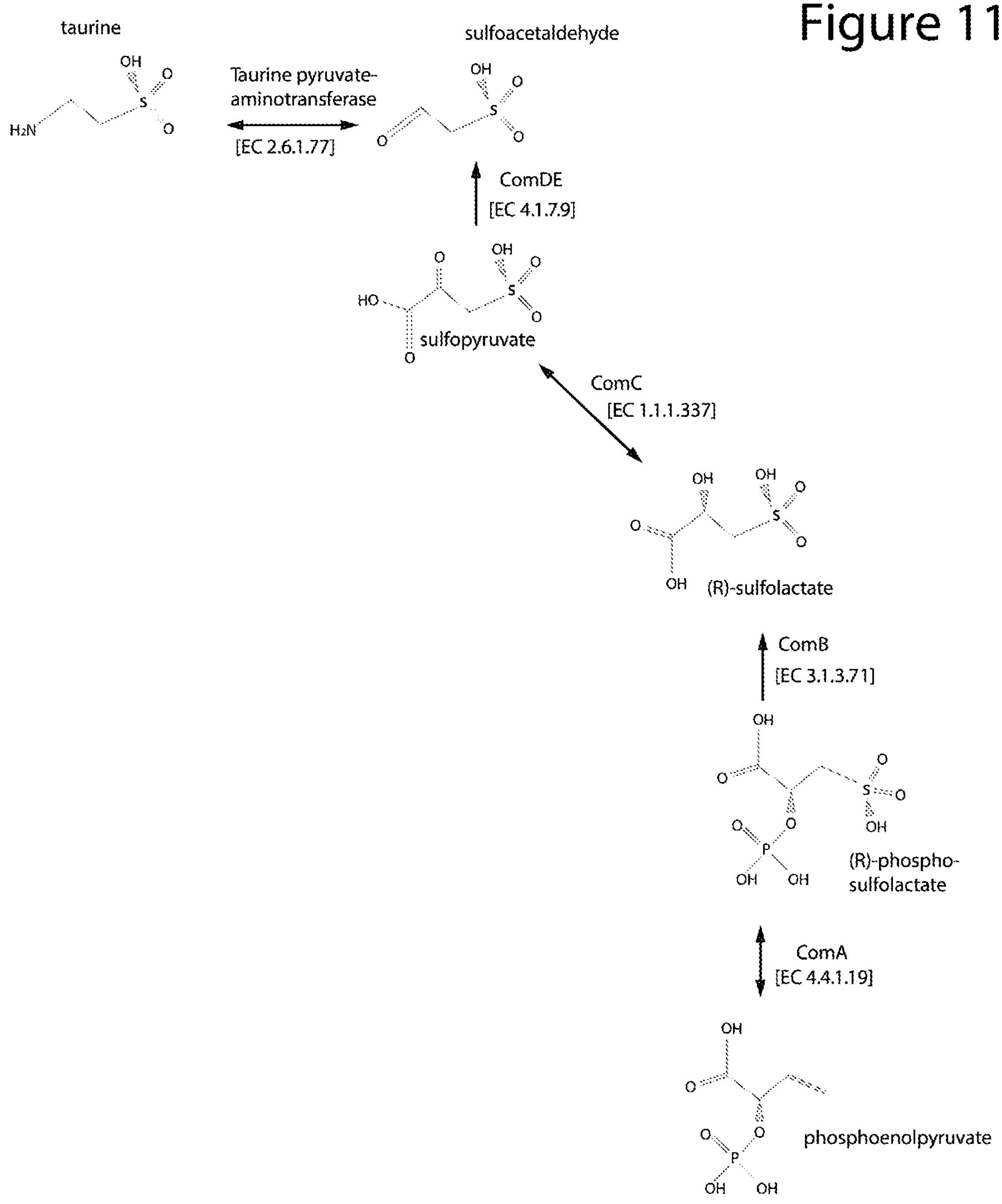
FIG. 11 depicts an embodiment of a biosynthetic pathway for production of taurine from phosphoenolpyruvate.

In some embodiments, a non-naturally occurring microorganism is provided that expresses one or more exogenous enzyme activity/ies for the conversion of phosphoenolpyruvate to taurine via the enzymes phosphosulfolactate synthase (ComA), 2-phospho-e-sulfolactate dehydrogenase (ComB), sulfolactate dehydrogenase (ComC), sulfopyruvate decarboxylase (ComDE), and taurine-pyruvate aminotransferase (Tpa), for example, one or more exogenous enzyme(s) of the ComA/ComB/ComC, ComDE/Tpa pathway for biosynthesis of taurine. This pathway for taurine biosynthesis is shown schematically in FIG. 11.

Non-naturally occurring microorganisms are provided that include the following enzymes or enzyme activities: phosphosulfolactate synthase (ComA) (EC 4.4.1.19), 2-phospho-3-sulfolactate phosphohydrolase (ComB) (EC 3.1.3.71), sulfolactate dehydrogenase (ComC) (EC 1.1.1.337), sulfopyruvate decarboxylase (ComDE) (EC 4.1.7.9), and taurine-pyruvate aminotransferase (Tpa) (EC 2.6.1.77), wherein at least one of these enzymes or enzyme activities is encoded by an exogenous polynucleotide with which the microorganism has been transformed. In some embodiments, ComA, ComB, ComC, ComDE, and Tpa enzymes or enzyme activities are encoded by one or more exogenous polynucleotide(s) (e.g., one, two, three, four, or five exogenous polynucleotide(s)) in the microorganism. In some embodiments, one or more of ComA, ComB, ComC, ComDE, and Tpa enzymes or enzyme activities is encoded by one or more exogenous polynucleotide(s) in the microorganism and the remaining activity/ies is/are endogenously expressed in the host cell from which the non-naturally occurring microorganism is derived, i.e., not expressed from exogenous polynucleotide(s).

In some embodiments, the non-naturally occurring microorganism includes an exogenous polynucleotide that encodes ComA comprising or consisting of the amino acid sequence depicted in SEQ ID NO:19, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:19. In some embodiments, the polynucleotide that encodes ComA comprises or consists of the polynucleotide sequence depicted in SEQ ID NO:20 or SEQ ID NO:67 or a polynucleotide having at least about 30, 35, 40, 45, 50, 55, 60, 65, 70, 75, 80, 85, 90, 95, 98, or 99% identity to SEQ ID NO:20 or SEQ ID NO:67. In some embodiments, the polynucleotide sequence is codon optimized for expression in the microorganism, e.g., SEQ ID NO:67.

In some embodiments, the non-naturally occurring microorganism includes an exogenous polynucleotide that encodes ComB comprising or consisting of the amino acid sequence depicted in SEQ ID NO:21, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:21. In some embodiments, the polynucleotide that encodes ComB comprises or consists of the polynucleotide sequence depicted in SEQ ID NO:22 or SEQ ID NO:68 or a polynucleotide having at least about 30, 35, 40, 45, 50, 55, 60, 65, 70, 75, 80, 85, 90, 95, 98, or 99% identity to SEQ ID NO:22 or SEQ ID NO:68. In some embodiments, the polynucleotide sequence is codon optimized for expression in the microorganism, e.g., SEQ ID NO:68.

In some embodiments, the non-naturally occurring microorganism includes an exogenous polynucleotide that encodes ComC comprising or consisting of the amino acid sequence depicted in SEQ ID NO:23, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:23. In some embodiments, the polynucleotide that encodes ComC comprises or consists of the polynucleotide sequence depicted in SEQ ID NO:24 or SEQ ID NO:69 or a polynucleotide having at least about 30, 35, 40, 45, 50, 55, 60, 65, 70, 75, 80, 85, 90, 95, 98, or 99% identity to SEQ ID NO:24 or SEQ ID NO:69. In some embodiments, the polynucleotide sequence is codon optimized for expression in the microorganism, e.g., SEQ ID NO:69.

In some embodiments, the non-naturally occurring microorganism includes an exogenous polynucleotide that encodes ComDE comprising or consisting of the amino acid sequence depicted in SEQ ID NO:25, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:25. In some embodiments, the polynucleotide that encodes ComDE comprises or consists of the polynucleotide sequence depicted in SEQ ID NO:26 or SEQ ID NO:55 or a polynucleotide having at least about 30, 35, 40, 45, 50, 55, 60, 65, 70, 75, 80, 85, 90, 95, 98, or 99% identity to SEQ ID NO:26 or SEQ ID NO:55. In some embodiments, the polynucleotide sequence is codon optimized for expression in the microorganism, e.g., SEQ ID NO:55.

In some embodiments, the non-naturally occurring microorganism includes an exogenous polynucleotide that encodes Tpa comprising or consisting of the amino acid sequence depicted in SEQ ID NO:27, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:27. In some embodiments, the polynucleotide that encodes Tpa comprises or consists of the polynucleotide sequence depicted in SEQ ID NO:28 or SEQ ID NO:56 or a polynucleotide having at least about 30, 35, 40, 45, 50, 55, 60, 65, 70, 75, 80, 85, 90, 95, 98, or 99% identity to SEQ ID NO:28 or SEQ ID NO:56. In some embodiments, the polynucleotide sequence is codon optimized for expression in the microorganism, e.g., SEQ ID NO:56.

In one embodiment, a non-naturally occurring *Methylobacterium* microorganism is provided that includes one or more exogenous polynucleotide(s) encoding ComA, ComB, ComC, and ComDE, and Tpa.

In one embodiment, a non-naturally occurring *Escherichia* microorganism is provided that includes one or more exogenous polynucleotide(s) encoding ComA, ComB, ComC, ComDE, and Tpa.

In one embodiment, a non-naturally occurring *Saccharomyces* microorganism is provided that includes one or more exogenous polynucleotide(s) encoding ComA, ComB, ComC, ComDE, and Tpa.

In one embodiment, a non-naturally occurring *Bacillus* microorganism is provided that includes one or more exogenous polynucleotide(s) encoding ComA, ComB, ComC, ComDE, and Tpa.

Conversion of Cysteate to Taurine Via AspAT, ComDE, and Tpa

Cysteate, which is an intermediate in some of the biosynthetic pathways described above (see FIGS. 4, 5, 6, 7, and 8) be converted to taurine via aspartate aminotransferase (AspAT) (EC 2.6.1.1), which converts cysteate to sulfopyruvate, sulfopyruvate decarboxylase (ComDE) (EC4.1.7.9), which converts sulfopyruvate to sulfoacetaldehyde, and taurine-pyruvate aminotransferase (Tpa) (EC 2.67.1.77), which converts sulfoacetaldehyde to taurine, instead of or in addition to CSAD or GAD. This is shown schematically in FIG. 12.

Figure 12:
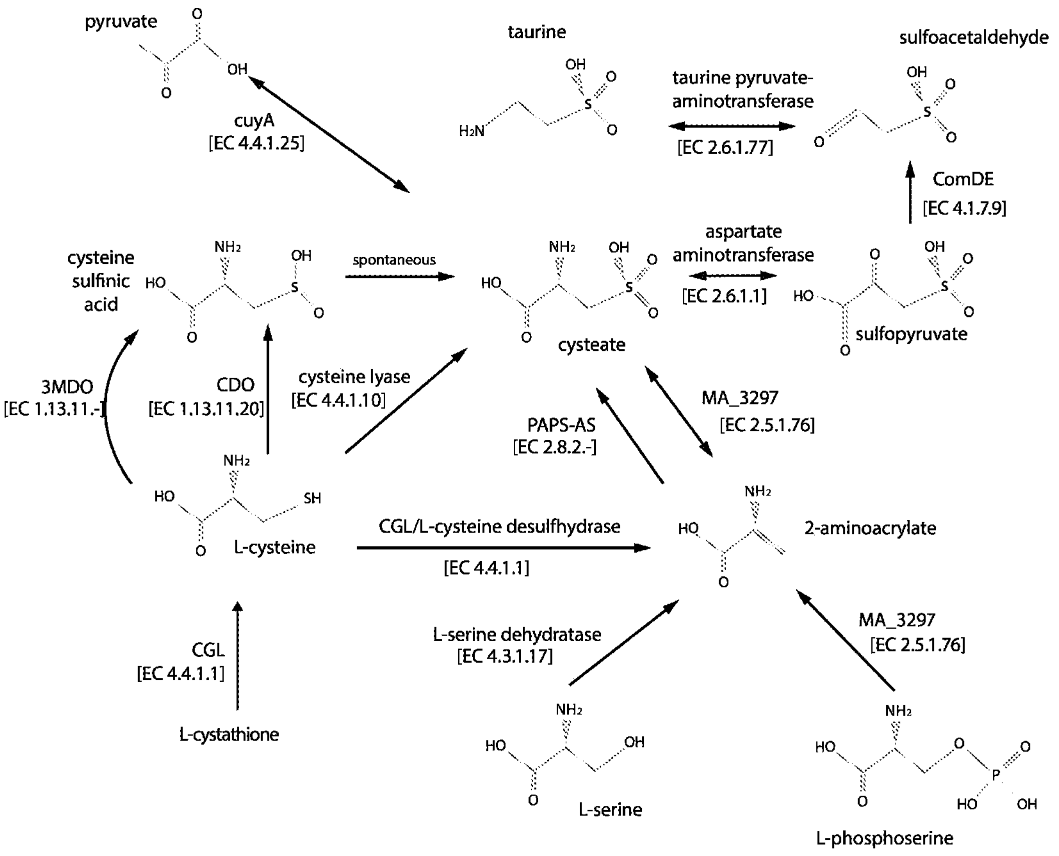
FIG. 12 depicts an embodiment of a biosynthetic pathway for production of taurine through taurine-pyruvate aminotransferase.

Non-naturally occurring microorganisms are provided that include the following enzymes or enzyme activities: aspartate aminotransferase (AspAT) (EC 2.6.1.1); sulfopyruvate decarboxylase (ComDE) (EC4.1.7.9); and taurine-pyruvate aminotransferase (Tpa) (EC 2.67.1.77), wherein at least one of these enzymes or enzyme activities is encoded by an exogenous polynucleotide with which the microorganism has been transformed, and optionally other enzyme activities for production of cysteate, as shown in FIG. 12, either endogenous to the microorganism or encoded by exogenous polynucleotide(s) with which the microorganism has been transformed.

In some embodiments, one or more of AspAT, ComDE, and Tpa enzymes or enzyme activities is encoded by exogenous polynucleotide(s) in the microorganism and the remaining activity/ies is/are endogenously expressed in the host cell from which the non-naturally occurring microorganism is derived, i.e., not expressed from an exogenous polynucleotide. In one embodiment, the microorganism expresses an endogenous AspAT activity and ComDE and Tpa are encoded by exogenous polynucleotide(s) in the microorganism.

In some embodiments, the non-naturally occurring microorganism includes an exogenous polynucleotide that encodes ComDE comprising or consisting of the amino acid sequence depicted in SEQ ID NO:25, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:25. In some embodiments, the polynucleotide that encodes ComDE comprises or consists of the polynucleotide sequence depicted in SEQ ID NO:26 or SEQ ID NO:55 or a polynucleotide having at least about 30, 35, 40, 45, 50, 55, 60, 65, 70, 75, 80, 85, 90, 95, 98, or 99% identity to SEQ ID NO:26 or SEQ ID NO:55. In some embodiments, the polynucleotide sequence is codon optimized for expression in the microorganism, e.g., SEQ ID NO:55.

In some embodiments, the non-naturally occurring microorganism includes an exogenous polynucleotide that encodes Tpa comprising or consisting of the amino acid sequence depicted in SEQ ID NO:27, or a variant or homolog thereof. In some embodiments, the exogenous polynucleotide encodes a polypeptide comprising or consisting of an amino acid sequence having at least about 30, 35, 40, 45, 50, 55, 60, 65, 70, 75, 80, 85, 90, 95, 98, or 99% identity to SEQ ID NO:27. In some embodiments, the polynucleotide that encodes Tpa comprises or consists of the polynucleotide sequence depicted in SEQ ID NO:28 or SEQ ID NO:56 or a polynucleotide having at least about 30, 35, 40, 45, 50, 55, 60, 65, 70, 75, 80, 85, 90, 95, 98, or 99% identity to SEQ ID NO:28 or SEQ ID NO:56. In some embodiments, the polynucleotide sequence is codon optimized for expression in the microorganism, e.g., SEQ ID NO:56.

In one embodiment, a non-naturally occurring *Methylobacterium* microorganism is provided that includes one or more exogenous polynucleotide(s) encoding ComDE and Tpa.

In one embodiment, a non-naturally occurring *Escherichia* microorganism is provided that includes one or more exogenous polynucleotide(s) encoding ComDE and Tpa.

In one embodiment, a non-naturally occurring *Saccharomyces* microorganism is provided that includes one or more exogenous polynucleotide(s) encoding ComDE and Tpa.

In one embodiment, a non-naturally occurring *Bacillus* microorganism is provided that includes one or more exogenous polynucleotide(s) encoding ComDE and Tpa.

Figure 13:
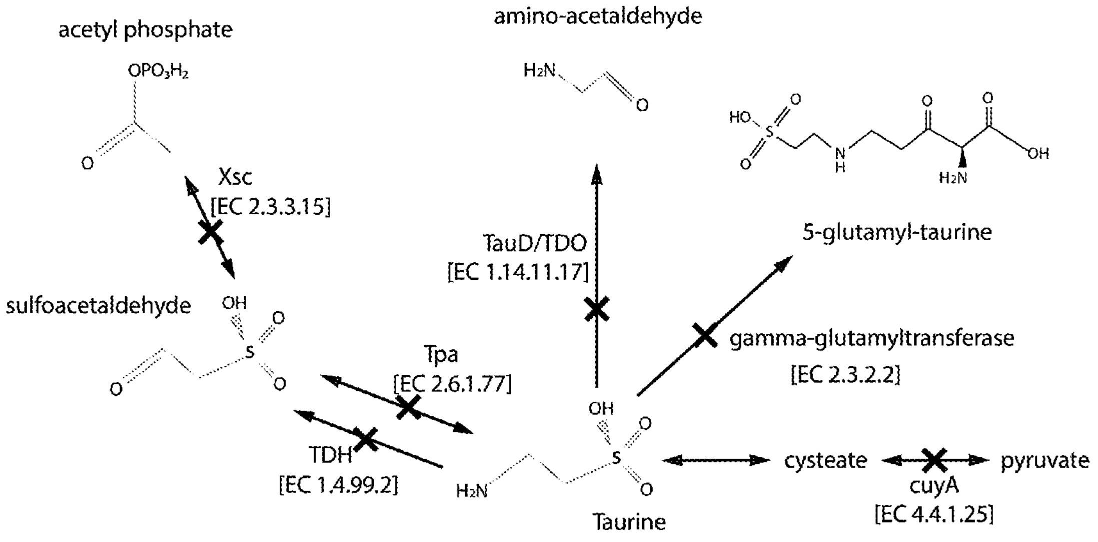
FIG. 13 depicts taurine and cysteate degradation pathways.

Mutations to Enhance Accumulation of Taurine or an Intermediate in Taurine Biosynthesis In some embodiments, a non-naturally occurring microorganism is provided that produces taurine, as described above, and that further includes a mutation in a pathway for degradation of taurine and/or in a pathway for degradation of an intermediate of taurine biosynthesis (e.g., a cysteate degradation pathway). In some embodiments, the microorganism includes deletion of one or more endogenous gene sequence that encodes an enzyme that degrades taurine or an intermediate in taurine biosynthesis (e.g., cysteate or sulfoacetaldehyde), thus enhancing accumulation of taurine in the microorganism. Taurine and cysteate degradation pathways are shown schematically in FIG. 13. Examples of enzymes in taurine degradation pathways include, but are not limited to, taurine dehydrogenase (TDH), taurine dioxygenase (TDO/TauD), gamma-glutamyltransferase, and taurine-pyruvate aminotransferase (Tpa). A non-limiting example of an enzyme in a cysteate degradation pathway is cysteate sulfo-lyase (CuyA). A non-limiting example of an enzyme in a sulfoacetaldehyde degradation pathway is sulfoacetaldehyde acetyltransferase (Xsc).

In some embodiments, the non-naturally occurring microorganism includes one or more mutation(s) or deletion of a gene sequence that encodes taurine dehydrogenase (TDH) (EC 1.4.99.2), thus reducing or eliminating activity of TDH in the microorganism in comparison to the host cell from which the microorganism was derived.

In some embodiments, the non-naturally occurring microorganism includes one or more mutation(s) or deletion of a gene sequence that encodes taurine dioxygenase (TDO)/TauD (EC 1.14.11.17), thus reducing or eliminating activity of TDO/TauD in the microorganism in comparison the host cell from which the microorganism was derived. In one embodiment, an *Escherichia* microorganism is provided with one or more mutation(s) or deletion of a gene sequence that encodes TDO/TauD, thus reducing or eliminating activity of this enzyme in the microorganism. In one embodiment, a *Saccharomyces* microorganism is provided with one or more mutation(s) or deletion of a gene sequence that encodes TDO/TauD, thus reducing or eliminating activity of this enzyme in the microorganism in comparison to the host cell from which the microorganism was derived. In one embodiment, a *Bacillus* microorganism is provided with one or more mutation(s) or deletion of a gene sequence that encodes TDO/TauD, thus reducing or eliminating activity of this enzyme in the microorganism in comparison to the host cell from which the microorganism was derived.

In some embodiments, the non-naturally occurring microorganism includes one or more mutation(s) or deletion of a gene sequence that encodes cysteate sulfo-lyase (CuyA) (EC 4.4.1.25), thus reducing or eliminating activity of CuyA in the microorganism in comparison to the host cell from which the microorganism was derived.

In some embodiments, the non-naturally occurring microorganism includes one or more mutation(s) or deletion of a gene sequence that encodes gamma-glutamyltransferase (EC 2.3.2.2), thus reducing or eliminating activity of gamma-glutamyltransferase in the microorganism in comparison the host cell from which the microorganism was derived. In one embodiment, a *Methylobacterium* microorganism is provided with one or more mutation(s) or deletion of a gene sequence that encodes gamma-glutamyltransferase, thus reducing or eliminating activity of this enzyme in the microorganism. In one embodiment, an *Escherichia* microorganism is provided with one or more mutation(s) or deletion of a gene sequence that encodes gamma-glutamyltransferase, thus reducing or eliminating activity of this enzyme in the microorganism in comparison to the host cell from which the microorganism was derived. In one embodiment, a *Bacillus* microorganism is provided with one or more mutation(s) or deletion of a gene sequence that encodes gamma-glutamyltransferase, thus reducing or eliminating activity of this enzyme in the microorganism in comparison to the host cell from which the microorganism was derived.

In some embodiments, the non-naturally occurring microorganism includes one or more mutations(s) or deletion of a gene sequence that encodes a taurine-pyruvate aminotransferase (Tpa) (EC 2.6.1.77), thus reducing or eliminating activity of taurine-pyruvate aminotransferase in the microorganism in comparison the host cell from which the microorganism was derived.

In some embodiments, the non-naturally occurring microorganism includes one or more mutations(s) or deletion of a gene sequence that encodes a sulfoacetaldehyde acetyltransferase (Xsc) (EC 2.3.3.15), thus reducing or eliminating activity of sulfoacetaldehyde acetyltransferase in the microorganism in comparison the host cell from which the microorganism was derived.

Transformation of Microorganisms

Numerous transformation protocols and constructs for introducing and expressing exogenous polynucleotides in host cells are known in the art.

In certain embodiments, genetic modifications will take advantage of freely replicating plasmid vectors for cloning. These may include small IncP vectors developed for use in *Methylobacterium*. These vectors may include pCM62, pCM66, or pHC41 for cloning. (Marx, C. J. and M. E. Lidstrom *Microbiology* (2001) 147: 2065-2075; Chou, H.-H. et al. *PLoS Genetics* (2009) 5: e1000652)

In certain embodiments, genetic modifications will take advantage of freely replicating expression plasmids such as pCM80, pCM160, pHC90, or pHC91. (Marx, C. J. and M. E. Lidstrom *Microbiology* (2001) 147: 2065-2075; Chou, H.-H. et al. *PLoS Genetics* (2009) 5: e1000652)

In certain embodiments, genetic modifications will utilize freely replicating expression plasmids that have the ability to respond to levels of inducing molecules such as cumate or anhydrotetracycline. These include pHC115, pLC 290, pLC291. (Chou, H.-H. et al. *PLoS Genetics* (2009) 5: e1000652; Chubiz, L. M. et al. *BMC Research Notes* (2013) 6: 183)

In certain embodiments, genetic modifications will utilize recyclable antibiotic marker systems such as the cre-lox system. This may include use of the pCM157, pCM158, pCM184, pCM351 series of plasmids developed for use in *M. extorquens*. (Marx, C. J. and M. E. Lidstrom *BioTechniques* (2002) 33: 1062-1067)

In certain embodiments, genetic modifications will utilize recyclable antibiotic marker systems such as the cre-lox system. This may include use of the pCM157, pCM158, pCM184, pCM351 series of plasmids developed for use in *M. extorquens* (Marx, C. J. and M. E. Lidstrom *BioTechniques* (2002) 33: 1062-1067).

In certain embodiments, genetic modifications will utilize transposon mutagenesis. This may include mini-Tn5 delivery systems such as pCM639 (D'Argenio, D. A. et al. *Journal of Bacteriology* (2001) 183: 1466-1471) demonstrated in *M. extorquens*. (Marx, C. J. et al. *Journal of Bacteriology* (2003) 185: 669-673)

In certain embodiments, genetic modifications will utilize expression systems introduced directly into a chromosomal locus. This may include pCM168, pCM172, and pHC01 plasmids developed for *M. extorquens* AM1. (Marx, C. J. and M. E. Lidstrom *Microbiology* (2001) 147: 2065-2075; Lee, M.-C. et al. *Evolution* (2009) 63: 2813-2830)

In certain embodiments, genetic modifications will utilize a sacB-based system for unmarked exchange of alleles due to the sucrose sensitivity provided by sacB expression. This may include the pCM433 vector originally tested with *M. extorquens*. (Marx, C. J. et al. *BMC Research Notes* (2008) 1: 1)

Microbial Cultures

Methods for producing taurine and/or taurine precursors are provided. The methods include culturing a non-naturally occurring microorganism as described herein in a culture medium under conditions suitable for growth of the microorganism and expression of enzymes for taurine biosynthesis as described herein, wherein biomass that includes taurine and/or taurine precursors is produced in the culture. In embodiments in which the microorganism also produces one or more carotenoid compound(s) (e.g., a microorganism that has been genetically modified or artificially pre-selected to produce elevated levels of one or more carotenoid compound(s)), biomass that includes taurine and/or taurine precursors and the one or more carotenoid compound(s) is produced.

The culture medium includes carbon source(s), nitrogen source(s), inorganic substances (e.g., inorganic salts), and any other substances required for the growth of the microorganism (e.g., vitamins, amino acids, etc.).

The carbon source may include sugars, such as glucose, sucrose, lactose, fructose, trehalose, mannose, mannitol, and maltose; organic acids, such as acetic acid, fumaric acid, citric acid, propionic acid, malic acid, pyruvic acid, malonic acid, and ascorbic acid; alcohols, such as ethanol, propanol, butanol, pentanol, hexanol, isobutanol, and glycerol; oil or fat, such as soybean oil, rice bran oil, olive oil, corn oil, sesame oil, linseed oil, and the like. The amount of the carbon source added varies according to the kind of the carbon source, for example, about 1 to about 100 g, or about 2 to about 50 g per liter of medium.

In some embodiments, a C1 carbon substrate is provided to a microorganism that is capable of converting such a substrate to organic products (e.g., microorganisms of the genera *Methylobacterium, Methylomonas, Methylobacter. Methylococcus, Methylosinus, Methylocyctis, Methylomicrobium*). In certain embodiments, the C1 carbon substrate is selected from methane, methanol, formaldehyde, formic acid, methylated amines, methylated thiols, and carbon dioxide. In certain embodiments, the C1 carbon substrate is selected from methanol, formaldehyde, and methylated amines. In certain embodiments, the C1 carbon substrate is methanol.

The nitrogen source may include potassium nitrate, ammonium nitrate, ammonium chloride, ammonium sulfate, ammonium phosphate, ammonia, urea, and the like, alone or in combination. Amount of the nitrogen source added varies according to the kind of the nitrogen source, for example, about 0.1 to about 30 g, or about 1 to about 10 g per liter of medium.

Inorganic salts may include potassium dihydrogen phosphate, dipotassium hydrogen phosphate, disodium hydrogen phosphate, magnesium sulfate, magnesium chloride, ferric sulfate, ferrous sulfate, ferric chloride, ferrous chloride, manganous sulfate, manganous chloride, zinc sulfate, zinc, chloride, cupric sulfate, calcium chloride, calcium carbonate, sodium carbonate, sodium sulfate, and the like, alone or in combination. Amount of inorganic salt varies according to the kind of the inorganic salt, for example, about 0.001 to about 10 g per liter of medium.

Special required substances, for example, vitamins, nucleic acids, yeast extract, peptone, meat extract, malt extract, corn steep liquor, soybean meal, dried yeast etc., may be included alone or in combination. Amount of the special required substance used varies according to the kind of the substance, for example, about 0.2 g to about 200 g, or about 3 to about 10 g per liter of medium.

Figure 2:
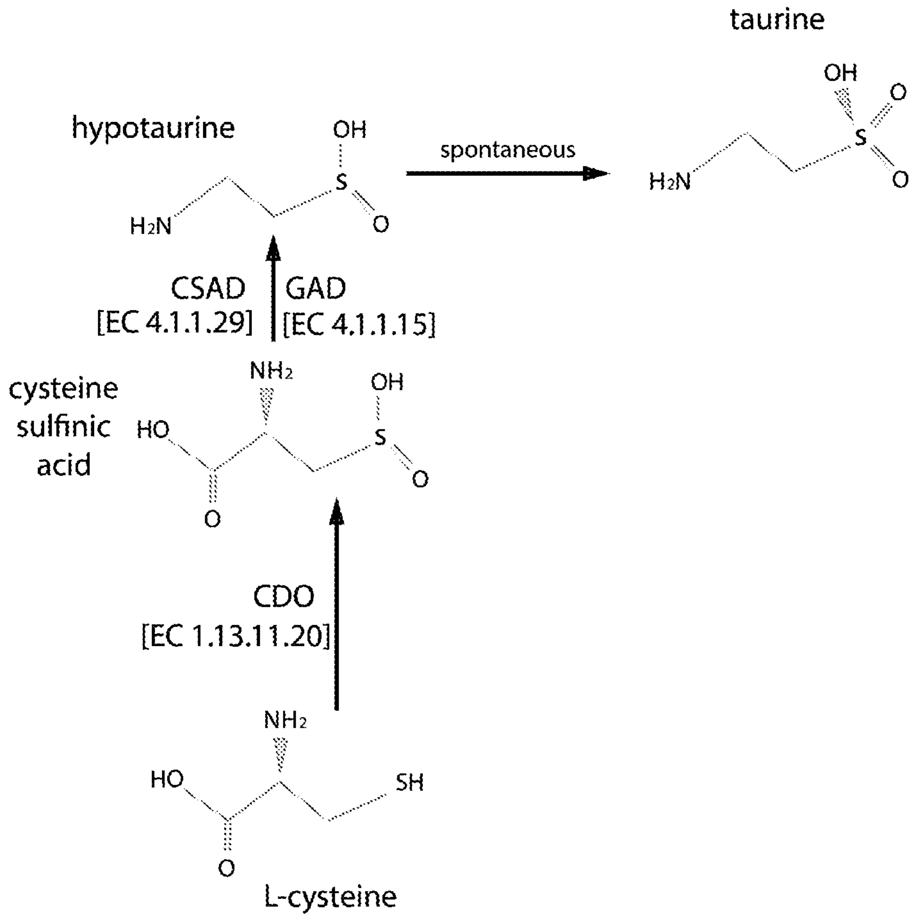
FIG. 2 depicts an embodiment of a biosynthetic pathway for production of taurine from L-cysteine.

In some embodiments, the pH of the culture medium is adjusted to pH about 2 to about 12, or about 6 to about 9. The medium may further include one or more buffer(s) to maintain the culture at the desired pH. Numerous buffers are known in the art and include phosphate, carbonate, acetate, PIPES, HEPES, and Tris buffers. A suitable buffer for a given microorganism can easily be determined by one of ordinary skill in the art. For *Methylobacterium*, a common medium, described by Lee, et al. (2009) *Evolution* 63:2813-2830, is a phosphate buffered medium that consists of 1 mL of trace metal solution (to 1 liter of deionized water the following are added in this order: 12.738 g of EDTA disodium salt dihydrate, 4.4 g of $ZnSO\text{-}7H_2O$, 1.466 g of $CaCI_2\text{-}2H_2O$, 1 0.012 g of $MnCI_2\text{-}4H_2O$, 0.22 g of $(NH_4)_6Mo_7O_{24}\text{-}4H_2O$, 0.314 g of $CuSO_4\text{-}5H_2O$, 0.322 g of $CoCl_2\text{-}6H_2O$, and 0.998 g of $Fe_3(SO_4)_2\text{-}7H_2O$; pH 5.0 is maintained after every addition), 100 mL of phosphate buffer (25.3 g of $K_2HPO_4$ and 22.5 g of $NaH_2PO_4$ in 1 liter of deionized water), 100 mL of sulfate solution (5 g of $(NH_4)_2(SO_4)$ and 0.98 g of $Mg(SO_4)_2$ in 1 liter of deionized water), and 799 mL of deionized water. All components are heat sterilized separately and then pooled together. An alternative medium recently developed for use with *Methylobacterium extorquens* takes advantage of an organic buffer and has a citrate-chelated trace metal mix. Culturing is carried out at temperature of 15° to 40° C., and preferably 20° to 35° C., usually for 1 to 20 days, and preferably 1 to 4 days, under aerobic conditions provided by shaking or aeration/agitation. Common practice with *Methylobacterium* is at 30° C. The protocol for making M-PIPES medium is described in Table Si of Delaney et al. (2013) PLoS One (8:e62957). FIG. 2 in U.S. Ser. No. 61/863,701 shows an exemplary recipe for medium optimized for use with *M. extorquens*.

In order to generate dense cultures of microorganisms, such as *Methylobacterium*, it may be advantageous to use a fed-batch method. Methanol can be tolerated well at 0.5-1% v/v (~120-240 mM), and thus this step size of addition can be used repeatedly. Critically, pH levels drop during culturing on methanol, such that the use of a base such as KOH or NaOH would be important to maintain the pH around 6.5. Aeration can be achieved via physical agitation, such as an impeller, via bubbling of filtered air or pure oxygen, or in combination. In order to reduce production costs, the buffer can be replaced from phosphates or PIPES to a carbonate-buffered medium.

Microbial cells may be separated from the culture, for example, by a conventional means such as centrifugation or filtration. The cells may be isolated whole, or may be lysed to release their contents for extraction or further processing. The cells or the medium may be subjected to an extraction with a suitable solvent.

Intracellular Taurine as a Molecular Chaperone and Antioxidant.

Microbial cells engineered to produce high levels of taurine or hypotaurine have increased levels of an important osmolyte known to promote protein folding and decrease oxidation (Warskulat et al. (2007) *Methods Enzymol* 428: 439-58; Abe et al. (2015) *Amino acids* 47(5):909-15; Fujii et al. (2007) *J Biochem* 141(5):697-707); Oliveira et al. (2010) Pharmacological Reports 62:185-193; Aruoma et al. (1988) *Biochem J* 256:251-55; Bucolo et al. (2016) *Acta Ophthalmologic* 95(256); Patel et al. (2016) *Exp Toxic Pathol* 68(2-3):103-12; Fontana et al. (2004) *Neurochemical Research* 29(1):111-116). When microbial cells are used to express a protein of interest, intracellular taurine or hypotaurine could aid in increasing protein folding or decreasing protein inactivation through oxidation. Thus the use of microorganisms engineered to accumulate intracellular taurine or hypotaurine could be used to increase the yield and/or specific activity of proteins of interest.

Production of intracellular taurine and/or hypotaurine to aid in protein folding has potential benefits, both for cost and effectiveness. In vivo production of taurine or hypotaurine should be less expensive than when taurine or hypotaurine are added externally. Intracellular protein production may also be more effective if it simultaneously allows for higher levels of taurine or hypotaurine. Transport from the cellular medium into cells generally requires a higher concentration of these substrates in the medium and/or requires cellular energy for active transport.

Compositions Containing Taurine and Taurine Precursors

Feed compositions are provided for use in aquaculture, or as animal feed, or as human nutritional supplements containing processed or unprocessed biomass from non-naturally occurring microorganism cells as described herein, as are methods of preparation of the feed compositions.

The feed compositions or nutritional supplements include taurine and/or one or more taurine precursor(s), e.g., cysteate, sulfoacetaldehyde, and/or hypotaurine, produced by the non-naturally occurring microorganism. In some embodiments, taurine and/or taurine precursor(s) produced by the microorganism is encapsulated in the microorganism in the feed composition or supplement, e.g., encapsulated in the lipid bilayer of the cell membrane of the microorganism. In some embodiments, taurine and/or taurine precursor(s) produced by the microbial biocatalyst is/are excreted into the culture medium and further purified, for example, using chromatographic or other separation and purification procedures. In some embodiments, taurine and/or taurine precursor(s) is/are chemically extracted from the producing microorganism.

Taurine and/or taurine precursor(s) can be accumulated and encapsulated by the microorganism or can be exported outside the cell. Conditions required for export may be continuous during microbial growth or can be stimulated by limitation of nutrients, e.g., biotin, or by the presence of an inhibitor of microbial growth, such as an antibiotic or surfactant.

In some embodiments, methods for separating and purifying taurine and/or taurine precursors from a culture containing microbial cells and microbially produced taurine may deploy ion exchange, e.g., ion exchange resins. In some embodiments, microbial cells may be separated by centrifugation, condensed, or filtered, and taurine and/or taurine precursors concentrated to, for example, at least about 80% purity.

In certain embodiments, biomass that is incorporated into a feed or nutritional supplement composition can be in a dry, or substantially dry, form, e.g., containing less than about 20%, 10%, 5%, or 2% of moisture. In certain embodiments, the cultures are isolated by removing substantially all supernatant, such as by filtering, sedimentation, or centrifugation. In certain embodiments, the collection of cultures and further processing of biomass excludes a bacterial lysis step, e.g., by use of detergents or ultrasound. In certain embodiments, the processed microbial cells maintain substantially whole cell membranes. In some embodiments, a substantial portion (e.g., more than about 5%, 10%, 20%, 30%, 50%, or 80%) of bacterial cells may maintain viability in the processed biomass.

The feed composition may contain at least about 1% of the biomass by weight. In certain embodiments, the feed composition is optimized for consumption by fish, seafood, humans, or other animals. For example, the feed may include one or more of EPA, DHA, and one or more essential amino acids.

Methods for preparing a feed composition are also provided. In some embodiments, the method includes: (a) culturing in an appropriate medium at least one non-naturally occurring microorganism as described above; (b) concentrating the medium to provide a biomass; (c) optionally providing additional feed components; and (d) producing the feed composition from the biomass. In certain embodiments, step (b) includes centrifugation. In certain embodiments, step (b) includes allowing the biomass to settle. In certain embodiments, step (b) includes filtration. In certain embodiments, the method further includes a pre-treatment of the biomass after step (a) with a chemical agent (e.g., a surfactant or solvent) to disrupt the cell membranes of the biomass. In certain embodiments, the method further includes mechanical disruption of the cell membranes of the biomass after step (a).

Examples of feedstuffs into which single cell protein enriched with taurine and/or taurine precursors, produced as described herein, may be incorporated include, for example, pet foods, such as cat foods, dog foods and the like, feeds for aquarium fish, cultured fish or crustaceans, etc., feed for farm-raised animals (including livestock and further including fish or crustaceans raised in aquaculture). The state of the biomass can be in whole cell, lysed or partially processed. The taurine and/or taurine precursors and/or other caloric or nutritional supplements produced in described herein can also be incorporated into food or vitamin supplements for human consumption. Food or feed material into which taurine and/or taurine precursors produced as described herein is incorporated is preferably palatable to the organism that is the intended recipient. This food or feed material may have any physical properties currently known for a food material (e.g., solid, liquid, soft). In some embodiments, feed produced as described herein will undergo a pelletization process, e.g., through a hot or cold extrusion process at an inclusion rate of less than about 1%, 5%, 10%, 20%, 25%, 30%, 40%, 50%, 60%, or 75%. In other scenarios, the taurine and/or taurine precursors-enriched protein can be consumed directly at 100% or combined with another substance in the form of liquid, baked goods or other to form, including but not limited to, various types of tablets, capsules, drinkable agents, gargles, etc.

Methods of producing fish or seafood are also provided, including farming fish or seafood, and providing a diet, which includes a feed composition as described herein, to the fish or seafood.

The following examples are intended to illustrate, but not limit the invention.

EXAMPLES

Example 1

Methods:

Expression plasmids were constructed utilizing standard molecular cloning techniques and codon optimized, synthetically-derived DNA (see Table 1). These plasmids were transformed into *Methylobacterium extorquens* or *Escherichia coli* BL21 (DE3).

*M. extorquens* strains were grown in a minimal media based on Choi et al (1989) *Appl Microbiol Bioeng* 17:392-6). This media was amended with 0.5% methanol, 10 ug/mL trimethylprim, and 50 ug/mL Kanamycin. For expression, a saturated *M. extorquens* culture was diluted 100 fold into 25 mL of fresh media in a 250 mL Erlenmeyer flask and shaken at 200 rpm at 30° C. At 24 hours and 36 hours, cultures were fed an additional 0.5% methanol and induced with 0.0125-0.05 ng/uL anhydrotetracy cline (ATC). *M. extorquens* cultures were harvested between 48 and 52 hours. Following centrifugation, the bacterial pellets were washed once with 1/20× phosphate buffered saline (PBS) and frozen at −20° C.

*E. coli* cultures were grown in LB (10 g Tryptone, 10 g NaCl, 5 g Yeast extract per liter) amended with 100 ug/mL carbenicillin and 125 uM isopropyl β-D-1-thiogalactopyranoside (IPTG). Following a 100-500 fold dilution, *E. coli* cultures were shaken at 200 rpm at 30° C. for 12-24 hours. Following centrifugation, the bacterial pellets were washed once with 1/20×PBS and frozen at −20° C.

To induce chaperones to aid in protein folding, Betaine (Bet) or Benzyl alcohol (BA) were added at 5-10 mm to cultures of *E. coli* or *M. extorquens*, as described in Marco et al. (2005) *Cell Stress & Chaperones* 10(4):329-339.

For extraction of intracellular free amino acids, frozen bacterial pellets were resuspended in 1:1 methanol:water and subjected to 3 to 4 freeze thaw cycles using dry-ice/ethanol slurry and a bath sonicator. Following centrifugation, the extraction supernatants were derivatized with the Waters AccQ-Tag Ultra Chemistry kit (176001235) utilizing the provided protocols. Derivatized samples were analyzed on a Waters Acquity H-Class UPLC equipped with a 3100 Mass spectrophotometer. Samples were compared to the included amino acid standard amended with taurine, hypotaurine, and L-cysteate. The presence of taurine or hypotaurine was confirmed by the presence of mass spec ions matching the correct derivatized amino acid mass at the same retention time as in the standard samples. Results are in Table 2.

Results:

TABLE 1

Expression constructs for taurine and hypotaurine production

| Plasmid Name | Vector | Genes present in plasmid | SEQ ID NOs |
|---|---|---|---|
| E2bA | pUC19 | CDO_Bacillus, CSAD | 50, 53 |
| E2rA | pUC19 | CDO_Rat, CSAD | 51, 53 |
| E5A | pUC19 | MA_3297, CSAD | 52, 53 |
| M1A | pLC291 | ADO, CSAD | 57, 54 |
| M1B | pLC291 | ADO, ComDE, TPA | 57, 55, 56 |
| M2bA | pLC291 | CDO_Bacillus, CSAD | 58, 54 |
| M2bB | pLC291 | CDO_Bacillus, ComDE, TPA | 58, 55, 56 |
| M2rA | pLC291 | CDO_Rat, CSAD | 59, 54 |
| M2rB | pLC291 | CDO_Rat, ComDE, TPA | 59, 55, 56 |
| M3A | pLC291 | 3MDO, CSAD | 60, 54 |
| M3B | pLC291 | 3MDO, ComDE, TPA | 60, 55, 56 |
| M4A | pLC291 | PAPS-AS, APSK, PAPSSS1, CSAD | 61, 62, 63, 54 |
| M4B | pLC291 | PAPS-AS, APSK, PAPSSS1, ComDE, TPA | 61, 62, 63, 55, 56 |
| M5A | pLC291 | MA_3297, CSAD | 64, 54 |
| M5B | pLC291 | MA_3297, ComDE, TPA | 64, 55, 56 |
| M6A | pLC291 | CGL/CD, PAP-AS, CSAD | 65, 61, 54 |
| M6B | pLC291 | CGL/CD, PAP-AS, ComDE, TPA | 65, 51, 55, 56 |
| M7A | pLC291 | CGL/CD, MA3297, CSAD | 65, 64, 54 |
| M7B | pLC291 | CGL/CD, MA3297, ComDE, TPA | 65, 64, 55, 56 |
| M8A | pLC291 | CuyA, CSAD | 66, 54 |
| M8B | pLC291 | CuyA, ComDE, TPA | 66, 55, 56 |
| M9A | pLC291 | ComA, ComB, ComC, CSAD | 67, 68, 69, 54 |
| M9B | pLC291 | ComA, ComB, ComC, ComDE, TPA | 67, 68, 69, 55, 56 |

TABLE 2

Detection and concentration of intracellular taurine or hypotaurine

| Plasmid Name | Organism | Taurine in cells (ppm) | Taurine in Media (ng/mL) | Hypo-taurine in cells (ppm) | Hypo-taurine in Media (ng/mL) |
|---|---|---|---|---|---|
| E2bA | *E. coli* BL21 | | 6 | | 54 |
| E2bA + Bet | *E. coli* BL21 | | | 2.7 | 9 |
| E2bA + BA | *E. coli* BL21 | | 12 | 1.4 | 22 |
| E2rA | *E. coli* BL21 | | 19 | 4.6 | 264 |
| E2rA + Bet | *E. coli* BL21 | 1.0 | 10 | 64.3 | 218 |
| E2rA + BA | *E. coli* BL21 | | 8 | 29.3 | 209 |
| E5A | *E. coli* BL21 | 24.8 | 122 | | 39 |
| E5A + Bet | *E. coli* BL21 | 9.8 | 88 | | 10 |
| E5A + BA | *E. coli* BL21 | 8.7 | 25 | | 48 |
| M2bA | *M. extorquens* | Peak in MS | 5 | 0.5 | 56 |
| M2bA + Bet | *M. extorquens* | | | | 419 |
| M2bB | *M. extorquens* | Peak in MS | | Peak in MS | |
| M2rA | *M. extorquens* | | | | 9 |
| M3A | *M. extorquens* | 0.2 | | | |
| M5A | *M. extorquens* | 3.9 | 55 | | |
| M5A + BA | *M. extorquens* | 6.7 | 60 | | |
| M5B | *M. extorquens* | 0.8 | | | |
| M5B + BA | *M. extorquens* | 1.2 | | | |
| M7A | *M. extorquens* | 12.4 | 144 | | |
| M7A + BA | *M. extorquens* | 6.0 | 75 | | |
| M7B | *M. extorquens* | 0.6 | | | |
| M7B + BA | *M. extorquens* | 2.2 | | | |

Amino Acid and Nucleotide Sequences

SEQ ID NO: 1
Description: L-serine dehydratase
Alias: Mext_3740, A9VXE2
Length: 453
Type: Protein
Organism: *Methylobacterium extorquens* PA1
>MISTFDLFKIGIGPSSSHTVGPMIAGRRFRETVLARGGIARISAEIYGSLAWTGRGHGTDVAILLGLMGHAPSTIDPDRTAPLA
DELRRTGDLGIPGVHFEPERDLVFNFKDILPLHTNGMRFRAYDAGDAPIEDQIFYSVGGGFVVTAAEAEAAAAGHAECVPPPLAF
GSGRELLDLTLRTGLTIPQIQLANELTLRPRDEIDAGLDAIRDAMFACIERGLRMDGELPGGLRVRRRAKRLYESLEATKLANSR
PAHEIMDWISLYALAVNEENASGGRVVTAPTNGAAGIVPAVLRYTRDFCPDWSDERGREFLLTAAAIGGLIKARASISGAEVGCQ
GEVGSAAAMAAAGLTAVLGGSAFQIENAAEIAMEHHLGMTCDPIAGLVQVPCIERNAFGANKAVVAASLSLRGDGQHRVSLDEVI
ETMRQTGHDMQAKYKETSLGGLAVNVAAC SEQ ID NO: 2
Description: L-serine dehydratase
Alias: Mext_3740, A9VXE2
Length: 1362
Type: DNA
Organism: *Methylobacterium extorquens* PA1
>atgATCAGCACCTTCGATCTGTTCAAGATCGGGATCGGTCCGTCGAGCTCCCACACCGTCGGGCCGATGATCGCCGGGCGCCGG
TTCCGCGAGACCGTACTCGCCCGCGGCGGCATCGCCCGCATCAGCGCCGAGATCTACGGCTCGCTCGCCTGGACCGGGCGCGGCC
ACGGCACCGACGTGGCGATCCTGCTCGGGCTCATGGGCCACGCGCCCTCCACCATCGACCCGGATCGGACGGCGCCGCTCGCCGA
CGAACTGCGCCGCACCGGCGATCTCGGCATTCCCGGCGTCCATTTCGAGCCCGAGCGCGACCTCGTCTTCAACTTCAAGGACATC
CTGCCGCTGCACACCAACGGCATGCGCTTTCGCGCCTACGATGCCGGGGACGCGCCGATCGAGGACCAGATCTTCTACTCGGTCG
GCGGCGGCTTCGTCGTCACCGCCGCCGAGGCGGAAGCTGCCGCGGCGGGTCATGCGGAGTGCGTGCCACCCCCGCTCGCCTTCGG
CAGCGGGCGTGAACTCCTCGACCTGACGCTACGCACCGGGCTGACGATCCCGCAGATCCAGCTCGCCAACGAGCTGACCCTGCGC
CCGCGCGACGAGATCGATGCCGGCCTCGACGCGATCCGCGATGCGATGTTCGCCTGCATCGAGCGCGGCCTGCGCATGGACGGCG
AATTGCCCGGCGGCCTGCGGGTGCGGCGGCGGGCCAAGCGGCTCTACGAGTCGCTGGAGGCGACGAAGCTCGCCAACAGCCGCCC
GGCCCACGAGATCATGGATTGGATCAGCCTCTACGCGCTCGCCGTCAACGAGGAGAACGCCTCGGGCGGCCGGGTGGTGACGGCG
CCGACCAACGGCGCGGCCGGCATCGTCCCGGCGGTGCTGCGCTACACCCGCGATTTCTGCCCCGATTGGAGCGACGAGCGCGGGC
GCGAGTTCCTGCTCACCGCCGCCGCCATCGGCGGGCTGATCAAGGCCCGTGCCTCGATCTCGGGGGCGGACGGTCGGCTGCCAGG
GCGAGGTCGGCTCGGCCGCGGCGATGGCGGCGGCGGGGCTGACCGCCGTGCTCGGCGGCTCGGCCTTCCAGATCGAGAACGCCGC
CGAGATCGCCATGGAGCACCATCTAGGCATGACCTGCGATCCGATCGCCGGCCTCGTGCAAGTGCCCTGCATCGAGCGCAACGCC
TTCGGCGCCAACAAGGCAGTGGTGGCGGCCTCGCTGTCGCTCCGCGGCGACGGCCAGCACCGGGTGAGCCTGGACGAGGTGATCG
AGACCATGCGCCAGACCGGCCACGACATGCAGGCCAAGTACAAGGAAACCTCGCTCGGGGGGCTAGCCGTCAACGTCGCCGCCTG
Ctga SEQ ID NO: 3
Description: sulfate adenylyltransferase subunit 1
Alias: Mext_2232
Length: 469
Type: DNA
Organism: *Methylobacterium extorquens* PA1
>MTIHQSPEAFGYDAFLRQHQNKEVLRFITCGSVDDGKSTLIGRLLHDTKQIFDDQVTALQRDSRKHGTQGGEVDLALLVDGLQA
EREQGITIDVAYRFFSTDRRSFIVADTPGHEQYTRNMATGASTADLAVILVDARHGLTRQSRRHALLVSLLGIRRVALAINKMDL
VGWSQDKFEAIVSGFQAFAAPLNFFEVRAIPLSAKNGDNVVLPGTAATWYTDVPLLRYLEEVPVKSEERAAAFRMPVQWVNRPNS
DFRGFSGLIASGSVAPGDAVTVAPSGKTSTIARIFTADGDLERASEGQSVTLVLADEVDASRGAVIATSDAPLTLTDSLDVRLFW
AAESDLVPGANLWAKVGTQTVNAVVKAVHRRIDPETGQAGPADKLAVNDIGDVTLTLDRQIAVDPYAENRDTGSLILIDRETTDT
AALGLVQRVVASSKVAPAPTASVTASAEPARSGGLLAGLKRLFGG SEQ ID NO: 4
Description: sulfate adenylyltransferase subunit 1
Alias: Mext_2232
Length: 1410
Type: DNA
Organism: *Methylobacterium extorquens* PA1
>atgACCATCCATCAGTCTCCGGAAGCGTTCGGCTACGACGCCTTCCTGCGTCAGCACCAGAACAAGGAAGTCCTGCGCTTCATC
ACCTGCGGCTCGGTCGATGACGGCAAGTCCACCCTGATCGGGCGGCTCCTGCACGACACCAAGCAGATCTTCGACGATCAGGTGA
CGGCGCTCCAGCGCGATTCGCGCAAGCACGGCACGCAGGGCGGCGAGGTCGATCTCGCCCTTCTGGTTGACGGACTCCAGGCCGA
GCGCGAGCAGGGCATCACCATCGATGTCGCCTACCGCTTCTTCTCGACCGACCGGCGCTCCTTCATCGTCGCCGACACCCCCGGC
CACGAGCAGTACACCCGCAACATGGCGACCGGCGCCTCGACCGCCGACCTCGCCGTGATCCTGGTGGACGCCCGCCACGGGCTGA
CCCGCCAGAGCCGGCGCCACGCGCTGCTGGTCTCGCTGCTCGGCATCCGCCGCGTCGCGCTCGCCATCAACAAGATGGACCTCGT
CGGCTGGTCGCAGGACAAGTTCGAGGCGATCGTCTCCGGCTTCCAGGCCTTTGCCGCGCCGCTGAACTTCACCGAGGTGCGGGCG
ATCCCGCTCTCGGCCAAGAACGGCGACAACGTCGTCCTGCCGGGCACCGCCGCGACCTGGTACACGGACGTTCCGCTGCTGCGCT
ATCTCGAAGAGGTGCCGGTGAAGTCGGAGGAGCGCGCCGCCGCCTTCCGCATGCCGGTGCAGTGGGTGAACCGCCCGAATTCCGA
CTTCCGCGGCTTCTCGGGGCTGATCGCCTCGGGCTCCGTCGCGCCGGGCGATGCCGTCACCGTCGCGCCTTCCGGCAAGACCTCG
ACGATCGCCCGCATCTTCACCGCCGACGGCGATCTGGAACGGGCGAGCGAGGGCCAGTCGGTGACGCTGGTGCTGGCCGACGAAG
TCGATGCCTCGCGCGGCGCGGTGATCGCGACCTCGGACGCACCGTTGACGCTGACCGACAGCCTCGACGTGCGCCTGTTCTGGGC
CGCCGAATCCGATCTCGTTCCCGGCGCCAACCTGTGGGCGAAGGTCGGCACGCAGACCGTCAACGCGGTGGTGAAGGCGGTGCAC
CGCCGGATCGATCCGGAGACGGGACAGGCCGGTCCGGCCGACAAGCTCGCGGTCAACGACATCGGCGACGTGACGCTGACCCTCG
ACCGGCAGATCGCGGTCGATCCCTATGCCGAGAACCGCGACACCGGCAGCCTGATCCTGATCGACCGTGAGACGACCGACACGGC
CGCGCTCGGCCTCGTGCAGAGGGTCGTTGCGTCGAGCAAGGTCGCTCCGGCGCCGACCGCGTCTGTGACGGCTTCGGCGGAGCCC
GCACGTAGCGGCGGTTTGCTGGCCGGCCTCAAGCGGCTGTTCGGCGGAtaa SEQ ID NO: 5
Description: sulfate adenylyltransferase subunit 2
Alias: Mext_2233
Length: 309
Type: Protein -continued Amino Acid and Nucleotide Sequences Organism: *Methylobacterium extorquens* PA1
>MSAAVAAPARTRLTHLQRLEAESIHIFREAVAEAENPVMLYSIGKDSSVLLHLALKAFAPGRLPFPLMHIDTTWKFREMIAFRD
RRAKELGLELIVHTNQDGLAKGVGPVSHGSEVHTDVMKTQALRQALDKYKYDVAFGGARRDEEASRAKERIVSLRNGQHRWDPKR
QRAEPWHLYNFKKRRGESFRVFPLSNWTELDIWLYIEQENIPIVPLYFAAERPVVERDGQLIMVDDERFPLEPGETPQQRQVRFR
TLGCYPLTGAVESPAATLPEIIGETLAARTSERQGRVIDKDGAGAMERKKQEGYF SEQ ID NO: 6
Description: sulfate adenylyltransferase subunit 2
Alias: Mext_2233
Length: 930
Type: DNA
Organism: *Methylobacterium extorquens* PA1
>atgAGCGCTGCCGTCGCCGCGCCCGCGCGCACCCGCCTGACGCATCTCCAGCGTCTCGAGGCCGAGAGCATCCACATCTTCCGG
GAGGCCGTCGCCGAGGCCGAGAACCCGGTGATGCTCTACTCGATCGGCAAGGATTCGTCGGTGCTGCTGCACCTGGCGCTGAAGG
CCTTCGCGCCGGGGCGCCTCCCGTTCCCCCTGATGCACATCGACACGACCTGGAAGTTCCGCGAGATGATCGCCTTCCGCGATCG
GCGAGCCAAGGAGCTCGGGCTCGAACTCATCGTGCACACGAATCAGGACGGGCTTGCCAAGGGCGTCGGCCCGGTCAGCCACGGC
TCGGAAGTGCATACCGACGTGATGAAGACGCAGGCCCTGCGGCAGGCGCTCGACAAGTACAAGTATGACGTGGCCTTCGGCGGCG
CCCGCCGGGACGAGGAGGCCAGCCGCGCCAAGGAGCGCATCGTGAGCCTGCGCAACGGCCAGCACCGCTGGGACCCGAAGCGCCA
GCGCGCCGAGCCGTGGCACCTCTACAATTTCAAGAAGCGGCGCGGCGAGAGTTTTCGCGTGTTCCCGCTATCCAACTGGACCGAA
TTGGATATCTGGCTCTACATCGAGCAGGAAAATATTCCGATCGTCCCGCTCTACTTCGCCGCCGAGCGCCCGGTGGTGGAGCGCG
ACGGCCAGCTCATCATGGTCGATGACGAGCGCTTTCCGCTGGAGCCGGGCGAGACCCCACAACAGCGGCAGGTCCGGTTCCGCAC
GCTCGGCTGCTACCCGCTGACCGGCGCGGTCGAGAGCCCGGCCGCGACCCTGCCGGAGATCATCGGCGAGACGCTGGCCGCCCGA
ACCTCGGAGCGCCAGGGCCGGGTCATCGACAAGGACGGCGCCGGCGCCATGGAGCGCAAGAAGCAGGAGGGCTATTTCtga SEQ ID NO: 7
Description: Adenylyl-Sulfate Kinase
Alias: cysC, NC_000913.3
Length: 201
Type: Protein
Organism: *Escherichia coli* K-12
>MALHDENVVWHSHPVTVQQRELHHGHRGVVLWFTGLSGSGKSTVAGALEEALHKLGVSTYLLDGDNVRHGLCSDLGFSDADRKE
NIRRVGEVANLMVEAGLVVLTAFISPHRAERQMVRERVGEGRFIEVFVDTPLAICEARDPKGLYKKARAGELRNFTGIDSVYEAP
ESAEIHLNGEQLVTNLVQQLLDLLRQNDIIRS SEQ ID NO: 8
Description: Adenylyl-Sulfate Kinase
Alias: cysC, NC_000913.3
Length: 606
Type: DNA
Organism: *Escherichia coli* K-12
>atgGCGCTGCATGACGAAAACGTCGTCTGGCATAGCCATCCGGTCACTGTGCAACAACGCGAGCTACACCACGGTCATCGTGGT
GTAGTGCTGTGGTTTACCGGCCTCTCCGGGTCCGGTAAATCAACGGTCGCCGGGGCGCTGGAGGAGGCGTTACATAAACTCGGCG
TCAGTACGTATCTGCTGGATGGCGACAATGTTCGCCACGGATTATGCAGCGATCTCGGTTTTAGCGATGCCGATCGTAAAGAGAA
TATCCGTCGCGTCGGTGAAGTGGCGAATTTGATGGTTGAAGCCGGACTGGTGGTGCTGACCGCATTTATCTCGCCACACCGCGCC
GAACGCCAGATGGTTCGCGAACGCGTAGGAGAAGGGCGCTTTATCGAAGTGTTTGTCGATACGCCGCTGGCGATTTGCGAAGCCC
GCGATCCCAAAGGCTTATATAAGAAAGCGCGTGCCGGTGAACTGCGCAACTTTACGGGAATAGATTCCGTTTACGAAGCGCCTGA
ATCGGCAGAAATTCATCTCAATGGTGAACAATTAGTAACAAATTTGGTACAGCAATTATTAGATCTGTTGAGACAGAACGATATT
ATCAGATCCtga SEQ ID NO: 9
Description: PAPS-AS
Alias: Q019P5
Length: 322
Type: Protein
Organism: *Ostreococcus tauri*
>MPRGWTKTRAYDSHHFDADAWSVVTPRAGDVIIATAYKSGTTWMQQIVSQLVFEGAAPAALGELSPWVDLRVPPREVKRGMIEG
LPSPRILKTHLPTTGLEYDENAKYIYVARDGRDAFMSLMNHYKNGNEAFYGALNGPGLKGAPLPTWEEACEGEGDEKLRALFDKW
LNTPWGQHPWEEDGWPFWSLFYNMKTWWDARESKNIIFVHFSDLKKDLKGQMRRIAKFLNAPIDESKFDAQVTACFFESMKGNAA
SVAPLGGALWKGGAETFINKGTNGRWRNVLTKEQVKQYEQVAEKRLGKDCAKWLANGGDMNGRGCVIM SEQ ID NO: 10
Description: PAPS-AS
Alias: OT_ostta05g01260
Length: 969
Type: DNA
Organism: *Ostreococcus tauri*
>atgCCGCGCGGATGGACGAAGACGCGCGCGTACGACTCGCATCACTTTGACGCCGACGCGTGGTCGGTGGTGACGCCTCGAGCG
GGTGACGTCATCATCGCCACCGCGTATAAATCTGGCACGACGTGGATGCAACAGATCGTGTCGCAACTCGTGTTCGAGGGCGCGG
CCCCGGCGGCGTTGGGGGAGCTCTCGCCGTGGGTGGATCTGCGCGTGCCCCCGCGGGAGGTGAAGCGAGGGATGATCGAGGGATT
GCCCTCGCCCCGGATCTTGAAGACGCATCTTCCGACGACGGGGTTGGAATACGACGAAAACGCGAAGTACATTTACGTCGCGCGG
GACGGCCGCGACGCGTTCATGTCTTTGATGAACCACTATAAGAACGGTAATGAAGCGTTTTACGGCGCGCTGAACGGCCCTGGGT
TAAAGGGCGCACCTTTGCCTACGTGGGAAGAGGCGTGCGAAGGCGAGGGCGACGAGAAACTTCGCGCGCTTTTTGACAAGTGGCT
CAACACGCCGTGGGGCCAGCACCCGTGGGAAGAAGACGGGTGGCCTTTCTGGTCTCTGTTCTATAACATGAAGACGTGGTGGGAC
GCGCGCGAATCCAAGAACATCATCTTCGTGCATTTTTCGGATTTGAAGAAGGATTTGAAGGGTCAGATGCGACGCATTGCGAAGT
TTTTGAACGCCCCGATCGATGAAAGCAAATTCGATGCGCAAGTCACAGCGTGCACGTTCGAGAGCATGAAGGGTAACGCCGCGAG
CGTCGCGCCTCTCGGTGGCGCGCTGTGGAAGGGCGGTGCGGAGACGTTCATTAACAAAGGTACCAACGGCCGGTGGAGGAACGTT -continued

| Amino Acid and Nucleotide Sequences |
| --- |

CTAACCAAGGAACAAGTCAAGCAGTACGAGCAGGTGGCTGAGAAACGGCTGGGTAAGGACTGCGCAAAGTGGCTCGCCAACGGCG
GCGATATGAACGGCCGTGGGTGCGTGATCATGtga SEQ ID NO: 11
Description: CSAD
Alias: ref|WP_006454033.1
Length: 488
Type: Protein
Organism: *Synechococcus* sp. PCC7335
>MFKASKYYNLLQQLENFFSTANSSSLLTKPIDPNVLKSQLSLDLPNEGKPVEELRTEITSYLNNALKTAHPSYFNQLWGGFNSA
CFMGDMLASATNTSMYTYEVAPAATLIEQALVTKMSGILGFKSADGQFTTGGSNGNLMAMAIARHHVLPTVKQDGMTSGPKLVAF
VSREAHYSFDKAAHILGLGTEQLWKVPVDSDGRMKPEALSELVDRARVQGSIPFFVAGTAGTTVRGAFDPFEEISAIAHQENLWF
HIDGAWGASVSLSATHRQLMAGANQADSLVWDAHKMMGMTLMCSLLLVKQRGQMLRTFSTAGTDYLFHDEVSAGEVPTESSTSST
ELPIEELPTDFGPATMECGRRVDALKLWLAWRHLGDRGWERLIDSYFELAQRAETIIDKHPSLELVSSRQSVNLCFRYLPQNKQQ
ADELTLKVRQALWETGTAMVNYAQVEGKTVFRLVICNNQTRSEDIERFFEALVAIARRLEQEMC SEQ ID NO: 12
Description: CSAD
Alias: ref|WP_006454033.1
Length: 1467
Type: DNA
Organism: *Synechococcus* sp. PCC7335
>ATGTTCAAAGCCTCCAAATACTACAACTTGTTGCAGCAGCTTGAAAATTTCTTTTCGACAGCTAATTCGTCGAGTCTGCTTACT
AAACCAATAGATCCTAACGTTTTGAAATCTCAACTTTCTTTGGATTTACCAAATGAGGGTAAACCTGTAGAAGAACTGCGAACGG
AGATTACTAGCTATTTGAATAACGCGCTGAAGACAGCTCATCCTAGCTATTTTAATCAGCTGTGGGGCGGTTTCAACTCAGCCTG
TTTCATGGGTGATATGCTTGCGAGTGCGACAAATACCTCGATGTATACCTACGAGGTGGCGCCGGCTGCTACTTTAATCGAGCAG
GCGCTAGTTACTAAGATGTCTGGCATCTTAGGGTTTAAGAGTGCCGATGGGCAGTTTACAACCGGAGGGAGTAACGGAAATTTGA
TGGCGATGGCGATCGCTCGCCATCATGTTCTACCGACTGTTAAGCAGGACGGTATGACCAGCGGCCCCAAACTAGTTGCTTTTGT
CTCTAGAGAGGCGCACTATTCTTTTGATAAAGCTGCTCATATATTGGGATTAGGAACAGAGCAGCTATGGAAAGTTCCTGTAGAC
AGCGATGGCAGAATGAAGCCGGAGGCATTATCTGAGCTAGTAGATAGAGCGCGTGTACAAGGCTCTATTCCTTTCTTTGTTGCCG
GAACTGCTGGAACAACTGTAAGAGGTGCCTTCGATCCGTTTGAAGAGATTAGCGCGATCGCCCACCAGGAAAACCTGTGGTTTCA
TATCGATGGAGCTTGGGGTGCTAGCGTATCGCTGAGCGCTACTCATCGACAGCTAATGGCTGGGGCAAACCAAGCAGACTCTCTG
GTGTGGGACGCACACAAAATGATGGGGATGACGCTGATGTGTTCTTTGCTGTTGGTCAAGCAGCGTGGTCAAATGTTAAGGACTT
TCTCTACTGCAGGCACCGACTATCTATTCCACGATGAAGTCTCTGCTGGGGAAGTGCCTACAGAATCATCAACATCATCAACAGA
ATTGCCCATAGAAGAACTACCAACAGACTTTGGCCCTGCAACTATGCACTGCGGTCGGCGTGTGGATGCACTCAAGCTTTGGCTA
GCCTGGCGGCACCTAGGCGATCGCGGCTGGGAAAGGCTAATCGACAGCTACTTTGAGCTGGCTCAGCGAGCAGAAACTATCATCG
ATAAGCATCCTTCGCTGGAGCTAGTGTCTTCGAGACAGTCGGTGAACCTATGCTTTCGGTATCTACCTCAGAACAAACAGCAGGC
CGATGAGCTGACGCTGAAAGTGCGACAGGCGCTGTGGGAAACCGGAACTGCGATGGTGAACTACGCTCAAGTAGAAGGCAAAACG
GTTTTTCGTTTGGTCATTTGCAACAATCAAACCCGCTCTGAGGACATCGAGCGTTTTTTCGAGGCTTTAGTAGCGATCGCCCGGC
GGTTAGAGCAGGAGATGTGCTGA SEQ ID NO: 13
Description: GadA
Length: 466
Type: Protein
Organism: *Escherichia coli* str k12 subs. MG1655
>MDQKLLTDFRSELLDSRFGAKAISTIAESKRFPLHEMRDDVAFQIINDELYLDGNARQNLATFCQTWDDENVHKLMDLSINKNW
IDKEEYPQSAAIDLRCVNMVADLWHAPAPKNGQAVGTNTIGSSEACMLGGMAMKWRWRKRMEAAGKPTDKPNLVCGPVQICWHKF
ARYWDVELREIPMRPGQLFMDPKRMIEACDENTIGVVPTFGVTYTGNYEFPQPLHDALDKFQADTGIDIDMEIDAASGGFLAPFV
APDIVWDFRLPRVKSISASGHKFGLAPLGCGWVIWRDEEALPQELVFNVDYLGGQIGTFAINFSRPAGQVIAQYYEFLRLGREGY
TKVQNASYQVAAYLADEIAKLGPYEFICTGRPDEGIPAVCFKLKDGEDPGYTLYDLSERLRLRGWQVPAFTLGGEATDIVVMRIM
CRRGFEMDFAELLLEDYKASLKYLSDHPKLQGIAQQNSFKHT SEQ ID NO: 14
Description: GadA
Length: 1401
Type: DNA
Organism: *Escherichia coli* str k12 subs. MG1655
>atgGACCAGAAGCTGTTAACGGATTTCCGCTCAGAACTACTCGATTCACGTTTTGGCGCAAAGGCCATTTCTACTATCGCGGAG
TCAAAACGATTTCCGCTGCACGAAATGCGCGATGATGTCGCATTTCAGATTATCAATGATGAATTATATCTTGATGGCAACGCTC
GTCAGAACCTGGCCACTTTCTGCCAGACCTGGGACGACGAAAACGTCCATAAATTGATGGATTTGTCGATCAATAAAAACTGGAT
CGACAAAGAAGAATATCCGCAATCCGCAGCCATCGACCTGCGTTGCGTAAATATGGTTGCCGATCTGTGGCATGCGCCTGCGCCG
AAAAATGGTCAGGCCGTTGGCACCAACACCATTGGTTCTTCCGAGGCCTGTATGCTCGGCGGGATGGCGATGAAATGGCGTTGGC
GCAAGCGTATGGAAGCTGCAGGCAAACCAACGGATAAACCAAACCTGGTGTGCGGTCCGGTACAAATCTGCTGGCATAAATTCGC
CCGCTACTGGGATGTGGAGCTGCGTGAGATCCCTATGCGCCCCGGTCAGTTGTTTATGGACCCGAAACGCATGATTGAAGCCTGT
GACGAAAACACCATCGGCGTGGTGCCGACTTTCGGCGTGACCTACACCGGTAACTATGAGTTCCCACAACCGCTGCACGATGCGC
TGGATAAATTCCAGGCCGACACCGGTATCGACATCGACATGCACATCGACGCTGCCAGCGGTGGCTTCCTGGCACCGTTCGTCGC
CCCGGATATCGTCTGGGACTTCCGCCTGCCGCGTGTGAAATCGATCAGTGCTTCAGGCCATAAATTCGGTCTGGCTCCGCTGGGC
TGCGGCTGGGTTATCTGGCGTGACGAAGAAGCGCTGCCGCAGGAACTGGTGTTCAACGTTGACTACCTGGGTGGTCAAATTGGTA
CTTTTGCCATCAACTTCTCCCGCCCGGCGGGTCAGGTAATTGCACAGTACTATGAATTCCTGCGCCTCGGTCGTGAAGGCTATAC
CAAAGTACAGAACGCCTCTTACCAGGTTGCCGCTTATCTGGCGGATGAAATCGCCAAACTGGGGCCGTATGAGTTCATCTGTACG
GGTCGCCCGGACGAAGGCATCCCGGCGGTTTGCTTCAAACTGAAAGATGGTGAAGATCCGGGATACACCCTGTACGACCTCTCTG
AACGTCTGCGTCTGCGCGGCTGGCAGGTTCCGGCCTTCACTCTCGGCGGTGAAGCCACCGACATCGTGGTGATGCGCATTATGTG
TCGTCGCGGCTTCGAAATGGACTTTGCTGAACTGTTGCTGGAAGACTACAAAGCCTCCCTGAAATATCTCAGCGATCACCCGAAA
CTGCAGGGTATTGCCCAGCAGAACAGCTTTAAACACACCtga -continued Amino Acid and Nucleotide Sequences SEQ ID NO: 15
Description: CDO
Alias: cdoA, BSU31140, O32085, CDO_*Bacillus*
Length: 161
Type: Protein
Organism: Bacillus subtilis
>MELYECIQDIFGGLKNPSVKDLATSLKQIPNAAKLSQPYIKEPDQYAYGRNAIYRNNELEIIVINIPPNKETTVHDHGQSIGCA
MVLEGKLLNSIYRSTGEHAELSNSYFVHEGECLISTKGLIHKMSNPTSERMVSLHVYSPPLEDMTVFEEQKEVLENS SEQ ID NO: 16
Description: CDO
Alias: cdoA, BSU31140, O32085, CDO_*Bacillus*
Length: 486
Type: DNA
Organism: *Bacillus subtilis*
>atgGAACTGTATGAGTGTATCCAAGACATTTTTGGCGGCTTGAAAAATCCATCGGTTAAAGATTTAGCAACGTCTTTAAAACAA
ATTCCAAACGCAGCAAAATTGAGTCAACCGTATATTAAGGAACCAGACCAGTACGCTTACGGCCGAAATGCCATCTATCGAAATA
ATGAATTGGAAATTATCGTGATTAACATTCCGCCAAACAAGGAGACAACAGTACACGATCATGGTCAATCCATTGGTTGTGCAAT
GGTGTTAGAAGGAAAGCTTCTTAATTCTATTTATCGTTCAACCGGCGAACACGCAGAACTCTCCAATTCATACTTTGTCCACGAA
GGAGAATGCCTTATTTCAACCAAAGGTTTAATTCACAAAATGTCCAATCCAACATCTGAACGAATGGTGTCTCTTCATGTCTACT
CCCCTCCTTTGGAAGACATGACGGTCTTTGAGGAACAAAAGGAGGTATTGGAAAATTCAtga SEQ ID NO: 17
Description: MA_3297
Length: 416
Type: Protein
Organism: *Methanosarcina acetivorans* str. C2A
>MGRFILKCLKCGREYSQEYRLTCENDDSFLRAEYLEKKLELRKQPGIGRFHSWLPVQEELTTEAGPITYKSEALARELGLSNLY
IGFSGYWPEKGAFIKTCSFKELEAHPTMQLLKESGGKAIVLASAGNTGRAFAHVSALTGTDVYIVVPDSGIPKLWLPEEPTDSIH
LISMTPGNDYTDAINLAGRIAKLPGMVPEGGARNVARREGMGTVMLDAAVTIGKMPDHYFQAVGSGTGGISAWEASLRLREDGRF
GSKLPKLQLTQNLPFVPMYNAWQEGRRDIIPEIDMKDAKKRIEETYATVLTNRAPPYSVTGGLYDALVDTDGIMYAVSKEEALDA
KALFESLEGIDILPPSAVAAASLLKAVEAGNVGKDDTILLNIAGGGFKRLKEDFTLFQIEPEITVSNPDVPLEELKL SEQ ID NO: 18
Description: MA_3297
Length: 1251
Type: DNA
Organism: *Methanosarcina acetivorans* str. C2A
>atgGGAAGATTCATATTAAAATGTCTGAAATGCGGCAGAGAATACAGCCAGGAATACAGGCTGACCTGCGAGAATGACGACTCC
TTTTTGCGGGCGGAATACCTTGAAAAAAAACTTGAGCTGAGAAAGCAGCCAGGGATAGGAAGATTTCACTCATGGCTTCCGGTTC
AGGAAGAGCTTACTACCGAAGCCGGGCCCATCACGTACAAAAGCGAAGCTCTTGCGAGGGAACTTGGGCTTTCGAATCTGTACAT
AGGGTTCAGCGGGTACTGGCCCGAGAAAGGAGCTTTTATCAAGACCTGCAGTTTCAAAGAACTCGAAGCCCATCCTACGATGCAG
CTTCTCAAGGAATCCGGGGGAAAAGCCATAGTCCTTGCCTCTGCAGGGAATACGGGGAGGGCTTTTGCACATGTTTCGGCACTTA
CCGGAACCGATGTTTATATCGTGGTTCCCGACTCAGGCATCCCTAAACTCTGGCTGCCTGAAGAACCGACCGATTCCATTCACCT
TATCAGCATGACTCCGGGGAACGATTACACCGATGCTATCAACCTTGCAGGAAGAATTGCAAAGCTTCCTGGAATGGTCCCTGAA
GGAGGAGCCAGAAACGTTGCCAGAAGAGAAGGAATGGGTACTGTAATGCTTGATGCAGCCGTAACCATAGGAAAGATGCCTGATC
ACTACTTCCAGGCTGTCGGAAGCGGGACGGGAGGAATCTCAGCCTGGGAAGCTTCTCTGCGCCTCAGAGAGGACGGGCGTTTTGG
TTCCAAACTTCCAAAGCTCCAGCTTACCCAGAATCTCCCCTTCGTTCCCATGTATAATGCATGGCAAGAAGGCAGGAGGGATATA
ATTCCCGAAATTGACATGAAAGATGCAAAGAAGCGGATCGAAGAGACCTACGCCACTGTACTTACCAACCGAGCACCACCTTACT
CCGTGACAGGCGGGCTCTATGACGCACTTGTCGATACGGACGGGATAATGTATGCAGTAAGCAAAGAAGAAGCCCTTGACGCAAA
AGCGCTTTTTGAGTCCCTTGAAGGAATAGATATCCTTCCCCCATCTGCCGTTGCTGCTGCTTCCCTCTTAAAAGCCGTGGAAGCC
GGAAATGTCGGAAAGGACGACACTATCCTCCTGAACATTGCAGGCGGAGGTTTCAAACGGCTGAAGGAAGACTTCACACTATTCC
AGATTGAACCTGAAATTACTGTCTCGAACCCGGATGTGCCGCTTGAGGAACTGAAGCTCtga SEQ ID NO: 19
Description: ComA
Alias: phosphosulfolactate synthase
Length: 252
Type: Protein
Organism: *Methanosphaera stadtmanae* DSM 3091
>MNAFKFLDEIGPVNTNTMVLDKALGYKTVEDMLTISGNYFNLLKYGWGTSILYDEEIIKDKNELYHSYNIRTYTGGTLFELANK
QNKIDEYFNEIDRLGFNAVEISDGSTTIDSDRRAQLINKSKELGFYTLSEIGKKNPQKDSEYTTQQRIDLINTDIEAGSDMVIIE
GRESGKNIGIYDDKGNVKKDDLTSIYENTPKEKVLWEAPQKNQQVELILTLSNDVNLGNINSNEIVSLETLRRGLRGDTLGKL SEQ ID NO: 20
Description: ComA
Alias: phosphosulfolactate synthase
Length: 759
Type: DNA
Organism: *Methanosphaera stadtmanae* DSM 3091
>atgAACGCTTTTAAGTTTCTAGATGAAATTGGACCAGTAAATACCAATACCATGGTTCTTGATAAGGCATTAGGATACAAAACA
GTTGAAGATATGTTAACAATTAGTGGAAACTATTTTAATCTATTGAAGTATGGATGGGGAACTTCAATATTATATGATGAAGAAA
TAATAAAAGATAAAAATGAATTATATCACTCATATAATATTAGAACATATACTGGTGGAACTTTATTTGAATTAGCAAATAAACA
AAATAAAATAGATGAATATTTTAATGAAATTGACAGATTAGGATTTAATGCTGTGGAAATATCTGATGGATCAACTACCATTGAC
AGTGATAGACGTGCACAGTTAATTAATAAATCAAAAGAATTAGGTTTCTACACTTTGAGTGAAATAGGTAAGAAAAATCCACAAA
AAGATTCTGAATATACAACACAACAACGTATAGATCTTATAAATACAGATATTGAAGCAGGTTCTGATATGGTTATTATTGAAGG -continued

| Amino Acid and Nucleotide Sequences |
|---|

ACGTGAAAGTGGTAAAAATATTGGTATATACGATGATAAAGGTAATGTAAAAAAAGATGATTTAACTTCAATCTATGAAAATACA
CCTAAAGAAAAAGTATTGTGGGAAGCTCCACAGAAAAATCAACAAGTAGAATTAATACTTACATTAAGTAATGATGTAAATCTTG
GAAACATTAATTCTAATGAAATAGTCTCCCTTGAAACATTACGTCGTGGATTAAGAGGAGACACTCTTGGAAAATTAtaa SEQ ID NO: 21
Description: ComB1
Length: 232
Type: Protein
Organism: *Methanosphaera stadtmanae* DSM 3091
>MKINVSLYNSRTNDLAIVIDLLRASTTISVALNTFKRIVPINDIDEAIKLKEKHNAILAGEIKSSDFDVSNSPVQISNYAGDTL
ILKTTNGTKVLENIKQRNSEVNILVGASINAKTVAQKALDIADNEIELVMAGRHQRFTIEDCIGAGIIINEIVNIAKEKNIYLEL
SESAKASKIISNNSNIIKQLINTSHSADKLRYLGFGEDIEICSLINKIDTVPIYKNNYIVSLD SEQ ID NO: 22
Description: ComB1
Length: 699
Type: DNA
Organism: *Methanosphaera stadtmanae* DSM 3091
>atgAAAATTAATGTAAGTTTATATAATTCACGAACCAATGATTTAGCTATAGTAATTGATTTATTAAGGGCAAGTACAACAATA
AGTGTAGCATTAAATACTTTTAAAAGAATTGTTCCGATTAATGATATAGATGAAGCTATTAAATTAAAAGAAAAACATAATGCAA
TATTGGCAGGTGAAATTAAATCATCAGATTTTGATGTTTCAAATTCACCAGTTCAAATATCAAATTATGCTGGTGATACATTAAT
TTTGAAAACAACAAATGGTACAAAGGTATTAGAAAATATAAAACAAAGAAATTCAGAAGTAAATATATTGGTTGGAGCATCAATA
AATGCAAAAACAGTAGCACAAAAGGCATTAGATATTGCAGATAATGAAATTGAATTAGTTATGGCAGGAAGACATCAAAGATTTA
CAATAGAGGATTGTATTGGTGCAGGAATAATTATTAATGAAATAGTAAACATAGCTAAAGAAAAAAATATATACTTAGAACTTTC
AGAATCAGCAAAAGCATCAAAAATAATATCAAATAATTCTAATATAATAAAACAATTAATAAATACTTCACACAGTGCAGATAAA
TTACGTTATCTTGGATTTGGTGAAGATATTGAAATATGTAGTTTAATTAACAAGATAGATACAGTTCCAATCTATAAGAATAATT
ACATAGTCTCATTAGATtaa SEQ ID NO: 23
Description: ComC
Alias: Sulfolactate dehydrogenase
Length: 342
Type: Protein
Organism: *Methanobacterium* sp. MB1
>MNITPEQELSLIIDILTKFDVPEDQASIIAEVTLDGDLKGFSSHGIGRFPQYIKGLECGHIKPHIEIVVEKETAATALINGNHG
FGHVVTYQAMKMAIEKAKEVGIGLVGIHNSNHFGVAGYYSDMALMEDIIGIVTANTEPAVAPIGGKEPILGTNPLAIGIPSGSHY
LSVDMATSASARGKLMEAKRLGEPIPENVALDSDGNPTTDPAEALKGSILPFGAHKGYALSLMIEVIAGPLVRASYGKGVTGTAD
PEVPCTKGDLIAAIDPSKFVDIDQFKEEVDDLISELKSTPNVMIPGDEEVLNVKRHQKEGIALDETLVQQLREIASNVDVDVSDI
LGD SEQ ID NO: 24
Description: ComC
Alias: Sulfolactate dehydrogenase
Length: 1029
Type: DNA
Organism: *Methanobacterium* sp. MB1
>atgAACATTACTCCAGAACAGGAATTATCCCTGATCATCGATATTTTAACTAAATTTGACGTACCTGAAGACCAAGCATCCATC
ATTGCCGAAGTGACACTAGACGGTGATCTTAAGGGTTTCTCATCTCATGGAATTGGTAGATTCCCCCAGTACATTAAGGGATTGG
AATGTGGTCATATCAAGCCCCACACAGAAATAGTTGTGGAGAAAGAAACTGCAGCCACCGCTCTGATAAATGGTAACCATGGTTT
TGGACATGTAGTAACCTACCAGGCCATGAAAATGGCCATAGAGAAAGCTAAAGAAGTAGGTATTGGTTTAGTGGGTATCCATAAC
TCCAACCACTTTGGAGTGGCTGGTTATTACTCCGACATGGCATTGATGGAAGATATCATTGGCATTGTAACTGCCAACACTGAAC
CAGCCGTGGCCCCTATTGGAGGGAAAGAACCAATACTGGGTACTAATCCCCTGGCCATAGGAATACCTTCCGGTAGCCACTATCT
CTCCGTGGACATGGCCACATCAGCTTCCGCCCGTGGAAAACTCATGGAAGCCAAACGTCTTGGTGAACCCATACCAGAAAATGTG
GCCCTGGATTCCGATGGAAATCCCACCACCGACCCAGCAGAAGCACTCAAAGGATCAATCCTCCCCTTCGGAGCCCATAAAGGAT
ATGCCTTATCCCTTATGATTGAAGTTATAGCCGGCCCACTGGTACGTGCCTCCTATGGTAAGGGAGTTACTGGAACAGCTGACCC
CGAGGTTCCCTGCACCAAAGGAGACCTGATTGCCGCCATTGACCCCTCCAAATTTGTGGATATAGACCAGTTTAAGGAAGAGGTG
GATGATCTTATAAGTGAATTAAAATCCACTCCTAATGTAATGATACCCGGAGATTTTGAAGTCTTAAATGTGAAACGTCACCAGA
AAGAAGGAATAGCTCTGGATGAAACCCTTGTACAGCAGTTAAGGGAAATCGCCAGCAATGTAGATGTGGATGTATCAGATATACT
GGGAGATtaa SEQ ID NO: 25
Description: ComDE
Alias: sulfopyruvate decarboxylase
Length: 387
Type: Protein
Organism: *Methanosarcina acetivorans* str. C2A
>MYVVNPEEKVIEIMKQTGIDLAATLPCDRIKNLLPLVSENFPEIKLTREENGVGICAGIYLAGGKPMMLIQSTGLGNMINALES
LNVTCKIPLPILASWRGVYKEGIEAQVPLGAHLPSILEGAGLTYTIIGETEKLPLLENVILDAFENSRPHIALVSPKVWEASECC
AWQAAGMPIKPEMERTCRFSLTSGTLKPFMLRNDAICTLASELDDEITVTNLGVPCKELYACRDRELNFYMFGSMGLVSSIGLGL
ALRSEKTVITFDGDGSLLMNPNALLEIAKEAPKNLIIIALDNGAYGSTGSQETCALRYIDLEIFANACGIQNTAKVNSKEGVIEA
FRKFKAMRELSFIHVILKPGNTNAPNIPMSPEEATKRFKETLDVKKF SEQ ID NO: 26
Description: ComDE
Alias: sulfopyruvate decarboxylase
Length: 1164
Type: DNA -continued Amino Acid and Nucleotide Sequences Organism: *Methanosarcina acetivorans* str. C2A
>atgTACGTGGTAAACCCGGAAGAAAAAGTAATAGAAATCATGAAACAAACAGGTATTGATCTTGCTGCAACGCTTCCCTGCGAC
AGGATCAAGAACCTGCTTCCCCTGGTCTCGGAAAATTTTCCAGAAATCAAATTGACAAGGGAAGAAAACGGAGTGGGGATCTGTG
CAGGCATCTACCTTGCAGGCGGAAAGCCAATGATGCTTATCCAGAGTACGGGGCTCGGGAATATGATCAATGCCCTTGAATCCCT
GAACGTAACCTGTAAAATCCCCCTTCCGATCCTGGCTAGCTGGCGCGGTGTATATAAAGAAGGCATCGAAGCTCAGGTTCCCCTG
GGAGCCCACCTCCCTTCCATCCTTGAAGGGGCGGACTTACATACACAATAATTGGCGAAACTGAAAAGCTTCCTCTTCTTGAAA
ATGTAATTCTTGACGCCTTTGAAAACTCGAGACCCCATATTGCCCTGGTCTCCCCTAAAGTTTGGGAAGCTTCGGAATGCTGTGC
TTGGCAGGCTGCAGGGATGCCGATAAAGCCGGAAATTATGGAAAGGACCTGCAGGTTTTCCCTCACAAGCGGGACTCTCAAGCCT
TTTATGCTCAGAAACGATGCAATCTGCACCTTAGCCTCCGAGCTTGATGACGAAATTACCGTGACAAACCTCGGAGTCCCCTGCA
AGGAGCTTTACGCCTGCAGGGACAGGGAACTCAACTTCTATATGTTCGGCTCCATGGGGCTTGTTTCTTCAATAGGGCTTGGTCT
TGCCCTGCGCTCGGAAAAGACAGTTATCACTTTTGACGGGGACGGGAGCCTTTTAATGAACCCAAATGCCCTCCTTGAAATTGCA
AAAGAAGCCCCGAAAAACCTCATAATCATTGCCCTTGACAACGGCGCCTATGGTTCTACAGGTTCTCAGGAGACCTGCGCCCTCC
GCTACATTGACCTTGAAATCTTTGCAAACGCCTGCGGGATTCAGAACACCGCCAAAGTGAACAGCAAAGAAGGGGTGATAGAAGC
TTTCAGGAAATTCAAAGCCATGAGAGAGCTCTCCTTTATCCATGTGATCCTGAAACCCGGGAACACAAATGCTCCCAATATTCCT
ATGAGCCCTGAAGAAGCAACAAAACGCTTCAAAGAAACACTGGATGTAAAAAAGTTTtaa SEQ ID NO: 27
Description: Taurine-pyruvate aminotransferase (Tpa)
Length: 456
Type: Protein
Organism: *Rhodococcus opacus*
>MVVDVTELRARARRHLGPHFTRKDTWESDFPVFVRGEGSYLIDTEGDRFLDGLAGLFCVNIGHGRDDIAKAASEQIGTLAYASN
WGSAHIPAIEASALIADLAPGDLGTTFFVNSGSEAVETAVKFARQYHRSQGNPQRTKIISREMAYHGTTLGALSVTQLPKIKDPF
GPLLPGVRSVPNTLGYLGDCGPANELDCIAAIEAVIEEEGAETIAAVFAEPVQNGRGALVPPDGYWAALRALCDKHGILLVSDEV
ICSFGRLGHWFGHGLTGVVPDMITFAKGSTSGYAPLGGLIVREQLVRELYDSPKGGVFTHGATWGGHPVSTAVAVANITAMRDEN
VLGNVSARGPKLRSALDSLMSSHRCVKDVRGTGFFYAIELMADSDSGREFTEQESLTVLRKVLPEAFARTKVILRGDDRGATMLM
ISPPLVADDEVLSELLHGIDSMLTDIEKAIQP SEQ ID NO: 28
Description: Taurine-pyruvate aminotransferase (Tpa)
Length: 1371
Type: DNA
Organism: *Rhodococcus opacus*
>atgGTCGTGGACGTCACCGAATTGCGAGCACGGGCCCGCCGGCACCTCGGACCTCATTTCACCCGTAAGGACACCTGGGAAAGC
GACTTTCCGGTGTTCGTTCGTGGCGAGGGAAGCTATCTGATCGACACCGAGGGGGACCGTTTCCTCGACGGTCTGGCAGGCCTGT
TCTGTGTGAACATCGGTCACGGCCGCGACGACATCGCCAAGGCGGCGAGCGAGCAGATCGGGACGCTGGCGTACGCCTCCAACTG
GGGCAGCGCCCACATTCCCGCGATCGAGGCGTCCGCGCTCATCGCGGACCTGGCGCCCGGTGATCTCGGGACGACCTTCTTCGTC
AACTCGGGTTCCGAGGCCGTGGAGACGGCCGTCAAGTTCGCCCGGCAGTACCACCGCAGCCAGGGCAACCCGCAGCGCACCAAGA
TCATCAGCCGCGAGATGGCGTATCACGGAACCACTCTCGGCGCCCTCTCGGTGACACAGCTGCCCAAGATCAAAGACCCGTTCGG
ACCGCTGCTGCCCGGGGTCCGCTCCGTACCCAACACCCTCGGTTACCTCGGCGACTGCGGCCCGGCGAACGAGCTCGACTGCATC
GCCGCGATCGAAGCCGTCATCGAGGAAGAGGGCGCCGAGACCATCGCCGCCGTGTTCGCCGAGCCGGTTCAGAACGGGCGCGGCG
CCCTCGTCCCGCCGGACGGATACTGGGCCGCGCTGCGCGCGCTGTGCGACAAGCACGGGATCCTGCTGGTCTCCGACGAGGTGAT
CTGCTCGTTCGGCCGCCTCGGACACTGGTTCGGGCACGGGCTGACCGGTGTGGTTCCCGACATGATCACGTTCGCGAAGGGCTCC
ACGTCCGGATACGCGCCGCTCGGCGGCCTGATCGTGCGTGAGCAGCTGGTTCGCGAGCTCTACGACTCGCCCAAGGGCGGCGTGT
TCACGCACGGCGCGACGTGGGGCGGACACCCGGTGTCGACTGCGGTGGCGGTCGCGAACATCACCGCGATGCGCGACGAGAACGT
GCTGGGCAACGTCTCCGCGCGCGGCCCGAAGTTGCGGTCGGCACTCGACTCGCTGATGAGCTCGCACCGCTGCGTCAAGGACGTG
CGCGGCACCGGCTTCTTCTACGCGATCGAGTTGATGGCCGACAGCGACAGCGGCCGCGAGTTCACCGAGCAGGAGTCGCTGACGG
TGTTGCGCAAGGTGCTGCCGGAGGCGTTCGCCCGCACCAAGGTGATCCTCCGCGGCGACGACCGCGGTGCCACGATGCTGATGAT
TTCGCCGCCACTCGTCGCCGACGACGAGGTGCTCTCGGAACTGCTCCACGGAATCGACAGCATGCTCACCGACATCGAAAAGGCA
ATCCAGCCGtag SEQ ID NO: 29
Description: gamma-glutamyltransferase/glutathione hydrolase/gamma-glutamyl-transpeptidase
Alias: MEXT_1030
Length: 625
Type: Protein
Organism: *Methylobacterium extorquens* PA1
>MSSRPHRRSSFSATFAKRQRRHPEPFSACGKSARLRRILSAHPGPSAILREPVARSRNAGGARWRGARQLPFAPTRGPDPASRP
VRSQVSSESVMPDTPVFAHAAVAAPHALAASAGQNVLAQGGNAIEAMVAMAAAIAVVYPHMNGIGGDGFWLIRERNGRVRGIEAC
GPAGQLATRARYREKELDAIPSRGPDAAVTVAGTVGGWRLALDMARAFGGRLPLDTILADAIRHARAGCPVSASEARYVPKELDT
LHDAPNFAATYLDDGKPYAAGAIRAQPKLADTLAQLAHAGLDDFYRGDIGREIASDLERLGAPVTRADLTAYAAKERAPLTLRRR
DATLYNFPPPTQGLAALIILGIFDRLNIAEPESTAHYHGLIEATKRAFAIRDRFVTDFDRLKGDPAAFLDPRRLDREAALIDMRR
AASIPVRSGEGDTVWMGAIDNDGMAVSFIQSVYWEYGSGTVLPGTGICWQNRGMSFSLDANAVNPLEPGRRPFHTLIPALAAFDD
GRVMSYGSMGGDGQPQFQAQIFTRYADYGMSVADAVDAPRLLYGRTWGAESLSVKVEDRFDPACIAALRRLGHDIEELGGAYIDS
LGHAGMLVRHVKDGRIEATHDPRSDGGAAGL SEQ ID NO: 30
Description: gamma-glutamyltransferase/glutathione hydrolase/gamma-glutamyl-transpeptidase
Alias: MEXT_1030
Length: 1878
Type: DNA
Organism: *Methylobacterium extorquens* PA1
>atgTCATCCCGCCCGCACCGGCGCAGTTCCTTTTCTGCAACATTTGCAAAAAGGCAGAGGCGCCACCCGGAACCATTTTCGGCT
TGTGGGAAATCCGCACGTCTCCGACGCATCCTGAGCGCGCATCCAGGGCCATCTGCGATCCTGCGGGAGCCGGTCGCGCGATCGC
GGAATGCCGGGGGTGCGCGGTGGCGGGGAGCACGGCAGTTGCCCTTCGCGCCGACGCGTGGTCCTGATCCTGCCTCTCGGCCCGT -continued

| Amino Acid and Nucleotide Sequences |
|---|

CCGATCTCAGGTTTCGTCAGAGTCCGTCATGCCCGACACGCCCGTCTTCGCCCATGCGGCCGTTGCCGCCCCCCACGCGCTGGCG
GCTTCGGCCGGTCAGAACGTACTGGCGCAGGGCGGCAACGCCATCGAGGCGATGGTCGCGATGGCCGCCGCCATCGCGGTGGTCT
ACCCGCACATGAACGGCATCGGCGGCGACGGCTTCTGGCTGATCCGCGAGCGGAACGGCCGCGTGCGCGGCATCGAGGCCTGCGG
ACCGGCCGGGCAGCTCGCGACCCGCGCCCGCTACCGGGAGAAGGAGCTCGACGCGATCCCCTCCCGCGGCCCCGACGCGGCAGTG
ACGGTGGCGGGCACCGTCGGCGGCTGGCGCCTCGCGCTCGACATGGCGCGCGCCTTCGGCGGCCGGCTCCCCCTCGATACGATTC
TGGCCGACGCCATCCGCCACGCTCGCGCAGGCTGCCCGGTCTCGGCCTCGGAAGCGCGCTACGTGCCAAAGGAACTCGACACGCT
GCACGACGCGCCGAATTTCGCTGCGACCTATCTCGATGACGGCAAGCCCTACGCGGCGGGCGCGATCCGGGCGCAGCCCAAGCTC
GCCGACACCCTGGCCCAGCTCGCCCATGCCGGGCTCGACGACTTCTACCGCGGCGATATCGGCCGCGAGATCGCCAGCGATCTGG
AACGTCTCGGCGCCCCCGTTACCCGCGCCGACCTCACCGCCTACGCGGCCAAGGAGCGGGCACCGCTGACCCTGCGGCGGCGCGA
CGCCACGCTCTACAACTTCCCGCCGCCGACCCAGGGCCTCGCGGCGCTGATCATCCTCGGGATCTTCGACCGGCTGAACATCGCC
GAGCCGGAGAGCACCGCGCATTATCACGGGCTGATCGAGGCGACGAAGCGCGCCTTCGCCATCCGCGACCGCTTCGTCACCGATT
TCGACCGCCTGAAGGGCGACCCCGCCGCCTTCCTCGATCCGAGGCGCCTCGACCGCGAGGCGGCCCTGATCGACATGCGGCGTGC
CGCGAGCATCCCGGTCCGCTCGGGCGAGGGCGACACCGTCTGGATGGGCGCGATCGACAACGACGGCATGGCCGTCTCCTTCATC
CAGTCGGTCTACTGGGAGTACGGCTCCGGCACGGTGCTGCCGGGAACCGGCATCTGCTGGCAGAACCGCGGCATGTCGTTCTCGC
TCGACGCGAACGCGGTGAACCCGCTGGAACCGGGCCGGCGCCCGTTCCACACCCTGATCCCGGCGCTGGCCGCCTTCGATGACGG
CCGGGTCATGTCCTACGGCTCCATGGGCGGTGACGGGCAGCCGCAGTTCCAGGCGCAGATCTTCACCCGCTACGCCGATTACGGG
ATGTCGGTGGCCGATGCGGTGGACGCGCCGCGCCTGCTCTACGGCCGCACCTGGGGCGCCGAGTCGCTGAGTGTGAAGGTCGAGG
ACCGCTTCGATCCGGCCTGCATCGCGGCGCTCCGGCGCCTGGGCCACGACATCGAGGAGCTGGGCGGCGCCTATATCGACTCGCT
GGGCCATGCCGGCATGCTGGTGCGCCATGTCAAAGACGGGCGGATCGAAGCGACGCACGATCCGCGCTCCGATGGCGGCGCGGCG
GGGCTTtga SEQ ID NO: 31
Description: PAPSS1-Bifunctional 3'-phosphoadenosine 5'-phosphosulfate synthase 1
Alias: E1C8P2
Length: 624
Type: Protein
Organism: *Gallus gallus*
>MELPESQCKKAKLSNRVPNWGMQRATNVTYQAHHVSRNKRGQVVGTRSGFRGCTVWLTGLSGAGKTTVSMALEEYLVCHGIPCY
TLDGDNIRQGLNKNLGFTPEDREENVRRIAEVAKLFADAGLVCITSFISPYAQDRNNARRIHEGASLPFFEVFVDAPLHVCEQRD
VKGLYKKARAGEIKGFTGIDSEYEKPEAPELVLKTDSCDVNDCVQQVVELLQERDIVPVDASYEVKELYVPENKLKLAKTDAESL
LTLEINKVDMQWVQVLAEGWATPLSGFMREREYLQCLHFDCLLDGGVINLSVPIVLTATQEDKERLDGCTAIALVYEGRRVAILR
NPEFYEHRKEERCARQWGTTCKDHPYIKMVMEQGNWLVGGDLQVLDRIYWNDGLDQYRLTPAELRQKFKEMNADAVFAFQLRNPV
HNGHALLMQDTHKQLLERGYRRPVLLLHPLGGWTKEDDVPLMWRMKQHAAVLEEGVLNPETTVVAIFPSPMMYAGPTEVQWHCRS
RMVAGANFYIVGRDPAGMPHPGTGKDLYEPTHGAKVLTMAPGLRALEIVPFRVAAYNKKKKSMDYYDSEHHEDFEFISGTHMRKL
AREGQNPPEGFMAPKAWTVLFEYYKSLEKA SEQ ID NO: 32
Description: PAPSS1-Bifunctional 3'-phosphoadenosine 5'-phosphosulfate synthase 1
Alias: E1C8P2
Length: 1875
Type: DNA
Organism: *Gallus gallus*
>ATCGAGCTGCCTGAGAGCCAGTGCAAGAAAGCGAAGCTGAGCAACAGGGTGCCGAACTGGGGAATGCAGAGGGCAACCAATGTT
ACCTACCAAGCTCATCATGTCAGCCGAAATAAGAGAGGCCAAGTGGTAGGAACAAGAAGTGGTTTCCGTGGATGCACAGTCTGGT
TAACAGGTCTATCTGGTGCTGGGAAGACCACAGTTAGCATGGCCCTGGAGGAGTATTTAGTATGCCATGGCATTCCATGCTACAC
GTTGGATGGTGACAATATTCGCCAAGGCCTTAATAAGAATCTGGGTTTCACTCCAGAAGATAGAGAAGAAAACGTCCGTCGGATT
GCTGAGGTTGCTAAACTGTTTGCAGATGCTGGTTTGGTGTGCATCACTAGTTTCATCTCTCCTTATGCTCAGGATCGTAATAATG
CTAGACGAATTCATGAAGGGGCCAGCTTGCCTTTTTTTGAAGTATTTGTGGATGCTCCTTTGCATGTCTGTGAACAAAGAGATGT
TAAGGGACTGTATAAGAAAGCCAGAGCTGGAGAAATTAAAGGCTTTACTGGGATTGACTCTGAGTATGAAAAACCAGAAGCCCCA
GAGCTTGTGCTGAAAACTGATTCCTGTGATGTGAACGATTGTGTACAACAAGTTGTGGAACTTCTTCAAGAGAGGGACATCGTAC
CAGTAGATGCCTCGTATGAGGTGAAAGAGCTTTATGTGCCAGAAAACAAACTGAAGTTGGCTAAAACTGATGCTGAGTCTCTGTT
AACCTTGGAAATAAATAAGGTGGATATGCAGTGGGTGCAAGTGTTGGCAGAAGGCTGGGCAACACCTCTGAGTGGCTTTATGAGA
GAGAGAGAATACCTGCAGTGCCTTCACTTTGACTGTCTCCTTGATGGGGGAGTCATTAATCTTTCAGTGCCTATAGTGCTAACAG
CTACACAGGAAGACAAGGAAAGACTGGATGGTTGTACAGCAATTGCATTAGTGTACGAGGGTCGCCGTGTGGCCATTCTCCGTAA
TCCAGAATTCTATGAGCATAGGAAAGAGGAACGCTGTGCGAGGCAGTGGGGAACAACATGCAAGGATCATCCTTACATAAAGATG
GTTATGGAGCAAGGGAACTGGCTTGTAGGTGGAGATTTACAGGTCCTTGATCGTATTTATTGGAATGATGGACTTGATCAGTACC
GTCTCACTCCAGCTGAACTAAGACAGAAGTTCAAGGAAATGAATGCTGATGCTGTCTTTGCATTCCAGTTACGCAACCCAGTGCA
CAATGGGCACGCACTTTTAATGCAGGATACTCATAAGCAGCTTTTGGAACGTGGCTACAGGCGTCCAGTTTTGCTCTTGCATCCA
CTTGGAGGCTGGACAAAGGAGGACGACGTTCCTCTCATGTGGCGCATGAAACAGCATGCTGCAGTACTGGAGGAGGGAGTCTTGA
ATCCAGAAACAACGGTAGTGGCTATATTCCCCTCCCCCATGATGTATGCTGGACCAACGGAGGTTCAGTGGCACTGCAGATCACG
GATGGTTGCAGGTGCTAACTTCTACATTGTGGGGCGAGATCCTGCAGGGATGCCGCACCCTGGTACTGGGAAAGATCTGTATGAA
CCAACCCATGGTGCCAAAGTGTTGACAATGGCCCCAGGCCTCCGAGCACTGGAAATTGTACCTTTCAGGGTTGCGGCTTATAACA
AGAAAAAGAAGTCCATGGACTACTATGACTCTGAGCACCATGAAGACTTTGAATTTATATCGGGGACCCACATGCGCAAGCTGGC
TCGAGAAGGACAAAACCCACCGGAAGGCTTCATGGCTCCTAAGGCTTGGACTGTGCTGACAGAATACTACAAATCCTTGGAGAAG
GCTTAG SEQ ID NO: 33
Description: p3MDO
Alias: Q9I0N5, PA2602
Length: 201
Type: Protein
Organism: *Pseudomonas aeruginosa* PAO1
>MSSILRLDRLRQFIGELATLLDSRPDESTLLAQAHPLLAELVHQDDWLPEDCARPDPQRYQQYLLHVDSRQRFSVVSFVWGPGQ
ITPVHDHRVWGLIGMLRGAEYSQPYAFDAGGRPHPSGARRRLEPGEVEALSPRIGDVHQVSNAFSDRTSISIHVYGANIGAVRRA
VFSAEGEEKPFISGYSNSRLPNIWDLSKENPA

SEQ ID NO: 34

-continued

| Amino Acid and Nucleotide Sequences |
|---|

Description: p3MDO
Alias: Q9I0N5, PA2602
Length: 606
Type: DNA
Organism: *Pseudomonas aeruginosa* PAO1
>atgTCATCCATCCTGCGCCTCGACCGCCTGCGCCAGTTCATCGGCGAGCTGGCGACACTGCTCGACAGCCGTCCCGACGAATCC
ACCCTGCTCGCCCAAGCCCACCCCCTGCTGGCCGAGCTGGTGCACCAGGACGACTGGCTGCCGGAAGACTGCGCCCGCCCCGATC
CACAGCGCTACCAACAGTACCTGCTGCATGTCGACTCACGGCAGCGCTTCTCGGTGGTCAGCTTCGTCTGGGGGCCGGGCCAGAT
CACACCGGTACACGATCATCGGGTCTGGGGCCTGATCGGCATGCTCCGCGGGGCCGAATACTCGCAGCCGTACGCCTTCGATGCG
GGGGGGCGTCCGCATCCCAGCGGAGCCCGTCGACGCCTGGAGCCCGGCGAGGTCGAAGCGCTGTCGCCACGCATTGGCGACGTGC
ACCAGGTGAGCAACGCCTTCAGCGACCGCACATCCATCAGTATCCACGTCTACGGCGCCAATATCGGTGCGGTACGGCGTGCCGT
GTTCAGCGCCGAAGGTGAGGAAAAACCCTTCATTTCCGGCTATTCCAACAGCCGCTTGCCCAATATCTGGGACCTGTCGAAAGAG
AACCCCGCAtga SEQ ID NO: 35
Description: Mammalian CDO
Alias: P21816, CDO_Rat
Length: 200
Type: Protein
Organism: *Rattus norvegicus*
MERFELLKPRTLADLIRILHELFAGDEVNVEEVQAVLEAYESNPAEWALYAKFDQYRYTRNLVDQGNGKFNLMILCWGEGHGSSI
HDHTDSHCFLKLLQGNLKETLFDWPDKKSNEMIKKSERTLRENQCAYINDSIGLHRVENVSHTEPAVSLHLYSPPFDTCHAFDQR
TGHKNKVTMTFHSKFGIRTPFTTSGSLENN SEQ ID NO: 36
Description: Mammalian CDO
Alias: P21816, M35266.1, CDO_Rat
Length: 603
Type: DNA
Organism: *Rattus norvegicus*
>ATGGAACGGACCGAGCTGCTGAAGCCCCGGACCCTGGCCGACCTCATCCGAATCTTGCATGAGCTCTTCGCCGGGGACGAAGTC
AATGTGGAGGAGGTGCAGGCTGTGCTGGAAGCCTACGAGAGCAATCCTGCCGAGTGGGCTTTGTATGCCAAATTCGATCAATACA
GGTATACCCGAAACCTTGTGGATCAAGGAAATGGGAAGTTTAATCTGATGATTCTGTGCTGGGGTGAAGGGCATGGCAGCAGTAT
TCACGATCACACGGACTCCCACTGCTTTTTGAAGCTGCTGCAAGGAAATCTAAAGGAGACATTGTTTGACTGGCCTGACAAGAAA
TCCAACGAGATGATCAAGAAGTCTGAAAGAACTTTGAGGGAAAATCAGTGTGCCTACATTAATGATTCTATTGGCTTACATCGAG
TAGAGAACGTCAGCCACACAGAGCCTGCTGTGAGCCTTCACTTGTACAGTCCACCTTTCGATACATGCCATGCCTTTGACCAACG
AACAGGGCATAAAAACAAAGTCACCATGACATTCCACAGCAAATTTGGAATCAGAACTCCATTTACAACTTCAGGTTCACTGGAG
AACAACTAA SEQ ID NO: 37
Description: cuyA
Length: 339
Type: Protein
Organism: *Ruegeria pomeroyi*
>MELARYPRRFIAHLPTPLERLDRLTAELGGPEIWIKRDDCTGLSTGGNKTRKLEFLMAEAELQGADMVMTQGATQSNHARQTAA
FAAKLGMDCHILLEDRTGSNNANYNNNGNVLLDHLHGATTEKRPGSGLDMNAEMEKVAEKFRADGRKVYTIPGGGSNPTGALGYV
NCAFEMLNQFNERGLKVDHIVHATGSAGTQAGLITGLQAMNAQIPLLGIGVRAPKPKQEENVYNLACATAEKLGCPGVVAREDVV
ANTDYVGEGYGIPFESGLEAIRMFAELEAILLDPVYSAKGAAGFIDLIRKGHFKKGERVVFLHTGGAVALFGYDNAFDYSGRWVA SEQ ID NO: 38
Description: cuyA
Length: 1020
Type: DNA
Organism: *Ruegeria pomeroyi*
>atgCATCTTGCCCGCTATCCCCGCCGCTTCATCGCCCATCTGCCGACGCCGCTGGAACGGCTGGACCGGCTGACCGCCGAACTG
GGCGGGCCCGAGATCTGGATCAAGCGCGACGACTGCACCGGCCTGTCCACCGGCGGCAACAAGACCCGCAAGCTGGAATTCCTGA
TGGCCGAGGCCGAGCTGCAAGGCGCTGACATGGTGATGACGCAGGGCGCGACCCAGTCCAACCATGCCCGCCAGACCGCCGCATT
CGCCGCCAAGCTGGGCATGGATTGCCATATCCTGCTCGAGGACCGGACCGGCTCGAACAACGCCAACTACAACAACAACGGCAAC
GTTCTGCTCGACCATCTGCATGGCGCCACCACTGAAAAGCGCCCCGGCAGCGGTCTGGACATGAATGCCGAGATGGAAAAGGTGG
CCGAGAAGTTCCGCGCCGACGGGCGCAAGGTCTATACCATCCCCGGCGGCGGCTCGAACCCGACCGGCGCGCTGGGATATGTCAA
CTGCGCTTTCGAGATGCTGAACCAGTTCAATGAGCGCGGGCTGAAGGTGGACCATATCGTGCATGCCACCGGCAGCGCGGGCACC
CAGGCAGGGCTGATCACCGGGCTTCAGGCGATGAACGCTCAGATCCCGCTCTTGGGCATCGGCGTGCGTGCGCCCAAGCCCAAGC
AGGAAGAGAATGTCTATAACCTGGCCTGCGCCACCGCCGAGAAGCTGGGTTGCCCCGGTGTCGTCGCGCGCGAGGACGTGGTGGC
CAATACCGACTATGTCGGCGAAGGCTATGGCATCCCGACCGAAAGCGGGCTGGAGGCGATCCGCATGTTCGCCGAGCTTGAGGCG
ATCCTGCTTGACCCGGTCTATTCGGCCAAGGGCGCGGCTGGCTTCATCGACCTGATCCGCAAGGGTCATTTCAAAAAGGGCGAGC
GGGTGGTGTTCCTGCATACCGGCGGCGCTGTGGCGCTGTTCGGCTATGACAACGCCTTTGACTATTCGGGACGCTGGGTGGCCta
a SEQ ID NO: 39
Description: promoter P_tac
Length: 74
Type: DNA
Organism: *Methylobacterium extorquens*
>GGTCGACTCTAGTTCTGAAATGAGCTGTTGACAATTAATCATCGGCTCGTATAATGTGTGGAGGCCTCATATGT SEQ ID NO: 40
Description: promoter P_tacA Amino Acid and Nucleotide Sequences Length: 80
Type: DNA
Organism: *Methylobacterium extorquens*
>GGTCGACTCTAGTAAGAAATCTGAAATGAGCTGTTGACAATTAATCATCGGCTCGTATAATGTGTGGAGGCCTCATATGT SEQ ID NO: 41
Description: promoter P_Lac
Length: 33
Type: DNA
Organism: *Methylobacterium extorquens*
>TTTACACTTTATGCTTCCGGCTCGTATGTTGTG SEQ ID NO: 42
Description: promoter P_R
Length: 109
Type: DNA
Organism: Bacteriophage 16-3
>CAACAACTTATACCATGGCCTACAAAAAGGCAAACAATGGTACTTGACGACTCATCACAACAATTGTAGTTGTAGATTGTAAAG
ATCTAGGGAGAGACCCCGAGGTACC SEQ ID NO: 43
Description: promoter PmxaF
Length: 101
Type: DNA
Organism: *Methylobacterium extorquens*
>CGACACTACGCCTTGGCACTTTTAGAATTGCCTTATCGTCCTGATAAGAAATGTCCGACCAGCTAAAGACATCGCGTCCAATCA
AAGCCTAGAAAATATAG SEQ ID NO: 44
Description: ADO (2-aminoethanol dioxygenase)
Alias: Gm237, NP_001005419.2
Length: 256
Type: Protein
Organism: *Mus musculus*
>MPRDNMASLIQRIARQACLTFRGSSTGSEGPAPGFPENLSLLKSLLTQVRAEDLNIAPRKALPQPLPRNLPPVTYMEIYEFEGF
SLGVFLLKSGTCIPLHDHPGMEGMLKVLYGTVRISCMDKLDTGAGHRRPPPEQQFEPPLQPLEREAVRPGVLRSRAEYYEASGPC
VLTPHRDNLHQIDAVDGPAAFLDILAPPYDPEDGRDCHYYRVVEPIRPKEASGSACDLPREVWLLETPQADDFWCEGEPYPGPKV
LP SEQ ID NO: 45
Description: ADO (2-aminoethanol dioxygenase)
Alias: Gm237, NP_001005419.2
Length: 771
Type: DNA
Organism: *Mus musculus*
>ATGCCCCGCGACAACATGGCCTCCCTGATCCAGCGCATCGCTCGCCAGGCGTGTCTCACCTTCCGCGGCAGCTCGACGGGCTCC
GAAGGGCCGGCGCCGGGCTTCCCGGAGAACCTGAGCCTGCTCAAGAGCCTGCTGACCCAGGTGCGCGCCGAGGACCTCAACATCG
CGCCGCGCAAGGCGCTGCCGCAGCCGCTGCCCCGCAACCTCCCGCCGGTCACCTACATGCACATCTACGAGACGGAGGGCTTCAG
CCTGGGCGTGTTCCTGCTCAAGAGCGGCACGTGCATCCCGCTGCACGACCACCCGGGCATGCACGGTATGCTCAAGGTGCTGTAC
GGCACGGTCCGCATCAGCTGCATGGACAAGCTGGACACGGGGGCCGGGCATCGGCGGCCGCCGCCAGAGCAGCAGTTCGAGCCCC
CGCTGCAGCCCTTGGAGCGGGAGGCCGTGCGACCGGGCGTGCTGCGTTCCCGGGCCGAGTACACCGAGGCCAGTGGGCCCTGCGT
GCTCACTCCACACCGGGACAACCTGCACCAGATTGATGCCGTGGACGGGCCAGCTGCCTTCCTGGACATCCTGGCCCCACCCTAC
GACCCGGAGGACGGCCGGGACTGCCACTATTACCGTGTAGTGGAGCCCATCAGACCCAAGGAGGCTTCCGGCTCTGCCTGCGACC
TTCCCCGAGAAGTGTGGCTCCTGGAGACACCACAGGCCGACGACTTCTGGTGCGAGGGAGAGCCCTATCCAGGCCCCAAGGTCCT
ACCTTGA SEQ ID NO: 46
Description: cystathionine gamma-lyase
Alias: mccB, B5U27250
Length: 379
Type: Protein
Organism: *Bacillus subtilis* 168
>MKKKTLMIHGGITGDEKTGAVSVPIYQVSTYKQPKAGQHTGYEYSRTANPTRTALEALVTELESGEAGYAFSSGMAAITAVMML
FNSGDHVVLTDDVYGGTYRVMTKVLNRLGIESTFVDTSSREEVEKAIRPNTKAIYIETPTNPLLKITDLTLMADIAKKAGVLLIV
DNTFNTPYFQQPLTLGADIVLHSATKYLGGHSDVVGGLVVTASKELGEELHFVQNSTGGVLGPQDSWLLMRGIKTLGLRMEAIDQ
NARKIASFLENHPAVQTLYYPGSSNHPGHELAKTQGAGFGGMISFDIGSEERVDAFLGNLKLFTIAESLGAVESLISVPARMTHA
SIPRERRLELGITDGLIRISVGIEDAEDLLEDIGQALENI SEQ ID NO: 47
Description: cystathionine gamma-lyase
Alias: mccB, BSU27250
Length: 1140
Type: DNA
Organism: *Bacillus subtilis* 168
>atgAAGAAAAAAACATTGATGATACATGGCGGAATCACAGGTGATGAGAAAACAGGCGCAGTTTCCGTGCCGATTTATCAAGTA
AGCACGTACAAGCAGCCGAAAGCAGGGCAGCATACAGGCTACGAGTATTCAAGAACGGCCAATCCGACTCGAACCGCTCTCGAAG
CACTTGTGACAGAACTGGAAAGCGGGGAAGCAGGCTATGCGTTCAGCTCAGGAATGGCTGCCATTACAGCGGTTATGATGCTGTT -continued Amino Acid and Nucleotide Sequences TAACAGCGGAGATCATGTCGTGTTGACTGATGATGTGTACGGCGGAACATATCGCGTGATGACAAAGGTGCTTAACCGTCTTGGC
ATTGAATCAACATTTGTTGATACGAGCAGCAGGGAAGAAGTTGAAAAAGCGATTCGCCCTAATACAAAAGCAATTTATATTGAAA
CACCGACAAACCCGTTGCTCAAAATCACCGACCTGACGCTCATGGCTGATATCGCAAAAAAAGCGGGTGTTCTGCTTATCGTAGA
CAATACCTTTAATACTCCTTATTTTCAACAGCCGCTTACTTTAGGCGCTGATATCGTACTGCACAGTGCGACAAAATATCTTGGC
GGACACAGTGATGTCGTCGGAGGTTTAGTTGTGACAGCTTCGAAAGAGCTTGGAGAAGAGCTGCATTTTGTGCAAAACTCCACAG
GCGGCGTGCTCGGCCCTCAAGATTCCTGGCTGTTAATGAGAGGAATCAAAACGTTGGGACTCAGAATGGAAGCGATCGATCAAAA
TGCGCGGAAAATCGCAAGCTTTCTTGAGAATCACCCTGCTGTCCAAACGTTATATTACCCTGGTTCTTCAAATCATCCCGGACAT
GAGCTTGCAAAAACGCAAGGAGCGGGCTTCGGCGGCATGATCTCCTTTGATATTGGCAGTGAAGAACGGGTTGATGCGTTTTTAG
GAAATCTGAAACTGTTTACCATTGCTGAAAGCCTGGGGGCGGTTGAAAGCTTAATTTCTGTTCCTGCAAGAATGACACATGCCTC
TATTCCGAGAGAACGCCGGCTTGAGCTCGGCATTACGGACGGCTTGATCAGAATTTCTGTAGGAATTGAAGATGCGGAAGACTTG
TTGGAAGATATCGGCCAAGCGCTTGAAAATATAtaa SEQ ID NO: 48
Description: Sulfoacetaldehyde acetyltransferase
Alias: Xsc
Length: 593
Type: Protein
Organism: *Paracoccus denitrificans*
>MRMTPEESFVKTLQLHGIEHAFGIIGSAMMPVSDLFPRAGITFWDCAHETNAGMMADGFTRSTGRMSMAIAQNGPGVTGFVTPV
KTAYWNHTPLLLVTPQAANRTIGQGGFQEMEQMRIFADCVCYQEEVRDPSRIPEVLNRVIMQAWRNSAPAQINIPRDFWTQVIDV
DLPQVVGFERPAGGERAVAEAARLLSEARFPVILSGAGVVLSGAIPDLVGLAERLDAPVCSNYQHNDSFPGSHPLAMGPLGYNGS
KAAMEIIARADVVLALGTRLNPFSTLPGYGIDYWPKDARIIQVDINADRIGLTKKVAVGIQGDAAKVARGILAQLAPAAGDAGRQ
ERRDLVAQTRSRWAQELSSLDHEEDDPGPEWNEQARARDAGLMSPRQAWRAIMQAVPKEATVSSDIGNNCAIGNAYPSFEAGRKY
LAPGLFGPCGYGFPAILGAKIGNPEVPVIGFAGDGAFGISMNEMTACGREDWPAITMVIFRNYQWGAEKRNTTLWYDNNFVGPEL
DRDTSYAKIAQACGLVGVQVRSQEELTAALHDAVERQMQGRETTFIEVLLNQELGEPFRRDAMKKPVAVAGIDPADMRPQQGAA SEQ ID NO: 49
Description: Sulfoacetaldehyde acetyltransferase
Alias: Xsc
Length: 1782
Type: DNA
Organism: *Paracoccus denitrificans*
>atgCGAATGACGACTGAGGAGTCTTTTGTCAAAACCCTTCAATTGCACGGGATCGAGCATGCCTTTGGCATTATCGGCTCTGCG
ATGATGCCTGTTTCGGACCTGTTTCCGCGGGCCGGGATCACGTTCTGGGACTGTGCGCATGAGACGAATGCCGGGATGATGGCGG
ACGGTTTCACGCGCTCGACGGGGCGGATGTCGATGGCGATCGCGCAGGAACGGTCCCGGGGTGACGGGGTTCGTGACGCCGGTCA
AGACGGCCTACTGGAACCACACGCCCTTGCTTCTGGTGACGCCGCAGGCGGCGAACCGGACCATCGGGCAGGGCGGTTTCCAGGA
GATGGAGCAGATGCGCATCTTCGCCGATTGCGTCTGCTACCAGGAGGAGGTGCGCGACCCGAGCCGCATCCCCGAGGTTCTGAAC
CGGGTGATCATGCAGGCCTGGCGCAACTCGGCGCCGGCGCAGATCAACATCCCGCGCGACTTCTGGACCCAGGTGATCGACGTGG
ATCTGCCGCAGGTGGTGGGCTTCGAGCGGCCGGCGGGCGGCGAGCGGGCGGTGGCCGAGGCGGCCAGGCTGCTCTCCGAGGCGCG
GTTCCCGGTGATCCTGTCGGGCGCCGGCGTGGTGCTGTCGGGCGCCATTCCCGACCTGGTCGGGCTGGCCGAGCGGCTGGATGCG
CCGGTCTGCTCGAACTACCAGCACAATGACAGCTTTCCGGGCAGCCATCCGCTGGCCATGGGGCCGCTGGGCTACAACGGCTCGA
AGGCGGCGATGGAGATCATCGCCCGGGCCGACGTGGTGCTGGCGCTGGGGACGCGGCTCAATCCGTTCTCGACCCTGCCGGGCTA
CGGCATCGACTACTGGCCGAAGGATGCCAGGATCATCCAGGTCGACATCAATGCCGACCGCATCGGGCTGACCAAGAAGGTGGCG
GTGGGCATCCAGGGCGATGCGGCCAAGGTGGCGCGCGGCATCCTGGCGCAGCTGGCCCCGGCCGCCGGCGATGCCGGGCGGCAGG
AGCGCCGCGACCTGGTGGCGCAGACCCGGTCCCGCTGGGCGCAGGAACTGTCGAGCCTGGACCACGAGGAGGACGATCCCGGCAC
CGAATGGAACGAGCAGGCGCGGGCCCGCGACGCCGGTCTGATGAGCCCGCGCCAGGCCTGGCGGGCGATCATGCAGGCGGTGCCG
AAGGAGGCGATCGTCAGCTCGGACATCGGCAACAACTGCGCCATCGGCAATGCCTATCCCAGCTTCGAGGCGGGGCGGAAATACC
TGGCGCCGGGGCTGTTCGGTCCCTGCGGCTACGGCTTCCCGGCGATCCTGGGGGCCAAGATCGGCAATCCGGAGGTGCCGGTGAT
CGGCTTTGCCGGCGACGGCGCCTTCGGGATCTCGATGAACGAGATGACCGCCTGCGGGCGCGAGGACTGGCCGGCGATCACCATG
GTGATCTTCCGCAACTACCAGTGGGGGGCGGAAAAGCGCAACACGACGCTGTGGTACGACAACAACTTCGTCGGCACCGAGCTCG
ACCGCGACACCTCCTATGCGAAGATCGCCCAGGCCTGCGGGCTGGTGGGCGTGCAGGTGCGCAGCCAGGAGGAGCTGACGGCGGC
GCTGCACGATGCGGTCGAGCGGCAGATGCAGGGCCGCGAGACCACCTTCATCGAGGTGCTCTTGAACCAGGAGCTGGGCGAGCCC
TTCCGCCGCGACGCGATGAAGAAGCCGGTGGCGGTGGCCGGCATCGACCCGGCCGACATGCGCCCGCAGCAGGGCGCCGCCtga SEQ ID NO: 50
Description: CDO
Alias: cdoA, BSU31140, O32085, CDO_*Bacillus*
Length: 486
Type: DNA
Codon Optimization: *E. coli*
>ATGGAACTGTATGAATGTATTCAGGATATTTTTGGTGGTCTGAAAAATCCGAGCGTTAAAGATCTGGCAACCAGCCTGAAACAG
ATTCCGAATGCAGCAAAACTGAGCCAGCCGTATATTAAAGAACCGGATCAGTATGCATATGGTCGTAATGCAATTTATCGTAATA
ATGAACTGGAAATTATTGTTATTAATATTCCGCCGAATAAAGAAACCACCGTTCATGATCATGGTCAGAGCATTGGTTGTGCAAT
GGTTCTGGAAGGTAAACTGCTGAATAGCATTTATCGTAGCACCGGTGAACATGCAGAACTGAGCAATAGCTATTTTGTTCATGAA
GGTGAATGTCTGATTAGCACCAAAGGTCTGATTCATAAAATGAGCAATCCGACCAGCGAACGTATGGTTAGCCTGCATGTTTATA
GCCCGCCGCTGGAAGATATGACCGTTTTTGAAGAACAGAAAGAAGTTCTGGAAAATAGCTGA SEQ ID NO: 51
Description: Mammalian CDO
Alias: P21816, M35266.1, CDO_Rat
Length: 603
Type: DNA
Codon Optimization: *E. coli*
>ATGGAACGTACCGAACTGCTGAAACCGCGTACCCTGGCAGATCTGATTCGTATTCTGCATGAACTGTTTGCCGGTGATGAAGTT
AATGTTGAAGAAGTTCAGGCAGTTCTGGAAGCATATGAAAGCAATCCGGCAGAATGGGCACTGTATGCAAAATTTGATCAGTATC
GTTATACCCGTAATCTGGTTGATCAGGGTAATGGTAAATTTAATCTGATGATTCTGTGTTGGGGTGAAGGTCATGGTAGCAGCAT
TCATGATCATACCGATAGCCATTGTTTTCTGAAACTGCTGCAGGGTAATCTGAAAGAAACCCTGTTTGATTGGCCGGATAAAAAA -continued Amino Acid and Nucleotide Sequences AGCAATGAAATGATTAAAAAAAGCGAACGTACCCTGCGTGAAAATCAGTGTGCATATATTAATGATAGCATTGGTCTGCATCGTG
TTGAAAATGTTAGCCATACCGAACCGGCAGTTAGCCTGCATCTGTATAGCCCGCCGTTTGATACCTGTCATGCATTTGATCAGCG
TACCGGTCATAAAAATAAAGTTACCATGACCTTTCATAGCAAATTTGGTATTCGTACCCCGTTTACCACCAGCGGTAGCCTGGAA
AATAATTAA SEQ ID NO: 52
Description: MA_3297
Length: 1251
Type: DNA
Codon Optimization: *E. coli*
>ATGGGTCGTTTTATTCTGAAATGTCTGAAATGTGGTCGTGAATATAGCCAGGAATATCGTCTGACCTGTGAAAATGATGATAGC
TTTCTGCGTGCAGAATATCTGGAAAAAAAACTGGAACTGCGTAAACAGCCGGGTATTGGTCGTTTTCATAGCTGGCTGCCGGTTC
AGGAAGAACTGACCACCGAAGCAGGTCCGATTACCTATAAAAGCGAAGCACTGGCACGTGAACTGGGTCTGAGCAATCTGTATAT
TGGTTTTAGCGGTTATTGGCCGGAAAAAGGTGCATTTATTAAAACCTGTAGCTTTAAAGAACTGGAAGCACATCCGACCATGCAG
CTGCTGAAAGAAAGCGGTGGTAAAGCAATTGTTCTGGCAAGCGCAGGTAATACCGGTCGTGCATTTGCACATGTTAGCGCACTGA
CCGGTACCGATGTTTATATTGTTGTTCCGGATAGCGGTATTCCGAAACTGTGGCTGCCGGAAGAACCGACCGATAGCATTCATCT
GATTAGCATGACCCCGGGTAATGATTATACCGATGCAATTAATCTGGCAGGTCGTATTGCAAAACTGCCGGGTATGGTTCCGGAA
GGTGGTGCACGTAATGTTGCACGTCGTGAAGGTATGGGTACCGTTATGCTGGATGCAGCAGTTACCATTGGTAAAATGCCGGATC
ATTATTTTCAGGCAGTTGGTAGCGGTACCGGTGGTATTAGCGCATGGGAAGCAAGCCTGCGTCTGCGTGAAGATGGTCGTTTTGG
TAGCAAACTGCCGAAACTGCAGCTGACCCAGAATCTGCCGTTTGTTCCGATGTATAATGCATGGCAGGAAGGTCGTCGTGATATT
ATTCCGGAAATTGATATGAAAGATGCAAAAAAACGTATTGAAGAAACCTATGCAACCGTTCTGACCAATCGTGCACCGCCGTATA
GCGTTACCGGTGGTCTGTATGATGCACTGGTTGATACCGATGGTATTATGTATGCAGTTAGCAAAGAAGAAGCACTGGATGCAAA
AGCACTGTTTGAAAGCCTGGAAGGTATTGATATTCTGCCGCCGAGCGCAGTTGCAGCAGCAAGCCTGCTGAAAGCAGTTGAAGCA
GGTAATGTTGGTAAAGATGATACCATTCTGCTGAATATTGCCGGTGGTGGTTTTAAACGTCTGAAAGAAGATTTACCCTGTTTC
AGATTGAACCGGAAATTACCGTTAGCAATCCGGATGTTCCGCTGGAAGAACTGAAACTGTGA SEQ ID NO: 53
Description: CSAD
Alias: ref|WP_006454033.1
Length: 1467
Type: DNA
Codon Optimization: *E. coli*
>ATGTTTAAAGCAAGCAAATATTATAATCTGCTGCAGCAGCTGGAAAATTTTTTTAGCACCGCAAATAGCAGCAGCCTGCTGACC
AAACCGATTGATCCGAATGTTCTGAAAAGCCAGCTGAGCCTGGATCTGCCGAATGAAGGTAAACCGGTTGAAGAACTGCGTACCG
AAATTACCAGCTATCTGAATAATGCACTGAAAACCGCACATCCGAGCTATTTTAATCAGCTGTGGGGTGGTTTTAATAGCGCATG
TTTTATGGGTGATATGCTGGCAAGCGCAACCAATACCAGCATGTATACCTATGAAGTTGCACCGGCAGCAACCCTGATTGAACAG
GCACTGGTTACCAAAATGAGCGGTATTCTGGGTTTTAAAAGCGCAGATGGTCAGTTTACCACCGGTGGTAGCAATGGTAATCTGA
TGGCAATGGCAATTGCACGTCATCATGTTCTGCCGACCGTTAAACAGGATGGTATGACCAGCGGTCCGAAACTGGTTGCATTTGT
TAGCCGTGAAGCACATTATAGCTTTGATAAAGCAGCACATATTCTGGGTCTGGGTACCGAACAGCTGTGGAAAGTTCCGGTTGAT
AGCGATGGTCGTATGAAACCGGAAGCACTGAGCGAACTGGTTGATCGTGCACGTGTTCAGGGTAGCATTCCGTTTTTTGTTGCAG
GTACCGCAGGTACCACCGTTCGTGGTGCATTTGATCCGTTTGAAGAAATTAGCGCAATTGCACATCAGGAAAATCTGTGGTTTCA
TATTGATGGTGCATGGGGTGCAAGCGTTAGCCTGAGCGCAACCCATCGTCAGCTGATGGCCGGTGCAAATCAGGCAGATAGCCTG
GTTTGGGATGCACATAAAATGATGGGTATGACCCTGATGTGTAGCCTGCTGCTGGTTAAACAGCGTGGTCAGATGCTGCGTACCT
TTAGCACCGCAGGTACCGATTATCTGTTTCATGATGAAGTTAGCGCCGGTGAAGTTCCGACCGAAAGCAGCACCAGCAGCACCGA
ACTGCCGATTGAAGAACTGCCGACCGATTTTGGTCCGGCAACCATGCATTGTGGTCGTCGTGTTGATGCACTGAAACTGTGGCTG
GCATGGCGTCATCTGGGTGATCGTGGTTGGGAACGTCTGATTGATAGCTATTTTGAACTGGCACAGCGTGCAGAAACCATTATTG
ATAAACATCCGAGCCTGGAACTGGTTAGCAGCCGTCAGAGCGTTAATCTGTGTTTTCGTTATCTGCCGCAGAATAAACAGCAGGC
AGATGAACTGACCCTGAAAGTTCGTCAGGCACTGTGGGAAACCGGTACCGCAATGGTTAATTATGCACAGGTTGAAGGTAAAACC
GTTTTTCGTCTGGTTATTTGTAATAATCAGACCCGTAGCGAAGATATTGAACGTTTTTTTGAAGCACTGGTTGCAATTGCACGTC
GTCTGGAACAGGAAATGTGTTGA SEQ ID NO: 54
Description: CSAD
Alias: ref|WP_006454033.1
Length: 1467
Type: DNA
Codon Optimization: *M. extorquens*
>ATGTTCAAGGCCTCGAAGTACTACAACCTCCTCCAGCAGCTCGAGAACTTCTTCTCGACCGCCAACTCGTCGTCGCTCCTCACC
AAGCCGATCGACCCGAACGTCCTCAAGTCGCAGCTTTCGCTCGACCTCCCGAACGAGGGCAAGCCGGTCGAGGAGCTCCGCACCG
AGATCACCTCGTACCTCAACAACGCCCTCAAGACCGCCCACCCGTCGTACTTCAACCAGCTCTGGGGCGGCTTCAACTCGGCCTG
CTTCATGGGCGATATGCTCGCCTCGGCCACCAATACCTCGATGTACACCTACGAGGTCGCCCCGGCCGCCACCCTCATCGAACAG
GCCCTCGTCACCAAGATGTCGGGCATCCTCGGCTTCAAGTCGGCTGATGGCCAGTTTACCACCGGCGGTTCGAACGGCAACCTCA
TGGCCATGGCCATCGCCCGCCACCACGTTCTCCCGACCGTCAAGCAGGATGGTATGACCTCGGGCCCGAAGCTCGTCGCCTTTGT
CTCGCGCGAAGCCCATTACTCGTTCGACAAGGCCGCCCACATCCTCGGCCTCGGCACCGAGCAGCTTTGGAAGGTCCCGGTCGAC
TCGGATGGCCGCATGAAGCCGGAAGCTCTTTCGGAGCTCGTTGACCGCGCCAGAGTCCAAGGCTCGATCCCGTTTTTCGTCGCTG
GCACCGCCGGCACCACCGTCCGTGGTGCCTTCGATCCGTTCGAGGAGATCTCGGCCATTGCCCACCAGGAGAACCTCTGGTTCCA
CATTGATGGCGCCTGGGGCGCCAGCGTCTCGCTTTCGGCCACCCACCGCCAACTCATGGCTGGTGCCAACCAGGCCGATTCGCTT
GTCTGGGATGCCCACAAGATGATGGGCATGACCCTCATGTGCTCGCTCCTCCTCGTCAAGCAGCGTGGCCAGATGCTCCGCACCT
TCTCGACCGCTGGCACCGACTACCTCTTCCACGACGAGGTCAGTGCTGGCGAGGTCCCGACCGAATCGTCGACCAGTTCGACCGA
ACTCCCGATCGAAGAGCTTCCGACCGACTTCGGCCCGGCCACCATGCATTGCGGTCGTCGCGTCGATGCTCTTAAACTTTGGCTC
GCCTGGCGCCACCTCGGTGATCGTGGCTGGGAGCGCCTCATCGACTCGTACTTCGAGCTCGCCCAGCGTGCCGAAACCATCATCG
ACAAGCACCCGTCGCTCGAGCTCGTCTCGTCGCGCCAGTCGGTCAACCTCTGCTTCCGCTACCTCCCGCAGAACAAGCAACAGGC
CGACGAGCTCACCCTTAAGGTCCGCCAGGCCCTCTGGGAGACGGGCACCGCCATGGTCAACTACGCCCAGGTCGAAGGCAAGACC
GTTTTCCGCCTCGTCATCTGCAACAATCAGACCCGCTCGGAGGACATCGAGCGCTTCTTCGAGGCCCTCGTCGCCATCGCCCGCC
GCCTCGAGCAGGAGATGTGCTGA

SEQ ID NO: 55

-continued

Amino Acid and Nucleotide Sequences

Description: ComDE
Alias: sulfopyruvate decarboxylase
Length: 1164
Type: DNA
Codon Optimization: *M. extorquens*
>ATGTACGTCGTCAACCCGGAGGAGAAGGTCATCGAGATCATGAAGCAGACCGGCATCGACCTCGCCGCCACCCTCCCGTGCGAC
CGCATCAAGAACCTCCTCCCGCTCGTCTCGGAGAACTTCCCGGAGATTAAGCTCACCCGCGAGGAGAACGGTGTCGGCATCTGCG
CCGGTATCTACCTCGCCGGCGGCAAGCCGATGATGCTCATCCAGTCGACCGGCCTCGGCAACATGATCAACGCCCTCGAGTCGCT
CAACGTGACCTGCAAGATCCCGCTCCCGATCCTTGCCTCGTGGCGCGGCGTCTATAAGGAAGGCATCGAAGCCCAGGTCCCGCTC
GGTGCCCACCTTCCTTCGATCCTTGAGGGTGCCGGCCTCACCTACACCATCATCGGCGAGACGGAGAAGCTCCCGCTCCTCGAGA
ACGTCATCCTTGACGCCTTCGAGAACTCGCGTCCGCATATCGCCCTCGTTTCGCCGAAGGTCTGGGAAGCCTCGGAATGCTGCGC
CTGGCAGGCCGCTGGCATGCCGATCAAGCCGGAGATTATGGAGCGCACGTGCCGTTTCTCGCTCACCTCGGGCACCCTCAAGCCG
TTCATGCTCCGCAACGATGCCATCTGCACCCTCGCCTCGGAGCTCGACGACGAGATCACCGTCACCAACCTCGGCGTCCCGTGTA
AGGAGCTCTACGCCTGCCGCGACCGCGAACTCAACTTCTACATGTTCGGCTCGATGGGCCTCGTCTCGTCGATCGGCCTCGGCCT
CGCCCTCCGCTCGGAAAAGACCGTCATCACCTTCGATGGCGACGGCTCGCTTCTCATGAACCCGAACGCCCTCCTCGAGATCGCC
AAGGAGGCCCCGAAGAACCTCATCATCATCGCCCTCGACAACGGCGCCTATGGCTCGACCGGCTCGCAGGAAACCTGCGCCCTCC
GCTACATCGATCTCGAGATCTTCGCCAACGCCTGCGGCATCCAGAACACCGCCAAGGTCAACTCGAAGGAGGGCGTCATCGAGGC
CTTCCGCAAGTTCAAGGCCATGCGCGAGCTCTCGTTCATCCACGTCATCCTCAAGCCGGGCAACACCAACGCCCCGAACATCCCG
ATGTCGCCGGAGGAGGCCACCAAGCGCTTCAAGGAAACCCTCGACGTCAAGAAGTTCTAA SEQ ID NO: 56
Description: Taurine-pyruvate aminotransferase (Tpa)
Length: 1393
Type: DNA
Codon Optimization: *M. extorquens*
>ATGGTCGTCGATGTCACCGAGTTACGTGCCCGCGCCCGCCGCCACCTCGGCCCGCATTTCACCCGCAAGGATACCTGGGAATCG
GATTTCCCGGTGTTCGTCCGCGGTGAAGGTTCGTACCTCATCGACACCGAAGGCGATCGCTTCCTCGACGGCCTCGCCGGTCTGT
TCTGCGTCAACATCGGCCATGGTCGCGACGACATCGCCAAGGCCGCCTCGGAACAGATTGGCACCCTTGCCTATGCCTCGAACTG
GGGCTCGGCCCACATCCCGGCTATTGAGGCCTCGGCTCTCATCGCCGATCTTGCCCCGGGCGATCTCGGCACTACCTTCTTCGTC
AACTCGGGTTCGGAGGCCGTCGAAACCGCCGTCAAGTTCGCCCGCCAGTACCACCGCTCGCAGGGTAATCCGCAGCGCACCAAAA
TCATCTCGCGCGAGATGGCCTACCATGGCACCACCCTCGGCGCCCTCAGTGTCACCCAGCTCCCTAAGATCAAGGACCCGTTCGG
TCCGCTTCTTCCGGGCGTTCGTTCGGTCCCGAATACCCTCGGCTACCTCGGTGATTGCGGTCCGGCCAACGAGCTCGATTGCATC
GCCGCCATCGAGGCCGTCATCGAGGAGGAGGGTGCCGAAACCATCGCTGCTGTGTTCGCCGAACCGGTCCAAAATGGCCGCGGTG
CCCTTGTCCCTCCTGATGGTTACTGGGCCGCTCTCCGCGCCCTCTGCGACAAGCATGGCATCCTCCTCGTCTCGGACGAAGTCAT
CTGCTCGTTCGGTCGCCTCGGCCACTGGTTCGGTCATGGCCTTACCGGCGTCGTCCCGGACATGATCACCTTCGCCAAGGGCTCG
ACCTCGGGCTATGCTCCTCTCGGTGGCTTGATCGTCCGCGAGCAGCTCGTCCGTGAGCTCTATGATTCGCCGAAGGGTGGCGTGT
TCACTCACGGCGCTACCTGGGGTGGCCATCCTGTCTCGACCGCCGTCGCTGTCGCCAACATCACCGCCATGCGCGATGAAAACGT
CCTTGGCAACGTCAGTGCCCGCGGCCCGAAGCTCCGCAGTGCTCTTGATTCGCTCATGTCGTCGCATCGCTGCGTCAAGGACGTC
CGTGGCACCGGCTTCTTCTATGCCATCGAGCTCATGGCCGACTCGGATAGTGGCCGCGAGTTCACCGAGCAGGAGTCGCTCACCG
TCCTCCGCAAAGTTCTCCCGGAGGCCTTCGCCCGCACCAAGGTCATCCTCCGTGGTGATGATCGTGGCGCCACCATGCTCATGAT
CTCGCCGCCGCTCGTCGCTGACGACGAAGTCCTCTCGGAGCTCCTCCACGGCATCGACTCGATGCTCACCGACATCGAGAAGGCC
ATCCAGCCGTAG SEQ ID NO: 57
Description: ADO (2-aminoethanol dioxygenase)
Alias: Gm237, NP_001005419.2
Length: 771
Type: DNA
Codon Optimization: *M. extorquens*
>ATGCCGCGTGATAACATGGCCTCGCTTATCCAGCGCATTGCCCGCCAAGCCTGCCTCACCTTCCGCGGTTCGAGTACCGGCTC
GGAGGGCCCGGCTCCGGGCTTCCCGGAAAACCTCTCGCTCCTCAAGTCGCTTCTCACCCAGGTCCGTGCCGAGGATCTTAACAT
CGCCCCGCGTAAGGCCCTCCCGCAGCCGCTCCCGCGCAACCTCCCGCCGGTCACCTACATGCACATCTACGAAACCGAGGGCTT
CTCGCTCGGCGTGTTCCTCCTCAAGTCGGGCACGTGCATCCCGCTCCACGACCACCCGGGCATGCACGGCATGCTCAAGGTCCT
CTACGGCACCGTCCGCATCTCGTGCATGGACAAGCTCGACACCGGTGCCGGCCATAGACGTCCGCCTCCGGAACAGCAGTTCGA
GCCTCCGCTTCAGCCGCTCGAACGCGAAGCCGTTCGCCCGGGCGTCCTTAGAAGTCGCGCCGAATACACCGAGGCCAGTGGTCC
GTGCGTCCTCACCCCGCACCGTGATAACCTCCATCAGATCGATGCCGTCGACGGCCCGGCCGCCTTCCTCGATATCCTCGCCCC
GCCGTACGACCCGGAGGATGGCCGCGATTGCCATTATTATCGCGTCGTCGAGCCGATCCGCCCGAAGGAAGCCTCGGGTTCGGC
CTGTGATCTCCCGCGCGAGGTCTGGCTCCTCGAAACCCCGCAGGCCGACGACTTTTGGTGCGAGGGTGAACCGTACCCGGGCCC
GAAGGTCCTCCCGTGA SEQ ID NO: 58
Description: CDO
Alias: cdoA, BSU31140, O32085, CDO_*Bacillus*
Length: 486
Type: DNA
Codon Optimization: *M. extorquens*
>ATGGAGCTCTACGAGTGCATCCAGGACATCTTCGGCGGCCTCAAGAACCCGTCGGTCAAGGACCTCGCCACCTCGCTCAAGCAG
ATCCCGAACGCCGCCAAGCTCTCGCAGCCGTACATCAAGGAGCCGGACCAGTACGCCTACGGCCGCAACGCCATCTACCGCAACA
ACGAGCTCGAGATCATCGTCATCAACATCCCGCCGAACAAGGAGACGACCGTCCACGACCACGGCCAGTCGATCGGCTGCGCCAT
GGTCCTCGAGGGCAAGCTCCTCAACTCGATCTACCGCTCGACCGGCGAGCACGCCGAGCTCTCGAACTCGTACTTCGTCCACGAG
GGCGAGTGCCTCATCTCGACCAAGGGCCTCATCCACAAGATGTCGAACCCGACCTCGGAGCGCATGGTGTCGCTCCACGTCTACT
CGCCGCCGCTCGAGGACATGACCGTGTTCGAGGAGCAGAAGGAGGTCCTCGAGAACTCGTGA SEQ ID NO: 59
Description: Mammalian CDO
Alias: P21816, M35266.1, CDO_Rat
Length: 1371

-continued

Amino Acid and Nucleotide Sequences

Type: DNA
Codon Optimization: *M. extorquens*
>ATGGAGCGCACCGAGCTCCTCAAGCCGCGCACCCTCGCCGACCTCATCCGCATCCTCCACGAGCTCTTCGCCGGCGACGAGGTC
AACGTCGAGGAGGTCCAGGCCGTCCTCGAGGCCTACGAGTCGAACCCGGCCGAGTGGGCCCTCTACGCCAAGTTCGACCAGTACC
GCTACACCCGCAACCTCGTCGACCAGGGCAACGGCAAGTTCAACCTCATGATCCTCTGCTGGGGCGAGGGCCACGGCTCGTCGAT
CCACGACCACACCGACTCGCACTGCTTCCTCAAGCTCCTCCAGGGCAACCTCAAGGAGACGCTCTTCGACTGGCCGGACAAGAAG
TCGAACGAGATGATCAAGAAGTCGGAGCGCACCCTCCGCGAGAACCAGTGCGCCTACATCAACGACTCGATCGGCCTCCACCGCG
TCGAGAACGTCTCGCACACCGAGCCGGCCGTCTCGCTCCACCTCTACTCGCCGCCGTTCGACACGTGCCACGCCTTCGACCAGCG
CACCGGCCACAAGAACAAGGTCACCATGACCTTCCACTCGAAGTTCGGCATCCGCACCCCGTTCACCACCTCGGGCTCGCTCGAG
AACAACTAA SEQ ID NO: 60
Description: p3MDO
Alias: Q9I0N5, PA2602
Length: 606
Type: DNA
Codon Optimization: *M. extorquens*
>ATGTCGTCGATCCTCCGCCTTGACCGTCTCCGCCAGTTCATCGGCGAGCTCGCCACCCTCCTCGATTCGCGCCCGGATGAATCG
ACCCTCCTCGCCCAGGCCCATCCGCTCCTCGCCGAACTTGTCCATCAGGATGACTGGCTCCCGGAGGATTGCGCCCGCCCGGACC
CGCAGCGCTATCAGCAGTACCTCCTCCACGTCGACTCGCGTCAGCGCTTCTCGGTCGTCTCGTTCGTCTGGGGCCCGGGTCAGAT
CACCCCGGTCCACGATCACCGCGTCTGGGGCCTCATCGGCATGCTTCGTGGCGCCGAGTACTCGCAGCCGTATGCCTTCGATGCC
GGTGGCAGACCGCATCCGTCGGGTGCCAGACGTCGCCTTGAGCCGGGCGAAGTCGAGGCTCTCTCGCCTCGCATCGGCGATGTCC
ACCAGGTGTCGAACGCCTTCTCGGACCGCACCTCGATCTCGATCCACGTCTACGGCGCTAACATCGGCGCCGTCCGCCGCGCCGT
GTTCTCGGCCGAGGGTGAGGAGAAGCCGTTCATCTCGGGCTACTCGAACTCGCGCCTCCCGAACATCTGGGACCTCTCGAAGGAG
AACCCGGCCTGA SEQ ID NO: 61
Description: PAPS-AS
Alias: OT_ostta05g01260
Length: 969
Type: DNA
Codon Optimization: *M. extorquens*
>ATGCCGCGCGGCTGGACCAAGACCCGCGCCTATGACTCGCATCATTTCGATGCCGACGCCTGGTCGGTCGTCACCCCGCGCGCC
GGTGATGTCATTATCGCCACCGCCTACAAGTCGGGCACCACCTGGATGCAGCAGATCGTCTCGCAGCTCGTTTTCGAGGGCGCCG
CCCCGGCTGCCCTCGGCGAACTTAGTCCTTGGGTCGATCTCCGTGTTCCTCCTCGCGAAGTCAAGCGCGGTATGATTGAGGGCCT
CCCGTCGCCGCGCATTCTCAAGACCCATCTCCCGACCACCGGCCTCGAGTATGACGAGAACGCCAAGTACATCTACGTCGCCCGC
GACGGCCGCGACGCCTTCATGTCGCTCATGAACCACTACAAGAACGGCAACGAGGCCTTCTATGGCGCCCTCAACGGCCCGGGCC
TCAAGGGTGCTCCGCTCCCGACCTGGGAAGAAGCTTGCGAGGGCGAGGGCGATGAAAAGCTCAGAGCCCTCTTCGACAAGTGGCT
CAACACCCCGTGGGGCCAGCACCCGTGGGAGGAGGACGGCTGGCCGTTCTGGTCGCTCTTCTACAACATGAAAACCTGGTGGGAC
GCCCGCGAGTCGAAGAACATCATCTTCGTCCACTTCTCGGACCTCAAGAAGGACCTCAAGGGCCAGATGCGCCGCATCGCCAAGT
TCCTCAACGCCCCGATCGACGAGTCGAAGTTTGACGCCCAGGTCACCGCCTGCACCTTCGAATCGATGAAGGGTAATGCCGCTTC
GGTCGCCCCTCTCGGCGGCGCCCTCTGGAAGGGCGGTGCCGAAACCTTCATCAACAAAGGCACTAACGGCCGCTGGCGCAACGTC
CTCACCAAGGAGCAGGTCAAGCAGTACGAGCAGGTCGCCGAGAAGCGCCTCGGCAAGGATTGCGCCAAGTGGCTCGCCAACGGCG
GCGATATGAACGGCCGCGGCTGCGTCATCATGTGA SEQ ID NO: 62
Description: Adenylyl-Sulfate Kinase
Alias: cysC, NC_000913.3
Length: 606
Type: DNA
Codon Optimization: *M. extorquens*
>ATGGCCCTCCACGACGAGAACGTCGTCTGGCACTCGCACCCGGTCACCGTCCAGCAGCGCGAACTCCATCATGGCCATCGCGGC
GTCGTCCTCTGGTTCACCGGCCTCTCGGGTTCGGGTAAATCGACCGTCGCCGGCGCCCTCGAAGAGGCCCTCCACAAGCTCGGTG
TCTCGACCTACCTCCTCGATGGCGATAACGTCCGCCACGGTCTGTGCTCGGATCTCGGCTTCTCGGACGCCGACCGCAAGGAGAA
CATCCGCCGCGTCGGCGAGGTCGCCAACCTCATGGTCGAAGCCGGTCTGGTCGTCCTCACCGCCTTCATCTCGCCGCATCGCGCT
GAACGCCAAATGGTCCGTGAGCGCGTCGGCGAGGGCCGCTTCATCGAGGTGTTCGTCGATACCCCGCTCGCCATCTGCGAAGCCC
GTGATCCGAAGGGCCTCTACAAGAAGGCCCGCGCCGGCGAGCTCCGCAACTTCACCGGTATCGACTCGGTCTACGAAGCCCCGGA
GTCGGCCGAGATCCATCTCAACGGCGAGCAGCTCGTCACCAACCTCGTCCAGCAGCTCCTCGACCTCCTCCGCCAGAACGACATC
ATCCGCTCGTGA SEQ ID NO: 63
Description: PAPSS1-Bifunctional 3'-phosphoadenosine 5'-phosphosulfate synthase 1
Alias: E1C8P2
Length: 1875
Type: DNA
Codon Optimization: *M. extorquens*
>ATGGAGCTCCCGGAGTCGCAGTGCAAGAAGGCCAAGCTCTCGAACCGCGTCCCGAACTGGGGCATGCAGCGCGCTACCAACGTC
ACCTACCAGGCCCACCATGTTTCGCGCAACAAGCGTGGCCAGGTCGTCGGTACTCGCAGTGGTTTCCGCGGTTGCACCGTTTGGC
TTACCGGCCTTTCGGGCGCTGGCAAGACCACCGTCAGTATGGCCCTCGAGGAGTATCTCGTCTGCCACGGCATCCCGTGCTATAC
CCTCGACGGCGACAACATCCGCCAGGGACTCAACAAGAATCTCGGCTTCACCCCGGAGGACCGCGAGGAAAACGTCCGCCGCATC
GCCGAGGTCGCTAAGCTCTTCGCCGATGCTGGCCTCGTCTGCATCACCAGTTTCATCTCGCCGTACGCTCAGGACCGCAACAATG
CCCGCCGCATCCACGAAGGTGCCTCGCTCCCGTTCTTCGAGGTGTTCGTCGATGCCCCGCTCCATGTCTGCGAACAGCGCGATGT
CAAAGGCCTCTACAAGAAGGCCCGCGCCGGCGAGATCAAGGGTTTCACCGGCATCGACTCGGAGTACGAGAAGCCTGAGGCCCCG
GAGCTCGTCCTTAAGACTGACTCGTGCGACGTCAACGACTGCGTCCAGCAGGTCGTCGAGCTCCTCCAGGAGCGCGACATTGTCC
CGGTCGACGCCTCGTACGAGGTCAAGGAGCTCTACGTCCCGGAGAACAAGCTCAAGCTCGCCAAGACCGATGCCGAGTCGCTCCT
TACCCTCGAGATCAACAAGGTCGATATGCAGTGGGTCCAGGTCCTCGCCGAGGGCTGGGCCACCCCGCTCTCGGGTTTCATGCGC
GAGCGCGAATACCTCCAGTGCCTTCATTTCGATTGCCTTCTCGATGGCGGCGTCATCAACCTCTCGGTTCCGATTGTCCTCACCG -continued Amino Acid and Nucleotide Sequences CTACCCAGGAGGACAAAGAACGTCTCGACGGCTGCACCGCCATCGCCCTCGTCTACGAGGGCCGTCGTGTCGCCATTCTTCGCAA
CCCGGAGTTCTACGAACACCGTAAGGAAGAGCGCTGCGCCCGTCAGTGGGGCACCACGTGCAAGGATCACCCGTACATCAAGATG
GTCATGGAGCAGGGCAACTGGCTCGTCGGCGGTGACCTCCAGGTTCTCGATCGCATCTACTGGAACGATGGCCTCGACCAGTATC
GCCTCACCCCGGCCGAACTCCGCCAGAAGTTCAAGGAGATGAACGCCGACGCCGTCTTTGCCTTCCAGCTCCGCAACCCGGTCCA
CAACGGTCATGCCCTCCTCATGCAAGACACCCACAAGCAGCTCCTCGAGCGCGGTTACCGTCGCCCTGTCCTCCTCCTCCATCCT
CTCGGCGGCTGGACCAAAGAGGATGACGTCCCGCTTATGTGGCGCATGAAACAGCACGCCGCCGTCCTCGAGGAAGGCGTCCTCA
ACCCGGAGACGACCGTCGTTGCCATCTTCCCGTCGCCTATGATGTATGCCGGTCCGACCGAGGTTCAGTGGCATTGCCGTTCGCG
CATGGTCGCTGGCGCCAACTTCTATATCGTCGGCCGTGATCCTGCCGGTATGCCGCATCCGGGCACCGGCAAAGACCTTTACGAA
CCGACTCATGGCGCCAAGGTTCTTACCATGGCCCCGGGCCTCCGTGCCCTCGAGATCGTCCCTTTCCGCGTCGCCGCCTACAACA
AGAAGAAGAAGTCGATGGACTACTACGACTCGGAGCACCATGAGGACTTCGAGTTCATCTCGGGCACCCATATGCGCAAGCTCGC
CCGCGAAGGCCAGAACCCGCCGGAGGGCTTCATGGCTCCGAAGGCTTGGACCGTCCTCACCGAATACTACAAGTCGCTCGAGAAG
GCCTAG SEQ ID NO: 64
Description: MA3297
Length: 1251
Type: DNA
Type: DNA
Codon Optimization: *M. extorquens*
>ATGGGCCGCTTCATCCTCAAGTGCCTCAAGTGCGGCCGCGAGTACTCGCAGGAGTACCGCCTGACCTGCGAGAACGACGACTCG
TTCCTCCGCGCCGAGTACCTCGAGAAGAAGCTCGAGCTCCGCAAGCAGCCGGGCATCGGCCGCTTCCACTCGTGGCTCCCGGTCC
AGGAGGAGCTCACCACCGAGGCCGGCCCGATCACCTACAAGTCGGAGGCCCTCGCCCGCGAGCTCGGCCTCTCGAACCTCTACAT
CGGCTTCTCGGGCTACTGGCCGGAGAAGGGCGCCTTCATCAAGACCTGCTCGTTCAAGGAGCTCGAGGCCCACCCGACCATGCAG
CTCCTCAAGGAGTCGGGCGGCAAGGCCATCGTCCTCGCCTCGGCCGGCAACACCGGCCGCGCCTTCGCCCACGTCTCGGCCCTCA
CCGGCACCGACGTCTACATCGTCGTCCCGGACTCGGGCATCCCGAAGCTCTGGCTCCCGGAGGAGCCGACCGACTCGATCCACCT
CATCTCGATGACCCCGGGCAACGACTACACCGACGCCATCAACCTCGCCGGCCGCATCGCCAAGCTCCCGGGCATGGTCCCGGAG
GGCGGCGCCCGCAACGTCGCCCGCCGCGAGGGCATGGGCACCGTCATGCTCGACGCCGCCGTCACCATCGGCAAGATGCCGGACC
ACTACTTCCAGGCCGTCGGCTCGGGCACCGGCGGCATCTCGGCCTGGGAGGCCTCGCTCCGCCTCCGCGAGGACGGCCGCTTCGG
CTCGAAGCTCCCGAAGCTCCAGCTCACCCAGAACCTCCCGTTCGTCCCGATGTACAACGCCTGGCAGGAGGGCCGCCGCGACATC
ATCCCGGAGATCGACATGAAGGACGCCAAGAAGCGCATCGAGGAAACCTACGCCACCGTCCTCACCAACCGCGCCCCGCCGTACT
CGGTCACCGGCGGCCTCTACGACGCCCTCGTCGACACCGACGGCATCATGTACGCCGTCTCGAAGGAGGAGGCCCTCGACGCCAA
GGCCCTCTTCGAGTCGCTCGAGGGCATCGACATCCTCCCGCCGTCGGCCGTCGCCGCCGCCTCGCTCCTCAAGGCCGTCGAGGCC
GGCAACGTCGGCAAGGACGACACCATCCTCCTCAACATCGCCGGCGGCGGCTTCAAGCGCCTCAAGGAGGACTTCACCCTCTTCC
AGATCGAGCCGGAGATCACCGTCTCGAACCCGGACGTCCCGCTCGAGGAGCTCAAGCTCTGA SEQ ID NO: 65
Description: Cystathionine gamma-lyase (CGL)
Alias: mccB, BSU27250
Length: 1140
Type: DNA
Codon Optimization: *M. extorquens*
>ATGAAGAAGAAAACCCTCATGATCCACGGCGGCATCACCGGCGACGAAAAGACCGGCGCCGTCTCGGTCCCGATCTATCAGGTG
TCGACCTACAAGCAGCCGAAGGCCGGCCAGCATACTGGCTACGAGTATTCGCGCACCGCCAACCCGACCAGAACCGCCTTAGAGG
CCCTCGTCACCGAGCTCGAAAGTGGCGAAGCCGGCTACGCCTTCTCGTCGGGTATGGCTGCCATCACCGCCGTCATGATGCTCTT
CAACTCGGGCGACCACGTCGTCCTCACCGACGACGTCTACGGCGGCACCTACCGCGTCATGACCAAGGTCCTCAACCGCCTCGGC
ATCGAGTCGACCTTCGTCGACACCTCGTCGCGCGAGGAGGTCGAGAAGGCCATCCGCCCGAACACCAAGGCCATCTACATCGAGA
CGCCGACCAACCCGCTCCTCAAGATCACCGACCTCACCCTCATGGCCGACATCGCCAAGAAGGCCGGCGTCCTCCTCATCGTCGA
CAACACCTTCAACACCCCGTACTTCCAGCAGCCGCTTACTCTCGGCGCCGACATCGTCCTCCATTCGGCCACCAAGTACCTCGGT
GGCCATTCGGATGTCGTCGGCGGCCTCGTTGTCACCGCCTCGAAGGAGCTCGGTGAGGAACTCCACTTCGTCCAGAACTCGACCG
GTGGCGTCCTCGGTCCGCAGGATAGTTGGCTCCTCATGCGCGGCATCAAGACCCTCGGCCTCCGCATGGAGGCCATCGATCAGAA
CGCCCGTAAGATCGCCTCGTTCCTCGAGAACCATCCGGCCGTCCAGACCCTCTATTACCCGGGCTCGTCGAACCATCCGGGTCAT
GAACTCGCCAAGACCCAGGGCGCTGGCTTCGGCGGCATGATCTCGTTCGATATCGGCTCGGAGGAGCGCGTCGACGCCTTCCTCG
GCAACCTCAAGCTCTTCACCATCGCCGAATCGCTTGGCGCCGTCGAGTCGCTTATCTCGGTTCCGGCCCGCATGACCCACGCCAG
TATCCCGCGTGAGCGTCGCCTTGAACTCGGCATCACCGATGGCCTCATCCGCATCTCGGTCGGCATCGAAGATGCCGAGGACCTC
CTCGAGGACATCGGCCAGGCCCTCGAGAACATCTAA SEQ ID NO: 66
Description: cuyA
Length: 1020
Type: DNA
Codon Optimization: *M. extorquens*
>ATGCATCTCGCCCGTTACCCGCGCCGCTTCATCGCCCATCTTCCGACTCCGCTCGAGAGACTCGACCGTCTCACCGCCGAACTC
GGTGGCCCGGAAATCTGGATCAAGCGCGACGATTGCACTGGCCTCTCGACCGGCGGCAACAAGACCCGCAAGCTCGAGTTCCTCA
TGGCCGAGGCCGAGCTCCAAGGCGCCGATATGGTCATGACCCAGGGTGCTACCCAGTCGAATCATGCTCGTCAGACCGCCGCCTT
CGCCGCCAAGCTCGGTATGGACTGCCACATCCTCCTCGAGGACCGCACCGGCTCGAACAACGCCAACTACAACAACAACGGCAAC
GTCCTCCTCGACCATCTCCACGGCGCCACCACCGAAAAGCGCCCGGGCTCGGGCCTCGATATGAACGCCGAAATGGAGAAGGTCG
CCGAGAAGTTCCGCGCCGATGGTCGCAAGGTCTACACCATCCCTGGCGGTGGTTCGAACCCGACCGGCGCCCTCGGTTACGTCAA
CTGCGCCTTCGAGATGCTCAACCAGTTCAACGAGCGCGGCCTCAAGGTCGACCACATCGTCCATGCCACCGGTAGTGCCGGCACC
CAAGCCGGCCTCATCACCGGCCTCCAGGCTATGAATGCCCAGATTCCGCTTCTTGGCATCGGTGTCCGTGCCCCGAAGCCGAAGC
AGGAAGAGAACGTCTATAATCTCGCCTGCGCCACCGCCGAGAAACTTGGCTGCCCGGGCGTCGTCGCTCGCGAGGACGTCGTCGC
CAATACCGACTATGTCGGTGAGGGCTATGGCATTCCTACCGAGTCGGGCCTCGAAGCCATCCGCATGTTCGCCGAGCTCGAAGCC
ATCCTCCTCGACCCGGTCTATTCGGCCAAGGGTGCCGCCGGCTTCATCGACCTTATCCGCAAGGGCCATTTTAAGAAGGGCGAGC
GCGTCGTCTTTCTCCACACCGGCGGCGCCGTCGCCCTCTTCGGCTACGACAACGCCTTCGACTACTCGGGCCGCTGGGTCGCCTA
A SEQ ID NO: 67
Description: ComA -continued

| Amino Acid and Nucleotide Sequences |
| --- |

Alias: phosphosulfolactate synthase
Length: 759Type: DNA
Codon Optimization: *M. extorquens*
>ATGAACGCCTTCAAGTTCCTCGACGAGATCGGCCCGGTCAACACCAACACCATGGTCCTCGACAAGGCCCTCGGCTACAAGACC
GTCGAGGACATGCTCACCATCTCGGGCAACTACTTCAACCTCCTCAAGTACGGCTGGGGCACCTCGATCCTCTACGACGAGGAGA
TCATCAAGGACAAGAACGAGCTCTACCACTCGTACAACATCCGCACCTACACCGGCGGCACCCTCTTCGAGCTCGCCAACAAGCA
GAACAAGATCGACGAGTACTTCAACGAGATCGATCGCCTCGGCTTCAACGCCGTCGAGATCTCGGATGGCTCGACCACCATCGAC
TCGGACCGCCGCGCCCAGCTCATCAACAAGTCGAAGGAGCTCGGCTTCTACACCCTCTCGGAGATCGGCAAGAAGAACCCGCAGA
AGGACTCGGAGTACACCACCCAGCAGCGCATCGACCTCATCAACACCGACATCGAGGCCGGCTCGGACATGGTCATCATCGAGGG
CCGCGAGTCGGGCAAGAACATCGGCATCTACGACGACAAGGGCAACGTCAAGAAGGACGACCTCACCTCGATCTACGAGAACACC
CCGAAGGAGAAGGTCCTCTGGGAGGCCCCGCAGAAGAACCAGCAGGTCGAGCTCATCCTCACCCTCTCGAACGACGTCAACCTCG
GCAACATCAACTCGAACGAAATCGTCTCGCTCGAAACCCTCCGCCGCGGCCTCCGCGGCGACACCCTCGGCAAGCTCTAA SEQ ID NO: 68
Description: ComB1
Length: 699
Type: DNA
Codon Optimization: *M. extorquens*
>ATGAAGATCAACGTCTCGCTCTACAACTCGCGCACCAACGACCTCGCCATCGTCATCGACCTCCTCCGCGCCTCGACCACCATC
TCGGTCGCCCTCAACACCTTCAAGCGCATCGTCCCGATCAACGACATCGACGAGGCCATCAAGCTCAAGGAGAAGCACAACGCCA
TCCTCGCCGGCGAGATCAAGTCGTCGGACTTCGACGTCTCGAACTCGCCGGTCCAGATCTCGAACTACGCCGGCGACACCCTCAT
CCTCAAGACCACCAACGGCACCAAGGTCCTCGAGAACATCAAGCAGCGCAACTCGGAGGTCAACATCCTCGTCGGCGCCTCGATC
AACGCCAAGACCGTCGCCCAGAAGGCCCTCGATATCGCCGATAACGAAATCGAACTCGTCATGGCCGGCCGCCATCAGCGCTTCA
CCATCGAGGACTGCATCGGCGCCGGCATCATCATCAACGAGATCGTCAACATCGCCAAGGAGAAGAACATCTACCTCGAGCTCTC
GGAGTCGGCCAAGGCCTCGAAGATCATCTCGAACAACTCGAACATCATCAAGCAGCTCATCAACACCTCGCACTCGGCCGACAAG
CTCCGCTACCTCGGCTTCGGCGAGGACATCGAGATCTGCTCGCTCATCAACAAGATCGACACCGTCCCGATCTACAAGAACAACT
ACATCGTCTCGCTCGACTAA SEQ ID NO: 69
Description: ComC
Alias: Sulfolactate dehydrogenase
Length: 1029
Type: DNA
Codon Optimization: *M. extorquens*
>ATGAACATCACCCCGGAGCAGGAGCTCTCGCTCATCATCGACATCCTCACCAAGTTCGACGTCCCGGAGGACCAGGCCTCGATC
ATCGCCGAGGTCACCCTCGATGGCGATCTCAAGGGCTTCTCGTCGCACGGCATCGGCCGTTTCCCGCAGTACATCAAGGGCCTCG
AATGCGGCCACATTAAGCCGCACACCGAGATCGTCGTCGAGAAGGAGACGGCCGCCACCGCCCTCATCAACGGCAACCACGGCTT
CGGCCACGTCGTCACCTACCAGGCCATGAAGATGGCCATCGAGAAGGCCAAGGAGGTCGGCATCGGCCTCGTCGGCATCCACAAC
TCGAACCACTTCGGCGTCGCCGGCTACTACTCGGACATGGCCCTCATGGAGGACATCATTGGTATCGTCACCGCCAACACCGAAC
CGGCCGTCGCCCCGATTGGCGGCAAAGAACCGATCCTTGGCACCAACCCGCTCGCCATCGGTATCCCGTCGGGCAGTCATTACCT
CTCGGTCGATATGGCCACCTCGGCCTCGGCCCGCGGTAAGCTCATGGAAGCCAAGCGCCTTGGCGAGCCGATCCCGGAAAATGTC
GCCCTCGATTCGGATGGCAACCCTACCACCGATCCGGCTGAGGCCCTTAAGGGCTCGATCCTCCCGTTCGGCGCCCACAAGGGCT
ATGCCCTCTCGCTCATGATCGAAGTCATCGCCGGTCCGCTTGTCCGCGCCTCGTATGGCAAGGGTGTCACCGGTACGGCCGACCC
GGAGGTTCCGTGCACTAAGGGCGATCTTATCGCTGCCATCGACCCGTCGAAGTTCGTCGACATCGACCAGTTCAAGGAGGAGGTC
GACGACCTCATCTCGGAGCTCAAGTCGACCCCGAACGTCATGATCCCGGGCGACTTCGAGGTCCTCAACGTCAAGCGCCACCAGA
AGGAGGGCATCGCCCTCGACGAGACGCTCGTCCAGCAGCTCCGCGAAATCGCCTCGAACGTCGACGTCGACGTCTCGGATATCCT
CGGCGACTAA SEQ ID NO: 70
Description: Cystathionine-β-lyase/L-cysteine desulfhydrase
Alias: MetC
Length: 395
Type: Protein
Organism: *E. coli*
>MADKKLDTQLVNAGRSKKYTLGAVNSVIQRASSLVFDSVEAKKHATRNRANGELFYGRRGTLTHFSLQQAMCELEGGAGCVLFP
CGAAAVANSILAFIEQGDHVLMTNTAYEPSQDFCSKILSKLGVTTSWFDPLIGADIVKHLQPNTKIVFLESPGSITMEVHDVPAI
VAAVRSVVPDAIIMIDNTWAAGVLFKALDFGIDVSIQAATKYLVGHSDAMIGTAVCNARCWEQLRENAYLMGQMVDADTAYITSR
GLRTLGVRLRQHHESSLKVAEWLAEHPQVARVNHPALPGSKGHEFWKRDFTGSSGLFSFVLKKKLNNEELANYLDNFSLFSMAYS
WGGYESLILANQPEHIAAIRPQGEIDFSGTLIRLHIGLEDVDDLIADLDAGFARIV SEQ ID NO: 71
Description: Cystathionine-β-lyase/L-cysteine desulfhydrase
Alias: MetC
Length: 1188
Type: DNA
Organism: *E. coli*
>atgGCGGACAAAAAGCTTGATACTCAACTGGTGAATGCAGGACGCAGCAAAAAATACACTCTCGGCGCGGTAAATAGCGTGATT
CAGCGCGCTTCTTCGCTGGTCTTTGACAGTGTAGAAGCCAAAAAACACGCGACACGTAATCGCGCCAATGGAGAGTTGTTCTATG
GACGGCGCGGAACGTTAACCCATTTCTCCTTACAACAAGCGATGTGTGAACTGGAAGGTGGCGCAGGCTGCGTGCTATTTCCCTG
CGGGGCGGCAGCGGTTGCTAATTCCATTCTTGCTTTTATCGAACAGGGCGATCATGTGTTGATGACCAACACCGCCTATGAACCG
AGTCAGGATTTCTGTAGCAAAATCCTCAGCAAACTGGGCGTAACGACATCATGGTTTGATCCGCTGATTGGTGCCGATATCGTTA
AGCATCTGCAGCCAAACACTAAAATCGTGTTTCTGGAATCGCCAGGCTCCATCACCATGGAAGTCCACGACGTTCCGGCGATTGT
TGCCGCCGTACGCAGTGTGGTGCCGGATGCCATCATTATGATCGACAACACCTGGGCAGCCGGTGTGCTGTTTAAGGCGCTGGAT
TTTGGCATCGATGTTTCTATTCAAGCCGCCACCAAATATCTGGTTGGGCATTCAGATGCGATGATTGGCACTGCCGTGTGCAATG
CCCGTTGCTGGGAGCAGCTACGGGAAAATGCCTATCTGATGGGCCAGATGGTCGATGCCGATACCGCCTATATAACCAGCCGTGG
CCTGCGCACATTAGGTGTGCGTTTGCGTCAACATCATGAAAGCAGTCTGAAAGTGGCTGAATGGCTGGCAGAACATCCGCAAGTT
GCGCGAGTTAACCACCCTGCTCTGCCTGGCAGTAAAGGTCACGAATTCTGGAAACGAGACTTTACAGGCAGCAGCGGGCTATTTT -continued

| Amino Acid and Nucleotide Sequences |
| --- |
| CCTTTGTGCTTAAGAAAAAACTCAATAATGAAGAGCTGGCGAACTATCTGGATAACTTCAGTTTATTCAGCATGGCCTACTCGTG<br>GGGCGGGTATGAATCGTTGATCCTGGCAAATCAACCAGAACATATCGCCGCCATTCGCCCACAAGGCGAGATCGATTTTAGCGGG<br>ACCTTGATTCGCCTGCATATTGGTCTGGAAGATGTCGACGATCTGATTGCCGATCTGGACGCCGGTTTTGCGCGAATTGTAtaa |
| SEQ ID NO: 72<br>Description: Cysteine synthase B with L-cysteine desulfhydrase activity<br>Alias: CysM<br>Length: 303<br>Type: Protein<br>Organism: *E. coli*<br>>MSTLEQTIGNTPLVKLQRMGPDNGSEVWLKLEGNNPAGSVKDRAALSMIVEAEKRGEIKPGDVLIEATSGNTGIALAMIAALKG<br>YRMKLLMPDNMSQERRAAMRAYGAELILVTKEQGMEGARDLALEMANRGEGKLLDQFNNPDNPYAHYTTTGPEIWQQTGGRITHF<br>VSSMGTTGTITGVSRFMREQSKPVTIVGLQPEEGSSIPGIRRWPTEYLPGIFNASLVDEVLDIHQRDAENTMRELAVREGIFCGV<br>SSGGAVAGALRVAKANPDAVVVAIICDRGDRYLSTGVFGEEHFSQGAGI |
| SEQ ID NO: 73<br>Description: Cysteine synthase B with L-cysteine desulfhydrase activity<br>Alias: CysM<br>Length: 912<br>Type: DNA<br>Organism: *E. coli*<br>>gtgAGTACATTAGAACAAACAATAGGCAATACGCCTCTGGTGAAGTTGCAGCGAATGGGGCCGGATAACGGCAGTGAAGTGTGG<br>TTAAAACTGGAAGGCAATAACCCGGCAGGTTCGGTGAAAGATCGTGCGGCACTTTCGATGATCGTCGAGGCGGAAAAGCGCGGGG<br>AAATTAAACCGGGTGATGTCTTAATCGAAGCCACCAGTGGTAACACCGGCATTGCGCTGGCAATGATTGCCGCGCTGAAAGGCTA<br>TCGCATGAAATTGCTGATGCCCGACAACATGAGCCAGGAACGCCGTGCGGCGATGCGTGCTTATGGTGCGGAACTGATTCTTGTC<br>ACCAAAGAGCAGGGCATGGAAGGTGCGCGCGATCTGGCGCTGGAGATGGCGAATCGTGGCGAAGGAAAGCTGCTCGATCAGTTCA<br>ATAATCCCGATAACCCTTATGCGCATTACACCACCACTGGGCCGGAAATCTGGCAGCAAACCGGCGGGCGCATCACTCATTTTGT<br>CTCCAGCATGGGGACGACCGGCACTATCACCGGCGTCTCACGCTTTATGCGCGAACAATCCAAACCGGTGACCATTGTCGGCCTG<br>CAACCGGAAGAGGGCAGCAGCATTCCCGGCATTCGCCGCTGGCCTACGGAATATCTGCCGGGGATTTTCAACGCTTCTCTGGTGG<br>ATGAGGTGCTGGATATTCATCAGCGCGATGCGGAAAACACCATGCGCGAACTGGCGGTGCGGGAAGGAATATTCTGTGGCGTCAG<br>CTCCGGCGGCGCGGTT |

GCCG-GAGCACTGCGGGTGGCAAAAGCTAACCCTGACGC-GGTGGTGGTGGCGATCATCTGC GATCGTGGC-GATCGCTACCTTTCTACCGGGGTGTTTGGG-GAAGAGCATTTTAGCCAGGGG GCGGGGATTtaa Although the foregoing invention has been described in some detail by way of illustration and examples for purposes of clarity of understanding, it will be apparent to those skilled in the art that certain changes and modifications may be practiced without departing from the spirit and scope of the invention, which is delineated in the appended claims. Therefore, the description should not be construed as limiting the scope of the invention.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A non-naturally occurring microorganism that produces taurine and/or at least one taurine precursor selected from the group consisting of: cysteate, sulfoacetaldehyde, and hypotaurine, wherein the microorganism is selected from the group consisting of: *Methylobacterium, Methylomonas, Methylobacter, Methylococcus, Methylosinus, Methylocyctis, Methylomicrobium, Methylpophilus, Methylobacillus, Methylobacterium, Hyphomicrobium, Xanthobacter, Bacillus, Paracoccus, Nocardia, Arthrobacter, Rhodopseudomonas, Pseudomonas*, and *Escherichia,* wherein said microorganism comprises one or more exogenous polynucleotide(s) that encodes one or more enzyme(s) that operate in a taurine biosynthetic pathway to produce the taurine and/or the at least one taurine precursor in the microorganism, and wherein the one or more enzyme(s) is selected from the group consisting of:

(a) 3-mercaptopropionate dioxygenase (p3MDO) enzyme, and either cysteine sulfinic acid decarboxylase (CSAD) enzyme or glutamate decarboxylase (GAD) enzyme, wherein the p3MDO enzyme is at least 90% identical to the amino acid sequence set forth in SEQ ID NO: 33, and the CSAD enzyme is at least 90% identical to the amino acid sequence set forth in SEQ ID NO: 11 or the GAD enzyme is at least 90% identical to the amino acid sequence set forth in SEQ ID NO: 13;

(b) one or more of cysteate synthase enzyme, and either CSAD enzyme or GAD enzyme, wherein the cysteate synthase enzyme is at least 90% identical to the amino acid sequence set forth in SEQ ID NO:17, and the CSAD enzyme is at least 90% identical to the amino acid sequence set forth in SEQ ID NO: 11 or the GAD enzyme is at least 90% identical to the amino acid sequence set forth in SEQ ID NO: 13;

(c) one or more of cysteate synthase enzyme and L-serine dehydratase enzyme, and either CSAD enzyme or GAD enzyme, wherein the cysteate synthase enzyme is at least 90% identical to the amino acid sequence set forth in SEQ ID NO:17, the L-serine dehydratase enzyme is at least 90% identical to the amino acid sequence set forth in SEQ ID NO:1, and the CSAD enzyme is at least 90% identical to the amino acid sequence set forth in SEQ ID NO: 11 or the GAD enzyme is at least 90% identical to the amino acid sequence set forth in SEQ ID NO: 13;

(d) cystathionine gamma lyase (CGL) enzyme and cysteate synthase enzyme, and either CSAD enzyme or GAD enzyme, wherein the CGL enzyme is at least 90% identical to the amino acid sequence set forth in SEQ ID NO: 46, 70, or 72, the cysteate synthase enzyme is at least 90% identical to the amino acid sequence set forth in SEQ ID NO:17, and the CSAD enzyme is at least 90% identical to the amino acid sequence set forth in SEQ ID NO: 11 or the GAD enzyme is at least 90% identical to the amino acid sequence set forth in SEQ ID NO: 13;

(e) cysteate synthase enzyme, sulfopyruvate decarboxylase (ComDE) enzyme, and taurine pyruvate aminotransferase (Tpa) enzyme, wherein the cysteate synthase enzyme is at least 90% identical to the amino acid sequence set forth in SEQ ID NO:17, the ComDE enzyme is at least 90% identical to the amino acid sequence set forth in SEQ ID NO:25, and the Tpa enzyme is at least 90% identical to SEQ ID NO:27; or (f) CGL enzyme, cysteate synthase enzyme, ComDE enzyme, and Tpa enzyme, wherein the CGL enzyme is at least 90% identical to the amino acid sequence set forth in SEQ ID NO: 46, 70, or 72, the cysteate synthase enzyme is at least 90% identical to the amino acid sequence set forth in SEQ ID NO:17, the ComDE enzyme is at least 90% identical to the amino acid sequence set forth in SEQ ID NO:25, and the Tpa enzyme is at least 90% identical to the amino acid sequence set forth in SEQ ID NO:27.

2. The non-naturally occurring microorganism of claim 1, wherein the microorganism is selected from the group consisting of: *Methylobacterium, Escherichia*, and *Bacillus.*

3. The non-naturally occurring microorganism of claim 1, wherein the microorganism is a methylotrophic bacterium.

4. The non-naturally occurring microorganism of claim 1, wherein said one or more exogenous polynucleotide(s) is codon optimized for expression in the microorganism.

5. The non-naturally occurring microorganism of claim 1, wherein said one or more exogenous polynucleotide(s) is operably linked to promoter(s) for expression in the microorganism.

6. The non-naturally occurring microorganism of claim 1, wherein the microorganism further comprises a deletion of one or more endogenous genes that encode one or more enzyme(s) that degrade taurine, cysteate, or sulfoacetaldehyde, and wherein said one or more enzyme(s) that degrade taurine, cysteate, or sulfoacetaldehyde comprises taurine dehydrogenase, Tpa, taurine dioxygenase, cysteate sulfo-lyase (CuyA), sulfoacetaldehyde acetyltransferase, and/or gamma-glutamyltransferase.

7. A method for producing biomass comprising taurine and/or taurine precursor(s), comprising: culturing the microorganism of claim 1 in a culture medium under conditions suitable for growth of the microorganism and expression of said enzyme(s) for production of taurine and/or taurine precursor(s), wherein biomass comprising said taurine and/or taurine precursor(s) is produced in the culture.

8. The non-naturally occurring microorganism of claim 1, wherein said microorganism is a *Methylobacterium* or *Escherichia* microorganism.

* * * * *

SEQUENCE LISTING

<160> NUMBER OF SEQ ID NOS: 73

<210> SEQ ID NO 1
<211> LENGTH: 453
<212> TYPE: PRT
<213> ORGANISM: Methylobacterium extorquens

<400> SEQUENCE: 1

Met Ile Ser Thr Phe Asp Leu Phe Lys Ile Gly Ile Gly Pro Ser Ser
1               5                   10                  15

Ser His Thr Val Gly Pro Met Ile Ala Gly Arg Arg Phe Arg Glu Thr
            20                  25                  30

Val Leu Ala Arg Gly Gly Ile Ala Arg Ile Ser Ala Glu Ile Tyr Gly
        35                  40                  45

Ser Leu Ala Trp Thr Gly Arg Gly His Gly Thr Asp Val Ala Ile Leu
    50                  55                  60

Leu Gly Leu Met Gly His Ala Pro Ser Thr Ile Asp Pro Asp Arg Thr
65                  70                  75                  80

Ala Pro Leu Ala Asp Glu Leu Arg Arg Thr Gly Asp Leu Gly Ile Pro
                85                  90                  95

```
Gly Val His Phe Glu Pro Glu Arg Asp Leu Val Phe Asn Phe Lys Asp
            100                 105                 110

Ile Leu Pro Leu His Thr Asn Gly Met Arg Phe Arg Ala Tyr Asp Ala
        115                 120                 125

Gly Asp Ala Pro Ile Glu Asp Gln Ile Phe Tyr Ser Val Gly Gly Gly
    130                 135                 140

Phe Val Val Thr Ala Ala Glu Ala Glu Ala Ala Ala Ala Gly His Ala
145                 150                 155                 160

Glu Cys Val Pro Pro Pro Leu Ala Phe Gly Ser Gly Arg Glu Leu Leu
                165                 170                 175

Asp Leu Thr Leu Arg Thr Gly Leu Thr Ile Pro Gln Ile Gln Leu Ala
            180                 185                 190

Asn Glu Leu Thr Leu Arg Pro Arg Asp Glu Ile Asp Ala Gly Leu Asp
        195                 200                 205

Ala Ile Arg Asp Ala Met Phe Ala Cys Ile Glu Arg Gly Leu Arg Met
    210                 215                 220

Asp Gly Glu Leu Pro Gly Gly Leu Arg Val Arg Arg Arg Ala Lys Arg
225                 230                 235                 240

Leu Tyr Glu Ser Leu Glu Ala Thr Lys Leu Ala Asn Ser Arg Pro Ala
                245                 250                 255

His Glu Ile Met Asp Trp Ile Ser Leu Tyr Ala Leu Ala Val Asn Glu
            260                 265                 270

Glu Asn Ala Ser Gly Gly Arg Val Val Thr Ala Pro Thr Asn Gly Ala
        275                 280                 285

Ala Gly Ile Val Pro Ala Val Leu Arg Tyr Thr Arg Asp Phe Cys Pro
    290                 295                 300

Asp Trp Ser Asp Glu Arg Gly Arg Glu Phe Leu Leu Thr Ala Ala Ala
305                 310                 315                 320

Ile Gly Gly Leu Ile Lys Ala Arg Ala Ser Ile Ser Gly Ala Glu Val
                325                 330                 335

Gly Cys Gln Gly Glu Val Gly Ser Ala Ala Ala Met Ala Ala Ala Gly
            340                 345                 350

Leu Thr Ala Val Leu Gly Gly Ser Ala Phe Gln Ile Glu Asn Ala Ala
        355                 360                 365

Glu Ile Ala Met Glu His His Leu Gly Met Thr Cys Asp Pro Ile Ala
    370                 375                 380

Gly Leu Val Gln Val Pro Cys Ile Glu Arg Asn Ala Phe Gly Ala Asn
385                 390                 395                 400

Lys Ala Val Val Ala Ala Ser Leu Ser Leu Arg Gly Asp Gly Gln His
                405                 410                 415

Arg Val Ser Leu Asp Glu Val Ile Glu Thr Met Arg Gln Thr Gly His
            420                 425                 430

Asp Met Gln Ala Lys Tyr Lys Glu Thr Ser Leu Gly Gly Leu Ala Val
        435                 440                 445

Asn Val Ala Ala Cys
    450
```

<210> SEQ ID NO 2
<211> LENGTH: 1362
<212> TYPE: DNA
<213> ORGANISM: Methylobacterium extorquens

<400> SEQUENCE: 2

```
atgatcagca ccttcgatct gttcaagatc gggatcggtc cgtcgagctc ccacaccgtc     60
gggccgatga tcgccgggcg ccggttccgc gagaccgtac tcgcccgcgg cggcatcgcc    120
cgcatcagcg ccgagatcta cggctcgctc gcctggaccg ggcgcggcca cggcaccgac    180
gtggcgatcc tgctcgggct catgggccac gcgccctcca ccatcgaccc ggatcggacg    240
gcgccgctcg ccgacgaact gcgccgcacc ggcgatctcg gcattcccgg cgtccatttc    300
gagcccgagc gcgacctcgt cttcaacttc aaggacatcc tgccgctgca caccaacggc    360
atgcgctttc gcgcctacga tgccggggac gcgccgatcg aggaccagat cttctactcg    420
gtcggcggcg gcttcgtcgt caccgccgcc gaggcggaag ctgccgcggc gggtcatgcg    480
gagtgcgtgc cacccccgct cgccttcggc agcgggcgtg aactcctcga cctgacgcta    540
cgcaccgggc tgacgatccc gcagatccag ctcgccaacg agctgaccct gcgcccgcgc    600
gacgagatcg atgccggcct cgacgcgatc cgcgatgcga tgttcgcctg catcgagcgc    660
ggcctgcgca tggacggcga attgcccggc ggcctgcggg tgcggcggcg ggccaagcgg    720
ctctacgagt cgctggaggc gacgaagctc gccaacagcc gcccggccca cgagatcatg    780
gattggatca gcctctacgc gctcgccgtc aacgaggaga acgcctcggg cggccgggtg    840
gtgacggcgc cgaccaacgg cgcggccggc atcgtcccgg cggtgctgcg ctacacccgc    900
gatttctgcc ccgattggag cgacgagcgc gggcgcgagt tcctgctcac cgccgccgcc    960
atcggcgggc tgatcaaggc ccgtgcctcg atctcggggg cggaggtcgg ctgccagggc   1020
gaggtcggct cggccgcggc gatggcggcg gcggggctga ccgccgtgct cggcggctcg   1080
gccttccaga tcgagaacgc cgccgagatc gccatggagc accatctagg catgacctgc   1140
gatccgatcg ccggcctcgt gcaagtgccc tgcatcgagc gcaacgcctt cggcgccaac   1200
aaggcagtgg tggcggcctc gctgtcgctc cgcggcgacg gccagcaccg ggtgagcctg   1260
gacgaggtga tcgagaccat gcgccagacc ggccacgaca tgcaggccaa gtacaaggaa   1320
acctcgctcg gggggctagc cgtcaacgtc gccgcctgct ga                      1362
```

<210> SEQ ID NO 3
<211> LENGTH: 469
<212> TYPE: PRT
<213> ORGANISM: Methylobacterium extorquens

<400> SEQUENCE: 3

```
Met Thr Ile His Gln Ser Pro Glu Ala Phe Gly Tyr Asp Ala Phe Leu
1               5                   10                  15

Arg Gln His Gln Asn Lys Glu Val Leu Arg Phe Ile Thr Cys Gly Ser
            20                  25                  30

Val Asp Asp Gly Lys Ser Thr Leu Ile Gly Arg Leu Leu His Asp Thr
        35                  40                  45

Lys Gln Ile Phe Asp Asp Gln Val Thr Ala Leu Gln Arg Asp Ser Arg
    50                  55                  60

Lys His Gly Thr Gln Gly Gly Glu Val Asp Leu Ala Leu Leu Val Asp
65                  70                  75                  80

Gly Leu Gln Ala Glu Arg Glu Gln Gly Ile Thr Ile Asp Val Ala Tyr
                85                  90                  95

Arg Phe Phe Ser Thr Asp Arg Arg Ser Phe Ile Val Ala Asp Thr Pro
            100                 105                 110
```

-continued

```
Gly His Glu Gln Tyr Thr Arg Asn Met Ala Thr Gly Ala Ser Thr Ala
        115                 120                 125

Asp Leu Ala Val Ile Leu Val Asp Ala Arg His Gly Leu Thr Arg Gln
    130                 135                 140

Ser Arg Arg His Ala Leu Leu Val Ser Leu Leu Gly Ile Arg Arg Val
145                 150                 155                 160

Ala Leu Ala Ile Asn Lys Met Asp Leu Val Gly Trp Ser Gln Asp Lys
                165                 170                 175

Phe Glu Ala Ile Val Ser Gly Phe Gln Ala Phe Ala Ala Pro Leu Asn
            180                 185                 190

Phe Thr Glu Val Arg Ala Ile Pro Leu Ser Ala Lys Asn Gly Asp Asn
        195                 200                 205

Val Val Leu Pro Gly Thr Ala Ala Thr Trp Tyr Thr Asp Val Pro Leu
    210                 215                 220

Leu Arg Tyr Leu Glu Glu Val Pro Val Lys Ser Glu Glu Arg Ala Ala
225                 230                 235                 240

Ala Phe Arg Met Pro Val Gln Trp Val Asn Arg Pro Asn Ser Asp Phe
                245                 250                 255

Arg Gly Phe Ser Gly Leu Ile Ala Ser Gly Ser Val Ala Pro Gly Asp
            260                 265                 270

Ala Val Thr Val Ala Pro Ser Gly Lys Thr Ser Thr Ile Ala Arg Ile
        275                 280                 285

Phe Thr Ala Asp Gly Asp Leu Glu Arg Ala Ser Glu Gly Gln Ser Val
    290                 295                 300

Thr Leu Val Leu Ala Asp Glu Val Asp Ala Ser Arg Gly Ala Val Ile
305                 310                 315                 320

Ala Thr Ser Asp Ala Pro Leu Thr Leu Thr Asp Ser Leu Asp Val Arg
                325                 330                 335

Leu Phe Trp Ala Ala Glu Ser Asp Leu Val Pro Gly Ala Asn Leu Trp
            340                 345                 350

Ala Lys Val Gly Thr Gln Thr Val Asn Ala Val Val Lys Ala Val His
        355                 360                 365

Arg Arg Ile Asp Pro Glu Thr Gly Gln Ala Gly Pro Ala Asp Lys Leu
    370                 375                 380

Ala Val Asn Asp Ile Gly Asp Val Thr Leu Thr Leu Asp Arg Gln Ile
385                 390                 395                 400

Ala Val Asp Pro Tyr Ala Glu Asn Arg Asp Thr Gly Ser Leu Ile Leu
                405                 410                 415

Ile Asp Arg Glu Thr Thr Asp Thr Ala Ala Leu Gly Leu Val Gln Arg
            420                 425                 430

Val Val Ala Ser Ser Lys Val Ala Pro Ala Pro Thr Ala Ser Val Thr
        435                 440                 445

Ala Ser Ala Glu Pro Ala Arg Ser Gly Gly Leu Leu Ala Gly Leu Lys
    450                 455                 460

Arg Leu Phe Gly Gly
465
```

<210> SEQ ID NO 4
<211> LENGTH: 1410
<212> TYPE: DNA
<213> ORGANISM: Methylobacterium extorquens -continued

<400> SEQUENCE: 4
atgaccatcc atcagtctcc ggaagcgttc ggctacgacg ccttcctgcg tcagcaccag 60
aacaaggaag tcctgcgctt catcacctgc ggctcggtcg atgacggcaa gtccaccctg 120
atcgggcggc tcctgcacga caccaagcag atcttcgacg atcaggtgac ggcgctccag 180
cgcgattcgc gcaagcacgg cacgcagggc ggcgaggtcg atctcgccct tctggttgac 240
ggactccagg ccgagcgcga gcagggcatc accatcgatg tcgcctaccg cttcttctcg 300
accgaccggc gctccttcat cgtcgccgac acccccggcc acgagcagta cacccgcaac 360
atggcgaccg gcgcctcgac cgccgacctc gccgtgatcc tggtggacgc ccgccacggg 420
ctgacccgcc agagccggcg ccacgcgctg ctggtctcgc tgctcggcat ccgccgcgtc 480
gcgctcgcca tcaacaagat ggacctcgtc ggctggtcgc aggacaagtt cgaggcgatc 540
gtctccggct tccaggcctt tgccgcgccg ctgaacttca ccgaggtgcg ggcgatcccg 600
ctctcggcca agaacggcga caacgtcgtc ctgccgggca ccgccgcgac ctggtacacg 660
gacgttccgc tgctgcgcta tctcgaagag gtgccggtga agtcggagga gcgcgccgcc 720
gccttccgca tgccggtgca gtgggtgaac cgcccgaatt ccgacttccg cggcttctcg 780
gggctgatcg cctcgggctc cgtcgcgccg ggcgatgccg tcaccgtcgc gccttccggc 840
aagacctcga cgatcgcccg catcttcacc gccgacggcg atctggaacg ggcgagcgag 900
ggccagtcgg tgacgctggt gctggccgac gaagtcgatg cctcgcgcgg cgcggtgatc 960
gcgacctcgg acgcaccgtt gacgctgacc gacagcctcg acgtgcgcct gttctgggcc 1020
gccgaatccg atctcgttcc cggcgccaac ctgtgggcga aggtcggcac gcagaccgtc 1080
aacgcggtgg tgaaggcggt gcaccgccgg atcgatccgg agacgggaca ggccggtccg 1140
gccgacaagc tcgcggtcaa cgacatcggc gacgtgacgc tgaccctcga ccggcagatc 1200
gcggtcgatc cctatgccga gaaccgcgac accggcagcc tgatcctgat cgaccgtgag 1260
acgaccgaca cggccgcgct cggcctcgtg cagagggtcg ttgcgtcgag caaggtcgct 1320
ccggcgccga ccgcgtctgt gacggcttcg gcggagcccg cacgtagcgg cggtttgctg 1380
gccggcctca agcggctgtt cggcggataa 1410

<210> SEQ ID NO 5
<211> LENGTH: 309
<212> TYPE: PRT
<213> ORGANISM: Methylobacterium extorquens

<400> SEQUENCE: 5

Met Ser Ala Ala Val Ala Ala Pro Ala Arg Thr Arg Leu Thr His Leu
1 5 10 15

Gln Arg Leu Glu Ala Glu Ser Ile His Ile Phe Arg Glu Ala Val Ala
20 25 30

Glu Ala Glu Asn Pro Val Met Leu Tyr Ser Ile Gly Lys Asp Ser Ser
35 40 45

Val Leu Leu His Leu Ala Leu Lys Ala Phe Ala Pro Gly Arg Leu Pro
50 55 60

Phe Pro Leu Met His Ile Asp Thr Thr Trp Lys Phe Arg Glu Met Ile
65 70 75 80

Ala Phe Arg Asp Arg Arg Ala Lys Glu Leu Gly Leu Glu Leu Ile Val
85 90 95

His Thr Asn Gln Asp Gly Leu Ala Lys Gly Val Gly Pro Val Ser His
100 105 110

-continued

```
Gly Ser Glu Val His Thr Asp Val Met Lys Thr Gln Ala Leu Arg Gln
        115                 120                 125

Ala Leu Asp Lys Tyr Lys Tyr Asp Val Ala Phe Gly Gly Ala Arg Arg
    130                 135                 140

Asp Glu Glu Ala Ser Arg Ala Lys Glu Arg Ile Val Ser Leu Arg Asn
145                 150                 155                 160

Gly Gln His Arg Trp Asp Pro Lys Arg Gln Arg Ala Glu Pro Trp His
                165                 170                 175

Leu Tyr Asn Phe Lys Lys Arg Arg Gly Glu Ser Phe Arg Val Phe Pro
            180                 185                 190

Leu Ser Asn Trp Thr Glu Leu Asp Ile Trp Leu Tyr Ile Glu Gln Glu
        195                 200                 205

Asn Ile Pro Ile Val Pro Leu Tyr Phe Ala Ala Glu Arg Pro Val Val
    210                 215                 220

Glu Arg Asp Gly Gln Leu Ile Met Val Asp Asp Glu Arg Phe Pro Leu
225                 230                 235                 240

Glu Pro Gly Glu Thr Pro Gln Gln Arg Gln Val Arg Phe Arg Thr Leu
                245                 250                 255

Gly Cys Tyr Pro Leu Thr Gly Ala Val Glu Ser Pro Ala Ala Thr Leu
            260                 265                 270

Pro Glu Ile Ile Gly Glu Thr Leu Ala Ala Arg Thr Ser Glu Arg Gln
        275                 280                 285

Gly Arg Val Ile Asp Lys Asp Gly Ala Gly Ala Met Glu Arg Lys Lys
    290                 295                 300

Gln Glu Gly Tyr Phe
305
```

<210> SEQ ID NO 6
<211> LENGTH: 930
<212> TYPE: DNA
<213> ORGANISM: Methylobacterium extorquens

<400> SEQUENCE: 6

```
atgagcgctg ccgtcgccgc gcccgcgcgc acccgcctga cgcatctcca gcgtctcgag     60

gccgagagca tccacatctt ccgggaggcc gtcgccgagg ccgagaaccc ggtgatgctc    120

tactcgatcg gcaaggattc gtcggtgctg ctgcacctgg cgctgaaggc cttcgcgccg    180

gggcgcctcc cgttccccct gatgcacatc gacacgacct ggaagttccg cgagatgatc    240

gccttccgcg atcggcgagc caaggagctc gggctcgaac tcatcgtgca cacgaatcag    300

gacgggcttg ccaagggcgt cggcccggtc agccacggct cggaagtgca taccgacgtg    360

atgaagacgc aggccctgcg gcaggcgctc gacaagtaca agtatgacgt ggccttcggc    420

ggcgcccgcc gggacgagga ggccagccgc gccaaggagc gcatcgtgag cctgcgcaac    480

ggccagcacc gctgggaccc gaagcgccag cgcgccgagc cgtggcacct ctacaatttc    540

aagaagcggc gcggcgagag ttttcgcgtg ttcccgctat ccaactggac cgaattggat    600

atctggctct acatcgagca ggaaaatatt ccgatcgtcc cgctctactt cgccgccgag    660

cgcccggtgg tggagcgcga cggccagctc atcatggtcg atgacgagcg ctttccgctg    720

gagccgggcg agaccccaca acagcggcag gtccggttcc gcacgctcgg ctgctacccg    780

ctgaccggcg cggtcgagag cccggccgcg accctgccgg agatcatcgg cgagacgctg    840

gccgcccgaa cctcggagcg ccagggccgg gtcatcgaca aggacggcgc cggcgccatg    900

gagcgcaaga agcaggaggg ctatttctga                                     930
```

<210> SEQ ID NO 7
<211> LENGTH: 201
<212> TYPE: PRT
<213> ORGANISM: Escherichia coli

<400> SEQUENCE: 7

```
Met Ala Leu His Asp Glu Asn Val Val Trp His Ser His Pro Val Thr
1               5                   10                  15

Val Gln Gln Arg Glu Leu His His Gly His Arg Gly Val Val Leu Trp
            20                  25                  30

Phe Thr Gly Leu Ser Gly Ser Gly Lys Ser Thr Val Ala Gly Ala Leu
        35                  40                  45

Glu Glu Ala Leu His Lys Leu Gly Val Ser Thr Tyr Leu Leu Asp Gly
    50                  55                  60

Asp Asn Val Arg His Gly Leu Cys Ser Asp Leu Gly Phe Ser Asp Ala
65                  70                  75                  80

Asp Arg Lys Glu Asn Ile Arg Arg Val Gly Glu Val Ala Asn Leu Met
                85                  90                  95

Val Glu Ala Gly Leu Val Val Leu Thr Ala Phe Ile Ser Pro His Arg
            100                 105                 110

Ala Glu Arg Gln Met Val Arg Glu Arg Val Gly Glu Gly Arg Phe Ile
        115                 120                 125

Glu Val Phe Val Asp Thr Pro Leu Ala Ile Cys Glu Ala Arg Asp Pro
    130                 135                 140

Lys Gly Leu Tyr Lys Lys Ala Arg Ala Gly Glu Leu Arg Asn Phe Thr
145                 150                 155                 160

Gly Ile Asp Ser Val Tyr Glu Ala Pro Glu Ser Ala Glu Ile His Leu
                165                 170                 175

Asn Gly Glu Gln Leu Val Thr Asn Leu Val Gln Gln Leu Leu Asp Leu
            180                 185                 190

Leu Arg Gln Asn Asp Ile Ile Arg Ser
        195                 200
```

<210> SEQ ID NO 8
<211> LENGTH: 606
<212> TYPE: DNA
<213> ORGANISM: Escherichia coli

<400> SEQUENCE: 8

```
atggcgctgc atgacgaaaa cgtcgtctgg catagccatc cggtcactgt gcaacaacgc     60

gagctacacc acggtcatcg tggtgtagtg ctgtggttta ccggcctctc cgggtccggt    120

aaatcaacgg tcgccggggc gctggaggag gcgttacata aactcggcgt cagtacgtat    180

ctgctggatg gcgacaatgt tcgccacgga ttatgcagcg atctcggttt tagcgatgcc    240

gatcgtaaag agaatatccg tcgcgtcggt gaagtggcga atttgatggt tgaagccgga    300

ctggtggtgc tgaccgcatt tatctcgcca caccgcgccg aacgccagat ggttcgcgaa    360

cgcgtaggag aagggcgctt tatcgaagtg tttgtcgata cgccgctggc gatttgcgaa    420

gcccgcgatc ccaaaggctt atataagaaa gcgcgtgccg gtgaactgcg caactttacg    480

ggaatagatt ccgtttacga agcgcctgaa tcggcagaaa ttcatctcaa tggtgaacaa    540

ttagtaacaa atttggtaca gcaattatta gatctgttga gacagaacga tattatcaga    600

tcctga                                                               606
```

-continued

<210> SEQ ID NO 9
<211> LENGTH: 322
<212> TYPE: PRT
<213> ORGANISM: Ostreococcus tauri

<400> SEQUENCE: 9

```
Met Pro Arg Gly Trp Thr Lys Thr Arg Ala Tyr Asp Ser His His Phe
1               5                   10                  15

Asp Ala Asp Ala Trp Ser Val Val Thr Pro Arg Ala Gly Asp Val Ile
            20                  25                  30

Ile Ala Thr Ala Tyr Lys Ser Gly Thr Thr Trp Met Gln Gln Ile Val
        35                  40                  45

Ser Gln Leu Val Phe Glu Gly Ala Ala Pro Ala Ala Leu Gly Glu Leu
    50                  55                  60

Ser Pro Trp Val Asp Leu Arg Val Pro Pro Arg Glu Val Lys Arg Gly
65                  70                  75                  80

Met Ile Glu Gly Leu Pro Ser Pro Arg Ile Leu Lys Thr His Leu Pro
                85                  90                  95

Thr Thr Gly Leu Glu Tyr Asp Glu Asn Ala Lys Tyr Ile Tyr Val Ala
            100                 105                 110

Arg Asp Gly Arg Asp Ala Phe Met Ser Leu Met Asn His Tyr Lys Asn
        115                 120                 125

Gly Asn Glu Ala Phe Tyr Gly Ala Leu Asn Gly Pro Gly Leu Lys Gly
    130                 135                 140

Ala Pro Leu Pro Thr Trp Glu Glu Ala Cys Glu Gly Glu Gly Asp Glu
145                 150                 155                 160

Lys Leu Arg Ala Leu Phe Asp Lys Trp Leu Asn Thr Pro Trp Gly Gln
                165                 170                 175

His Pro Trp Glu Glu Asp Gly Trp Pro Phe Trp Ser Leu Phe Tyr Asn
            180                 185                 190

Met Lys Thr Trp Trp Asp Ala Arg Glu Ser Lys Asn Ile Ile Phe Val
        195                 200                 205

His Phe Ser Asp Leu Lys Lys Asp Leu Lys Gly Gln Met Arg Arg Ile
    210                 215                 220

Ala Lys Phe Leu Asn Ala Pro Ile Asp Glu Ser Lys Phe Asp Ala Gln
225                 230                 235                 240

Val Thr Ala Cys Thr Phe Glu Ser Met Lys Gly Asn Ala Ala Ser Val
                245                 250                 255

Ala Pro Leu Gly Gly Ala Leu Trp Lys Gly Gly Ala Glu Thr Phe Ile
            260                 265                 270

Asn Lys Gly Thr Asn Gly Arg Trp Arg Asn Val Leu Thr Lys Glu Gln
        275                 280                 285

Val Lys Gln Tyr Glu Gln Val Ala Glu Lys Arg Leu Gly Lys Asp Cys
    290                 295                 300

Ala Lys Trp Leu Ala Asn Gly Gly Asp Met Asn Gly Arg Gly Cys Val
305                 310                 315                 320

Ile Met
```

<210> SEQ ID NO 10
<211> LENGTH: 969
<212> TYPE: DNA
<213> ORGANISM: Ostreococcus tauri -continued

<400> SEQUENCE: 10

```
atgccgcgcg gatggacgaa gacgcgcgcg tacgactcgc atcactttga cgccgacgcg      60
tggtcggtgg tgacgcctcg agcgggtgac gtcatcatcg ccaccgcgta taaatctggc     120
acgacgtgga tgcaacagat cgtgtcgcaa ctcgtgttcg agggcgcggc cccggcggcg     180
ttgggggagc tctcgccgtg ggtggatctg cgcgtgcccc cgcgggaggt gaagcgaggg     240
atgatcgagg gattgccctc gccccggatc ttgaagacgc atcttccgac gacggggttg     300
gaatacgacg aaaacgcgaa gtacatttac gtcgcgcggg acggccgcga cgcgttcatg     360
tctttgatga accactataa gaacggtaat gaagcgtttt acggcgcgct gaacggccct     420
gggttaaagg gcgcaccttt gcctacgtgg gaagaggcgt gcgaaggcga gggcgacgag     480
aaacttcgcg cgctttttga caagtggctc aacacgccgt ggggccagca cccgtgggaa     540
gaagacgggt ggcctttctg gtctctgttc tataacatga agacgtggtg ggacgcgcgc     600
gaatccaaga acatcatctt cgtgcatttt tcggatttga agaaggattt gaagggtcag     660
atgcgacgca ttgcgaagtt tttgaacgcc ccgatcgatg aaagcaaatt cgatgcgcaa     720
gtcacagcgt gcacgttcga gagcatgaag ggtaacgccg cgagcgtcgc gcctctcggt     780
ggcgcgctgt ggaagggcgg tgcggagacg ttcattaaca aaggtaccaa cggccggtgg     840
aggaacgttc taaccaagga acaagtcaag cagtacgagc aggtggctga gaaacggctg     900
ggtaaggact gcgcaaagtg gctcgccaac ggcggcgata tgaacggccg tgggtgcgtg     960
atcatgtga                                                              969
```

<210> SEQ ID NO 11
<211> LENGTH: 488
<212> TYPE: PRT
<213> ORGANISM: Synechoccocus sp.

<400> SEQUENCE: 11

```
Met Phe Lys Ala Ser Lys Tyr Tyr Asn Leu Leu Gln Gln Leu Glu Asn
1               5                   10                  15

Phe Phe Ser Thr Ala Asn Ser Ser Ser Leu Leu Thr Lys Pro Ile Asp
            20                  25                  30

Pro Asn Val Leu Lys Ser Gln Leu Ser Leu Asp Leu Pro Asn Glu Gly
        35                  40                  45

Lys Pro Val Glu Glu Leu Arg Thr Glu Ile Thr Ser Tyr Leu Asn Asn
    50                  55                  60

Ala Leu Lys Thr Ala His Pro Ser Tyr Phe Asn Gln Leu Trp Gly Gly
65                  70                  75                  80

Phe Asn Ser Ala Cys Phe Met Gly Asp Met Leu Ala Ser Ala Thr Asn
                85                  90                  95

Thr Ser Met Tyr Thr Tyr Glu Val Ala Pro Ala Ala Thr Leu Ile Glu
            100                 105                 110

Gln Ala Leu Val Thr Lys Met Ser Gly Ile Leu Gly Phe Lys Ser Ala
        115                 120                 125

Asp Gly Gln Phe Thr Thr Gly Gly Ser Asn Gly Asn Leu Met Ala Met
    130                 135                 140

Ala Ile Ala Arg His His Val Leu Pro Thr Val Lys Gln Asp Gly Met
145                 150                 155                 160

Thr Ser Gly Pro Lys Leu Val Ala Phe Val Ser Arg Glu Ala His Tyr
                165                 170                 175
```

-continued

Ser Phe Asp Lys Ala Ala His Ile Leu Gly Leu Gly Thr Glu Gln Leu
180 185 190

Trp Lys Val Pro Val Asp Ser Asp Gly Arg Met Lys Pro Glu Ala Leu
195 200 205

Ser Glu Leu Val Asp Arg Ala Arg Val Gln Gly Ser Ile Pro Phe Phe
210 215 220

Val Ala Gly Thr Ala Gly Thr Thr Val Arg Gly Ala Phe Asp Pro Phe
225 230 235 240

Glu Glu Ile Ser Ala Ile Ala His Gln Glu Asn Leu Trp Phe His Ile
245 250 255

Asp Gly Ala Trp Gly Ala Ser Val Ser Leu Ser Ala Thr His Arg Gln
260 265 270

Leu Met Ala Gly Ala Asn Gln Ala Asp Ser Leu Val Trp Asp Ala His
275 280 285

Lys Met Met Gly Met Thr Leu Met Cys Ser Leu Leu Leu Val Lys Gln
290 295 300

Arg Gly Gln Met Leu Arg Thr Phe Ser Thr Ala Gly Thr Asp Tyr Leu
305 310 315 320

Phe His Asp Glu Val Ser Ala Gly Glu Val Pro Thr Glu Ser Ser Thr
325 330 335

Ser Ser Thr Glu Leu Pro Ile Glu Glu Leu Pro Thr Asp Phe Gly Pro
340 345 350

Ala Thr Met His Cys Gly Arg Arg Val Asp Ala Leu Lys Leu Trp Leu
355 360 365

Ala Trp Arg His Leu Gly Asp Arg Gly Trp Glu Arg Leu Ile Asp Ser
370 375 380

Tyr Phe Glu Leu Ala Gln Arg Ala Glu Thr Ile Ile Asp Lys His Pro
385 390 395 400

Ser Leu Glu Leu Val Ser Ser Arg Gln Ser Val Asn Leu Cys Phe Arg
405 410 415

Tyr Leu Pro Gln Asn Lys Gln Gln Ala Asp Glu Leu Thr Leu Lys Val
420 425 430

Arg Gln Ala Leu Trp Glu Thr Gly Thr Ala Met Val Asn Tyr Ala Gln
435 440 445

Val Glu Gly Lys Thr Val Phe Arg Leu Val Ile Cys Asn Asn Gln Thr
450 455 460

Arg Ser Glu Asp Ile Glu Arg Phe Phe Glu Ala Leu Val Ala Ile Ala
465 470 475 480

Arg Arg Leu Glu Gln Glu Met Cys
485

<210> SEQ ID NO 12
<211> LENGTH: 1467
<212> TYPE: DNA
<213> ORGANISM: Synechoccocus sp.

<400> SEQUENCE: 12
atgttcaaag cctccaaata ctacaacttg ttgcagcagc ttgaaaattt cttttcgaca 60
gctaattcgt cgagtctgct tactaaacca atagatccta acgttttgaa atctcaactt 120
tctttggatt taccaaatga gggtaaacct gtagaagaac tgcgaacgga gattactagc 180
tatttgaata acgcgctgaa gacagctcat cctagctatt ttaatcagct gtggggcggt 240
ttcaactcag cctgtttcat gggtgatatg cttgcgagtg cgacaaatac ctcgatgtat 300

-continued acctacgagg tggcgccggc tgctacttta atcgagcagg cgctagttac taagatgtct 360
ggcatcttag ggtttaagag tgccgatggg cagtttacaa ccggagggag taacggaaat 420
ttgatggcga tggcgatcgc tcgccatcat gttctaccga ctgttaagca ggacggtatg 480
accagcggcc ccaaactagt tgcttttgtc tctagagagg cgcactattc ttttgataaa 540
gctgctcata tattgggatt aggaacagag cagctatgga aagttcctgt agacagcgat 600
ggcagaatga agccggaggc attatctgag ctagtagata gagcgcgtgt acaaggctct 660
attcctttct ttgttgccgg aactgctgga acaactgtaa gaggtgcctt cgatccgttt 720
gaagagatta gcgcgatcgc ccaccaggaa aacctgtggt ttcatatcga tggagcttgg 780
ggtgctagcg tatcgctgag cgctactcat cgacagctaa tggctggggc aaaccaagca 840
gactctctgg tgtgggacgc acacaaaatg atggggatga cgctgatgtg ttctttgctg 900
ttggtcaagc agcgtggtca aatgttaagg actttctcta ctgcaggcac cgactatcta 960
ttccacgatg aagtctctgc tggggaagtg cctacagaat catcaacatc atcaacagaa 1020
ttgcccatag aagaactacc aacagacttt ggccctgcaa ctatgcactg cggtcggcgt 1080
gtggatgcac tcaagctttg gctagcctgg cggcacctag gcgatcgcgg ctgggaaagg 1140
ctaatcgaca gctactttga gctggctcag cgagcagaaa ctatcatcga taagcatcct 1200
tcgctggagc tagtgtcttc gagacagtcg gtgaacctat gctttcggta tctacctcag 1260
aacaaacagc aggccgatga gctgacgctg aaagtgcgac aggcgctgtg ggaaaccgga 1320
actgcgatgg tgaactacgc tcaagtagaa ggcaaaacgg tttttcgttt ggtcatttgc 1380
aacaatcaaa cccgctctga ggacatcgag cgtttttttcg aggctttagt agcgatcgcc 1440
cggcggttag agcaggagat gtgctga 1467

<210> SEQ ID NO 13
<211> LENGTH: 466
<212> TYPE: PRT
<213> ORGANISM: Escherichia coli

<400> SEQUENCE: 13

Met Asp Gln Lys Leu Leu Thr Asp Phe Arg Ser Glu Leu Leu Asp Ser
1 5 10 15

Arg Phe Gly Ala Lys Ala Ile Ser Thr Ile Ala Glu Ser Lys Arg Phe
20 25 30

Pro Leu His Glu Met Arg Asp Asp Val Ala Phe Gln Ile Ile Asn Asp
35 40 45

Glu Leu Tyr Leu Asp Gly Asn Ala Arg Gln Asn Leu Ala Thr Phe Cys
50 55 60

Gln Thr Trp Asp Asp Glu Asn Val His Lys Leu Met Asp Leu Ser Ile
65 70 75 80

Asn Lys Asn Trp Ile Asp Lys Glu Glu Tyr Pro Gln Ser Ala Ala Ile
85 90 95

Asp Leu Arg Cys Val Asn Met Val Ala Asp Leu Trp His Ala Pro Ala
100 105 110

Pro Lys Asn Gly Gln Ala Val Gly Thr Asn Thr Ile Gly Ser Ser Glu
115 120 125

Ala Cys Met Leu Gly Gly Met Ala Met Lys Trp Arg Trp Arg Lys Arg
130 135 140

Met Glu Ala Ala Gly Lys Pro Thr Asp Lys Pro Asn Leu Val Cys Gly
145 150 155 160

```
Pro Val Gln Ile Cys Trp His Lys Phe Ala Arg Tyr Trp Asp Val Glu
                165                 170                 175

Leu Arg Glu Ile Pro Met Arg Pro Gly Gln Leu Phe Met Asp Pro Lys
            180                 185                 190

Arg Met Ile Glu Ala Cys Asp Glu Asn Thr Ile Gly Val Val Pro Thr
        195                 200                 205

Phe Gly Val Thr Tyr Thr Gly Asn Tyr Glu Phe Pro Gln Pro Leu His
    210                 215                 220

Asp Ala Leu Asp Lys Phe Gln Ala Asp Thr Gly Ile Asp Ile Asp Met
225                 230                 235                 240

His Ile Asp Ala Ala Ser Gly Gly Phe Leu Ala Pro Phe Val Ala Pro
                245                 250                 255

Asp Ile Val Trp Asp Phe Arg Leu Pro Arg Val Lys Ser Ile Ser Ala
            260                 265                 270

Ser Gly His Lys Phe Gly Leu Ala Pro Leu Gly Cys Gly Trp Val Ile
        275                 280                 285

Trp Arg Asp Glu Glu Ala Leu Pro Gln Glu Leu Val Phe Asn Val Asp
    290                 295                 300

Tyr Leu Gly Gly Gln Ile Gly Thr Phe Ala Ile Asn Phe Ser Arg Pro
305                 310                 315                 320

Ala Gly Gln Val Ile Ala Gln Tyr Tyr Glu Phe Leu Arg Leu Gly Arg
                325                 330                 335

Glu Gly Tyr Thr Lys Val Gln Asn Ala Ser Tyr Gln Val Ala Ala Tyr
            340                 345                 350

Leu Ala Asp Glu Ile Ala Lys Leu Gly Pro Tyr Glu Phe Ile Cys Thr
        355                 360                 365

Gly Arg Pro Asp Glu Gly Ile Pro Ala Val Cys Phe Lys Leu Lys Asp
    370                 375                 380

Gly Glu Asp Pro Gly Tyr Thr Leu Tyr Asp Leu Ser Glu Arg Leu Arg
385                 390                 395                 400

Leu Arg Gly Trp Gln Val Pro Ala Phe Thr Leu Gly Gly Glu Ala Thr
                405                 410                 415

Asp Ile Val Val Met Arg Ile Met Cys Arg Arg Gly Phe Glu Met Asp
            420                 425                 430

Phe Ala Glu Leu Leu Leu Glu Asp Tyr Lys Ala Ser Leu Lys Tyr Leu
        435                 440                 445

Ser Asp His Pro Lys Leu Gln Gly Ile Ala Gln Gln Asn Ser Phe Lys
    450                 455                 460

His Thr
465
```

<210> SEQ ID NO 14
<211> LENGTH: 1401
<212> TYPE: DNA
<213> ORGANISM: Escherichia coli

<400> SEQUENCE: 14

```
atggaccaga agctgttaac ggatttccgc tcagaactac tcgattcacg ttttggcgca     60

aaggccattt ctactatcgc ggagtcaaaa cgatttccgc tgcacgaaat gcgcgatgat    120

gtcgcatttc agattatcaa tgatgaatta tatcttgatg gcaacgctcg tcagaacctg    180

gccactttct gccagacctg ggacgacgaa aacgtccata aattgatgga tttgtcgatc    240

aataaaaact ggatcgacaa agaagaatat ccgcaatccg cagccatcga cctgcgttgc    300
```

-continued

```
gtaaatatgg ttgccgatct gtggcatgcg cctgcgccga aaaatggtca ggccgttggc    360

accaacacca ttggttcttc cgaggcctgt atgctcggcg ggatggcgat gaaatggcgt    420

tggcgcaagc gtatggaagc tgcaggcaaa ccaacggata aaccaaacct ggtgtgcggt    480

ccggtacaaa tctgctggca taaattcgcc cgctactggg atgtggagct gcgtgagatc    540

cctatgcgcc ccggtcagtt gtttatggac ccgaaacgca tgattgaagc ctgtgacgaa    600

aacaccatcg gcgtggtgcc gactttcggc gtgacctaca ccggtaacta tgagttccca    660

caaccgctgc acgatgcgct ggataaattc caggccgaca ccggtatcga catcgacatg    720

cacatcgacg ctgccagcgg tggcttcctg gcaccgttcg tcgccccgga tatcgtctgg    780

gacttccgcc tgccgcgtgt gaaatcgatc agtgcttcag gccataaatt cggtctggct    840

ccgctgggct gcggctgggt tatctggcgt gacgaagaag cgctgccgca ggaactggtg    900

ttcaacgttg actacctggg tggtcaaatt ggtacttttg ccatcaactt ctcccgcccg    960

gcgggtcagg taattgcaca gtactatgaa ttcctgcgcc tcggtcgtga aggctatacc   1020

aaagtacaga acgcctctta ccaggttgcc gcttatctgg cggatgaaat cgccaaactg   1080

gggccgtatg agttcatctg tacgggtcgc ccggacgaag gcatcccggc ggtttgcttc   1140

aaactgaaag atggtgaaga tccgggatac accctgtacg acctctctga acgtctgcgt   1200

ctgcgcggct ggcaggttcc ggccttcact ctcggcggtg aagccaccga catcgtggtg   1260

atgcgcatta tgtgtcgtcg cggcttcgaa atggactttg ctgaactgtt gctggaagac   1320

tacaaagcct ccctgaaata tctcagcgat cacccgaaac tgcagggtat tgcccagcag   1380

aacagcttta aacacacctg a                                              1401
```

```
<210> SEQ ID NO 15
<211> LENGTH: 161
<212> TYPE: PRT
<213> ORGANISM: Bacillus subtilis

<400> SEQUENCE: 15

Met Glu Leu Tyr Glu Cys Ile Gln Asp Ile Phe Gly Gly Leu Lys Asn
1               5                   10                  15

Pro Ser Val Lys Asp Leu Ala Thr Ser Leu Lys Gln Ile Pro Asn Ala
            20                  25                  30

Ala Lys Leu Ser Gln Pro Tyr Ile Lys Glu Pro Asp Gln Tyr Ala Tyr
        35                  40                  45

Gly Arg Asn Ala Ile Tyr Arg Asn Asn Glu Leu Glu Ile Ile Val Ile
    50                  55                  60

Asn Ile Pro Pro Asn Lys Glu Thr Thr Val His Asp His Gly Gln Ser
65                  70                  75                  80

Ile Gly Cys Ala Met Val Leu Glu Gly Lys Leu Leu Asn Ser Ile Tyr
                85                  90                  95

Arg Ser Thr Gly Glu His Ala Glu Leu Ser Asn Ser Tyr Phe Val His
            100                 105                 110

Glu Gly Glu Cys Leu Ile Ser Thr Lys Gly Leu Ile His Lys Met Ser
        115                 120                 125

Asn Pro Thr Ser Glu Arg Met Val Ser Leu His Val Tyr Ser Pro Pro
    130                 135                 140

Leu Glu Asp Met Thr Val Phe Glu Glu Gln Lys Glu Val Leu Glu Asn
145                 150                 155                 160

Ser
```

```
<210> SEQ ID NO 16
<211> LENGTH: 486
<212> TYPE: DNA
<213> ORGANISM: Bacillus subtilis

<400> SEQUENCE: 16

atggaactgt atgagtgtat ccaagacatt tttggcggct tgaaaaatcc atcggttaaa      60

gatttagcaa cgtctttaaa acaaattcca aacgcagcaa aattgagtca accgtatatt     120

aaggaaccag accagtacgc ttacggccga aatgccatct atcgaaataa tgaattggaa     180

attatcgtga ttaacattcc gccaaacaag gagacaacag tacacgatca tggtcaatcc     240

attggttgtg caatggtgtt agaaggaaag cttcttaatt ctatttatcg ttcaaccggc     300

gaacacgcag aactctccaa ttcatacttt gtccacgaag gagaatgcct tatttcaacc     360

aaaggtttaa ttcacaaaat gtccaatcca acatctgaac gaatggtgtc tcttcatgtc     420

tactcccctc ctttggaaga catgacggtc tttgaggaac aaaaggaggt attggaaaat     480

tcatga                                                                486


<210> SEQ ID NO 17
<211> LENGTH: 416
<212> TYPE: PRT
<213> ORGANISM: Methanosarcina acetivorans

<400> SEQUENCE: 17

Met Gly Arg Phe Ile Leu Lys Cys Leu Lys Cys Gly Arg Glu Tyr Ser
1               5                   10                  15

Gln Glu Tyr Arg Leu Thr Cys Glu Asn Asp Asp Ser Phe Leu Arg Ala
            20                  25                  30

Glu Tyr Leu Glu Lys Lys Leu Glu Leu Arg Lys Gln Pro Gly Ile Gly
        35                  40                  45

Arg Phe His Ser Trp Leu Pro Val Gln Glu Glu Leu Thr Thr Glu Ala
    50                  55                  60

Gly Pro Ile Thr Tyr Lys Ser Glu Ala Leu Ala Arg Glu Leu Gly Leu
65                  70                  75                  80

Ser Asn Leu Tyr Ile Gly Phe Ser Gly Tyr Trp Pro Glu Lys Gly Ala
                85                  90                  95

Phe Ile Lys Thr Cys Ser Phe Lys Glu Leu Glu Ala His Pro Thr Met
            100                 105                 110

Gln Leu Leu Lys Glu Ser Gly Gly Lys Ala Ile Val Leu Ala Ser Ala
        115                 120                 125

Gly Asn Thr Gly Arg Ala Phe Ala His Val Ser Ala Leu Thr Gly Thr
    130                 135                 140

Asp Val Tyr Ile Val Val Pro Asp Ser Gly Ile Pro Lys Leu Trp Leu
145                 150                 155                 160

Pro Glu Glu Pro Thr Asp Ser Ile His Leu Ile Ser Met Thr Pro Gly
                165                 170                 175

Asn Asp Tyr Thr Asp Ala Ile Asn Leu Ala Gly Arg Ile Ala Lys Leu
            180                 185                 190

Pro Gly Met Val Pro Glu Gly Gly Ala Arg Asn Val Ala Arg Arg Glu
        195                 200                 205

Gly Met Gly Thr Val Met Leu Asp Ala Ala Val Thr Ile Gly Lys Met
    210                 215                 220

Pro Asp His Tyr Phe Gln Ala Val Gly Ser Gly Thr Gly Gly Ile Ser
225                 230                 235                 240
```

```
Ala Trp Glu Ala Ser Leu Arg Leu Arg Glu Asp Gly Arg Phe Gly Ser
                245                 250                 255

Lys Leu Pro Lys Leu Gln Leu Thr Gln Asn Leu Pro Phe Val Pro Met
            260                 265                 270

Tyr Asn Ala Trp Gln Glu Gly Arg Arg Asp Ile Ile Pro Glu Ile Asp
        275                 280                 285

Met Lys Asp Ala Lys Lys Arg Ile Glu Glu Thr Tyr Ala Thr Val Leu
    290                 295                 300

Thr Asn Arg Ala Pro Pro Tyr Ser Val Thr Gly Gly Leu Tyr Asp Ala
305                 310                 315                 320

Leu Val Asp Thr Asp Gly Ile Met Tyr Ala Val Ser Lys Glu Glu Ala
                325                 330                 335

Leu Asp Ala Lys Ala Leu Phe Glu Ser Leu Glu Gly Ile Asp Ile Leu
            340                 345                 350

Pro Pro Ser Ala Val Ala Ala Ala Ser Leu Leu Lys Ala Val Glu Ala
        355                 360                 365

Gly Asn Val Gly Lys Asp Asp Thr Ile Leu Leu Asn Ile Ala Gly Gly
    370                 375                 380

Gly Phe Lys Arg Leu Lys Glu Asp Phe Thr Leu Phe Gln Ile Glu Pro
385                 390                 395                 400

Glu Ile Thr Val Ser Asn Pro Asp Val Pro Leu Glu Glu Leu Lys Leu
                405                 410                 415


<210> SEQ ID NO 18
<211> LENGTH: 1251
<212> TYPE: DNA
<213> ORGANISM: Methanosarcina acetivorans

<400> SEQUENCE: 18

atgggaagat tcatattaaa atgtctgaaa tgcggcagag aatacagcca ggaatacagg      60

ctgacctgcg agaatgacga ctcctttttg cgggcggaat accttgaaaa aaaacttgag     120

ctgagaaagc agccagggat aggaagattt cactcatggc ttccggttca ggaagagctt     180

actaccgaag ccgggcccat cacgtacaaa agcgaagctc ttgcgaggga acttgggctt     240

tcgaatctgt acatagggtt cagcgggtac tggcccgaga aaggagcttt tatcaagacc     300

tgcagtttca aagaactcga agcccatcct acgatgcagc ttctcaagga atccggggga     360

aaagccatag tccttgcctc tgcagggaat acggggaggg cttttgcaca tgtttcggca     420

cttaccggaa ccgatgttta tatcgtggtt cccgactcag gcatccctaa actctggctg     480

cctgaagaac cgaccgattc cattcacctt atcagcatga ctccggggaa cgattacacc     540

gatgctatca accttgcagg aagaattgca aagcttcctg gaatggtccc tgaaggagga     600

gccagaaacg ttgccagaag agaaggaatg ggtactgtaa tgcttgatgc agccgtaacc     660

ataggaaaga tgcctgatca ctacttccag gctgtcggaa gcgggacggg aggaatctca     720

gcctgggaag cttctctgcg cctcagagag gacgggcgtt ttggttccaa acttccaaag     780

ctccagctta cccagaatct ccccttcgtt cccatgtata atgcatggca agaaggcagg     840

agggatataa ttcccgaaat tgacatgaaa gatgcaaaga agcggatcga agagacctac     900

gccactgtac ttaccaaccg agcaccacct tactccgtga caggcgggct ctatgacgca     960

cttgtcgata cggacgggat aatgtatgca gtaagcaaag aagaagccct tgacgcaaaa    1020

gcgctttttg agtcccttga aggaatagat atccttcccc catctgccgt tgctgctgct    1080

tccctcttaa aagccgtgga agccggaaat gtcggaaagg acgacactat cctcctgaac    1140
```

```
attgcaggcg gaggtttcaa acggctgaag gaagacttca cactattcca gattgaacct   1200

gaaattactg tctcgaaccc ggatgtgccg cttgaggaac tgaagctctg a           1251


<210> SEQ ID NO 19
<211> LENGTH: 252
<212> TYPE: PRT
<213> ORGANISM: Methanosphaera stadtmanae

<400> SEQUENCE: 19

Met Asn Ala Phe Lys Phe Leu Asp Glu Ile Gly Pro Val Asn Thr Asn
1               5                   10                  15

Thr Met Val Leu Asp Lys Ala Leu Gly Tyr Lys Thr Val Glu Asp Met
            20                  25                  30

Leu Thr Ile Ser Gly Asn Tyr Phe Asn Leu Leu Lys Tyr Gly Trp Gly
        35                  40                  45

Thr Ser Ile Leu Tyr Asp Glu Glu Ile Ile Lys Asp Lys Asn Glu Leu
    50                  55                  60

Tyr His Ser Tyr Asn Ile Arg Thr Tyr Thr Gly Gly Thr Leu Phe Glu
65                  70                  75                  80

Leu Ala Asn Lys Gln Asn Lys Ile Asp Glu Tyr Phe Asn Glu Ile Asp
                85                  90                  95

Arg Leu Gly Phe Asn Ala Val Glu Ile Ser Asp Gly Ser Thr Thr Ile
            100                 105                 110

Asp Ser Asp Arg Arg Ala Gln Leu Ile Asn Lys Ser Lys Glu Leu Gly
        115                 120                 125

Phe Tyr Thr Leu Ser Glu Ile Gly Lys Lys Asn Pro Gln Lys Asp Ser
    130                 135                 140

Glu Tyr Thr Thr Gln Gln Arg Ile Asp Leu Ile Asn Thr Asp Ile Glu
145                 150                 155                 160

Ala Gly Ser Asp Met Val Ile Ile Glu Gly Arg Glu Ser Gly Lys Asn
                165                 170                 175

Ile Gly Ile Tyr Asp Asp Lys Gly Asn Val Lys Lys Asp Asp Leu Thr
            180                 185                 190

Ser Ile Tyr Glu Asn Thr Pro Lys Glu Lys Val Leu Trp Glu Ala Pro
        195                 200                 205

Gln Lys Asn Gln Gln Val Glu Leu Ile Leu Thr Leu Ser Asn Asp Val
    210                 215                 220

Asn Leu Gly Asn Ile Asn Ser Asn Glu Ile Val Ser Leu Glu Thr Leu
225                 230                 235                 240

Arg Arg Gly Leu Arg Gly Asp Thr Leu Gly Lys Leu
                245                 250


<210> SEQ ID NO 20
<211> LENGTH: 759
<212> TYPE: DNA
<213> ORGANISM: Methanosphaera stadtmanae

<400> SEQUENCE: 20

atgaacgctt ttaagtttct agatgaaatt ggaccagtaa ataccaatac catggttctt     60

gataaggcat taggatacaa aacagttgaa gatatgttaa caattagtgg aaactatttt    120

aatctattga agtatggatg gggaacttca atattatatg atgaagaaat aataaaagat    180

aaaaatgaat tatatcactc atataatatt agaacatata ctggtggaac tttatttgaa    240

ttagcaaata aacaaaataa aatagatgaa tattttaatg aaattgacag attaggattt    300
```

-continued

```
aatgctgtgg aaatatctga tggatcaact accattgaca gtgatagacg tgcacagtta    360

attaataaat caaaagaatt aggtttctac actttgagtg aaataggtaa gaaaaatcca    420

caaaaagatt ctgaatatac aacacaacaa cgtatagatc ttataaatac agatattgaa    480

gcaggttctg atatggttat tattgaagga cgtgaaagtg gtaaaaatat tggtatatac    540

gatgataaag gtaatgtaaa aaaagatgat ttaacttcaa tctatgaaaa tacacctaaa    600

gaaaaagtat tgtgggaagc tccacagaaa aatcaacaag tagaattaat acttacatta    660

agtaatgatg taaatcttgg aaacattaat tctaatgaaa tagtctccct tgaaacatta    720

cgtcgtggat taagaggaga cactcttgga aaattataa                          759
```

<210> SEQ ID NO 21
<211> LENGTH: 232
<212> TYPE: PRT
<213> ORGANISM: Methanosphaera stadtmanae

<400> SEQUENCE: 21

```
Met Lys Ile Asn Val Ser Leu Tyr Asn Ser Arg Thr Asn Asp Leu Ala
1               5                   10                  15

Ile Val Ile Asp Leu Leu Arg Ala Ser Thr Thr Ile Ser Val Ala Leu
            20                  25                  30

Asn Thr Phe Lys Arg Ile Val Pro Ile Asn Asp Ile Asp Glu Ala Ile
        35                  40                  45

Lys Leu Lys Glu Lys His Asn Ala Ile Leu Ala Gly Glu Ile Lys Ser
    50                  55                  60

Ser Asp Phe Asp Val Ser Asn Ser Pro Val Gln Ile Ser Asn Tyr Ala
65                  70                  75                  80

Gly Asp Thr Leu Ile Leu Lys Thr Thr Asn Gly Thr Lys Val Leu Glu
                85                  90                  95

Asn Ile Lys Gln Arg Asn Ser Glu Val Asn Ile Leu Val Gly Ala Ser
            100                 105                 110

Ile Asn Ala Lys Thr Val Ala Gln Lys Ala Leu Asp Ile Ala Asp Asn
        115                 120                 125

Glu Ile Glu Leu Val Met Ala Gly Arg His Gln Arg Phe Thr Ile Glu
    130                 135                 140

Asp Cys Ile Gly Ala Gly Ile Ile Ile Asn Glu Ile Val Asn Ile Ala
145                 150                 155                 160

Lys Glu Lys Asn Ile Tyr Leu Glu Leu Ser Glu Ser Ala Lys Ala Ser
                165                 170                 175

Lys Ile Ile Ser Asn Asn Ser Asn Ile Ile Lys Gln Leu Ile Asn Thr
            180                 185                 190

Ser His Ser Ala Asp Lys Leu Arg Tyr Leu Gly Phe Gly Glu Asp Ile
        195                 200                 205

Glu Ile Cys Ser Leu Ile Asn Lys Ile Asp Thr Val Pro Ile Tyr Lys
    210                 215                 220

Asn Asn Tyr Ile Val Ser Leu Asp
225                 230
```

<210> SEQ ID NO 22
<211> LENGTH: 699
<212> TYPE: DNA
<213> ORGANISM: Methanosphaera stadtmanae

<400> SEQUENCE: 22
atgaaaatta atgtaagttt atataattca cgaaccaatg atttagctat agtaattgat 60
ttattaaggg caagtacaac aataagtgta gcattaaata cttttaaaag aattgttccg 120
attaatgata tagatgaagc tattaaatta aaagaaaaac ataatgcaat attggcaggt 180
gaaattaaat catcagattt tgatgtttca aattcaccag ttcaaatatc aaattatgct 240
ggtgatacat taattttgaa aacaacaaat ggtacaaagg tattagaaaa tataaaacaa 300
agaaattcag aagtaaatat attggttgga gcatcaataa atgcaaaaac agtagcacaa 360
aaggcattag atattgcaga taatgaaatt gaattagtta tggcaggaag acatcaaaga 420
tttacaatag aggattgtat tggtgcagga ataattatta atgaaatagt aaacatagct 480
aaagaaaaaa atatatactt agaactttca gaatcagcaa aagcatcaaa aataatatca 540
aataattcta atataataaa acaattaata aatacttcac acagtgcaga taaattacgt 600
tatcttggat ttggtgaaga tattgaaata tgtagtttaa ttaacaagat agatacagtt 660
ccaatctata agaataatta catagtctca ttagattaa 699

<210> SEQ ID NO 23
<211> LENGTH: 342
<212> TYPE: PRT
<213> ORGANISM: Methanobacterium sp.

<400> SEQUENCE: 23

Met Asn Ile Thr Pro Glu Gln Glu Leu Ser Leu Ile Ile Asp Ile Leu
1 5 10 15

Thr Lys Phe Asp Val Pro Glu Asp Gln Ala Ser Ile Ile Ala Glu Val
20 25 30

Thr Leu Asp Gly Asp Leu Lys Gly Phe Ser Ser His Gly Ile Gly Arg
35 40 45

Phe Pro Gln Tyr Ile Lys Gly Leu Glu Cys Gly His Ile Lys Pro His
50 55 60

Thr Glu Ile Val Val Glu Lys Glu Thr Ala Ala Thr Ala Leu Ile Asn
65 70 75 80

Gly Asn His Gly Phe Gly His Val Val Thr Tyr Gln Ala Met Lys Met
85 90 95

Ala Ile Glu Lys Ala Lys Glu Val Gly Ile Gly Leu Val Gly Ile His
100 105 110

Asn Ser Asn His Phe Gly Val Ala Gly Tyr Tyr Ser Asp Met Ala Leu
115 120 125

Met Glu Asp Ile Ile Gly Ile Val Thr Ala Asn Thr Glu Pro Ala Val
130 135 140

Ala Pro Ile Gly Gly Lys Glu Pro Ile Leu Gly Thr Asn Pro Leu Ala
145 150 155 160

Ile Gly Ile Pro Ser Gly Ser His Tyr Leu Ser Val Asp Met Ala Thr
165 170 175

Ser Ala Ser Ala Arg Gly Lys Leu Met Glu Ala Lys Arg Leu Gly Glu
180 185 190

Pro Ile Pro Glu Asn Val Ala Leu Asp Ser Asp Gly Asn Pro Thr Thr
195 200 205

Asp Pro Ala Glu Ala Leu Lys Gly Ser Ile Leu Pro Phe Gly Ala His
210 215 220

Lys Gly Tyr Ala Leu Ser Leu Met Ile Glu Val Ile Ala Gly Pro Leu
225 230 235 240

```
Val Arg Ala Ser Tyr Gly Lys Gly Val Thr Gly Thr Ala Asp Pro Glu
                245                 250                 255

Val Pro Cys Thr Lys Gly Asp Leu Ile Ala Ala Ile Asp Pro Ser Lys
            260                 265                 270

Phe Val Asp Ile Asp Gln Phe Lys Glu Glu Val Asp Asp Leu Ile Ser
        275                 280                 285

Glu Leu Lys Ser Thr Pro Asn Val Met Ile Pro Gly Asp Phe Glu Val
    290                 295                 300

Leu Asn Val Lys Arg His Gln Lys Glu Gly Ile Ala Leu Asp Glu Thr
305                 310                 315                 320

Leu Val Gln Gln Leu Arg Glu Ile Ala Ser Asn Val Asp Val Asp Val
                325                 330                 335

Ser Asp Ile Leu Gly Asp
            340


<210> SEQ ID NO 24
<211> LENGTH: 1029
<212> TYPE: DNA
<213> ORGANISM: Methanobacterium sp.

<400> SEQUENCE: 24

atgaacatta ctccagaaca ggaattatcc ctgatcatcg atattttaac taaatttgac     60

gtacctgaag accaagcatc catcattgcc gaagtgacac tagacggtga tcttaagggt    120

ttctcatctc atggaattgg tagattcccc cagtacatta agggattgga atgtggtcat    180

atcaagcccc acacagaaat agttgtggag aaagaaactg cagccaccgc tctgataaat    240

ggtaaccatg gttttggaca tgtagtaacc taccaggcca tgaaaatggc catagagaaa    300

gctaaagaag taggtattgg tttagtgggt atccataact ccaaccactt tggagtggct    360

ggttattact ccgacatggc attgatggaa gatatcattg gcattgtaac tgccaacact    420

gaaccagccg tggcccctat tggagggaaa gaaccaatac tgggtactaa tcccctggcc    480

ataggaatac cttccggtag ccactatctc tccgtggaca tggccacatc agcttccgcc    540

cgtggaaaac tcatggaagc caaacgtctt ggtgaaccca taccagaaaa tgtggccctg    600

gattccgatg gaaatcccac caccgaccca gcagaagcac tcaaaggatc aatcctcccc    660

ttcggagccc ataaaggata tgccttatcc cttatgattg aagttatagc cggcccactg    720

gtacgtgcct cctatggtaa gggagttact ggaacagctg accccgaggt tccctgcacc    780

aaaggagacc tgattgccgc cattgacccc tccaaatttg tggatataga ccagtttaag    840

gaagaggtgg atgatcttat aagtgaatta aaatccactc ctaatgtaat gatacccgga    900

gattttgaag tcttaaatgt gaaacgtcac cagaaagaag gaatagctct ggatgaaacc    960

cttgtacagc agttaaggga aatcgccagc aatgtagatg tggatgtatc agatatactg   1020

ggagattaa                                                           1029


<210> SEQ ID NO 25
<211> LENGTH: 387
<212> TYPE: PRT
<213> ORGANISM: Methanosarcina acetivorans

<400> SEQUENCE: 25

Met Tyr Val Val Asn Pro Glu Glu Lys Val Ile Glu Ile Met Lys Gln
1               5                   10                  15

Thr Gly Ile Asp Leu Ala Ala Thr Leu Pro Cys Asp Arg Ile Lys Asn
            20                  25                  30
```

```
Leu Leu Pro Leu Val Ser Glu Asn Phe Pro Glu Ile Lys Leu Thr Arg
        35                  40                  45

Glu Glu Asn Gly Val Gly Ile Cys Ala Gly Ile Tyr Leu Ala Gly Gly
    50                  55                  60

Lys Pro Met Met Leu Ile Gln Ser Thr Gly Leu Gly Asn Met Ile Asn
65                  70                  75                  80

Ala Leu Glu Ser Leu Asn Val Thr Cys Lys Ile Pro Leu Pro Ile Leu
                85                  90                  95

Ala Ser Trp Arg Gly Val Tyr Lys Glu Gly Ile Glu Ala Gln Val Pro
            100                 105                 110

Leu Gly Ala His Leu Pro Ser Ile Leu Glu Gly Ala Gly Leu Thr Tyr
        115                 120                 125

Thr Ile Ile Gly Glu Thr Glu Lys Leu Pro Leu Leu Glu Asn Val Ile
    130                 135                 140

Leu Asp Ala Phe Glu Asn Ser Arg Pro His Ile Ala Leu Val Ser Pro
145                 150                 155                 160

Lys Val Trp Glu Ala Ser Glu Cys Cys Ala Trp Gln Ala Ala Gly Met
                165                 170                 175

Pro Ile Lys Pro Glu Ile Met Glu Arg Thr Cys Arg Phe Ser Leu Thr
            180                 185                 190

Ser Gly Thr Leu Lys Pro Phe Met Leu Arg Asn Asp Ala Ile Cys Thr
        195                 200                 205

Leu Ala Ser Glu Leu Asp Asp Glu Ile Thr Val Thr Asn Leu Gly Val
    210                 215                 220

Pro Cys Lys Glu Leu Tyr Ala Cys Arg Asp Arg Glu Leu Asn Phe Tyr
225                 230                 235                 240

Met Phe Gly Ser Met Gly Leu Val Ser Ser Ile Gly Leu Gly Leu Ala
                245                 250                 255

Leu Arg Ser Glu Lys Thr Val Ile Thr Phe Asp Gly Asp Gly Ser Leu
            260                 265                 270

Leu Met Asn Pro Asn Ala Leu Leu Glu Ile Ala Lys Glu Ala Pro Lys
        275                 280                 285

Asn Leu Ile Ile Ile Ala Leu Asp Asn Gly Ala Tyr Gly Ser Thr Gly
    290                 295                 300

Ser Gln Glu Thr Cys Ala Leu Arg Tyr Ile Asp Leu Glu Ile Phe Ala
305                 310                 315                 320

Asn Ala Cys Gly Ile Gln Asn Thr Ala Lys Val Asn Ser Lys Glu Gly
                325                 330                 335

Val Ile Glu Ala Phe Arg Lys Phe Lys Ala Met Arg Glu Leu Ser Phe
            340                 345                 350

Ile His Val Ile Leu Lys Pro Gly Asn Thr Asn Ala Pro Asn Ile Pro
        355                 360                 365

Met Ser Pro Glu Glu Ala Thr Lys Arg Phe Lys Glu Thr Leu Asp Val
    370                 375                 380

Lys Lys Phe
385
```

<210> SEQ ID NO 26
<211> LENGTH: 1164
<212> TYPE: DNA
<213> ORGANISM: Methanosarcina acetivorans

<400> SEQUENCE: 26

```
atgtacgtgg taaacccgga agaaaaagta atagaaatca tgaaacaaac aggtattgat     60
cttgctgcaa cgcttccctg cgacaggatc aagaacctgc ttcccctggt ctcggaaaat    120
tttccagaaa tcaaattgac aagggaagaa aacggagtgg ggatctgtgc aggcatctac    180
cttgcaggcg gaaagccaat gatgcttatc cagagtacgg ggctcgggaa tatgatcaat    240
gcccttgaat ccctgaacgt aacctgtaaa atccccccttc cgatcctggc tagctggcgc    300
ggtgtatata aagaaggcat cgaagctcag gttcccctgg gagcccacct cccttccatc    360
cttgaagggg ccggacttac atacacaata attggcgaaa ctgaaaagct tcctcttctt    420
gaaaatgtaa ttcttgacgc ctttgaaaac tcgagacccc atattgccct ggtctcccct    480
aaagtttggg aagcttcgga atgctgtgct tggcaggctg cagggatgcc gataaagccg    540
gaaattatgg aaaggacctg caggttttcc ctcacaagcg ggactctcaa gccttttatg    600
ctcagaaacg atgcaatctg caccttagcc tccgagcttg atgacgaaat taccgtgaca    660
aacctcggag tcccctgcaa ggagctttac gcctgcaggg acagggaact caacttctat    720
atgttcggct ccatggggct tgtttcttca atagggcttg gtcttgccct gcgctcggaa    780
aagacagtta tcacttttga cggggacggg agccttttaa tgaacccaaa tgccctcctt    840
gaaattgcaa aagaagcccc gaaaaacctc ataatcattg cccttgacaa cggcgcctat    900
ggttctacag gttctcagga gacctgcgcc ctccgctaca ttgaccttga aatctttgca    960
aacgcctgcg ggattcagaa caccgccaaa gtgaacagca aagaaggggt gatagaagct   1020
ttcaggaaat tcaaagccat gagagagctc tcctttatcc atgtgatcct gaaacccggg   1080
aacacaaatg ctcccaatat tcctatgagc cctgaagaag caacaaaacg cttcaaagaa   1140
acactggatg taaaaaagtt ttaa                                          1164
```

<210> SEQ ID NO 27
<211> LENGTH: 456
<212> TYPE: PRT
<213> ORGANISM: Rhodococcus opacus

<400> SEQUENCE: 27

```
Met Val Val Asp Val Thr Glu Leu Arg Ala Arg Ala Arg Arg His Leu
1               5                   10                  15

Gly Pro His Phe Thr Arg Lys Asp Thr Trp Glu Ser Asp Phe Pro Val
            20                  25                  30

Phe Val Arg Gly Glu Gly Ser Tyr Leu Ile Asp Thr Glu Gly Asp Arg
        35                  40                  45

Phe Leu Asp Gly Leu Ala Gly Leu Phe Cys Val Asn Ile Gly His Gly
    50                  55                  60

Arg Asp Asp Ile Ala Lys Ala Ala Ser Glu Gln Ile Gly Thr Leu Ala
65                  70                  75                  80

Tyr Ala Ser Asn Trp Gly Ser Ala His Ile Pro Ala Ile Glu Ala Ser
                85                  90                  95

Ala Leu Ile Ala Asp Leu Ala Pro Gly Asp Leu Gly Thr Thr Phe Phe
            100                 105                 110

Val Asn Ser Gly Ser Glu Ala Val Glu Thr Ala Val Lys Phe Ala Arg
        115                 120                 125

Gln Tyr His Arg Ser Gln Gly Asn Pro Gln Arg Thr Lys Ile Ile Ser
    130                 135                 140
```

-continued

```
Arg Glu Met Ala Tyr His Gly Thr Thr Leu Gly Ala Leu Ser Val Thr
145                 150                 155                 160

Gln Leu Pro Lys Ile Lys Asp Pro Phe Gly Pro Leu Leu Pro Gly Val
                165                 170                 175

Arg Ser Val Pro Asn Thr Leu Gly Tyr Leu Gly Asp Cys Gly Pro Ala
            180                 185                 190

Asn Glu Leu Asp Cys Ile Ala Ala Ile Glu Ala Val Ile Glu Glu Glu
        195                 200                 205

Gly Ala Glu Thr Ile Ala Ala Val Phe Ala Glu Pro Val Gln Asn Gly
    210                 215                 220

Arg Gly Ala Leu Val Pro Pro Asp Gly Tyr Trp Ala Ala Leu Arg Ala
225                 230                 235                 240

Leu Cys Asp Lys His Gly Ile Leu Leu Val Ser Asp Glu Val Ile Cys
                245                 250                 255

Ser Phe Gly Arg Leu Gly His Trp Phe Gly His Gly Leu Thr Gly Val
            260                 265                 270

Val Pro Asp Met Ile Thr Phe Ala Lys Gly Ser Thr Ser Gly Tyr Ala
        275                 280                 285

Pro Leu Gly Gly Leu Ile Val Arg Glu Gln Leu Val Arg Glu Leu Tyr
    290                 295                 300

Asp Ser Pro Lys Gly Gly Val Phe Thr His Gly Ala Thr Trp Gly Gly
305                 310                 315                 320

His Pro Val Ser Thr Ala Val Ala Val Ala Asn Ile Thr Ala Met Arg
                325                 330                 335

Asp Glu Asn Val Leu Gly Asn Val Ser Ala Arg Gly Pro Lys Leu Arg
            340                 345                 350

Ser Ala Leu Asp Ser Leu Met Ser Ser His Arg Cys Val Lys Asp Val
        355                 360                 365

Arg Gly Thr Gly Phe Phe Tyr Ala Ile Glu Leu Met Ala Asp Ser Asp
    370                 375                 380

Ser Gly Arg Glu Phe Thr Glu Gln Glu Ser Leu Thr Val Leu Arg Lys
385                 390                 395                 400

Val Leu Pro Glu Ala Phe Ala Arg Thr Lys Val Ile Leu Arg Gly Asp
                405                 410                 415

Asp Arg Gly Ala Thr Met Leu Met Ile Ser Pro Pro Leu Val Ala Asp
            420                 425                 430

Asp Glu Val Leu Ser Glu Leu Leu His Gly Ile Asp Ser Met Leu Thr
        435                 440                 445

Asp Ile Glu Lys Ala Ile Gln Pro
    450                 455
```

<210> SEQ ID NO 28
<211> LENGTH: 1371
<212> TYPE: DNA
<213> ORGANISM: Rhodococcus opacus

<400> SEQUENCE: 28

```
atggtcgtgg acgtcaccga attgcgagca cgggcccgcc ggcacctcgg acctcatttc      60

acccgtaagg acacctggga aagcgacttt ccggtgttcg ttcgtggcga gggaagctat     120

ctgatcgaca ccgaggggga ccgtttcctc gacggtctgg caggcctgtt ctgtgtgaac     180

atcggtcacg gccgcgacga catcgccaag gcggcgagcg agcagatcgg gacgctggcg     240

tacgcctcca actggggcag cgcccacatt cccgcgatcg aggcgtccgc gctcatcgcg     300
```

-continued

```
gacctggcgc ccggtgatct cgggacgacc ttcttcgtca actcgggttc cgaggccgtg    360

gagacggccg tcaagttcgc ccggcagtac caccgcagcc agggcaaccc gcagcgcacc    420

aagatcatca gccgcgagat ggcgtatcac ggaaccactc tcggcgccct ctcggtgaca    480

cagctgccca agatcaaaga cccgttcgga ccgctgctgc ccggggtccg ctccgtaccc    540

aacaccctcg gttacctcgg cgactgcggc ccggcgaacg agctcgactg catcgccgcg    600

atcgaagccg tcatcgagga agagggcgcc gagaccatcg ccgccgtgtt cgccgagccg    660

gttcagaacg ggcgcggcgc cctcgtcccg ccggacggat actgggccgc gctgcgcgcg    720

ctgtgcgaca agcacgggat cctgctggtc tccgacgagg tgatctgctc gttcggccgc    780

ctcggacact ggttcgggca cgggctgacc ggtgtggttc ccgacatgat cacgttcgcg    840

aagggctcca cgtccggata cgcgccgctc ggcggcctga tcgtgcgtga gcagctggtt    900

cgcgagctct acgactcgcc caagggcggc gtgttcacgc acggcgcgac gtggggcgga    960

cacccggtgt cgactgcggt ggcggtcgcg aacatcaccg cgatgcgcga cgagaacgtg   1020

ctgggcaacg tctccgcgcg cggcccgaag ttgcggtcgg cactcgactc gctgatgagc   1080

tcgcaccgct gcgtcaagga cgtgcgcggc accggcttct tctacgcgat cgagttgatg   1140

gccgacagcg acagcggccg cgagttcacc gagcaggagt cgctgacggt gttgcgcaag   1200

gtgctgccgg aggcgttcgc ccgcaccaag gtgatcctcc gcggcgacga ccgcggtgcc   1260

acgatgctga tgatttcgcc gccactcgtc gccgacgacg aggtgctctc ggaactgctc   1320

cacggaatcg acagcatgct caccgacatc gaaaaggcaa tccagccgta g            1371


<210> SEQ ID NO 29
<211> LENGTH: 625
<212> TYPE: PRT
<213> ORGANISM: Methylobacterium extorquens

<400> SEQUENCE: 29

Met Ser Ser Arg Pro His Arg Arg Ser Ser Phe Ser Ala Thr Phe Ala
1               5                   10                  15

Lys Arg Gln Arg Arg His Pro Glu Pro Phe Ser Ala Cys Gly Lys Ser
            20                  25                  30

Ala Arg Leu Arg Arg Ile Leu Ser Ala His Pro Gly Pro Ser Ala Ile
        35                  40                  45

Leu Arg Glu Pro Val Ala Arg Ser Arg Asn Ala Gly Gly Ala Arg Trp
    50                  55                  60

Arg Gly Ala Arg Gln Leu Pro Phe Ala Pro Thr Arg Gly Pro Asp Pro
65                  70                  75                  80

Ala Ser Arg Pro Val Arg Ser Gln Val Ser Ser Glu Ser Val Met Pro
                85                  90                  95

Asp Thr Pro Val Phe Ala His Ala Ala Val Ala Ala Pro His Ala Leu
            100                 105                 110

Ala Ala Ser Ala Gly Gln Asn Val Leu Ala Gln Gly Gly Asn Ala Ile
        115                 120                 125

Glu Ala Met Val Ala Met Ala Ala Ala Ile Ala Val Val Tyr Pro His
    130                 135                 140

Met Asn Gly Ile Gly Gly Asp Gly Phe Trp Leu Ile Arg Glu Arg Asn
145                 150                 155                 160

Gly Arg Val Arg Gly Ile Glu Ala Cys Gly Pro Ala Gly Gln Leu Ala
                165                 170                 175

Thr Arg Ala Arg Tyr Arg Glu Lys Glu Leu Asp Ala Ile Pro Ser Arg
            180                 185                 190
```

```
Gly Pro Asp Ala Ala Val Thr Val Ala Gly Thr Val Gly Gly Trp Arg
        195                 200                 205

Leu Ala Leu Asp Met Ala Arg Ala Phe Gly Gly Arg Leu Pro Leu Asp
    210                 215                 220

Thr Ile Leu Ala Asp Ala Ile Arg His Ala Arg Ala Gly Cys Pro Val
225                 230                 235                 240

Ser Ala Ser Glu Ala Arg Tyr Val Pro Lys Glu Leu Asp Thr Leu His
                245                 250                 255

Asp Ala Pro Asn Phe Ala Ala Thr Tyr Leu Asp Asp Gly Lys Pro Tyr
            260                 265                 270

Ala Ala Gly Ala Ile Arg Ala Gln Pro Lys Leu Ala Asp Thr Leu Ala
        275                 280                 285

Gln Leu Ala His Ala Gly Leu Asp Asp Phe Tyr Arg Gly Asp Ile Gly
    290                 295                 300

Arg Glu Ile Ala Ser Asp Leu Glu Arg Leu Gly Ala Pro Val Thr Arg
305                 310                 315                 320

Ala Asp Leu Thr Ala Tyr Ala Ala Lys Glu Arg Ala Pro Leu Thr Leu
                325                 330                 335

Arg Arg Arg Asp Ala Thr Leu Tyr Asn Phe Pro Pro Pro Thr Gln Gly
            340                 345                 350

Leu Ala Ala Leu Ile Ile Leu Gly Ile Phe Asp Arg Leu Asn Ile Ala
        355                 360                 365

Glu Pro Glu Ser Thr Ala His Tyr His Gly Leu Ile Glu Ala Thr Lys
    370                 375                 380

Arg Ala Phe Ala Ile Arg Asp Arg Phe Val Thr Asp Phe Asp Arg Leu
385                 390                 395                 400

Lys Gly Asp Pro Ala Ala Phe Leu Asp Pro Arg Arg Leu Asp Arg Glu
                405                 410                 415

Ala Ala Leu Ile Asp Met Arg Arg Ala Ala Ser Ile Pro Val Arg Ser
            420                 425                 430

Gly Glu Gly Asp Thr Val Trp Met Gly Ala Ile Asp Asn Asp Gly Met
        435                 440                 445

Ala Val Ser Phe Ile Gln Ser Val Tyr Trp Glu Tyr Gly Ser Gly Thr
    450                 455                 460

Val Leu Pro Gly Thr Gly Ile Cys Trp Gln Asn Arg Gly Met Ser Phe
465                 470                 475                 480

Ser Leu Asp Ala Asn Ala Val Asn Pro Leu Glu Pro Gly Arg Arg Pro
                485                 490                 495

Phe His Thr Leu Ile Pro Ala Leu Ala Ala Phe Asp Asp Gly Arg Val
            500                 505                 510

Met Ser Tyr Gly Ser Met Gly Gly Asp Gly Gln Pro Gln Phe Gln Ala
        515                 520                 525

Gln Ile Phe Thr Arg Tyr Ala Asp Tyr Gly Met Ser Val Ala Asp Ala
    530                 535                 540

Val Asp Ala Pro Arg Leu Leu Tyr Gly Arg Thr Trp Gly Ala Glu Ser
545                 550                 555                 560

Leu Ser Val Lys Val Glu Asp Arg Phe Asp Pro Ala Cys Ile Ala Ala
                565                 570                 575

Leu Arg Arg Leu Gly His Asp Ile Glu Glu Leu Gly Gly Ala Tyr Ile
            580                 585                 590

Asp Ser Leu Gly His Ala Gly Met Leu Val Arg His Val Lys Asp Gly
        595                 600                 605
```

-continued

```
Arg Ile Glu Ala Thr His Asp Pro Arg Ser Asp Gly Gly Ala Ala Gly
    610                 615                 620

Leu
625


<210> SEQ ID NO 30
<211> LENGTH: 1878
<212> TYPE: DNA
<213> ORGANISM: Methylobacterium extorquens

<400> SEQUENCE: 30

atgtcatccc gcccgcaccg gcgcagttcc ttttctgcaa catttgcaaa aaggcagagg      60

cgccacccgg aaccattttc ggcttgtggg aaatccgcac gtctccgacg catcctgagc     120

gcgcatccag ggccatctgc gatcctgcgg gagccggtcg cgcgatcgcg gaatgccggg     180

ggtgcgcggt ggcggggagc acggcagttg cccttcgcgc cgacgcgtgg tcctgatcct     240

gcctctcggc ccgtccgatc tcaggtttcg tcagagtccg tcatgcccga cacgcccgtc     300

ttcgcccatg cggccgttgc cgccccccac gcgctggcgg cttcggccgg tcagaacgta     360

ctggcgcagg gcggcaacgc catcgaggcg atggtcgcga tggccgccgc catcgcggtg     420

gtctacccgc acatgaacgg catcggcggc gacggcttct ggctgatccg cgagcggaac     480

ggccgcgtgc gcggcatcga ggcctgcgga ccggccgggc agctcgcgac ccgcgcccgc     540

taccgggaga aggagctcga cgcgatcccc tcccgcggcc ccgacgcggc agtgacggtg     600

gcgggcaccg tcggcggctg gcgcctcgcg ctcgacatgg cgcgcgcctt cggcggccgg     660

ctccccctcg atacgattct ggccgacgcc atccgccacg ctcgcgcagg ctgcccggtc     720

tcggcctcgg aagcgcgcta cgtgccaaag gaactcgaca cgctgcacga cgcgccgaat     780

ttcgctgcga cctatctcga tgacggcaag ccctacgcgg cgggcgcgat ccgggcgcag     840

cccaagctcg ccgacaccct ggcccagctc gcccatgccg ggctcgacga cttctaccgc     900

ggcgatatcg gccgcgagat cgccagcgat ctggaacgtc tcggcgcccc cgttacccgc     960

gccgacctca ccgcctacgc ggccaaggag cgggcaccgc tgaccctgcg gcggcgcgac    1020

gccacgctct acaacttccc gccgccgacc cagggcctcg cggcgctgat catcctcggg    1080

atcttcgacc ggctgaacat cgccgagccg gagagcaccg cgcattatca cgggctgatc    1140

gaggcgacga agcgcgcctt cgccatccgc gaccgcttcg tcaccgattt cgaccgcctg    1200

aagggcgacc ccgccgcctt cctcgatccg aggcgcctcg accgcgaggc ggccctgatc    1260

gacatgcggc gtgccgcgag catcccggtc cgctcgggcg agggcgacac cgtctggatg    1320

ggcgcgatcg acaacgacgg catggccgtc tccttcatcc agtcggtcta ctgggagtac    1380

ggctccggca cggtgctgcc gggaaccggc atctgctggc agaaccgcgg catgtcgttc    1440

tcgctcgacg cgaacgcggt gaacccgctg gaaccgggcc ggcgcccgtt ccacaccctg    1500

atcccggcgc tggccgcctt cgatgacggc cgggtcatgt cctacggctc catgggcggt    1560

gacgggcagc cgcagttcca ggcgcagatc ttcacccgct acgccgatta cgggatgtcg    1620

gtggccgatg cggtggacgc gccgcgcctg ctctacggcc gcacctgggg cgccgagtcg    1680

ctgagtgtga aggtcgagga ccgcttcgat ccggcctgca tcgcggcgct ccggcgcctg    1740

ggccacgaca tcgaggagct gggcggcgcc tatatcgact cgctgggcca tgccggcatg    1800

ctggtgcgcc atgtcaaaga cgggcggatc gaagcgacgc acgatccgcg ctccgatggc    1860

ggcgcggcgg ggctttga                                                  1878
```

-continued

<210> SEQ ID NO 31
<211> LENGTH: 624
<212> TYPE: PRT
<213> ORGANISM: Gallus gallus

<400> SEQUENCE: 31

```
Met Glu Leu Pro Glu Ser Gln Cys Lys Lys Ala Lys Leu Ser Asn Arg
1               5                   10                  15

Val Pro Asn Trp Gly Met Gln Arg Ala Thr Asn Val Thr Tyr Gln Ala
            20                  25                  30

His His Val Ser Arg Asn Lys Arg Gly Gln Val Val Gly Thr Arg Ser
        35                  40                  45

Gly Phe Arg Gly Cys Thr Val Trp Leu Thr Gly Leu Ser Gly Ala Gly
    50                  55                  60

Lys Thr Thr Val Ser Met Ala Leu Glu Glu Tyr Leu Val Cys His Gly
65                  70                  75                  80

Ile Pro Cys Tyr Thr Leu Asp Gly Asp Asn Ile Arg Gln Gly Leu Asn
                85                  90                  95

Lys Asn Leu Gly Phe Thr Pro Glu Asp Arg Glu Glu Asn Val Arg Arg
            100                 105                 110

Ile Ala Glu Val Ala Lys Leu Phe Ala Asp Ala Gly Leu Val Cys Ile
        115                 120                 125

Thr Ser Phe Ile Ser Pro Tyr Ala Gln Asp Arg Asn Asn Ala Arg Arg
    130                 135                 140

Ile His Glu Gly Ala Ser Leu Pro Phe Phe Glu Val Phe Val Asp Ala
145                 150                 155                 160

Pro Leu His Val Cys Glu Gln Arg Asp Val Lys Gly Leu Tyr Lys Lys
                165                 170                 175

Ala Arg Ala Gly Glu Ile Lys Gly Phe Thr Gly Ile Asp Ser Glu Tyr
            180                 185                 190

Glu Lys Pro Glu Ala Pro Glu Leu Val Leu Lys Thr Asp Ser Cys Asp
        195                 200                 205

Val Asn Asp Cys Val Gln Gln Val Val Glu Leu Leu Gln Glu Arg Asp
    210                 215                 220

Ile Val Pro Val Asp Ala Ser Tyr Glu Val Lys Glu Leu Tyr Val Pro
225                 230                 235                 240

Glu Asn Lys Leu Lys Leu Ala Lys Thr Asp Ala Glu Ser Leu Leu Thr
                245                 250                 255

Leu Glu Ile Asn Lys Val Asp Met Gln Trp Val Gln Val Leu Ala Glu
            260                 265                 270

Gly Trp Ala Thr Pro Leu Ser Gly Phe Met Arg Glu Arg Glu Tyr Leu
        275                 280                 285

Gln Cys Leu His Phe Asp Cys Leu Leu Asp Gly Gly Val Ile Asn Leu
    290                 295                 300

Ser Val Pro Ile Val Leu Thr Ala Thr Gln Glu Asp Lys Glu Arg Leu
305                 310                 315                 320

Asp Gly Cys Thr Ala Ile Ala Leu Val Tyr Glu Gly Arg Arg Val Ala
                325                 330                 335

Ile Leu Arg Asn Pro Glu Phe Tyr Glu His Arg Lys Glu Glu Arg Cys
            340                 345                 350

Ala Arg Gln Trp Gly Thr Thr Cys Lys Asp His Pro Tyr Ile Lys Met
        355                 360                 365

Val Met Glu Gln Gly Asn Trp Leu Val Gly Gly Asp Leu Gln Val Leu
    370                 375                 380
```

```
Asp Arg Ile Tyr Trp Asn Asp Gly Leu Asp Gln Tyr Arg Leu Thr Pro
385                 390                 395                 400

Ala Glu Leu Arg Gln Lys Phe Lys Glu Met Asn Ala Asp Ala Val Phe
                405                 410                 415

Ala Phe Gln Leu Arg Asn Pro Val His Asn Gly His Ala Leu Leu Met
            420                 425                 430

Gln Asp Thr His Lys Gln Leu Leu Glu Arg Gly Tyr Arg Arg Pro Val
        435                 440                 445

Leu Leu Leu His Pro Leu Gly Gly Trp Thr Lys Glu Asp Asp Val Pro
    450                 455                 460

Leu Met Trp Arg Met Lys Gln His Ala Ala Val Leu Glu Glu Gly Val
465                 470                 475                 480

Leu Asn Pro Glu Thr Thr Val Val Ala Ile Phe Pro Ser Pro Met Met
                485                 490                 495

Tyr Ala Gly Pro Thr Glu Val Gln Trp His Cys Arg Ser Arg Met Val
            500                 505                 510

Ala Gly Ala Asn Phe Tyr Ile Val Gly Arg Asp Pro Ala Gly Met Pro
        515                 520                 525

His Pro Gly Thr Gly Lys Asp Leu Tyr Glu Pro Thr His Gly Ala Lys
    530                 535                 540

Val Leu Thr Met Ala Pro Gly Leu Arg Ala Leu Glu Ile Val Pro Phe
545                 550                 555                 560

Arg Val Ala Ala Tyr Asn Lys Lys Lys Lys Ser Met Asp Tyr Tyr Asp
                565                 570                 575

Ser Glu His His Glu Asp Phe Glu Phe Ile Ser Gly Thr His Met Arg
            580                 585                 590

Lys Leu Ala Arg Glu Gly Gln Asn Pro Pro Glu Gly Phe Met Ala Pro
        595                 600                 605

Lys Ala Trp Thr Val Leu Thr Glu Tyr Tyr Lys Ser Leu Glu Lys Ala
    610                 615                 620
```

<210> SEQ ID NO 32
<211> LENGTH: 1875
<212> TYPE: DNA
<213> ORGANISM: Gallus gallus

<400> SEQUENCE: 32

```
atggagctgc ctgagagcca gtgcaagaaa gcgaagctga gcaacagggt gccgaactgg     60

ggaatgcaga gggcaaccaa tgttacctac caagctcatc atgtcagccg aaataagaga    120

ggccaagtgg taggaacaag aagtggtttc cgtggatgca cagtctggtt aacaggtcta    180

tctggtgctg ggaagaccac agttagcatg gccctggagg agtatttagt atgccatggc    240

attccatgct acacgttgga tggtgacaat attcgccaag gccttaataa gaatctgggt    300

ttcactccag aagatagaga agaaaacgtc cgtcggattg ctgaggttgc taaactgttt    360

gcagatgctg gtttggtgtg catcactagt ttcatctctc cttatgctca ggatcgtaat    420

aatgctagac gaattcatga aggggccagc ttgccttttt ttgaagtatt tgtggatgct    480

cctttgcatg tctgtgaaca aagagatgtt aagggactgt ataagaaagc cagagctgga    540

gaaattaaag gctttactgg gattgactct gagtatgaaa aaccagaagc cccagagctt    600

gtgctgaaaa ctgattcctg tgatgtgaac gattgtgtac aacaagttgt ggaacttctt    660

caagagaggg acatcgtacc agtagatgcc tcgtatgagg tgaaagagct ttatgtgcca    720

gaaaacaaac tgaagttggc taaaactgat gctgagtctc tgttaacctt ggaaataaat    780
```

-continued

```
aggtggata tgcagtgggt gcaagtgttg gcagaaggct gggcaacacc tctgagtggc    840
tttatgagag agagagaata cctgcagtgc cttcactttg actgtctcct tgatggggga    900
gtcattaatc tttcagtgcc tatagtgcta acagctacac aggaagacaa ggaaagactg    960
gatggttgta cagcaattgc attagtgtac gagggtcgcc gtgtggccat tctccgtaat   1020
ccagaattct atgagcatag gaaagaggaa cgctgtgcga ggcagtgggg aacaacatgc   1080
aaggatcatc cttacataaa gatggttatg gagcaaggga actggcttgt aggtggagat   1140
ttacaggtcc ttgatcgtat ttattggaat gatggacttg atcagtaccg tctcactcca   1200
gctgaactaa gacagaagtt caaggaaatg aatgctgatg ctgtctttgc attccagtta   1260
cgcaacccag tgcacaatgg gcacgcactt ttaatgcagg atactcataa gcagcttttg   1320
gaacgtggct acaggcgtcc agttttgctc ttgcatccac ttggaggctg gacaaaggag   1380
gacgacgttc ctctcatgtg gcgcatgaaa cagcatgctg cagtactgga ggagggagtc   1440
ttgaatccag aaacaacggt agtggctata ttcccctccc ccatgatgta tgctggacca   1500
acggaggttc agtggcactg cagatcacgg atggttgcag gtgctaactt ctacattgtg   1560
gggcgagatc ctgcagggat gccgcaccct ggtactggga aagatctgta tgaaccaacc   1620
catggtgcca aagtgttgac aatggcccca ggcctccgag cactggaaat tgtacctttc   1680
agggttgcgg cttataacaa gaaaaagaag tccatggact actatgactc tgagcaccat   1740
gaagactttg aatttatatc ggggacccac atgcgcaagc tggctcgaga aggacaaaac   1800
ccaccggaag gcttcatggc tcctaaggct tggactgtgc tgacagaata ctacaaatcc   1860
ttggagaagg cttag                                                    1875
```

<210> SEQ ID NO 33
<211> LENGTH: 201
<212> TYPE: PRT
<213> ORGANISM: Pseudomonas aeruginosa

<400> SEQUENCE: 33

```
Met Ser Ser Ile Leu Arg Leu Asp Arg Leu Arg Gln Phe Ile Gly Glu
1               5                   10                  15

Leu Ala Thr Leu Leu Asp Ser Arg Pro Asp Glu Ser Thr Leu Leu Ala
            20                  25                  30

Gln Ala His Pro Leu Leu Ala Glu Leu Val His Gln Asp Asp Trp Leu
        35                  40                  45

Pro Glu Asp Cys Ala Arg Pro Asp Pro Gln Arg Tyr Gln Gln Tyr Leu
    50                  55                  60

Leu His Val Asp Ser Arg Gln Arg Phe Ser Val Val Ser Phe Val Trp
65                  70                  75                  80

Gly Pro Gly Gln Ile Thr Pro Val His Asp His Arg Val Trp Gly Leu
                85                  90                  95

Ile Gly Met Leu Arg Gly Ala Glu Tyr Ser Gln Pro Tyr Ala Phe Asp
            100                 105                 110

Ala Gly Gly Arg Pro His Pro Ser Gly Ala Arg Arg Arg Leu Glu Pro
        115                 120                 125

Gly Glu Val Glu Ala Leu Ser Pro Arg Ile Gly Asp Val His Gln Val
    130                 135                 140

Ser Asn Ala Phe Ser Asp Arg Thr Ser Ile Ser Ile His Val Tyr Gly
145                 150                 155                 160

Ala Asn Ile Gly Ala Val Arg Arg Ala Val Phe Ser Ala Glu Gly Glu
                165                 170                 175
```

```
Glu Lys Pro Phe Ile Ser Gly Tyr Ser Asn Ser Arg Leu Pro Asn Ile
            180                 185                 190

Trp Asp Leu Ser Lys Glu Asn Pro Ala
        195                 200


<210> SEQ ID NO 34
<211> LENGTH: 606
<212> TYPE: DNA
<213> ORGANISM: Pseudomonas aeruginosa

<400> SEQUENCE: 34

atgtcatcca tcctgcgcct cgaccgcctg cgccagttca tcggcgagct ggcgacactg      60

ctcgacagcc gtcccgacga atccaccctg ctcgcccaag cccacccccct gctggccgag    120

ctggtgcacc aggacgactg gctgccggaa gactgcgccc gccccgatcc acagcgctac    180

caacagtacc tgctgcatgt cgactcacgg cagcgcttct cggtggtcag cttcgtctgg    240

gggccgggcc agatcacacc ggtacacgat catcgggtct ggggcctgat cggcatgctc    300

cgcggggccg aatactcgca gccgtacgcc ttcgatgcgg gggggcgtcc gcatcccagc    360

ggagcccgtc gacgcctgga gcccggcgag gtcgaagcgc tgtcgccacg cattggcgac    420

gtgcaccagg tgagcaacgc cttcagcgac cgcacatcca tcagtatcca cgtctacggc    480

gccaatatcg gtgcggtacg gcgtgccgtg ttcagcgccg aaggtgagga aaaacccttc    540

atttccggct attccaacag ccgcttgccc aatatctggg acctgtcgaa agagaacccc    600

gcatga                                                                606


<210> SEQ ID NO 35
<211> LENGTH: 200
<212> TYPE: PRT
<213> ORGANISM: Rattus norvegicus

<400> SEQUENCE: 35

Met Glu Arg Thr Glu Leu Leu Lys Pro Arg Thr Leu Ala Asp Leu Ile
1               5                   10                  15

Arg Ile Leu His Glu Leu Phe Ala Gly Asp Glu Val Asn Val Glu Glu
            20                  25                  30

Val Gln Ala Val Leu Glu Ala Tyr Glu Ser Asn Pro Ala Glu Trp Ala
        35                  40                  45

Leu Tyr Ala Lys Phe Asp Gln Tyr Arg Tyr Thr Arg Asn Leu Val Asp
    50                  55                  60

Gln Gly Asn Gly Lys Phe Asn Leu Met Ile Leu Cys Trp Gly Glu Gly
65                  70                  75                  80

His Gly Ser Ser Ile His Asp His Thr Asp Ser His Cys Phe Leu Lys
                85                  90                  95

Leu Leu Gln Gly Asn Leu Lys Glu Thr Leu Phe Asp Trp Pro Asp Lys
            100                 105                 110

Lys Ser Asn Glu Met Ile Lys Lys Ser Glu Arg Thr Leu Arg Glu Asn
        115                 120                 125

Gln Cys Ala Tyr Ile Asn Asp Ser Ile Gly Leu His Arg Val Glu Asn
    130                 135                 140

Val Ser His Thr Glu Pro Ala Val Ser Leu His Leu Tyr Ser Pro Pro
145                 150                 155                 160

Phe Asp Thr Cys His Ala Phe Asp Gln Arg Thr Gly His Lys Asn Lys
                165                 170                 175

Val Thr Met Thr Phe His Ser Lys Phe Gly Ile Arg Thr Pro Phe Thr
            180                 185                 190
```

```
Thr Ser Gly Ser Leu Glu Asn Asn
        195                 200


<210> SEQ ID NO 36
<211> LENGTH: 603
<212> TYPE: DNA
<213> ORGANISM: Rattus norvegicus

<400> SEQUENCE: 36

atggaacgga ccgagctgct gaagccccgg accctggccg acctcatccg aatcttgcat      60

gagctcttcg ccggggacga agtcaatgtg gaggaggtgc aggctgtgct ggaagcctac     120

gagagcaatc ctgccgagtg ggctttgtat gccaaattcg atcaatacag gtatacccga     180

aaccttgtgg atcaaggaaa tgggaagttt aatctgatga ttctgtgctg gggtgaaggg     240

catggcagca gtattcacga tcacacggac tcccactgct ttttgaagct gctgcaagga     300

aatctaaagg agacattgtt tgactggcct gacaagaaat ccaacgagat gatcaagaag     360

tctgaaagaa ctttgaggga aaatcagtgt gcctacatta atgattctat tggcttacat     420

cgagtagaga acgtcagcca cacagagcct gctgtgagcc ttcacttgta cagtccacct     480

ttcgatacat gccatgcctt tgaccaacga acagggcata aaaacaaagt caccatgaca     540

ttccacagca aatttggaat cagaactcca tttacaactt caggttcact ggagaacaac     600

taa                                                                   603


<210> SEQ ID NO 37
<211> LENGTH: 339
<212> TYPE: PRT
<213> ORGANISM: Ruegeria pomeroyi

<400> SEQUENCE: 37

Met His Leu Ala Arg Tyr Pro Arg Arg Phe Ile Ala His Leu Pro Thr
1               5                   10                  15

Pro Leu Glu Arg Leu Asp Arg Leu Thr Ala Glu Leu Gly Gly Pro Glu
            20                  25                  30

Ile Trp Ile Lys Arg Asp Asp Cys Thr Gly Leu Ser Thr Gly Gly Asn
        35                  40                  45

Lys Thr Arg Lys Leu Glu Phe Leu Met Ala Glu Ala Glu Leu Gln Gly
    50                  55                  60

Ala Asp Met Val Met Thr Gln Gly Ala Thr Gln Ser Asn His Ala Arg
65                  70                  75                  80

Gln Thr Ala Ala Phe Ala Ala Lys Leu Gly Met Asp Cys His Ile Leu
                85                  90                  95

Leu Glu Asp Arg Thr Gly Ser Asn Asn Ala Asn Tyr Asn Asn Asn Gly
            100                 105                 110

Asn Val Leu Leu Asp His Leu His Gly Ala Thr Thr Glu Lys Arg Pro
        115                 120                 125

Gly Ser Gly Leu Asp Met Asn Ala Glu Met Glu Lys Val Ala Glu Lys
    130                 135                 140

Phe Arg Ala Asp Gly Arg Lys Val Tyr Thr Ile Pro Gly Gly Gly Ser
145                 150                 155                 160

Asn Pro Thr Gly Ala Leu Gly Tyr Val Asn Cys Ala Phe Glu Met Leu
                165                 170                 175

Asn Gln Phe Asn Glu Arg Gly Leu Lys Val Asp His Ile Val His Ala
            180                 185                 190
```

```
Thr Gly Ser Ala Gly Thr Gln Ala Gly Leu Ile Thr Gly Leu Gln Ala
        195                 200                 205

Met Asn Ala Gln Ile Pro Leu Leu Gly Ile Gly Val Arg Ala Pro Lys
    210                 215                 220

Pro Lys Gln Glu Glu Asn Val Tyr Asn Leu Ala Cys Ala Thr Ala Glu
225                 230                 235                 240

Lys Leu Gly Cys Pro Gly Val Val Ala Arg Glu Asp Val Val Ala Asn
                245                 250                 255

Thr Asp Tyr Val Gly Glu Gly Tyr Gly Ile Pro Thr Glu Ser Gly Leu
            260                 265                 270

Glu Ala Ile Arg Met Phe Ala Glu Leu Glu Ala Ile Leu Leu Asp Pro
        275                 280                 285

Val Tyr Ser Ala Lys Gly Ala Ala Gly Phe Ile Asp Leu Ile Arg Lys
    290                 295                 300

Gly His Phe Lys Lys Gly Glu Arg Val Val Phe Leu His Thr Gly Gly
305                 310                 315                 320

Ala Val Ala Leu Phe Gly Tyr Asp Asn Ala Phe Asp Tyr Ser Gly Arg
                325                 330                 335

Trp Val Ala
```

<210> SEQ ID NO 38
<211> LENGTH: 1020
<212> TYPE: DNA
<213> ORGANISM: Ruegeria pomeroyi

<400> SEQUENCE: 38

```
atgcatcttg cccgctatcc ccgccgcttc atcgcccatc tgccgacgcc gctggaacgg     60

ctggaccggc tgaccgccga actgggcggg cccgagatct ggatcaagcg cgacgactgc    120

accggcctgt ccaccggcgg caacaagacc cgcaagctgg aattcctgat ggccgaggcc    180

gagctgcaag gcgctgacat ggtgatgacg cagggcgcga cccagtccaa ccatgcccgc    240

cagaccgccg cattcgccgc caagctgggc atggattgcc atatcctgct cgaggaccgg    300

accggctcga acaacgccaa ctacaacaac aacggcaacg ttctgctcga ccatctgcat    360

ggcgccacca ctgaaaagcg ccccggcagc ggtctggaca tgaatgccga gatggaaaag    420

gtggccgaga agttccgcgc cgacgggcgc aaggtctata ccatccccgg cggcggctcg    480

aacccgaccg gcgcgctggg atatgtcaac tgcgctttcg agatgctgaa ccagttcaat    540

gagcgcgggc tgaaggtgga ccatatcgtg catgccaccg gcagcgcggg cacccaggca    600

gggctgatca ccgggcttca ggcgatgaac gctcagatcc cgctcttggg catcggcgtg    660

cgtgcgccca agcccaagca ggaagagaat gtctataacc tggcctgcgc caccgccgag    720

aagctgggtt gccccggtgt cgtcgcgcgc gaggacgtgg tggccaatac cgactatgtc    780

ggcgaaggct atggcatccc gaccgaaagc gggctggagg cgatccgcat gttcgccgag    840

cttgaggcga tcctgcttga cccggtctat tcggccaagg gcgcggctgg cttcatcgac    900

ctgatccgca agggtcattt caaaaagggc gagcgggtgg tgttcctgca taccggcggc    960

gctgtggcgc tgttcggcta tgacaacgcc tttgactatt cgggacgctg ggtggcctaa   1020
```

<210> SEQ ID NO 39
<211> LENGTH: 74
<212> TYPE: DNA
<213> ORGANISM: Methylobacterium extorquens

<400> SEQUENCE: 39
ggtcgactct agttctgaaa tgagctgttg acaattaatc atcggctcgt ataatgtgtg 60
gaggcctcat atgt 74

<210> SEQ ID NO 40
<211> LENGTH: 80
<212> TYPE: DNA
<213> ORGANISM: Methylobacterium extorquens

<400> SEQUENCE: 40
ggtcgactct agtaagaaat ctgaaatgag ctgttgacaa ttaatcatcg gctcgtataa 60
tgtgtggagg cctcatatgt 80

<210> SEQ ID NO 41
<211> LENGTH: 33
<212> TYPE: DNA
<213> ORGANISM: Methylobacterium extorquens

<400> SEQUENCE: 41
tttacacttt atgcttccgg ctcgtatgtt gtg 33

<210> SEQ ID NO 42
<211> LENGTH: 109
<212> TYPE: DNA
<213> ORGANISM: Unknown
<220> FEATURE:
<223> OTHER INFORMATION: Description of Unknown:
Bacteriophage 16-3 sequence

<400> SEQUENCE: 42
caacaactta taccatggcc tacaaaaagg caaacaatgg tacttgacga ctcatcacaa 60
caattgtagt tgtagattgt aaagatctag ggagagaccc cgaggtacc 109

<210> SEQ ID NO 43
<211> LENGTH: 101
<212> TYPE: DNA
<213> ORGANISM: Methylobacterium extorquens

<400> SEQUENCE: 43
cgacactacg ccttggcact tttagaattg ccttatcgtc ctgataagaa atgtccgacc 60
agctaaagac atcgcgtcca atcaaagcct agaaaatata g 101

<210> SEQ ID NO 44
<211> LENGTH: 256
<212> TYPE: PRT
<213> ORGANISM: Mus musculus

<400> SEQUENCE: 44

Met Pro Arg Asp Asn Met Ala Ser Leu Ile Gln Arg Ile Ala Arg Gln
1 5 10 15

Ala Cys Leu Thr Phe Arg Gly Ser Ser Thr Gly Ser Glu Gly Pro Ala
20 25 30

Pro Gly Phe Pro Glu Asn Leu Ser Leu Leu Lys Ser Leu Leu Thr Gln
35 40 45

Val Arg Ala Glu Asp Leu Asn Ile Ala Pro Arg Lys Ala Leu Pro Gln
50 55 60

Pro Leu Pro Arg Asn Leu Pro Pro Val Thr Tyr Met His Ile Tyr Glu
65 70 75 80

```
Thr Glu Gly Phe Ser Leu Gly Val Phe Leu Leu Lys Ser Gly Thr Cys
                85                  90                  95

Ile Pro Leu His Asp His Pro Gly Met His Gly Met Leu Lys Val Leu
            100                 105                 110

Tyr Gly Thr Val Arg Ile Ser Cys Met Asp Lys Leu Asp Thr Gly Ala
        115                 120                 125

Gly His Arg Arg Pro Pro Pro Glu Gln Gln Phe Glu Pro Pro Leu Gln
    130                 135                 140

Pro Leu Glu Arg Glu Ala Val Arg Pro Gly Val Leu Arg Ser Arg Ala
145                 150                 155                 160

Glu Tyr Thr Glu Ala Ser Gly Pro Cys Val Leu Thr Pro His Arg Asp
                165                 170                 175

Asn Leu His Gln Ile Asp Ala Val Asp Gly Pro Ala Ala Phe Leu Asp
            180                 185                 190

Ile Leu Ala Pro Pro Tyr Asp Pro Glu Asp Gly Arg Asp Cys His Tyr
        195                 200                 205

Tyr Arg Val Val Glu Pro Ile Arg Pro Lys Glu Ala Ser Gly Ser Ala
    210                 215                 220

Cys Asp Leu Pro Arg Glu Val Trp Leu Leu Glu Thr Pro Gln Ala Asp
225                 230                 235                 240

Asp Phe Trp Cys Glu Gly Glu Pro Tyr Pro Gly Pro Lys Val Leu Pro
                245                 250                 255


<210> SEQ ID NO 45
<211> LENGTH: 771
<212> TYPE: DNA
<213> ORGANISM: Mus musculus

<400> SEQUENCE: 45

atgccccgcg acaacatggc ctccctgatc cagcgcatcg ctcgccaggc gtgtctcacc      60

ttccgcggca gctcgacggg ctccgaaggg ccggcgccgg gcttcccgga gaacctgagc     120

ctgctcaaga gcctgctgac ccaggtgcgc gccgaggacc tcaacatcgc gccgcgcaag     180

gcgctgccgc agccgctgcc ccgcaacctc ccgccggtca cctacatgca catctacgag     240

acggagggct tcagcctggg cgtgttcctg ctcaagagcg gcacgtgcat cccgctgcac     300

gaccacccgg gcatgcacgg tatgctcaag gtgctgtacg gcacggtccg catcagctgc     360

atggacaagc tggacacggg ggccgggcat cggcggccgc cgccagagca gcagttcgag     420

cccccgctgc agcccttgga gcgggaggcc gtgcgaccgg gcgtgctgcg ttcccgggcc     480

gagtacaccg aggccagtgg gccctgcgtg ctcactccac accgggacaa cctgcaccag     540

attgatgccg tggacgggcc agctgccttc ctggacatcc tggccccacc ctacgacccg     600

gaggacggcc gggactgcca ctattaccgt gtagtggagc ccatcagacc caaggaggct     660

tccggctctg cctgcgacct tccccgagaa gtgtggctcc tggagacacc acaggccgac     720

gacttctggt gcgagggaga gccctatcca ggccccaagg tcctaccttg a              771


<210> SEQ ID NO 46
<211> LENGTH: 379
<212> TYPE: PRT
<213> ORGANISM: Bacillus subtilis

<400> SEQUENCE: 46

Met Lys Lys Lys Thr Leu Met Ile His Gly Gly Ile Thr Gly Asp Glu
1               5                   10                  15
```

```
Lys Thr Gly Ala Val Ser Val Pro Ile Tyr Gln Val Ser Thr Tyr Lys
            20                  25                  30

Gln Pro Lys Ala Gly Gln His Thr Gly Tyr Glu Tyr Ser Arg Thr Ala
        35                  40                  45

Asn Pro Thr Arg Thr Ala Leu Glu Ala Leu Val Thr Glu Leu Glu Ser
    50                  55                  60

Gly Glu Ala Gly Tyr Ala Phe Ser Ser Gly Met Ala Ala Ile Thr Ala
65                  70                  75                  80

Val Met Met Leu Phe Asn Ser Gly Asp His Val Val Leu Thr Asp Asp
                85                  90                  95

Val Tyr Gly Gly Thr Tyr Arg Val Met Thr Lys Val Leu Asn Arg Leu
            100                 105                 110

Gly Ile Glu Ser Thr Phe Val Asp Thr Ser Ser Arg Glu Glu Val Glu
        115                 120                 125

Lys Ala Ile Arg Pro Asn Thr Lys Ala Ile Tyr Ile Glu Thr Pro Thr
    130                 135                 140

Asn Pro Leu Leu Lys Ile Thr Asp Leu Thr Leu Met Ala Asp Ile Ala
145                 150                 155                 160

Lys Lys Ala Gly Val Leu Leu Ile Val Asp Asn Thr Phe Asn Thr Pro
                165                 170                 175

Tyr Phe Gln Gln Pro Leu Thr Leu Gly Ala Asp Ile Val Leu His Ser
            180                 185                 190

Ala Thr Lys Tyr Leu Gly Gly His Ser Asp Val Val Gly Gly Leu Val
        195                 200                 205

Val Thr Ala Ser Lys Glu Leu Gly Glu Glu Leu His Phe Val Gln Asn
    210                 215                 220

Ser Thr Gly Gly Val Leu Gly Pro Gln Asp Ser Trp Leu Leu Met Arg
225                 230                 235                 240

Gly Ile Lys Thr Leu Gly Leu Arg Met Glu Ala Ile Asp Gln Asn Ala
                245                 250                 255

Arg Lys Ile Ala Ser Phe Leu Glu Asn His Pro Ala Val Gln Thr Leu
            260                 265                 270

Tyr Tyr Pro Gly Ser Ser Asn His Pro Gly His Glu Leu Ala Lys Thr
        275                 280                 285

Gln Gly Ala Gly Phe Gly Gly Met Ile Ser Phe Asp Ile Gly Ser Glu
    290                 295                 300

Glu Arg Val Asp Ala Phe Leu Gly Asn Leu Lys Leu Phe Thr Ile Ala
305                 310                 315                 320

Glu Ser Leu Gly Ala Val Glu Ser Leu Ile Ser Val Pro Ala Arg Met
                325                 330                 335

Thr His Ala Ser Ile Pro Arg Glu Arg Arg Leu Glu Leu Gly Ile Thr
            340                 345                 350

Asp Gly Leu Ile Arg Ile Ser Val Gly Ile Glu Asp Ala Glu Asp Leu
        355                 360                 365

Leu Glu Asp Ile Gly Gln Ala Leu Glu Asn Ile
    370                 375
```

<210> SEQ ID NO 47
<211> LENGTH: 1140
<212> TYPE: DNA
<213> ORGANISM: Bacillus subtilis -continued

<400> SEQUENCE: 47

```
atgaagaaaa aaacattgat gatacatggc ggaatcacag gtgatgagaa aacaggcgca      60
gtttccgtgc cgatttatca agtaagcacg tacaagcagc cgaaagcagg gcagcataca     120
ggctacgagt attcaagaac ggccaatccg actcgaaccg ctctcgaagc acttgtgaca     180
gaactggaaa gcggggaagc aggctatgcg ttcagctcag gaatggctgc cattacagcg     240
gttatgatgc tgtttaacag cggagatcat gtcgtgttga ctgatgatgt gtacggcgga     300
acatatcgcg tgatgacaaa ggtgcttaac cgtcttggca ttgaatcaac atttgttgat     360
acgagcagca gggaagaagt tgaaaaagcg attcgcccta atacaaaagc aatttatatt     420
gaaacaccga caaacccgtt gctcaaaatc accgacctga cgctcatggc tgatatcgca     480
aaaaaagcgg gtgttctgct tatcgtagac aataccttta atactcctta ttttcaacag     540
ccgcttactt taggcgctga tatcgtactg cacagtgcga caaaatatct tggcggacac     600
agtgatgtcg tcggaggttt agttgtgaca gcttcgaaag agcttggaga agagctgcat     660
tttgtgcaaa actccacagg cggcgtgctc ggccctcaag attcctggct gttaatgaga     720
ggaatcaaaa cgttgggact cagaatggaa gcgatcgatc aaaatgcgcg gaaaatcgca     780
agctttcttg agaatcaccc tgctgtccaa acgttatatt accctggttc ttcaaatcat     840
cccggacatg agcttgcaaa aacgcaagga gcgggcttcg gcggcatgat ctcctttgat     900
attggcagtg aagaacgggt tgatgcgttt ttaggaaatc tgaaactgtt taccattgct     960
gaaagcctgg gggcggttga aagcttaatt tctgttcctg caagaatgac acatgcctct    1020
attccgagag aacgccggct tgagctcggc attacggacg gcttgatcag aatttctgta    1080
ggaattgaag atgcggaaga cttgttggaa gatatcggcc aagcgcttga aaatatataa    1140
```

<210> SEQ ID NO 48
<211> LENGTH: 593
<212> TYPE: PRT
<213> ORGANISM: Paracoccus denitrificans

<400> SEQUENCE: 48

```
Met Arg Met Thr Thr Glu Glu Ser Phe Val Lys Thr Leu Gln Leu His
1               5                   10                  15

Gly Ile Glu His Ala Phe Gly Ile Ile Gly Ser Ala Met Met Pro Val
            20                  25                  30

Ser Asp Leu Phe Pro Arg Ala Gly Ile Thr Phe Trp Asp Cys Ala His
        35                  40                  45

Glu Thr Asn Ala Gly Met Met Ala Asp Gly Phe Thr Arg Ser Thr Gly
    50                  55                  60

Arg Met Ser Met Ala Ile Ala Gln Asn Gly Pro Gly Val Thr Gly Phe
65                  70                  75                  80

Val Thr Pro Val Lys Thr Ala Tyr Trp Asn His Thr Pro Leu Leu Leu
                85                  90                  95

Val Thr Pro Gln Ala Ala Asn Arg Thr Ile Gly Gln Gly Gly Phe Gln
            100                 105                 110

Glu Met Glu Gln Met Arg Ile Phe Ala Asp Cys Val Cys Tyr Gln Glu
        115                 120                 125

Glu Val Arg Asp Pro Ser Arg Ile Pro Glu Val Leu Asn Arg Val Ile
    130                 135                 140

Met Gln Ala Trp Arg Asn Ser Ala Pro Ala Gln Ile Asn Ile Pro Arg
145                 150                 155                 160
```

-continued

```
Asp Phe Trp Thr Gln Val Ile Asp Val Asp Leu Pro Gln Val Val Gly
                165                 170                 175

Phe Glu Arg Pro Ala Gly Gly Glu Arg Ala Val Ala Glu Ala Ala Arg
            180                 185                 190

Leu Leu Ser Glu Ala Arg Phe Pro Val Ile Leu Ser Gly Ala Gly Val
        195                 200                 205

Val Leu Ser Gly Ala Ile Pro Asp Leu Val Gly Leu Ala Glu Arg Leu
    210                 215                 220

Asp Ala Pro Val Cys Ser Asn Tyr Gln His Asn Asp Ser Phe Pro Gly
225                 230                 235                 240

Ser His Pro Leu Ala Met Gly Pro Leu Gly Tyr Asn Gly Ser Lys Ala
                245                 250                 255

Ala Met Glu Ile Ile Ala Arg Ala Asp Val Val Leu Ala Leu Gly Thr
            260                 265                 270

Arg Leu Asn Pro Phe Ser Thr Leu Pro Gly Tyr Gly Ile Asp Tyr Trp
        275                 280                 285

Pro Lys Asp Ala Arg Ile Ile Gln Val Asp Ile Asn Ala Asp Arg Ile
    290                 295                 300

Gly Leu Thr Lys Lys Val Ala Val Gly Ile Gln Gly Asp Ala Ala Lys
305                 310                 315                 320

Val Ala Arg Gly Ile Leu Ala Gln Leu Ala Pro Ala Ala Gly Asp Ala
                325                 330                 335

Gly Arg Gln Glu Arg Arg Asp Leu Val Ala Gln Thr Arg Ser Arg Trp
            340                 345                 350

Ala Gln Glu Leu Ser Ser Leu Asp His Glu Glu Asp Asp Pro Gly Thr
        355                 360                 365

Glu Trp Asn Glu Gln Ala Arg Ala Arg Asp Ala Gly Leu Met Ser Pro
    370                 375                 380

Arg Gln Ala Trp Arg Ala Ile Met Gln Ala Val Pro Lys Glu Ala Ile
385                 390                 395                 400

Val Ser Ser Asp Ile Gly Asn Asn Cys Ala Ile Gly Asn Ala Tyr Pro
                405                 410                 415

Ser Phe Glu Ala Gly Arg Lys Tyr Leu Ala Pro Gly Leu Phe Gly Pro
            420                 425                 430

Cys Gly Tyr Gly Phe Pro Ala Ile Leu Gly Ala Lys Ile Gly Asn Pro
        435                 440                 445

Glu Val Pro Val Ile Gly Phe Ala Gly Asp Gly Ala Phe Gly Ile Ser
    450                 455                 460

Met Asn Glu Met Thr Ala Cys Gly Arg Glu Asp Trp Pro Ala Ile Thr
465                 470                 475                 480

Met Val Ile Phe Arg Asn Tyr Gln Trp Gly Ala Glu Lys Arg Asn Thr
                485                 490                 495

Thr Leu Trp Tyr Asp Asn Asn Phe Val Gly Thr Glu Leu Asp Arg Asp
            500                 505                 510

Thr Ser Tyr Ala Lys Ile Ala Gln Ala Cys Gly Leu Val Gly Val Gln
        515                 520                 525

Val Arg Ser Gln Glu Glu Leu Thr Ala Ala Leu His Asp Ala Val Glu
    530                 535                 540

Arg Gln Met Gln Gly Arg Glu Thr Thr Phe Ile Glu Val Leu Leu Asn
545                 550                 555                 560

Gln Glu Leu Gly Glu Pro Phe Arg Arg Asp Ala Met Lys Lys Pro Val
                565                 570                 575
```

```
Ala Val Ala Gly Ile Asp Pro Ala Asp Met Arg Pro Gln Gln Gly Ala
            580                 585                 590

Ala


<210> SEQ ID NO 49
<211> LENGTH: 1782
<212> TYPE: DNA
<213> ORGANISM: Paracoccus denitrificans

<400> SEQUENCE: 49

atgcgaatga cgactgagga gtcttttgtc aaaacccttc aattgcacgg gatcgagcat      60

gcctttggca ttatcggctc tgcgatgatg cctgtttcgg acctgtttcc gcgggccggg     120

atcacgttct gggactgtgc gcatgagacg aatgccggga tgatggcgga cggtttcacg     180

cgctcgacgg ggcggatgtc gatggcgatc gcgcagaacg gtcccggggt gacggggttc     240

gtgacgccgg tcaagacggc ctactggaac cacacgccct tgcttctggt gacgccgcag     300

gcggcgaacc ggaccatcgg gcagggcggt ttccaggaga tggagcagat gcgcatcttc     360

gccgattgcg tctgctacca ggaggaggtg cgcgacccga gccgcatccc cgaggttctg     420

aaccgggtga tcatgcaggc ctggcgcaac tcggcgccgg cgcagatcaa catcccgcgc     480

gacttctgga cccaggtgat cgacgtggat ctgccgcagg tggtgggctt cgagcggccg     540

gcgggcggcg agcgggcggt ggccgaggcg gccaggctgc tctccgaggc gcggttcccg     600

gtgatcctgt cgggcgccgg cgtggtgctg tcgggcgcca ttcccgacct ggtcgggctg     660

gccgagcggc tggatgcgcc ggtctgctcg aactaccagc acaatgacag ctttccgggc     720

agccatccgc tggccatggg gccgctgggc tacaacggct cgaaggcggc gatggagatc     780

atcgcccggg ccgacgtggt gctggcgctg gggacgcggc tcaatccgtt ctcgaccctg     840

ccgggctacg gcatcgacta ctggccgaag gatgccagga tcatccaggt cgacatcaat     900

gccgaccgca tcgggctgac caagaaggtg gcggtgggca tccagggcga tgcggccaag     960

gtggcgcgcg gcatcctggc gcagctggcc ccggccgccg gcgatgccgg gcggcaggag    1020

cgccgcgacc tggtggcgca gacccggtcc cgctgggcgc aggaactgtc gagcctggac    1080

cacgaggagg acgatcccgg caccgaatgg aacgagcagg cgcgggcccg cgacgccggt    1140

ctgatgagcc cgcgccaggc ctggcgggcg atcatgcagg cggtgccgaa ggaggcgatc    1200

gtcagctcgg acatcggcaa caactgcgcc atcggcaatg cctatcccag cttcgaggcg    1260

gggcggaaat acctggcgcc ggggctgttc ggtccctgcg gctacggctt cccggcgatc    1320

ctgggggcca agatcggcaa tccggaggtg ccggtgatcg gctttgccgg cgacggcgcc    1380

ttcgggatct cgatgaacga gatgaccgcc tgcgggcgcg aggactggcc ggcgatcacc    1440

atggtgatct tccgcaacta ccagtggggg gcggaaaagc gcaacacgac gctgtggtac    1500

gacaacaact tcgtcggcac cgagctcgac cgcgacacct cctatgcgaa gatcgcccag    1560

gcctgcgggc tggtgggcgt gcaggtgcgc agccaggagg agctgacggc ggcgctgcac    1620

gatgcggtcg agcggcagat gcagggccgc gagaccacct tcatcgaggt gctcttgaac    1680

caggagctgg gcgagccctt ccgccgcgac gcgatgaaga agccggtggc ggtggccggc    1740

atcgacccgg ccgacatgcg cccgcagcag ggcgccgcct ga                       1782


<210> SEQ ID NO 50
<211> LENGTH: 486
<212> TYPE: DNA
<213> ORGANISM: Artificial Sequence
```

<220> FEATURE:
<223> OTHER INFORMATION: Description of Artificial Sequence: Synthetic
polynucleotide

<400> SEQUENCE: 50

```
atggaactgt atgaatgtat tcaggatatt tttggtggtc tgaaaaatcc gagcgttaaa     60

gatctggcaa ccagcctgaa acagattccg aatgcagcaa aactgagcca gccgtatatt    120

aaagaaccgg atcagtatgc atatggtcgt aatgcaattt atcgtaataa tgaactggaa    180

attattgtta ttaatattcc gccgaataaa gaaaccaccg ttcatgatca tggtcagagc    240

attggttgtg caatggttct ggaaggtaaa ctgctgaata gcatttatcg tagcaccggt    300

gaacatgcag aactgagcaa tagctatttt gttcatgaag gtgaatgtct gattagcacc    360

aaaggtctga ttcataaaat gagcaatccg accagcgaac gtatggttag cctgcatgtt    420

tatagcccgc cgctggaaga tatgaccgtt tttgaagaac agaaagaagt tctggaaaat    480

agctga                                                               486
```

<210> SEQ ID NO 51
<211> LENGTH: 603
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 51

```
atggaacgta ccgaactgct gaaaccgcgt accctggcag atctgattcg tattctgcat     60

gaactgtttg ccggtgatga agttaatgtt gaagaagttc aggcagttct ggaagcatat    120

gaaagcaatc cggcagaatg ggcactgtat gcaaaatttg atcagtatcg ttatacccgt    180

aatctggttg atcagggtaa tggtaaattt aatctgatga ttctgtgttg gggtgaaggt    240

catggtagca gcattcatga tcataccgat agccattgtt ttctgaaact gctgcagggt    300

aatctgaaag aaaccctgtt tgattggccg gataaaaaaa gcaatgaaat gattaaaaaa    360

agcgaacgta ccctgcgtga aaatcagtgt gcatatatta atgatagcat tggtctgcat    420

cgtgttgaaa atgttagcca taccgaaccg gcagttagcc tgcatctgta tagcccgccg    480

tttgatacct gtcatgcatt tgatcagcgt accggtcata aaaataaagt taccatgacc    540

tttcatagca aatttggtat tcgtaccccg tttaccacca gcggtagcct ggaaaataat    600

taa                                                                  603
```

<210> SEQ ID NO 52
<211> LENGTH: 1251
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 52

```
atgggtcgtt ttattctgaa atgtctgaaa tgtggtcgtg aatatagcca ggaatatcgt     60

ctgacctgtg aaaatgatga tagctttctg cgtgcagaat atctggaaaa aaaactggaa    120

ctgcgtaaac agccgggtat tggtcgtttt catagctggc tgccggttca ggaagaactg    180

accaccgaag caggtccgat tacctataaa agcgaagcac tggcacgtga actgggtctg    240

agcaatctgt atattggttt tagcggttat tggccggaaa aaggtgcatt tattaaaacc    300

tgtagcttta aagaactgga agcacatccg accatgcagc tgctgaaaga aagcggtggt    360
```

-continued

```
aaagcaattg ttctggcaag cgcaggtaat accggtcgtg catttgcaca tgttagcgca    420

ctgaccggta ccgatgttta tattgttgtt ccggatagcg gtattccgaa actgtggctg    480

ccggaagaac cgaccgatag cattcatctg attagcatga ccccgggtaa tgattatacc    540

gatgcaatta atctggcagg tcgtattgca aaactgccgg gtatggttcc ggaaggtggt    600

gcacgtaatg ttgcacgtcg tgaaggtatg ggtaccgtta tgctggatgc agcagttacc    660

attggtaaaa tgccggatca ttattttcag gcagttggta gcggtaccgg tggtattagc    720

gcatgggaag caagcctgcg tctgcgtgaa gatggtcgtt ttggtagcaa actgccgaaa    780

ctgcagctga cccagaatct gccgtttgtt ccgatgtata atgcatggca ggaaggtcgt    840

cgtgatatta ttccggaaat tgatatgaaa gatgcaaaaa aacgtattga agaaacctat    900

gcaaccgttc tgaccaatcg tgcaccgccg tatagcgtta ccggtggtct gtatgatgca    960

ctggttgata ccgatggtat tatgtatgca gttagcaaag aagaagcact ggatgcaaaa   1020

gcactgtttg aaagcctgga aggtattgat attctgccgc cgagcgcagt tgcagcagca   1080

agcctgctga aagcagttga agcaggtaat gttggtaaag atgataccat tctgctgaat   1140

attgccggtg gtggttttaa acgtctgaaa gaagatttta ccctgtttca gattgaaccg   1200

gaaattaccg ttagcaatcc ggatgttccg ctggaagaac tgaaactgtg a            1251
```

<210> SEQ ID NO 53
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
atgtttaaag caagcaaata ttataatctg ctgcagcagc tggaaaattt ttttagcacc     60

gcaaatagca gcagcctgct gaccaaaccg attgatccga atgttctgaa aagccagctg    120

agcctggatc tgccgaatga aggtaaaccg gttgaagaac tgcgtaccga aattaccagc    180

tatctgaata atgcactgaa aaccgcacat ccgagctatt ttaatcagct gtggggtggt    240

tttaatagcg catgttttat gggtgatatg ctggcaagcg caaccaatac cagcatgtat    300

acctatgaag ttgcaccggc agcaaccctg attgaacagg cactggttac caaaatgagc    360

ggtattctgg gttttaaaag cgcagatggt cagtttacca ccggtggtag caatggtaat    420

ctgatggcaa tggcaattgc acgtcatcat gttctgccga ccgttaaaca ggatggtatg    480

accagcggtc cgaaactggt tgcatttgtt agccgtgaag cacattatag ctttgataaa    540

gcagcacata ttctgggtct gggtaccgaa cagctgtgga aagttccggt tgatagcgat    600

ggtcgtatga aaccggaagc actgagcgaa ctggttgatc gtgcacgtgt tcagggtagc    660

attccgtttt ttgttgcagg taccgcaggt accaccgttc gtggtgcatt tgatccgttt    720

gaagaaatta gcgcaattgc acatcaggaa aatctgtggt ttcatattga tggtgcatgg    780

ggtgcaagcg ttagcctgag cgcaacccat cgtcagctga tggccggtgc aaatcaggca    840

gatagcctgg tttgggatgc acataaaatg atgggtatga ccctgatgtg tagcctgctg    900

ctggttaaac agcgtggtca gatgctgcgt acctttagca ccgcaggtac cgattatctg    960

tttcatgatg aagttagcgc cggtgaagtt ccgaccgaaa gcagcaccag cagcaccgaa   1020

ctgccgattg aagaactgcc gaccgatttt ggtccggcaa ccatgcattg tggtcgtcgt   1080

gttgatgcac tgaaactgtg gctggcatgg cgtcatctgg gtgatcgtgg ttgggaacgt   1140
```

ctgattgata gctattttga actggcacag cgtgcagaaa ccattattga taaacatccg 1200
agcctggaac tggttagcag ccgtcagagc gttaatctgt gttttcgtta tctgccgcag 1260
aataaacagc aggcagatga actgaccctg aaagttcgtc aggcactgtg ggaaaccggt 1320
accgcaatgg ttaattatgc acaggttgaa ggtaaaaccg tttttcgtct ggttatttgt 1380
aataatcaga cccgtagcga agatattgaa cgtttttttg aagcactggt tgcaattgca 1440
cgtcgtctgg aacaggaaat gtgttga 1467

<210> SEQ ID NO 54
<211> LENGTH: 1467
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54
atgttcaagg cctcgaagta ctacaacctc ctccagcagc tcgagaactt cttctcgacc 60
gccaactcgt cgtcgctcct caccaagccg atcgacccga acgtcctcaa gtcgcagctt 120
tcgctcgacc tcccgaacga gggcaagccg gtcgaggagc tccgcaccga gatcacctcg 180
tacctcaaca acgccctcaa gaccgcccac ccgtcgtact tcaaccagct ctggggcggc 240
ttcaactcgg cctgcttcat gggcgatatg ctcgcctcgg ccaccaatac ctcgatgtac 300
acctacgagg tcgccccggc cgccaccctc atcgaacagg ccctcgtcac caagatgtcg 360
ggcatcctcg gcttcaagtc ggctgatggc cagtttacca ccggcggttc gaacggcaac 420
ctcatggcca tggccatcgc ccgccaccac gttctcccga ccgtcaagca ggatggtatg 480
acctcgggcc cgaagctcgt cgcctttgtc tcgcgcgaag cccattactc gttcgacaag 540
gccgcccaca tcctcggcct cggcaccgag cagctttgga aggtcccggt cgactcggat 600
ggccgcatga agccggaagc tctttcggag ctcgttgacc gcgccagagt ccaaggctcg 660
atcccgtttt tcgtcgctgg caccgccggc accaccgtcc gtggtgcctt cgatccgttc 720
gaggagatct cggccattgc ccaccaggag aacctctggt tccacattga tggcgcctgg 780
ggcgccagcg tctcgctttc ggccacccac cgccaactca tggctggtgc caaccaggcc 840
gattcgcttg tctgggatgc ccacaagatg atgggcatga ccctcatgtg ctcgctcctc 900
ctcgtcaagc agcgtggcca gatgctccgc accttctcga ccgctggcac cgactacctc 960
ttccacgacg aggtcagtgc tggcgaggtc ccgaccgaat cgtcgaccag ttcgaccgaa 1020
ctcccgatcg aagagcttcc gaccgacttc ggcccggcca ccatgcattg cggtcgtcgc 1080
gtcgatgctc ttaaactttg gctcgcctgg cgccacctcg gtgatcgtgg ctgggagcgc 1140
ctcatcgact cgtacttcga gctcgcccag cgtgccgaaa ccatcatcga caagcacccg 1200
tcgctcgagc tcgtctcgtc gcgccagtcg gtcaacctct gcttccgcta cctcccgcag 1260
aacaagcaac aggccgacga gctcaccctt aaggtccgcc aggccctctg ggagacgggc 1320
accgccatgg tcaactacgc ccaggtcgaa ggcaagaccg ttttccgcct cgtcatctgc 1380
aacaatcaga cccgctcgga ggacatcgag cgcttcttcg aggccctcgt cgccatcgcc 1440
cgccgcctcg agcaggagat gtgctga 1467

<210> SEQ ID NO 55
<211> LENGTH: 1164
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 55

```
atgtacgtcg tcaacccgga ggagaaggtc atcgagatca tgaagcagac cggcatcgac     60
ctcgccgcca ccctcccgtg cgaccgcatc aagaacctcc tcccgctcgt ctcggagaac    120
ttcccggaga ttaagctcac ccgcgaggag aacggtgtcg gcatctgcgc cggtatctac    180
ctcgccggcg gcaagccgat gatgctcatc cagtcgaccg gcctcggcaa catgatcaac    240
gccctcgagt cgctcaacgt gacctgcaag atcccgctcc cgatccttgc ctcgtggcgc    300
ggcgtctata aggaaggcat cgaagcccag gtcccgctcg gtgcccacct tccttcgatc    360
cttgagggtg ccggcctcac ctacaccatc atcggcgaga cggagaagct cccgctcctc    420
gagaacgtca tccttgacgc cttcgagaac tcgcgtccgc atatcgccct cgtttcgccg    480
aaggtctggg aagcctcgga atgctgcgcc tggcaggccg ctggcatgcc gatcaagccg    540
gagattatgg agcgcacgtg ccgtttctcg ctcacctcgg gcaccctcaa gccgttcatg    600
ctccgcaacg atgccatctg caccctcgcc tcggagctcg acgacgagat caccgtcacc    660
aacctcggcg tcccgtgtaa ggagctctac gcctgccgcg accgcgaact caacttctac    720
atgttcggct cgatgggcct cgtctcgtcg atcggcctcg gcctcgccct ccgctcggaa    780
aagaccgtca tcaccttcga tggcgacggc tcgcttctca tgaacccgaa cgccctcctc    840
gagatcgcca aggaggcccc gaagaacctc atcatcatcg ccctcgacaa cggcgcctat    900
ggctcgaccg gctcgcagga aacctgcgcc ctccgctaca tcgatctcga gatcttcgcc    960
aacgcctgcg gcatccagaa caccgccaag gtcaactcga aggagggcgt catcgaggcc   1020
ttccgcaagt tcaaggccat gcgcgagctc tcgttcatcc acgtcatcct caagccgggc   1080
aacaccaacg ccccgaacat cccgatgtcg ccggaggagg ccaccaagcg cttcaaggaa   1140
accctcgacg tcaagaagtt ctaa                                          1164
```

<210> SEQ ID NO 56
<211> LENGTH: 1371
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 56

```
atggtcgtcg atgtcaccga gttacgtgcc cgcgcccgcc gccacctcgg cccgcatttc     60
acccgcaagg atacctggga atcggatttc ccggtgttcg tccgcggtga aggttcgtac    120
ctcatcgaca ccgaaggcga tcgcttcctc gacggcctcg ccggtctgtt ctgcgtcaac    180
atcggccatg gtcgcgacga catcgccaag gccgcctcgg aacagattgg cacccttgcc    240
tatgcctcga actggggctc ggcccacatc ccggctattg aggcctcggc tctcatcgcc    300
gatcttgccc cgggcgatct cggcactacc ttcttcgtca actcgggttc ggaggccgtc    360
gaaaccgccg tcaagttcgc ccgccagtac caccgctcgc agggtaatcc gcagcgcacc    420
aaaatcatct cgcgcgagat ggcctaccat ggcaccaccc tcggcgccct cagtgtcacc    480
cagctcccta agatcaagga cccgttcggt ccgcttcttc cgggcgttcg ttcggtcccg    540
aataccctcg gctacctcgg tgattgcggt ccggccaacg agctcgattg catcgccgcc    600
atcgaggccg tcatcgagga ggagggtgcc gaaaccatcg ctgctgtgtt cgccgaaccg    660
```

gtccaaaatg gccgcggtgc ccttgtccct cctgatggtt actgggccgc tctccgcgcc 720
ctctgcgaca agcatggcat cctcctcgtc tcggacgaag tcatctgctc gttcggtcgc 780
ctcggccact ggttcggtca tggccttacc ggcgtcgtcc cggacatgat caccttcgcc 840
aagggctcga cctcgggcta tgctcctctc ggtggcttga tcgtccgcga gcagctcgtc 900
cgtgagctct atgattcgcc gaagggtggc gtgttcactc acggcgctac ctggggtggc 960
catcctgtct cgaccgccgt cgctgtcgcc aacatcaccg ccatgcgcga tgaaaacgtc 1020
cttggcaacg tcagtgcccg cggcccgaag ctccgcagtg ctcttgattc gctcatgtcg 1080
tcgcatcgct gcgtcaagga cgtccgtggc accggcttct tctatgccat cgagctcatg 1140
gccgactcgg atagtggccg cgagttcacc gagcaggagt cgctcaccgt cctccgcaaa 1200
gttctcccgg aggccttcgc ccgcaccaag gtcatcctcc gtggtgatga tcgtggcgcc 1260
accatgctca tgatctcgcc gccgctcgtc gctgacgacg aagtcctctc ggagctcctc 1320
cacggcatcg actcgatgct caccgacatc gagaaggcca tccagccgta g 1371

<210> SEQ ID NO 57
<211> LENGTH: 771
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57
atgccgcgtg ataacatggc ctcgcttatc cagcgcattg cccgccaagc ctgcctcacc 60
ttccgcggtt cgagtaccgg ctcggagggc ccggctccgg gcttcccgga aaacctctcg 120
ctcctcaagt cgcttctcac ccaggtccgt gccgaggatc ttaacatcgc cccgcgtaag 180
gccctcccgc agccgctccc gcgcaacctc ccgccggtca cctacatgca catctacgaa 240
accgagggct tctcgctcgg cgtgttcctc ctcaagtcgg gcacgtgcat cccgctccac 300
gaccacccgg gcatgcacgg catgctcaag gtcctctacg gcaccgtccg catctcgtgc 360
atggacaagc tcgacaccgg tgccggccat agacgtccgc ctccggaaca gcagttcgag 420
cctccgcttc agccgctcga acgcgaagcc gttcgcccgg gcgtccttag aagtcgcgcc 480
gaatacaccg aggccagtgg tccgtgcgtc ctcaccccgc accgtgataa cctccatcag 540
atcgatgccg tcgacggccc ggccgccttc ctcgatatcc tcgccccgcc gtacgacccg 600
gaggatggcc gcgattgcca ttattatcgc gtcgtcgagc cgatccgccc gaaggaagcc 660
tcgggttcgg cctgtgatct cccgcgcgag gtctggctcc tcgaaacccc gcaggccgac 720
gacttttggt gcgagggtga accgtacccg ggcccgaagg tcctcccgtg a 771

<210> SEQ ID NO 58
<211> LENGTH: 486
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58
atggagctct acgagtgcat ccaggacatc ttcggcggcc tcaagaaccc gtcggtcaag 60
gacctcgcca cctcgctcaa gcagatcccg aacgccgcca agctctcgca gccgtacatc 120
aaggagccgg accagtacgc ctacggccgc aacgccatct accgcaacaa cgagctcgag 180
atcatcgtca tcaacatccc gccgaacaag gagacgaccg tccacgacca cggccagtcg 240
atcggctgcg ccatggtcct cgagggcaag ctcctcaact cgatctaccg ctcgaccggc 300
gagcacgccg agctctcgaa ctcgtacttc gtccacgagg gcgagtgcct catctcgacc 360
aagggcctca tccacaagat gtcgaacccg acctcggagc gcatggtgtc gctccacgtc 420
tactcgccgc cgctcgagga catgaccgtg ttcgaggagc agaaggaggt cctcgagaac 480
tcgtga 486

<210> SEQ ID NO 59
<211> LENGTH: 603
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59
atggagcgca ccgagctcct caagccgcgc accctcgccg acctcatccg catcctccac 60
gagctcttcg ccggcgacga ggtcaacgtc gaggaggtcc aggccgtcct cgaggcctac 120
gagtcgaacc cggccgagtg ggccctctac gccaagttcg accagtaccg ctacacccgc 180
aacctcgtcg accagggcaa cggcaagttc aacctcatga tcctctgctg gggcgagggc 240
cacggctcgt cgatccacga ccacaccgac tcgcactgct tcctcaagct cctccagggc 300
aacctcaagg agacgctctt cgactggccg gacaagaagt cgaacgagat gatcaagaag 360
tcggagcgca ccctccgcga gaaccagtgc gcctacatca acgactcgat cggcctccac 420
cgcgtcgaga acgtctcgca caccgagccg gccgtctcgc tccacctcta ctcgccgccg 480
ttcgacacgt gccacgcctt cgaccagcgc accggccaca agaacaaggt caccatgacc 540
ttccactcga agttcggcat ccgcaccccg ttcaccacct cgggctcgct cgagaacaac 600
taa 603

<210> SEQ ID NO 60
<211> LENGTH: 606
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60
atgtcgtcga tcctccgcct tgaccgtctc cgccagttca tcggcgagct cgccaccctc 60
ctcgattcgc gcccggatga atcgaccctc ctcgcccagg cccatccgct cctcgccgaa 120
cttgtccatc aggatgactg gctcccggag gattgcgccc gcccggaccc gcagcgctat 180
cagcagtacc tcctccacgt cgactcgcgt cagcgcttct cggtcgtctc gttcgtctgg 240
ggcccgggtc agatcacccc ggtccacgat caccgcgtct ggggcctcat cggcatgctt 300
cgtggcgccg agtactcgca gccgtatgcc ttcgatgccg gtggcagacc gcatccgtcg 360
ggtgccagac gtcgccttga gccgggcgaa gtcgaggctc tctcgcctcg catcggcgat 420
gtccaccagg tgtcgaacgc cttctcggac cgcacctcga tctcgatcca cgtctacggc 480
gctaacatcg gcgccgtccg ccgcgccgtg ttctcggccg agggtgagga gaagccgttc 540
atctcgggct actcgaactc gcgcctcccg aacatctggg acctctcgaa ggagaacccg 600
gcctga 606

<210> SEQ ID NO 61

<211> LENGTH: 969
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 61
atgccgcgcg gctggaccaa gacccgcgcc tatgactcgc atcatttcga tgccgacgcc 60
tggtcggtcg tcaccccgcg cgccggtgat gtcattatcg ccaccgccta caagtcgggc 120
accacctgga tgcagcagat cgtctcgcag ctcgttttcg agggcgccgc cccggctgcc 180
ctcggcgaac ttagtccttg ggtcgatctc cgtgttcctc ctcgcgaagt caagcgcggt 240
atgattgagg gcctcccgtc gccgcgcatt ctcaagaccc atctcccgac caccggcctc 300
gagtatgacg agaacgccaa gtacatctac gtcgcccgcg acggccgcga cgccttcatg 360
tcgctcatga accactacaa gaacggcaac gaggccttct atggcgccct caacggcccg 420
ggcctcaagg gtgctccgct cccgacctgg gaagaagctt gcgagggcga gggcgatgaa 480
aagctcagag ccctcttcga caagtggctc aacaccccgt ggggccagca cccgtgggag 540
gaggacggct ggccgttctg gtcgctcttc tacaacatga aacctggtg ggacgcccgc 600
gagtcgaaga acatcatctt cgtccacttc tcggacctca agaaggacct caagggccag 660
atgcgccgca tcgccaagtt cctcaacgcc ccgatcgacg agtcgaagtt tgacgcccag 720
gtcaccgcct gcaccttcga atcgatgaag ggtaatgccg cttcggtcgc ccctctcggc 780
ggcgccctct ggaagggcgg tgccgaaacc ttcatcaaca aaggcactaa cggccgctgg 840
cgcaacgtcc tcaccaagga gcaggtcaag cagtacgagc aggtcgccga gaagcgcctc 900
ggcaaggatt gcgccaagtg gctcgccaac ggcggcgata tgaacggccg cggctgcgtc 960
atcatgtga 969

<210> SEQ ID NO 62
<211> LENGTH: 606
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 62
atggccctcc acgacgagaa cgtcgtctgg cactcgcacc cggtcaccgt ccagcagcgc 60
gaactccatc atggccatcg cggcgtcgtc ctctggttca ccggcctctc gggttcgggt 120
aaatcgaccg tcgccggcgc cctcgaagag gccctccaca agctcggtgt ctcgacctac 180
ctcctcgatg gcgataacgt ccgccacggt ctgtgctcgg atctcggctt ctcggacgcc 240
gaccgcaagg agaacatccg ccgcgtcggc gaggtcgcca acctcatggt cgaagccggt 300
ctggtcgtcc tcaccgcctt catctcgccg catcgcgctg aacgccaaat ggtccgtgag 360
cgcgtcggcg agggccgctt catcgaggtg ttcgtcgata ccccgctcgc catctgcgaa 420
gcccgtgatc cgaagggcct ctacaagaag gcccgcgccg gcgagctccg caacttcacc 480
ggtatcgact cggtctacga agccccggag tcggccgaga tccatctcaa cggcgagcag 540
ctcgtcacca acctcgtcca gcagctcctc gacctcctcc gccagaacga catcatccgc 600
tcgtga 606

<210> SEQ ID NO 63
<211> LENGTH: 1875

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63
atggagctcc cggagtcgca gtgcaagaag gccaagctct cgaaccgcgt cccgaactgg 60
ggcatgcagc gcgctaccaa cgtcacctac caggcccacc atgtttcgcg caacaagcgt 120
ggccaggtcg tcggtactcg cagtggtttc cgcggttgca ccgtttggct taccggcctt 180
tcgggcgctg gcaagaccac cgtcagtatg gccctcgagg agtatctcgt ctgccacggc 240
atcccgtgct ataccctcga cggcgacaac atccgccagg gactcaacaa gaatctcggc 300
ttcaccccgg aggaccgcga ggaaaacgtc cgccgcatcg ccgaggtcgc taagctcttc 360
gccgatgctg gcctcgtctg catcaccagt ttcatctcgc cgtacgctca ggaccgcaac 420
aatgcccgcc gcatccacga aggtgcctcg ctcccgttct tcgaggtgtt cgtcgatgcc 480
ccgctccatg tctgcgaaca gcgcgatgtc aaaggcctct acaagaaggc ccgcgccggc 540
gagatcaagg gtttcaccgg catcgactcg gagtacgaga agcctgaggc cccggagctc 600
gtccttaaga ctgactcgtg cgacgtcaac gactgcgtcc agcaggtcgt cgagctcctc 660
caggagcgcg acattgtccc ggtcgacgcc tcgtacgagg tcaaggagct ctacgtcccg 720
gagaacaagc tcaagctcgc caagaccgat gccgagtcgc tccttaccct cgagatcaac 780
aaggtcgata tgcagtgggt ccaggtcctc gccgagggct gggccacccc gctctcgggt 840
ttcatgcgcg agcgcgaata cctccagtgc cttcatttcg attgccttct cgatggcggc 900
gtcatcaacc tctcggttcc gattgtcctc accgctaccc aggaggacaa agaacgtctc 960
gacggctgca ccgccatcgc cctcgtctac gagggccgtc gtgtcgccat tcttcgcaac 1020
ccggagttct acgaacaccg taaggaagag cgctgcgccc gtcagtgggg caccacgtgc 1080
aaggatcacc cgtacatcaa gatggtcatg gagcagggca actggctcgt cggcggtgac 1140
ctccaggttc tcgatcgcat ctactggaac gatggcctcg accagtatcg cctcaccccg 1200
gccgaactcc gccagaagtt caaggagatg aacgccgacg ccgtctttgc cttccagctc 1260
cgcaacccgg tccacaacgg tcatgccctc ctcatgcaag acacccacaa gcagctcctc 1320
gagcgcggtt accgtcgccc tgtcctcctc ctccatcctc tcggcggctg gaccaaagag 1380
gatgacgtcc cgcttatgtg gcgcatgaaa cagcacgccg ccgtcctcga ggaaggcgtc 1440
ctcaacccgg agacgaccgt cgttgccatc ttcccgtcgc ctatgatgta tgccggtccg 1500
accgaggttc agtggcattg ccgttcgcgc atggtcgctg gcgccaactt ctatatcgtc 1560
ggccgtgatc ctgccggtat gccgcatccg ggcaccggca aagaccttta cgaaccgact 1620
catggcgcca aggttcttac catggccccg ggcctccgtg ccctcgagat cgtccctttc 1680
cgcgtcgccg cctacaacaa gaagaagaag tcgatggact actacgactc ggagcaccat 1740
gaggacttcg agttcatctc gggcacccat atgcgcaagc tcgcccgcga aggccagaac 1800
ccgccggagg gcttcatggc tccgaaggct tggaccgtcc tcaccgaata ctacaagtcg 1860
ctcgagaagg cctag 1875

<210> SEQ ID NO 64
<211> LENGTH: 1251
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 64

```
atgggccgct tcatcctcaa gtgcctcaag tgcggccgcg agtactcgca ggagtaccgc      60
ctgacctgcg agaacgacga ctcgttcctc cgcgccgagt acctcgagaa gaagctcgag     120
ctccgcaagc agccgggcat cggccgcttc cactcgtggc tcccggtcca ggaggagctc     180
accaccgagg ccggcccgat cacctacaag tcggaggccc tcgcccgcga gctcggcctc     240
tcgaacctct acatcggctt ctcgggctac tggccggaga agggcgcctt catcaagacc     300
tgctcgttca aggagctcga ggcccacccg accatgcagc tcctcaagga gtcgggcggc     360
aaggccatcg tcctcgcctc ggccggcaac accggccgcg ccttcgccca cgtctcggcc     420
ctcaccggca ccgacgtcta catcgtcgtc ccggactcgg gcatcccgaa gctctggctc     480
ccggaggagc cgaccgactc gatccacctc atctcgatga ccccgggcaa cgactacacc     540
gacgccatca acctcgccgg ccgcatcgcc aagctcccgg gcatggtccc ggagggcggc     600
gcccgcaacg tcgcccgccg cgagggcatg ggcaccgtca tgctcgacgc cgccgtcacc     660
atcggcaaga tgccggacca ctacttccag gccgtcggct cgggcaccgg cggcatctcg     720
gcctgggagg cctcgctccg cctccgcgag gacggccgct tcggctcgaa gctcccgaag     780
ctccagctca cccagaacct cccgttcgtc ccgatgtaca acgcctggca ggagggccgc     840
cgcgacatca tcccggagat cgacatgaag gacgccaaga agcgcatcga ggaaacctac     900
gccaccgtcc tcaccaaccg cgccccgccg tactcggtca ccggcggcct ctacgacgcc     960
ctcgtcgaca ccgacggcat catgtacgcc gtctcgaagg aggaggccct cgacgccaag    1020
gccctcttcg agtcgctcga gggcatcgac atcctcccgc cgtcggccgt cgccgccgcc    1080
tcgctcctca aggccgtcga ggccggcaac gtcggcaagg acgacaccat cctcctcaac    1140
atcgccggcg gcggcttcaa gcgcctcaag gaggacttca ccctcttcca gatcgagccg    1200
gagatcaccg tctcgaaccc ggacgtcccg ctcgaggagc tcaagctctg a             1251
```

<210> SEQ ID NO 65
<211> LENGTH: 1140
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
atgaagaaga aaaccctcat gatccacggc ggcatcaccg gcgacgaaaa gaccggcgcc      60
gtctcggtcc cgatctatca ggtgtcgacc tacaagcagc cgaaggccgg ccagcatact     120
ggctacgagt attcgcgcac cgccaacccg accagaaccg ccttagaggc cctcgtcacc     180
gagctcgaaa gtggcgaagc cggctacgcc ttctcgtcgg gtatggctgc catcaccgcc     240
gtcatgatgc tcttcaactc gggcgaccac gtcgtcctca ccgacgacgt ctacggcggc     300
acctaccgcg tcatgaccaa ggtcctcaac cgcctcggca tcgagtcgac cttcgtcgac     360
acctcgtcgc gcgaggaggt cgagaaggcc atccgcccga acaccaaggc catctacatc     420
gagacgccga ccaacccgct cctcaagatc accgacctca ccctcatggc cgacatcgcc     480
aagaaggccg gcgtcctcct catcgtcgac aacaccttca acaccccgta cttccagcag     540
ccgcttactc tcggcgccga catcgtcctc cattcggcca ccaagtacct cggtggccat     600
tcggatgtcg tcggcggcct cgttgtcacc gcctcgaagg agctcggtga ggaactccac     660
```

```
ttcgtccaga actcgaccgg tggcgtcctc ggtccgcagg atagttggct cctcatgcgc    720

ggcatcaaga ccctcggcct ccgcatggag gccatcgatc agaacgcccg taagatcgcc    780

tcgttcctcg agaaccatcc ggccgtccag accctctatt acccgggctc gtcgaaccat    840

ccgggtcatg aactcgccaa gacccagggc gctggcttcg gcggcatgat ctcgttcgat    900

atcggctcgg aggagcgcgt cgacgccttc ctcggcaacc tcaagctctt caccatcgcc    960

gaatcgcttg gcgccgtcga gtcgcttatc tcggttccgg cccgcatgac ccacgccagt   1020

atcccgcgtg agcgtcgcct tgaactcggc atcaccgatg gcctcatccg catctcggtc   1080

ggcatcgaag atgccgagga cctcctcgag gacatcggcc aggccctcga gaacatctaa   1140
```

```
<210> SEQ ID NO 66
<211> LENGTH: 1020
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

atgcatctcg cccgttaccc gcgccgcttc atcgcccatc ttccgactcc gctcgagaga     60

ctcgaccgtc tcaccgccga actcggtggc ccggaaatct ggatcaagcg cgacgattgc    120

actggcctct cgaccggcgg caacaagacc cgcaagctcg agttcctcat ggccgaggcc    180

gagctccaag gcgccgatat ggtcatgacc cagggtgcta cccagtcgaa tcatgctcgt    240

cagaccgccg ccttcgccgc caagctcggt atggactgcc acatcctcct cgaggaccgc    300

accggctcga acaacgccaa ctacaacaac aacggcaacg tcctcctcga ccatctccac    360

ggcgccacca ccgaaaagcg cccgggctcg ggcctcgata tgaacgccga aatggagaag    420

gtcgccgaga agttccgcgc cgatggtcgc aaggtctaca ccatccctgg cggtggttcg    480

aacccgaccg gcgccctcgg ttacgtcaac tgcgccttcg agatgctcaa ccagttcaac    540

gagcgcggcc tcaaggtcga ccacatcgtc catgccaccg gtagtgccgg cacccaagcc    600

ggcctcatca ccggcctcca ggctatgaat gcccagattc cgcttcttgg catcggtgtc    660

cgtgccccga agccgaagca ggaagagaac gtctataatc tcgcctgcgc caccgccgag    720

aaacttggct gcccgggcgt cgtcgctcgc gaggacgtcg tcgccaatac cgactatgtc    780

ggtgagggct atggcattcc taccgagtcg ggcctcgaag ccatccgcat gttcgccgag    840

ctcgaagcca tcctcctcga cccggtctat tcggccaagg gtgccgccgg cttcatcgac    900

cttatccgca agggccattt taagaagggc gagcgcgtcg tctttctcca caccggcggc    960

gccgtcgccc tcttcggcta cgacaacgcc ttcgactact cgggccgctg ggtcgcctaa   1020
```

```
<210> SEQ ID NO 67
<211> LENGTH: 759
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

atgaacgcct tcaagttcct cgacgagatc ggcccggtca acaccaacac catggtcctc     60

gacaaggccc tcggctacaa gaccgtcgag gacatgctca ccatctcggg caactacttc    120

aacctcctca agtacggctg ggcacctcg atcctctacg acgaggagat catcaaggac    180
```

-continued

```
aagaacgagc tctaccactc gtacaacatc cgcacctaca ccggcggcac cctcttcgag    240

ctcgccaaca agcagaacaa gatcgacgag tacttcaacg agatcgatcg cctcggcttc    300

aacgccgtcg agatctcgga tggctcgacc accatcgact cggaccgccg cgcccagctc    360

atcaacaagt cgaaggagct cggcttctac accctctcgg agatcggcaa gaagaacccg    420

cagaaggact cggagtacac cacccagcag cgcatcgacc tcatcaacac cgacatcgag    480

gccggctcgg acatggtcat catcgagggc cgcgagtcgg gcaagaacat cggcatctac    540

gacgacaagg gcaacgtcaa gaaggacgac ctcacctcga tctacgagaa caccccgaag    600

gagaaggtcc tctgggaggc ccccgcagaag aaccagcagg tcgagctcat cctcaccctc    660

tcgaacgacg tcaacctcgg caacatcaac tcgaacgaaa tcgtctcgct cgaaaccctc    720

cgccgcggcc tccgcggcga caccctcggc aagctctaa                          759
```

<210> SEQ ID NO 68
<211> LENGTH: 699
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
atgaagatca acgtctcgct ctacaactcg cgcaccaacg acctcgccat cgtcatcgac     60

ctcctccgcg cctcgaccac catctcggtc gccctcaaca ccttcaagcg catcgtcccg    120

atcaacgaca tcgacgaggc catcaagctc aaggagaagc acaacgccat cctcgccggc    180

gagatcaagt cgtcggactt cgacgtctcg aactcgccgg tccagatctc gaactacgcc    240

ggcgacaccc tcatcctcaa gaccaccaac ggcaccaagg tcctcgagaa catcaagcag    300

cgcaactcgg aggtcaacat cctcgtcggc gcctcgatca acgccaagac cgtcgcccag    360

aaggccctcg atatcgccga taacgaaatc gaactcgtca tggccggccg ccatcagcgc    420

ttcaccatcg aggactgcat cggcgccggc atcatcatca acgagatcgt caacatcgcc    480

aaggagaaga acatctacct cgagctctcg gagtcggcca aggcctcgaa gatcatctcg    540

aacaactcga acatcatcaa gcagctcatc aacacctcgc actcggccga caagctccgc    600

tacctcggct tcggcgagga catcgagatc tgctcgctca tcaacaagat cgacaccgtc    660

ccgatctaca agaacaacta catcgtctcg ctcgactaa                          699
```

<210> SEQ ID NO 69
<211> LENGTH: 1029
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

```
atgaacatca ccccggagca ggagctctcg ctcatcatcg acatcctcac caagttcgac     60

gtcccggagg accaggcctc gatcatcgcc gaggtcaccc tcgatggcga tctcaagggc    120

ttctcgtcgc acggcatcgg ccgtttcccg cagtacatca agggcctcga atgcggccac    180

attaagccgc acaccgagat cgtcgtcgag aaggagacgg ccgccaccgc cctcatcaac    240

ggcaaccacg gcttcggcca cgtcgtcacc taccaggcca tgaagatggc catcgagaag    300

gccaaggagg tcggcatcgg cctcgtcggc atccacaact cgaaccactt cggcgtcgcc    360

ggctactact cggacatggc cctcatggag gacatcattg gtatcgtcac cgccaacacc    420
```

gaaccggccg tcgccccgat tggcggcaaa gaaccgatcc ttggcaccaa cccgctcgcc 480
atcggtatcc cgtcgggcag tcattacctc tcggtcgata tggccacctc ggcctcggcc 540
cgcggtaagc tcatggaagc caagcgcctt ggcgagccga tcccggaaaa tgtcgccctc 600
gattcggatg gcaaccctac caccgatccg gctgaggccc ttaagggctc gatcctcccg 660
ttcggcgccc acaagggcta tgccctctcg ctcatgatcg aagtcatcgc cggtccgctt 720
gtccgcgcct cgtatggcaa gggtgtcacc ggtacggccg acccggaggt tccgtgcact 780
aagggcgatc ttatcgctgc catcgacccg tcgaagttcg tcgacatcga ccagttcaag 840
gaggaggtcg acgacctcat ctcggagctc aagtcgaccc cgaacgtcat gatcccgggc 900
gacttcgagg tcctcaacgt caagcgccac cagaaggagg gcatcgccct cgacgagacg 960
ctcgtccagc agctccgcga aatcgcctcg aacgtcgacg tcgacgtctc ggatatcctc 1020
ggcgactaa 1029

<210> SEQ ID NO 70
<211> LENGTH: 395
<212> TYPE: PRT
<213> ORGANISM: Escherichia coli

<400> SEQUENCE: 70

Met Ala Asp Lys Lys Leu Asp Thr Gln Leu Val Asn Ala Gly Arg Ser
1 5 10 15

Lys Lys Tyr Thr Leu Gly Ala Val Asn Ser Val Ile Gln Arg Ala Ser
20 25 30

Ser Leu Val Phe Asp Ser Val Glu Ala Lys Lys His Ala Thr Arg Asn
35 40 45

Arg Ala Asn Gly Glu Leu Phe Tyr Gly Arg Arg Gly Thr Leu Thr His
50 55 60

Phe Ser Leu Gln Gln Ala Met Cys Glu Leu Glu Gly Gly Ala Gly Cys
65 70 75 80

Val Leu Phe Pro Cys Gly Ala Ala Ala Val Ala Asn Ser Ile Leu Ala
85 90 95

Phe Ile Glu Gln Gly Asp His Val Leu Met Thr Asn Thr Ala Tyr Glu
100 105 110

Pro Ser Gln Asp Phe Cys Ser Lys Ile Leu Ser Lys Leu Gly Val Thr
115 120 125

Thr Ser Trp Phe Asp Pro Leu Ile Gly Ala Asp Ile Val Lys His Leu
130 135 140

Gln Pro Asn Thr Lys Ile Val Phe Leu Glu Ser Pro Gly Ser Ile Thr
145 150 155 160

Met Glu Val His Asp Val Pro Ala Ile Val Ala Ala Val Arg Ser Val
165 170 175

Val Pro Asp Ala Ile Ile Met Ile Asp Asn Thr Trp Ala Ala Gly Val
180 185 190

Leu Phe Lys Ala Leu Asp Phe Gly Ile Asp Val Ser Ile Gln Ala Ala
195 200 205

Thr Lys Tyr Leu Val Gly His Ser Asp Ala Met Ile Gly Thr Ala Val
210 215 220

Cys Asn Ala Arg Cys Trp Glu Gln Leu Arg Glu Asn Ala Tyr Leu Met
225 230 235 240

Gly Gln Met Val Asp Ala Asp Thr Ala Tyr Ile Thr Ser Arg Gly Leu
245 250 255

```
Arg Thr Leu Gly Val Arg Leu Arg Gln His His Glu Ser Ser Leu Lys
            260                 265                 270

Val Ala Glu Trp Leu Ala Glu His Pro Gln Val Ala Arg Val Asn His
        275                 280                 285

Pro Ala Leu Pro Gly Ser Lys Gly His Glu Phe Trp Lys Arg Asp Phe
    290                 295                 300

Thr Gly Ser Ser Gly Leu Phe Ser Phe Val Leu Lys Lys Lys Leu Asn
305                 310                 315                 320

Asn Glu Glu Leu Ala Asn Tyr Leu Asp Asn Phe Ser Leu Phe Ser Met
                325                 330                 335

Ala Tyr Ser Trp Gly Gly Tyr Glu Ser Leu Ile Leu Ala Asn Gln Pro
            340                 345                 350

Glu His Ile Ala Ala Ile Arg Pro Gln Gly Glu Ile Asp Phe Ser Gly
        355                 360                 365

Thr Leu Ile Arg Leu His Ile Gly Leu Glu Asp Val Asp Asp Leu Ile
    370                 375                 380

Ala Asp Leu Asp Ala Gly Phe Ala Arg Ile Val
385                 390                 395
```

<210> SEQ ID NO 71
<211> LENGTH: 1188
<212> TYPE: DNA
<213> ORGANISM: Escherichia coli

<400> SEQUENCE: 71

```
atggcggaca aaaagcttga tactcaactg gtgaatgcag gacgcagcaa aaaatacact     60

ctcggcgcgg taaatagcgt gattcagcgc gcttcttcgc tggtctttga cagtgtagaa    120

gccaaaaaac acgcgacacg taatcgcgcc aatggagagt tgttctatgg acggcgcgga    180

acgttaaccc atttctcctt acaacaagcg atgtgtgaac tggaaggtgg cgcaggctgc    240

gtgctatttc cctgcggggc ggcagcggtt gctaattcca ttcttgcttt tatcgaacag    300

ggcgatcatg tgttgatgac caacaccgcc tatgaaccga gtcaggattt ctgtagcaaa    360

atcctcagca aactgggcgt aacgacatca tggtttgatc cgctgattgg tgccgatatc    420

gttaagcatc tgcagccaaa cactaaaatc gtgtttctgg aatcgccagg ctccatcacc    480

atggaagtcc acgacgttcc ggcgattgtt gccgccgtac gcagtgtggt gccggatgcc    540

atcattatga tcgacaacac ctgggcagcc ggtgtgctgt ttaaggcgct ggattttggc    600

atcgatgttt ctattcaagc cgccaccaaa tatctggttg ggcattcaga tgcgatgatt    660

ggcactgccg tgtgcaatgc ccgttgctgg gagcagctac gggaaaatgc ctatctgatg    720

ggccagatgg tcgatgccga taccgcctat ataaccagcc gtggcctgcg cacattaggt    780

gtgcgtttgc gtcaacatca tgaaagcagt ctgaaagtgg ctgaatggct ggcagaacat    840

ccgcaagttg cgcgagttaa ccaccctgct ctgcctggca gtaaaggtca cgaattctgg    900

aaacgagact ttacaggcag cagcgggcta ttttcctttg tgcttaagaa aaaactcaat    960

aatgaagagc tggcgaacta tctggataac ttcagtttat tcagcatggc ctactcgtgg   1020

ggcgggtatg aatcgttgat cctggcaaat caaccagaac atatcgccgc cattcgccca   1080

caaggcgaga tcgattttag cgggaccttg attcgcctgc atattggtct ggaagatgtc   1140

gacgatctga ttgccgatct ggacgccggt tttgcgcgaa ttgtataa                1188
```

<210> SEQ ID NO 72
<211> LENGTH: 303
<212> TYPE: PRT

<213> ORGANISM: Escherichia coli

<400> SEQUENCE: 72

```
Met Ser Thr Leu Glu Gln Thr Ile Gly Asn Thr Pro Leu Val Lys Leu
1               5                   10                  15

Gln Arg Met Gly Pro Asp Asn Gly Ser Glu Val Trp Leu Lys Leu Glu
            20                  25                  30

Gly Asn Asn Pro Ala Gly Ser Val Lys Asp Arg Ala Ala Leu Ser Met
        35                  40                  45

Ile Val Glu Ala Glu Lys Arg Gly Glu Ile Lys Pro Gly Asp Val Leu
    50                  55                  60

Ile Glu Ala Thr Ser Gly Asn Thr Gly Ile Ala Leu Ala Met Ile Ala
65                  70                  75                  80

Ala Leu Lys Gly Tyr Arg Met Lys Leu Leu Met Pro Asp Asn Met Ser
                85                  90                  95

Gln Glu Arg Arg Ala Ala Met Arg Ala Tyr Gly Ala Glu Leu Ile Leu
            100                 105                 110

Val Thr Lys Glu Gln Gly Met Glu Gly Ala Arg Asp Leu Ala Leu Glu
        115                 120                 125

Met Ala Asn Arg Gly Glu Gly Lys Leu Leu Asp Gln Phe Asn Asn Pro
    130                 135                 140

Asp Asn Pro Tyr Ala His Tyr Thr Thr Thr Gly Pro Glu Ile Trp Gln
145                 150                 155                 160

Gln Thr Gly Gly Arg Ile Thr His Phe Val Ser Ser Met Gly Thr Thr
                165                 170                 175

Gly Thr Ile Thr Gly Val Ser Arg Phe Met Arg Glu Gln Ser Lys Pro
            180                 185                 190

Val Thr Ile Val Gly Leu Gln Pro Glu Glu Gly Ser Ser Ile Pro Gly
        195                 200                 205

Ile Arg Arg Trp Pro Thr Glu Tyr Leu Pro Gly Ile Phe Asn Ala Ser
    210                 215                 220

Leu Val Asp Glu Val Leu Asp Ile His Gln Arg Asp Ala Glu Asn Thr
225                 230                 235                 240

Met Arg Glu Leu Ala Val Arg Glu Gly Ile Phe Cys Gly Val Ser Ser
                245                 250                 255

Gly Gly Ala Val Ala Gly Ala Leu Arg Val Ala Lys Ala Asn Pro Asp
            260                 265                 270

Ala Val Val Val Ala Ile Ile Cys Asp Arg Gly Asp Arg Tyr Leu Ser
        275                 280                 285

Thr Gly Val Phe Gly Glu Glu His Phe Ser Gln Gly Ala Gly Ile
    290                 295                 300
```

<210> SEQ ID NO 73
<211> LENGTH: 912
<212> TYPE: DNA
<213> ORGANISM: Escherichia coli

<400> SEQUENCE: 73

```
gtgagtacat tagaacaaac aataggcaat acgcctctgg tgaagttgca gcgaatgggg      60

ccggataacg gcagtgaagt gtggttaaaa ctggaaggca ataacccggc aggttcggtg     120

aaagatcgtg cggcactttc gatgatcgtc gaggcggaaa agcgcgggga aattaaaccg     180

ggtgatgtct taatcgaagc caccagtggt aacaccggca ttgcgctggc aatgattgcc     240

gcgctgaaag gctatcgcat gaaattgctg atgcccgaca acatgagcca ggaacgccgt     300
```

-continued

```
gcggcgatgc gtgcttatgg tgcggaactg attcttgtca ccaaagagca gggcatggaa    360

ggtgcgcgcg atctggcgct ggagatggcg aatcgtggcg aaggaaagct gctcgatcag    420

ttcaataatc ccgataaccc ttatgcgcat tacaccacca ctgggccgga aatctggcag    480

caaaccggcg ggcgcatcac tcattttgtc tccagcatgg ggacgaccgg cactatcacc    540

ggcgtctcac gctttatgcg cgaacaatcc aaaccggtga ccattgtcgg cctgcaaccg    600

gaagagggca gcagcattcc cggcattcgc cgctggccta cggaatatct gccggggatt    660

ttcaacgctt ctctggtgga tgaggtgctg gatattcatc agcgcgatgc ggaaaacacc    720

atgcgcgaac tggcggtgcg ggaaggaata ttctgtggcg tcagctccgg cggcgcggtt    780

gccggagcac tgcgggtggc aaaagctaac cctgacgcgg tggtggtggc gatcatctgc    840

gatcgtggcg atcgctacct ttctaccggg gtgtttgggg aagagcattt tagccagggg    900

gcggggattt aa                                                        912
```